(12) United States Patent
Varner

(10) Patent No.: US 9,403,908 B2
(45) Date of Patent: Aug. 2, 2016

(54) METHOD FOR ALTERING HEMATOPOIETIC PROGENITOR CELL ADHESION, DIFFERENTIATION, AND MIGRATION

(75) Inventor: Judith A. Varner, Encinitas, CA (US)

(73) Assignee: The Regents of the University of California, Oakland, CA (US)

( * ) Notice: Subject to any disclaimer, the term of this patent is extended or adjusted under 35 U.S.C. 154(b) by 1786 days.

(21) Appl. No.: 10/573,944

(22) PCT Filed: Sep. 28, 2004

(86) PCT No.: PCT/US2004/031825
§ 371 (c)(1),
(2), (4) Date: Mar. 14, 2007

(87) PCT Pub. No.: WO2005/033275
PCT Pub. Date: Apr. 14, 2005

(65) Prior Publication Data
US 2009/0130124 A1 May 21, 2009

Related U.S. Application Data

(60) Provisional application No. 60/507,202, filed on Sep. 29, 2003.

(51) Int. Cl.
| | | |
|---|---|---|
| A61K 35/28 | (2015.01) |
| C07K 16/28 | (2006.01) |
| A61K 38/07 | (2006.01) |
| A61K 38/08 | (2006.01) |
| G01N 33/50 | (2006.01) |
| G01N 33/68 | (2006.01) |
| A61K 39/00 | (2006.01) |

(52) U.S. Cl.
CPC ............. *C07K 16/2842* (2013.01); *A61K 38/07* (2013.01); *A61K 38/08* (2013.01); *G01N 33/5008* (2013.01); *G01N 33/5029* (2013.01); *G01N 33/5044* (2013.01); *G01N 33/5058* (2013.01); *G01N 33/5064* (2013.01); *G01N 33/5073* (2013.01); *G01N 33/68* (2013.01); *A61K 2039/505* (2013.01); *G01N 2333/70546* (2013.01); *G01N 2500/00* (2013.01)

(58) Field of Classification Search
None
See application file for complete search history.

(56) References Cited

U.S. PATENT DOCUMENTS

| | | |
|---|---|---|
| 4,244,496 A | 1/1981 | Litz |
| 4,639,512 A | 1/1987 | Audibert |
| 4,950,480 A | 8/1990 | Barber |
| 5,061,620 A | 10/1991 | Tsukamoto |
| 5,194,254 A | 3/1993 | Barber |
| 5,199,942 A | 4/1993 | Gillis |
| 5,225,347 A | 7/1993 | Goldberg |
| 5,246,921 A | 9/1993 | Reddy |
| 5,270,163 A | 12/1993 | Gold |
| 5,442,043 A | 8/1995 | Fukuta |
| 5,500,357 A | 3/1996 | Taira |
| 5,527,895 A | 6/1996 | Hampel |
| 5,541,103 A | 7/1996 | Kanz |
| 5,545,806 A | 8/1996 | Lonberg |
| 5,569,825 A | 10/1996 | Lonberg |
| 5,574,142 A | 11/1996 | Meyer, Jr. |
| 5,622,699 A | 4/1997 | Ruoslahti |
| 5,625,126 A | 4/1997 | Lonberg |
| 5,736,146 A | 4/1998 | Cohen |
| 5,750,105 A | 5/1998 | Newman |
| 5,760,029 A | 6/1998 | Jadhav |
| 5,780,426 A | 7/1998 | Palladino |
| 5,980,887 A | 11/1999 | Isner |
| 6,071,532 A | 6/2000 | Chaikof |
| 6,110,687 A | 8/2000 | Nilsen |
| 6,117,631 A | 9/2000 | Nilsen |
| 6,184,206 B1 | 2/2001 | Smith |
| 6,252,043 B1 | 6/2001 | Hession |
| 6,645,489 B2 | 11/2003 | Pykett |

FOREIGN PATENT DOCUMENTS

| | | |
|---|---|---|
| EP | 0140308 | 10/2001 |
| EP | 0842943 | 2/2003 |
| WO | WO92/00995 | 1/1992 |
| WO | WO94/11027 | 5/1994 |
| WO | WO95/15973 | 6/1995 |
| WO | WO96/00581 | 1/1996 |
| WO | WO96/06108 | 2/1996 |
| WO | WO96/20216 | 7/1996 |
| WO | WO96/22966 | 8/1996 |
| WO | WO97/02289 | 1/1997 |
| WO | WO98/42656 | 10/1998 |
| WO | WO00/39292 | 6/2000 |
| WO | WO03/019136 | 3/2003 |

OTHER PUBLICATIONS

Schofield et al, 1997, Blood , v.90, pp. 1858-1866.*
U.S. Appl. No. 60/507,202, filed Sep. 29, 2003, J. Varner.
Asahara et al. *Isolation of Putative Progenitor Endothelial Cells for Angiogenesis*, (1997) Science 275,964-967.
Atherton et al., Peptide *Synthesis. Part 7.' Solid-phase Synthesis of Conotoxin G1*, J. Chem. Soc. Trans. 1: 2065 (1985).
Ausprunk, *Vascularization of Normal and Neoplastic Tissues Grafted to the Chick Chorioallantois*, Amer. 3. Path., 79, No. 3: 597-610 (1975).

(Continued)

*Primary Examiner* — Michail Belyavskyi
(74) *Attorney, Agent, or Firm* — Medlen & Carroll, LLP

(57) ABSTRACT

The present invention satisfies the need in the art by providing methods for altering hematopoietic progenitor cell adhesion and/or migration to a target tissue, and for altering hematopoietic progenitor cell differentiation into a second cell type. The invention also provides methods for screening test compounds for altering the level of hematopoietic progenitor cell adhesion and/or migration to a target tissue, and for altering hematopoietic progenitor cell differentiation into a second cell type. The invention further provides methods for isolating hematopoietic progenitor cells.

19 Claims, 41 Drawing Sheets

(56) References Cited

OTHER PUBLICATIONS

Bartolome et al. *Rapid Up-Regulation of_4 Integrin-mediated Leukocyte Adhesion by Transforming Growth Factor-_1* (2003) Mol. Biol. Cell 14,54-66).
Belicci et al. *Human Skin-Derived Stem Cells Migrate Throughout Forebrain and Differentiate Into Astrocytes After Injection Into Adult Mouse Brain* (2004) J. Neurosci Res. 77,475-86.
Blondelle et al., *Soluble combinatorial libraries of organic, peptidomimetic and peptide diversities*, Trends Anal. Chem. 14:83-92 (1995).
Bochner et al., *Adhesion of Human Basophils, Eosinophils, and Neutrophils to Interleukin I-activated Human Vaacular Endothelial Cells: Contributions of Endothelial Cell Adhesion Molecules* J. Exp. Med. (1991) 173(6): 1553-7.
Boehm et al. *Bone marrow—derived immune cells regulate vascular disease through a p27Kip1—dependent mechanism*, (2004) J. Clin. Invest. 1 14,419-426.
Brando et al., *EC3, a Heterodimeric Disintegrin from Echis carinatus, Inhibits Human and Murine α4 Integrin and Attenuates Lymphocyte Infiltration of Langerhans Islets in Pancreas and Salivary Glands in Nonobese Diabetic Mice* Biochem. Biophys. Res. Commun. (2000) 267(1): 413-417.
Brooks et al., *Requirement of Vascular Integrin cV4I3 for Angiogenesis*, Science. 1994 264:569-71.
Cardarelli et al., *Cyclic RGD Peptide Inhibits a4pl Interaction with Connecting Segment 1 and Vascular Cell Adhesion Molecule*, J. Biol. Chem. (1994) 269(28): 18668-73.
Carlsson and Glad, *Monoclonal Antibodies into the 90's: The All Purpose Tool*, (1989) Bio/Technology 7: 567-73.
Carmeliet, *Angiogenesis in Health and Disease*, (2003) Nat. Med. 9,653-660.
Carmeliet et al., *Angiogenesis in cancer and other diseases*, Nature, Sep. 14, 2000; 407(6801): 249-57.
Chisholm et al., *Monoclonal antibodies to the integrin a-4 subunit inhibit the murine contact hypersensitivity response*, (1993) European J. Immunol. 23: 682-688.
Clements et al., *Identification of a key integrin-binding sequence in VCAM-1 homologous to the LDV active site in fibronectin*, J. Cell Sci. (1994) 107 (Pt 8): 2127-35).
Craddock et al., *Antibodies to VLA4 Integrin Mobilize Long-Term Repopulating Cells and Augment Cytokine-Induced Mobilization in Primates and Mice*, (1997) Blood 90,4779-4788.
Curley et al., *Integrin antagonists*, (1999) Cell. Mol. Life Sci., 56:427-441.
Cursiefen et al. *VEG F-A stimulates lymphangiogenesis and hernangiogenesis in inflammatory neovascularization via macrophage recruitment*, (2004) J. Clin. Invest. 1 13:1040-1050.
de Kruif et al., *Biosynthetically lipid-modified human scFv fragments from phage display libraries as targeting molecules for immunoliposomes*, FEBS Lett., 399:232-236 (1996).
Ding et al., *Synthesis and Biological Activity of Oligosaccharide Libraries*, Adv. Expt. Med. Biol. 376:261-269 (1995).
Dittel et al., *Regulation of Human B-Cell Precursor Adhesion to Bone Marrow Stromal Cells by Cytokines That Exert Opposing Effects on the Expression of Vascular Cell Adhesion Molecule-1 (VCAM-1)*, (1993) Blood 81:2272-2282.
Drabick et al., *Covalent Polymyxin B Conjugate with Human Immunoglobulin Gas an Antiendotoxin Reagent*, (1998) Antirnicrob. Agents Chemother. 42:5 83-5 88.
Dudgeon et al., *Expression and characterization of a very-late antigen-4 (a4βl) integrin-binding fragment of vascular cell-adhesion molecule-1*, Eur. J. Biochem. (1994) 226(2): 517-23.
Ecker and Crook, *Combinatorial Drug Discovery: Which Methods will Produce the Greatest Value?*, Bio/Technology 13:35 1-360 (1995).
Elices et al., *VCAM-1 on Activated Endothelium Interacts with the Leukocyte Integrin VLA-4 at a Site Distinct from the VLA=4/Fibronectin Binding Site*, (1990) Cell 60,577-584.
Elices et al., *Expression and Functional Significance of Alternatively Spliced CS1 Fibronectin in Rheumatoid Arthritis Microvasculature*, J Clin Invest. (1994) 93(1): 405-16.
Friede et al.., *Selective induction of protection against influenza virus infection in mice by a lipid-peptide conjugate delivered in liposomes*, (1994) Vaccine 12:791-797.
Garcia-Pardo et al., *Two Novel Monoclonal Antibodies to Fibronectin That Recognize the HEP II and CS-I Regions Respectively: Their Differential Effect on Lymphocyte Adhesion*, (1992) Biochemical and Biophysical Research Communications 186 (1): 135-42.
Gordon et al., *Applications of Combinatorial Technologies to Drug Discovery. 2. Combinatorial Organic Synthesis, Library Screening Strategies, and Future Directions'*, J. Med. Chern. 37: 1385-1401 (1994).
Grant et al., *Two Different Laminin Domains Mediate the Differentiation of Human Endothelial Cells into Capillary-like Structures In Vitro*, Cell, 5 8: 933-943 (1989).
Gronthos et al., *Molecular and cellular characterisation of highly purified stromal stem cells derived from human bone marrow*, (2003). J. Cell Sci. 116, 1827-1835.
Guan et al., *Lymphoid Cells Recognize an Alternatively Spliced Segment of Fibronectin via the Integrin Receptor a&*, (1990) Cell 60,5 3-6 1.
Guerrier-Takada et al., *The RNA Moiety of Ribonuclease P is the Catalytic Subunit of the Enzyme*, (1983) Cell 35: 849-857.
Hanahan et al., *Patterns and Emerging Mechanisms Review, of the Angiogenic Switch during Tumorigenesis*, (1996) Cell 86,353-364.
Hambor et al., *Functional Consequences of Anti-Sense RNA-Mediated Inhibition of CD8 Surface Expression in a Human T Cell Clone*, (1988) J. Exp. Med. 168: 1237-1 245.
Hashimoto et al., *Bone marrow-derived progenitor cells in pulmonary fibrosis*, (2004) J. Clin. Invest. 113,243-252.
Hattori et al., *Vascular Endothelial Growth Factor and Angiopoietin-1 Stimulate Postnatal Hematopoiesis by Recruitment of Vasculogenic and Hematopoietic Stem Cells*, (2001) J. Exp. Med. 193, 1005-1014.
Hatzopoulos et al., *Isolation and characterization of endothelial progenitor cells from mouse embryos*, (1998) Development 125: 1457-1468.
Hemler et al., *Characterization of the Cell Surface Heterodimer VLA-4 and Related Peptides*, (1987) J. Biol. Chem. 262: 11478.
Hemler et al. *The VLA Protein Family Characterization of Five Distinct Cell Surface Heterodimers Each With a Common 130,000 Molecular Weight P Subunit*, (1987) J. Biol. Chem. 262,3300-3309.
Hofacker et al., *Fast Folding and Comparison of RNA Secondary Structures*, (1994) Monatshefie F. Chemie 125: 167-188.
Holzmann et al., *Identification of a Murine Peyer's Patch-Specific Lymphocyte Homing Receptor as an Integrin Molecule with an a Chain Homologous to Human VLA-4a*, (1989) Cell 56: 37-46).
Humphries et al., *A Synthetic Peptide from Fibronectin Inhibits Experimental Metastasis of Murine Melanoma Cells*, Science, 233: 467-470 (1986).
Humphries et al., *Investigation of the Biological Effects of Anti-Cell Adhesive Synthetic Peptides That Inhibit Experimental Metastasis of B16-F1O Murine Melanoma Cells*, J. Clin. Invest., 81: 782-790 (1988).
Huse et al., *Generation of a Large Combinatorial Library of the Immunoglobulin Repertoire in Phage Lambda*, Science 246: 1275-128 1 (1989).
Issekutz, *Inhibition of In Vivo Lymphocyte Homing to Lymphoid Tissues by Migration to Inflammation and the TA-2 Monoclonal Antibody*, (1991) J. Immunol 147:4178-4184.
Jackson et al., *Potent r4â1 Peptide Antagonists as Potential Anti-Inflammatory Agents*, J. Med. Chem. (1997) 40(21): 3359-68.
Jain et al., *Role of bone marrow-derived cells in tumor angiogenesis and treatment*, (2003) Cancer Cell 3,515-5 16.
Kalka et al., *Transplantation of ex vivo expanded endothelial progenitor cells for therapeutic neovascularization*, Proc Natl Acad Sci U S A. Mar. 28, 2000; 97(7): 3422-7.
Kamber et al., *The Synthesis of Cystine Peptides by Iodine Oxidation of S-Trityl-cysteine and S-Acetamidomethyl-cysteine Peptides'*, Helv. Chim. Acta 63: 899 (1980).

(56) References Cited

OTHER PUBLICATIONS

Kamps et al., *Preparation and characterization of conjugates of (modified) human serum albumin and liposomes: drug carriers with an intrinsic anti-HIV activity*, (1996) Biochim. Biophys. Acta 1278:183-19.

Karaoglu et al., *Functional Characterization of Ost3p Loss of the 34-kD Subunit of the Saccharomyces cerevisiae Oligosaccharyltransferase Results in Biased Underglycosylation of Acceptor Substrates*, J. Cell Biol. 130: 567-577; (1995).

Kawamoto 25 et al. *Therapeutic Potential of Ex Vivo Expanded Endothelial Progenitor Cells for Myocardial Ischemia*, (2001) Circulation 103,634-637.

Kennedy, *Anti-idiotypes and Immunity*, (1986) Sci. 10 Am. 255:48-56.

Kikuta et al. *Mobilization of hematopoietic primitive and committed progenitor cells into blood in mice by anti-vascular adhesion molecule-1 antibody alone or in combination with granulocyte colony-stimulating factor*, Exp. Hematol. 2000,vol. 28, pp. 311-317.

Kim et al., *Regulation of Angiogenesis in Vivo by Ligation of Integrin a5b1 with the Central Cell-Binding Domain of Fibronectin*, Am J Pathol. Apr. 2000; 156 (4): 1345-62).

Kinashi et al. *Adhesion Molecules in Hematopoietic Cells*, (1994) Blood Cells 20: 25-44).

Koivunen et al. *Isolation of a Highly Specific Ligand for the ois(3i Integrin from a Phage Display Library*,J. Cell Biol., 124: 373-380 (1994).

Kruger et al. *Self-Splicing RNA: Autoexcision and Autocyclization of the Ribosomal RNA Intervening Sequence of Tetrahymena*, (1982) Cell 3 1: 147-1 57.

Kwee et al. *Defective development of the embryonic and extraembryonic circulatory systems in vascular cell adhesion molecule (VCAM-1) deficient mice*, (1995) Development 121; 489-503.

LaBarge et al. *Biological Progression from Adult Bone Marrow to Mononucleate Muscle Stem Cell toMultinucleate Muscle Fiber in Response to Injury*, (2002) Cell. 11 1, 589-601.

Liang et al., *Parallel Synthesis and Screening of a Solid Phase Carbohydrate Library*,Science 274: 1520-1 522 (1996).

Lin et al. *Very late antigen 4 (VLA4) agents*, (1998) Current Opinion in Chemical Biology 2:453-457.

Lin et al. *Selective, Tight-Binding Inhibitors of Integrin r4â1 That Inhibit Allergic Airway Responses*, (1999) J. Med. Chem., 42:920-934.

Lyden et al. *Impaired recruitment of bone-marrow-derived endothelial and hematopoietic precursor cells blocks tumor angiogenesis and growth*, (2001) Nat. Med. 7, 1194-201.

Marcinkiewicz et al., *EC3, a Novel Heterodimeric Disintegrin from Echis carinatus Venom, Inhibits a4 and a5 Integrins in an RGD-independent Manner*, J. Biol. Chem. (1999) 274(18): 1 2468-73.

Markus-Sekura, *Techniques for Using Antisense Oligodeoxyribonucleotides to Study Gene Expression*, (1988) Anal. Biochem. 172:289-295.

McCaskill, *The Equilibrium Partition Function and Base PairBinding Probabilities for RNA Secondary Structure*, (1990) Biopolyrners 29: 1 105-1 1 1.

Melder et al. *During angiogenisis, vascular endothelial growth and basic fibroblast growth factor regulate natural killer cell adhesion to tumor endothelium*, (1996) Nat Med. 2:992-997.

Miyake et al. *A VCAM-like Adhesion Molecule on Murine Bone Marrow Stromal Cells Mediates Binding of Lymphocyte Precursors in Culture*, (1991) J. Cell Biol.114, 557-56.

Miyake et al. *Requirement for VLA-4 and VLA-5 Integrins in Lymphoma Cells Binding to and Migration beneath Stromal Cells in Culture*, (1992) J. Cell Biol., 119,653-662.

Morales-Ducret et al., *~q /@ l Integrin (VLA-4) Ligands in Arthritis Vascular Cell Adhesion Molecule-1 Expression in Synovium and on Fibroblast-Like Synoviocytesl*, J. Immunol. 1992 149 (4): 1424-3 1.

Mostafavi-Pour et al. *Identification of a novel heparin-binding site in the alternatively spliced IIICS region of fibronectin: roles of integrins and proteoglycans in cell adhesion to fibronectin splice variants*, (2001) Matrix Biology 20(1): 63-73.

Munoz et al. *A novel region of the a4 integrin subunit with a modulatory role in VLA-4-mediated cell adhesion to fibronectin*, (1997) Biochem J., 327, 27-733.

Nakao et al. *Synergistic Effect of TNF-_in Soluble VCAM-1-Induced Angiogenesis Through_4 Integrins1*, J. Immunol. 2003 Un 1; 170 (11): 5704-11).

Needham et al. *Activation Dependent and Independent VLA-4 Binding Sites on Vascular Cell Adhesion Molecule-1*, (1994) Cell Adhes. Commun. 2:87-99.

Nowlin et al., *A Novel Cyclic Pentapeptide Inhibits a401 and a501Integrin-mediated Cell Adhesion*, J. Biol. Chem. Sep. 25, 1993,268(27): 20352.

Ossonowski and Reich, *Experimental Model for Quantitative Study of Metastasis1*, Cancer Res., 30: 2300-2309 (1980).

Otani et al., *Bone marrow-derived stem cells target retinal astrocytes and can promote or inhibit retinal angiogenesis*, (2004) J. Clin. Invest. 114,765-774.

Otani et al. *Rescue of retinal degeneration by intravitreally injected adult bonemarrow-derived lineage-negative hematopoietic stem cells*, (2002) Nat. Med. 8, 1004-1010 (2002).

Papayannopoulou et al. *Molecular pathways in bone marrow homing: dominant role of a4b1 over b2-integrins and selectins*, (2001); Blood 98,2403-241 1.

Peichev et al., *Expression of VEGFR-2 and AC133 by circulating human CD341 cells identifies a population of functional endothelial precursors*, Blood. Feb. 1, 2000; 95(3): 952-8).

Pitot, H. C., *The Language of Oncology*, (1978) Dekker, Marcel (Ed.); Fundamentals of Oncology, New York pp. 15-28.

Plaue, *Synthesis of cyclic peptides on solid support, Application to analogs of hemagglutinin of influenza virus*, Int. J. Peptide Protein Res., 35: 5 10-5 17 (1990).

Postigo et al. *The or4P1/VCAM-1 adhesion pathway in physiology and disease*, Research in Immunol. 1993 France, vol. 144, No. 9, pp. 723-735.

Priller et al. *Neogenesis of cerebellar Purkinje neurons from gene-marked bone marrow cells in vivo*, (2001) J. Cell Biol. 155, 733-738.

Puttaraju et al. *A circular trans-acting hepatitis delta virus ribozyme*, (1993) Nucl. Acids Res. 21:4253-4258.

Quackenbush et al. *Identification of Several Cell Surface Proteins of Non-T, Non-Bacute Lymphoblastic Leukemia by Using Monoclonal Antibodies*, (1985) J. Immunol 134: 1276-1285.

Rafii et al. *Therapeutic stem and progenitor cell transplantation for organ vascularization and regeneration*, (2003) Nat. Med. 9,702-12.

Religa et al. *Smooth-Muscle Progenitor Cells of Bone Marroworigin Contribute to the Development of Neointimal Thickenings in Rat Aortic Allografts and Injured Rat Carotid Arteries1*, (2002) Transplantation 74, 13 10-13 15.

Rose et al. *Soluble VCAM-1 binding to a4 integrins is cell-type specific and activation dependent and is disrupted during apoptosis in T cells*, (2000) Blood 95:602-609.

Rosen et al., *Roles for the Integrin VLA-4 and Its Counter Receptor VCAM-1 in Myogenesis*, Cell. Jun. 26, 1992; 69(7): 1107-19).

Ruzinova et al. *Effect of angiogenesis inhibition by Id loss and the contribution of bone-marrow-derived endothelial cells in spontaneous murine tumors*, (2003) 35 Cancer Cell. 4: 277-289.

Sanchez-Madrid et al. *VLA-3: A novel polypeptide association within the VLA molecular complex: cell distribution and biochemical characterization*, (1986) Eur. J. Immunol. 16, 1342-1349.

Shahinian et al. *A novel strategy affords high-yield coupling of antibody Fab fragments to liposomes*, (1995) Biochim. Biophys. Acta 1239:157-167.

Sheremata et al., *A safety and pharmacokinetic study of intravenous natalizumab in patients with MS*, (1999) Neurology 52: No. 5, Mar. 23 199.

Simmons et al. *Vascular Cell Adhesion Molecule-1 Expressed by Bone Marrow Stromal Cells Mediates the Binding of Hematopoietic Progenitor Cells*, (1992) Blood. 80, 3 8 8-395.

Sioud et al., *Prevention of human immunodeficiency virus type 1 integrase expression in Escherichia coli by a ribozyme*, (1991) Proc. Natl. Acad. Sci. USA 88:7303-7307.

Souers et al. *Novel Inhibitors of a4131 Integrin Receptor Interactions Through Library Synthesis and Screening*, (1998) Bioorg. Med. Chern. Lett., 8:2297-2302.

(56) References Cited

OTHER PUBLICATIONS

Takahashi et al. *Ischemia- and cytokine-induced mobilization of bone marrow-derived endothelial progenitor cells for neovascularization*, (1999) Nat. Med. 5,434-438.

Tam et al., *Disulfide Bond Formation in Peptides by Dimethyl Sulfoxide. Scope and Applications*, (1991) J. Am. Chem. Soc., 11 3: 6657-6662.

Tamaki et al. *Identification of myogenic-endothelial progenitor cells in the interstitial spaces of skeletal muscle*, (2002) J. Cell Biol. 157, 571-577.

Teixido et al., *Role of Ih, and I#2 Integrins in the Adhesion of Human CD34hI Stem Cells to Bone Marrow Stroma*, J. Clin. Invest. 1992, vol. 90, pp. 358-367.

Terskikh, Gene *expression analysis of purified hematopoietic stem cells and committed progenitors*, (2003) Blood 102,94-10.

Torrente et al., *Identification of a putative pathway for the muscle homing of stem cells in a muscular dystrophy model*, (2003) J. Cell Biol. 162,5 11-520.

Torrente et al., *Human circulating AC133+ stem cells restore dystrophin expression and ameliorate function in dystrophic skeletal muscle*, (2004) J. Clin. Invest. 114, 182-19.

Tubridy et al., *The effect of anti-cw4 integrin antibody on brain lesion activity in MS*, (1999) Neurology 53(3): 466-72.

Ulbrich et al., *Leukocyte and endothelial cell adhesion molecules as targets for therapeutic interventions in inflammatory disease*, Trends in Pharma. Sci., vol. 24, No. 12, Dec. 2003, pp. 640-647.

Urbich et al., *Endothelial Progenitor Cells Functional Characterization*, Trends in Cardio. Med., vol. 14, No. 8, Nov. 2004 pp. 318-322.

Verheul et al, *Monopalmitic acid-peptide conjugates induce cytotoxic T cell responses against malarial epitopes: importance of spacer amino acids*, (1995) J. Immunol. Methods 182:219-226.

Ward et al., *Binding activities of a repertoire of single immunoglobulin variable domains secreted from Escherichia coli*, Nature 341: 544-546 (1989).

Wayner et al., *Identification and Characterization of the T Lymphocyte Adhesion Receptor for an Alternative Cell Attachment Domain (CS-1) in Plasma Fibronectin*, J. Cell Biol. (1989) 109(3): 1321-30.

Wayner et al., *Activation-dependent Recognition by Hematopoietic Cells of the LDV Sequence in the V Region of Fibronectin*, J. Cell Biol. (1992) 116(2): 489-97.

Winter et al., *Humanized antibodies*, Immunol. Today 14:243-246 (1993).

Wolfe, Stephen L. (Ed.), "Molecular and Cellular Biology," Wadsworth Publishing Company (1993) p. 575.

Wu et al., *Reversible Cleavage and Ligation of Hepatitis Delta Virus RNA*, (1989) Science 243:652-655.

Yang et al., *Cell adhesion events mediated by a4 integrins are essential in placental and cardiac development*, (1995) Development 121, 549-5 60.

Yednock et al., *a4b1 Integrin-dependent Cell Adhesion is Regulated by a Low Affinity Receptor Pool That is Conformationally Responsive to Ligand*, (1995) J. Biol. Chem. 270:28740-28750.

York et al., *The structures of arabinoxyloglucans produced by solanaceous plants*, Carb. Res. 285:99-128 (1996).

Zimmer et al. *Peptides*, 393-394 (1992), ESCOM Science Publishers, B.V., 1993.

Ryan et al. *Inhibition of Human Bone Marrow Lymphoid Progenitor Colonies by Antibodies to VLA Integrins'*, (1992) J. of Immunol. U.S., vol. 149, No. 11, pp. 3759-3764.

\* cited by examiner

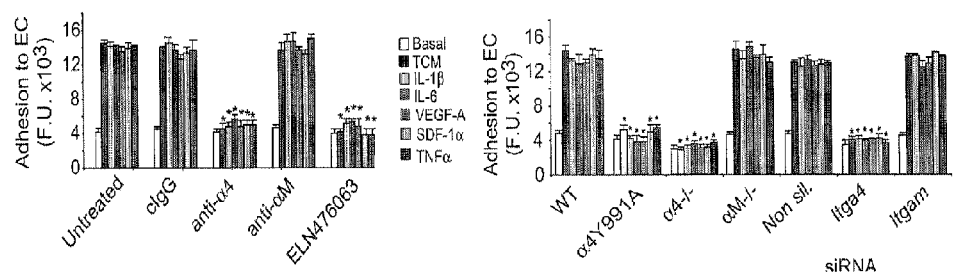

Figure 1: Antagonists of Integrin α4β1 and genetic mutation of α4 suppress progenitor cell adhesion to endothelial cells equally well. (A) Adhesion of stimulated myeloid cells to EC in the presence of medium (untreated), control IgG (cIgG), anti-α4, or anti-αM integrin antibody, or small molecule inhibitor of integrin α4 (ELN476063) (n = 3), *p < 0.001 versus IgG. (B) Adhesion to EC of stimulated WT, α4Y991A, α4-/-, αM-/- and integrin α4 (Itga4) or αM (Itgam) siRNA transfected myeloid cells (n = 3), *p < 0.001 versus WT. From Schmid et al, Cancer Cell 19, 715–727, June 14, 2011

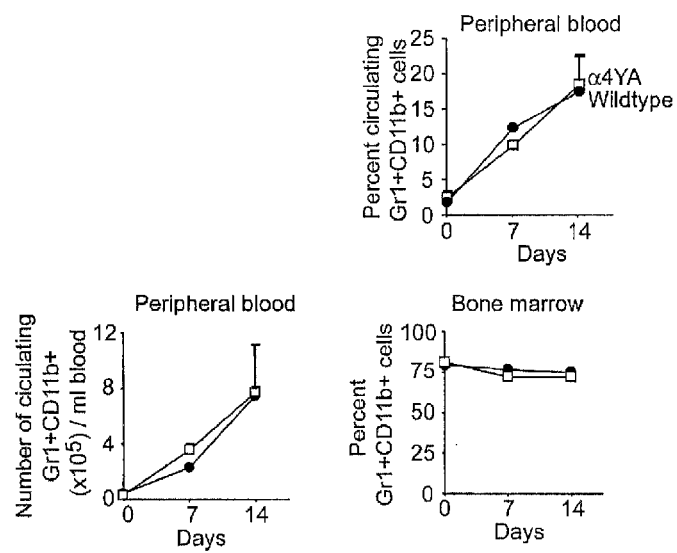
Figure 2: Inhibition of α4 integrin has no effect on myeloid progenitor cell content in peripheral blood or bone marrow. Percent and total number of CD11b+Gr1+ cells in peripheral blood and bone marrow of WT or α4Y991A mice with LLC tumors. Varner lab, unpublished.

Fig. 3A

```
  1 mpgkmvvilg asnilwimfa asqafkiett pesrylaqig dsvsltcstt gcespffswr
 61 tqidsplngk vtnegttstl tmnpvsfgne hsylctatce srklekgiqv eiysfpkdpe
121 ihlsgpleag kpitvkcsva dvypfdrlei dlkgdhlmk sqefledadr ksletkslev
181 tftpviedig kvlvcraklh idemdsvptv rqavkelqvy ispkntvisv npstklqegg
241 svtmtcsseg lpapeifwsk kldngnlqhl sgnatltlia mrmedsgiyv cegvnligkn
301 rkevelivqe kpftveispg priaaqigds vmltcsvmgc espsfswrtq idsplsgkvr
361 segtnstltl spvsfenehs ylctvtcghk klekgiqvel ysfprdpeie msgglvngss
421 vtvsckvpsv ypldrleiel lkgetileni efledtdmks lenkslemtf iptiedtgka
481 lvcqaklhid dmefepkqrq stqtlyvnva prdttvlvsp ssileegssv nmtclsqgfp
541 apkilwsrql pngelqplse natltlistk medsgvylce ginqagrsrk eveliiqvtp
601 kdikltafps esvkegdtvi isctcgnvpe twiilkkkae tgdtvlksid gaytirkaql
661 kdagvyeces knkvgsqlrs ltldvqgren nkdyfspell vlyfasslii paigmiiyfa
721 rkanmkgsys lveaqkskv
```

Fig. 3B

```
  1 mpgkmvvilg asnilwimfa asqafkiett pesrylaqig dsvsltcstt gcespffswr
 61 tqidsplngk vtnegttstl tmnpvsfgne hsylctatce srklekgiqv eiysfpkdpe
121 ihlsgpleag kpitvkcsva dvypfdrlei dlkgdhlmk sqefledadr ksletkslev
181 tftpviedig kvlvcraklh idemdsvptv rqavkelqvy ispkntvisv npstklqegg
241 svtmtcsseg lpapeifwsk kldngnlqhl sgnatltlia mrmedsgiyv cegvnligkn
301 rkevelivqa fprdpeiems gglvngssvt vsckvpsvyp ldrleiellk getilenief
361 ledtdmksle nkslemtfip tiedtgkalv cqaklhiddm efepkqrqst qtlyvnvapr
421 dttvlvspss ileegssvnm tclsqgfpap kilwsrqlpn gelqplsena tltlistkme
481 dsgvylcegi nqagrsrkev eliiqvtpkd ikltafpses vkegdtviis ctcgnvpetw
541 iilkkkaetg dtvlksidga ytirkaqlkd agvyeceskn kvgsqlrslt ldvqgrennk
601 dyfspellvl yfasslipa igmiiyfark anmkgsyslv eaqkskv
```

Fig. 4

```
   1 mlrgpgpgll llavqclgta vpstgasksk rqaqqmvqpq spvavsqskp gcydngkhyq
  61 inqqwertyl gnalvctcyg gsrgfncesk peaeetcfdk ytgntyrvgd tyerpkdsmi
 121 wdctcigagr grisctianr cheggqsyki gdtwrrphet ggymleovcl gngkgewtck
 181 piaekcfdha agtsyvvget wekpyqgwmm vdctclgegs gritctsrnr cndqdtrtsy
 241 rigdtwskkd nrgnllqcic tgngrgewkc erhtsvqtts sgsgpftdvr aavyqpqphp
 301 qpppyghcvt dsgvvysvgm qwlktqgnkq mlctclgngv scqetavtqt yggnsngepc
 361 vlpftyngrt fyscttegrq dghlwcstts nyeqdqkysf ctdhtvlvqt qggnsngalc
 421 hfpflynnhn ytdctsegrr dnmkwcgttq nydadqkfgf cpmaaheeic ttnegvmyri
 481 gdqwdkqhdm ghmmrctcvg ngrgewtcia ysqlrdqciv dditynvndt fhkrheeghm
 541 lnctcfgqgr grwkcdpvdq cqdsetgtfy qigdswekyv hgvryqcycy grgigewhcq
 601 plqtypsssg pvevfitetp sqpnshpiqw napqpshisk yilrwrpkns vgrwkeatip
 661 ghlnsytikg lkpgvvyegq lisiqqyghq evtrfdfttt ststpvtsnt vtgettpfsp
 721 lvatsesvte itassfvvsw vsasdtvsgf rveyelseeg depqyldlps tatsvnipdl
 781 lpgrkyivnv yqisedgeqs lilstsqtta pdappdptvd qvddtsivvr wsrpqapitg
 841 yrivyspsve gsstelnlpe tansvtlsdl qpgvqyniti yaveenqest pvviqqettg
 901 tprsdtvpsp rdlqfvevtd vkvtimwtpp esavtgyrvd vipvnlpgeh gqrlpismt
 961 faevtglspg vtyyfkvfav shgreskplt aqqttkldap tnlqfvnetd stvlvrwtpp
1021 raqitgyrlt vgltrrgqpr qynvgpsvsk yplrnlqpas eytvslvaik gnqespkatg
1081 vfttlqpgss ippyntevte ttivitwtpa prigfklgvr psqggeapre vtsdsgsivv
1141 sgltpgveyv ytiqvlrdgq erdapivnkv vtplspptnl hleanpdtgv ltvswerstt
1201 pditgyritt tptngqqgns leevvhadqs sctfdnlspg leynvsvytv kddkesvpis
1261 dtiipavppp tdlrftnigp dtmrvtwapp psidltnflv ryspvkneed vaelsispsd
1321 navvltnllp gteyvvsvss vyeqhestpl rgrqktglds ptgidfsdit ansftvhwia
1381 pratitgyri rhhpehfsgr predrvphsr nsitltnltp gteyvvsiva lngreespll
1441 igqqstvsdv prdlevvaat ptslliswda pavtvryyri tygetggnsp vqeftvpgsk
1501 statisglkp gvdytitvya vtgrgdspas skpisinyrt eidkpsqmqv tdvqdnsisv
1561 kwlpssspvt gyrvtttpkn gpgptktkta gpdqtemtie glqptveyvv svyaqnpsge
1621 sqplvqtavt nidrpkglaf tdvdvdsiki awespqgqvs ryrvtysspe dgihelfpap
1681 dgeedtaelq glrpgseytv svvalhddme sqpligtqst aipaptdlkf tqvtptslsa
1741 qwtppnvqlt gyrvrvtpke ktgpmkeinl apdsssvvvs glmvatkyev svyalkdtlt
1801 srpaqgvvtt lenvspprra rvtdatetti tiswrtktet itgfqvdavp angqtpiqrt
1861 ikpdvrsyti tglqpgtdyk iylytlndna rsspvvidas taidapsnlr flattpnsll
1921 vswqpprari tgyiikyekp gspprevvpr prpgvteati tglepgteyt iyvialknnq
1981 ksepligrkk tdelpqlvtl phpnlhgpei ldvpstvqkt pfvthpgydt gngiqlpgts
2041 gqqpsvgqqm ifeehgfrrt tppttatpir hrprpyppnv geeiqighip redvdyhlyp
2101 hgpglnpnas tgqealsqtt iswapfqdts eyiischpvg tdeeplqfrv pgtstsatlt
2161 gltrgatyni ivealkdqqr hkvreevvtv gnsvneglnq ptddscfdpy tvshyavgde
2221 wermsesgfk llcqclgfgs ghfrcdssrw chdngvnyki gekwdrqgen gqmmsctclg
2281 ngkgefkcdp heatcyddgk tyhvgeqwqk eylgaicsct cfggqrgwrc dncrrpggep
2341 spegttgqsy nqysqryhqr tntnvncpie cfmpldvqad redsre
```

Fig. 8A

```
   1 gocatoccgc gctctgcggg ctgggaggcc cgggccagga cgcgagtcct gcgcagccga
  61 ggttccccag cgcccctgc agcgcgcgt aggcagagac ggagcccggc cctgcgcctc
 121 cgcaccacgc ccgggacccc accagcggc ccgtaccogg agaagcagcg cgagcacccg
 181 aagctcccgg ctggcggcag aaaccgggag tggggccggg cgagtgcgcg gcatccoagg
 241 ccggcccgaa cgctccgccc gcggtgggcc gacttcccct cctcttccct ctctccttcc
 301 tttagcccgc tggcgccgga cacgctgcgc ctcatctctt ggggcgttct tcccgttgg
 361 ccaaccgtcg catccgtgc aactttgggg tagtggccgt ttagtgttga atgttcccca
 421 ccgagagcgc atggcttggg aagcgaggcg cgaaccoggc ccccgaaggg ccgccgtccg
 481 ggagacggtg atgctgttgc tgtgcctggg ggtcccgacc ggccgcccct acaacgtgga
 541 cactgagagc gcgctgcttt accagggccc ccacaacacg ctgttcgget actcggtcgt
 601 gctgcacagc cacggggcga accgatggct cctagtgggt gcgcccactg ccaactggct
 661 cgccaacgct tcagtgatca atcccgggc gatttacaga tgcaggatcg gaaagaatcc
 721 cggccagacg tgcgaacagc tccagctggg tagccctaat ggagaacctt gtggaaagac
 781 ttgtttggaa gagagagaca atcagtggtt gggggtcaca ctttccagac agccaggaga
 841 aaatggatcc atcgtgactt gtgggcatag atggaaaaat atatttacaa taaagaatga
 901 aaataagctc cccactggtg gttgctatgg agtgccccct gatttacgaa cagaactgag
 961 taaaagaata gctccgtgtt atcaagatta tgtgaaaaaa tttggagaaa attttgcatc
1021 atgtcaagct ggaatatcca gttttacac aaaggattta attgtgatgg gggccccagg
1081 atcatcttac tggactggct ctcttttgt ctacaatata actacaaata aatacaaggc
1141 tttttttagac aaacaaaatc aagtaaaatt tggaagttat ttaggatatt cagtcggagc
1201 tggtcatttt cggagccagc atactaccga agtagtcgga ggagctcctc aacatgagca
1261 gattggtaag gcatatatat tcagcattga tgaaaaagaa ctaaatatct tacatgaaat
1321 gaaaggtaaa aagcttggat cgtactttgg agcttctgtc tgtgctgtgg acctcaatgc
1381 agatggcttc tcagatctgc tcgtgggagc acccatgcag agcaccatca gagaggaagg
1441 aagagtgttt gtgtacatca actctggctc gggagcagta atgaatgcaa tggaaacaaa
1501 cctcgttgga agtgacaaat atgctgcaag atttggggaa tctatagtta atcttggcga
1561 cattgacaat gatggctttg aagatgttgc tatcggagct ccacaagaag atgacttgca
1621 aggtgctatt tatatttaca atggccgtgc agatgggatc tcgtcaacct tctcacagag
1681 aattgaagga cttcagatca gcaaatcgtt aagtatgttt ggacagtcta tatcaggaca
1741 aattgatgca gataataatg gctatgtaga tgtagcagtt ggtgctttc ggtctgattc
1801 tgctgtcttg ctaaggacaa gaactgtagt aattgttgac gttctttaa gccaccctga
1861 gtcagtaaat agaacgaaat ttgactgtgt tgaaaatgga tggccttctg tgtgcataga
1921 tctaacactt tgttttctcat ataagggcaa ggaagttcca ggttacattg ttttgttta
1981 taacatgagt ttggatgtga acagaaaggc agagtctcca ccaagattct atttctctto
2041 taatgaact tctgacgtga ttacaggaag catacaggtg tccagcagag aagctaactg
2101 tagaacacat caagcattta tgcggaaaga tgtgcgggac atcctcaccc caattcagat
2161 tgaagctgct taccaccttg gtcctcatgt catcagtaaa cgaagtacag aggaattccc
2221 accacttcag ccaattcttc agcagaagaa agaaaaagac ataatgaaaa aaacaataaa
2281 ctttgcaagg ttttgtgccc atgaaaattg ttctgctgat ttacaggttt ctgcaaagat
2341 tgggtttttg aagcccatg aaaataaaac atatcttgct gttgggagta tgaagacatt
2401 gatgttgaat gtgtccttgt ttaatgctgg agatgatgca tatgaaacga ctctacatgt
2461 caaactaccc gtgggtcttt atttcattaa gatttttagag ctggaagaga agcaaataaa
2521 ctgtgaagtc acagataact ctggcgtggt acaacttgac tgcagtattg gctatatata
```

Fig. 8B

```
2581 tgtagatcat ctctcaagga tagatattag ctttctcctg gatgtgagct cactcagcag
2641 agcggaagag gacctcagta tcacagtgca tgctacctgt gaaaatgaag aggaaatgga
2701 caatctaaag cacagcagag tgactgtagc aataccttta aaatatgagg ttaagctgac
2761 tgttcatggg tttgtaaacc caacttcatt tgtgtatgga tcaaatgatg aaaatgagcc
2821 tgaaacgtgc atggtggaga aaatgaactt aactttccat gttatcaaca ctggcaatag
2881 tatggctccc aatgttagtg tggaaataat ggtaccaaat tcttttagcc cccaaactga
2941 taagctgttc aacattttgg atgtccagac tactactgga gaatgccact ttgaaaatta
3001 tcaaagagtg tgtgcattag agcagcaaaa gagtgcaatg cagaccttga aaggcatagt
3061 ccggttcttg tccaagactg ataagaggct attgtactgc ataaaagctg atccacattg
3121 tttaaatttc ttgtgtaatt ttgggaaaat ggaaagtgga aaagaagcca gtgttcatat
3181 ccaactggaa ggccggccat ccatttaga aatggatgag acttcagcac tcaagtttga
3241 aataagagca acaggttttc cagagccaaa tccaagagta attgaactaa acaaggatga
3301 gaatgttgcg catgttctac tggaaggact acatcatcaa agacccaaac gttatttcac
3361 catagtgatt atttcaagta gcttgctact tggacttatt gtacttctat tgatctcata
3421 tgttatgtgg aaggctggct tctttaaaag acaatacaaa tctatcctac aagaagaaaa
3481 cagaagagac agtggagtt atatcaacag taaaagcaat gatgattaag gacttctttc
3541 aaattgagag aatggaaaac ag
```

Fig. 9A

```
   1 gccatcccgc gctctgcggg ctgggaggcc cgggccagga cgcgagtcct gcgcagccga
  61 ggttccccag cgcccctgc agccgcgcgt aggcagagac ggagcccggc cctgcgcctc
 121 cgcaccacgc ccgggacccc acccagcggc ccgtacccgg agaagcagcg cgagcacccg
 181 aagctcccgg ctggcggcag aaaccgggag tggggccggg cgagtgcgcg gcatcccagg
 241 ccggcccgaa cgctccgccc gcggtgggcc gacttcccct cctcttccct ctctccttcc
 301 tttagcccgc tggcgccgga cacgctgcgc ctcatctctt ggggcgttct tccccgttgg
 361 ccaaccgtcg catcccgtgc aactttgggg tagtggccgt ttagtgttga atgttcccca
 421 ccgagagcgc atggcttggg aagcgaggcg cgaacccggc ccccgaaggg ccgccgtccg
 481 ggagacggtg atgctgttgc tgtgcctggg ggtcccgacc ggccgcccct acaacgtgga
 541 cactgagagc gcgctgcttt accagggccc ccacaacacg ctgttcggct actcggtcgt
 601 gctgcacagc cacggggcga accgatggct cctagtgggt gcgcccactg ccaactggct
 661 cgccaacgct tcagtgatca atcccggggc gatttacaga tgcaggatcg gaaagaatcc
 721 cggccagacg tgcgaacagc tccagctggg tagccctaat ggagaacctt gtggaaagac
 781 ttgtttggaa gagagagaca atcagtggtt ggggtcaca ctttccagac agccaggaga
 841 aaatggatcc atcgtgactt gtgggcatag atggaaaaat atattttaca taaagaatga
 901 aaataagctc cccactggtg gttgctatgg agtgcccct gatttacgaa cagaactgag
 961 taaaagaata gctccgtgtt atcaagatta tgtgaaaaaa tttggagaaa attttgcatc
1021 atgtcaagct ggaatatcca gttttacac aaaggattta attgtgatgg gggcccagg
1081 atcatcttac tggactggct ctctttttgt ctacaatata actacaaata aatacaaggc
1141 tttttttagac aaacaaaatc aagtaaaatt tggaagttat ttaggatatt cagtcggagc
1201 tggtcatttt cggagccagc atactaccga agtagtcgga ggagctcctc aacatgagca
1261 gattggtaag gcatatatat tcagcattga tgaaaaagaa ctaaatatct tacatgaaat
1321 gaaaggtaaa aagcttggat cgtactttgg agcttctgtc tgtgctgtgg acctcaatgc
1381 agatggcttc tcagatctgc tcgtgggagc acccatgcag agcaccatca gagaggaagg
1441 aagagtgttt gtgtacatca actctggctc ggggagcagta atgaatgcaa tggaaacaaa
1501 cctcgttgga agtgacaaat atgctgcaag atttgggaa tctatagtta atcttggcga
1561 cattgacaat gatggctttg aagatgttgc tatcggagct ccacaagaag atgacttgca
1621 aggtgctatt tatatttaca atggccgtgc agatgggatc tcgtcaacct tctcacagag
1681 aattgaagga cttcagatca gcaaatcgtt aagtatgttt ggacagtcta tcaggaca
1741 aattgatgca gataataatg gctatgtaga tgtagcagtt ggtgcttttc ggtctgattc
1801 tgctgtcttg ctaaggacaa gacctgtagt aattgttgac gcttctttaa gccaccctga
1861 gtcagtaaat agaacgaaat ttgactgtgt tgaaatgga tggccttctg tgtgcataga
1921 tctaacactt tgtttctcat ataagggcaa ggaagttcca ggttacattg ttttgtttta
1981 taacatgagt ttggatgtga acagaaaggc agagtctcca ccaagattct atttctcttc
2041 taatggaact totgacgtga ttacaggaag catacaggtg tcaagcagag aagctaactg
2101 tagaacacat caagcattta tgcggaaaga tgtgcgggac atcctcaccc caattcagat
2161 tgaagctgct taccaccttg gtcctcatgt catcagtaaa cgaagtacag aggaattccc
2221 accacttcag ccaattcttc agcagaagaa agaaaaagac ataatgaaaa aaacaataaa
2281 ctttgcaagg ttttgtgccc atgaaaattg ttctgctgat ttacaggttt ctgcaaagat
2341 tgggttttttg aagcccatg aaaataaaac atatcttgct gttgggagta tgaagacatt
2401 gatgttgaat gtgtccttgt ttaatgctgg agatgatgca tatgaaacga ctctacatgt
2461 caaactaccc gtgggtctt atttcattaa gatttttagag ctggaagaga agcaaataaa
```

Fig. 9B

```
2521 ctgtgaagtc acagataact ctggcgtggt acaacttgac tgcagtattg gctatatata
2581 tgtagatcat ctctcaagga tagatattag ctttctcctg gatgtgagct cactcagcag
2641 agcggaagag gacctcagta tcacagtgca tgctacctgt gaaaatgaag aggaaatgga
2701 caatctaaag cacagcagag tgactgtagc aataccttta aaatatgagg ttaagctgac
2761 tgttcatggg tttgtaaacc caacttcatt tgtgtatgga tcaaatgatg aaaatgagcc
2821 tgaaacgtgc atggtggaga aaatgaactt aactttccat gttatcaaca ctggcaatag
2881 tatggctccc aatgttagtg tggaaataat ggtaccaaat tcttttagcc cccaaactga
2941 taagctgttc aacattttgg atgtccagac tactactgga gaatgccact ttgaaaatta
3001 tcaaagagtg tgtgcattag agcagcaaaa gagtgcaatg cagaccttga aaggcatagt
3061 ccggttcttg tccaagactg ataagaggct attgtactgc ataaaagctg atccacattg
3121 tttaaatttc ttgtgtaatt ttgggaaaat ggaaagtgga aaagaagcca gtgttcatat
3181 ccaactggaa ggccggccat ccattttaga aatggatgag acttcagcac tcaagtttga
3241 aataagagca acaggttttc cagagccaaa tccaagagta attgaactaa acaaggatga
3301 gaatgttgcg catgttctac tggaaggact acatcatcaa agacccaaac gttatttcac
3361 catagtgatt atttcaagta gcttgctact tggacttatt gtacttctat tgatctcata
3421 tgttatgtgg aaggctggct tctttaaaag acaatacaaa tctatcctac aagaagaaaa
3481 cagaagagac agttggagtt atatcaacag taaaagcaat gatgattaag gacttctttc
3541 aaattgagag aatggaaaac ag
```

Fig. 10A

```
   1 gtccgccaaa acctgcgcgg atagggaaga acagcacccc ggcgccgatt gccgtaccaa
  61 acaagcctaa cgtccgctgg gccccggacg ccgcgcggaa aagatgaatt tacaaccaat
 121 tttctggatt ggactgatca gttcagtttg ctgtgtgttt gctcaaacag atgaaaatag
 181 atgtttaaaa gcaaatgcca aatcatgtgg agaatgtata caagcagggc caaattgtgg
 241 gtggtgcaca aattcaacat ttttacagga aggaatgcct acttctgcac gatgtgatga
 301 tttagaagcc ttaaaaaaga agggttgccc tccagatgac atagaaaatc ccagaggctc
 361 caaagatata aagaaaaata aaaatgtaac caaccgtagc aaaggaacag cagagaagct
 421 caagccagag gatattcatc agatccaacc acagcagttg gttttgcgat taagatcagg
 481 ggagccacag acatttacat taaaattcaa gagagctgaa gactatccca ttgacctcta
 541 ctaccttatg gacctgtctt attcaatgaa agacgatttg gagaatgtaa aaagtcttgg
 601 aacagatctg atgaatgaaa tgaggaggat tacttcggac ttcagaattg gatttggctc
 661 atttgtggaa aagactgtga tgcctttacat tagcacaaca ccagctaagc tcaggaaccc
 721 ttgcacaagt gaacagaact gcaccacccc atttagctac aaaaatgtgc tcagtcttac
 781 taataaagga gaagtattta atgaacttgt tggaaaacag cgcatatctg gaaatttgga
 841 ttctccagaa ggtggtttcg atgccatcat gcaagttgca gtttgtggat cactgattgg
 901 ctggaggaat gttacacggc tgctggtgtt ttccacagat gccgggttttc actttgctgg
 961 agatgggaaa cttggtggca ttgttttacc aaatgatgga caatgtcacc tggaaaataa
1021 tatgtacaca atgagccatt attatgatta tccttctatt gctcacctta tccagaaact
1081 gagtgaaaat aatattcaga caattttttgc agttactgaa gaatttcagc ctgtttacaa
1141 ggagctgaaa aacttgatcc ctaagtcagc agtaggaaca ttatctgcaa attctagcaa
1201 tgtaattcag ttgatcattg atgcatacaa ttcccttttcc tcagaagtca ttttggaaaa
1261 cggcaaattg tcagaaggag taacaataag ttacaaatct tactgcaaga acggggtgaa
1321 tggaacaggg gaaaatggaa gaaaatgttc caatatttcc attggagatg aggttcaatt
1381 tgaaattagc ataacttcaa ataagtgtcc aaaaaaggat tctgacagct ttaaaattag
1441 gcctctgggc tttacggagg aagtagaggt tattcttcag tacatctgtg aatgtgaatg
1501 ccaaagcgaa ggcatccctg aaagtccaa gtgtcatgaa ggaaatggga catttgagtg
1561 tggcgcgtgc aggtgcaatg aagggcgtgt tggtagacat tgtgaatgca gcacagatga
1621 agttaacagt gaagacatgg atgcttactg caggaaagaa aacagttcag aaatctgcag
1681 taacaatgga gagtgcgtct gcggacagtg tgtttgtagg aagagggata atacaaatga
1741 aatttattct ggcaaattct gcgagtgtga taatttcaac tgtgatagat ccaatggctt
1801 aatttgtgga ggaaatggtg tttgcaagtg tcgtgtgtgt gagtgcaacc ccaactacac
1861 tggcagtgca tgtgactgtt ctttggatac tagtacttgt gaagccagca cggacagat
1921 ctgcaatggc cggggcatct gcgagtgtgg tgtctgtaag tgtacagatc cgaagtttca
1981 agggcaaacg tgtgagatgt gtcagacctg ccttggtgtc tgtgctgagc ataaagaatg
2041 tgttcagtgc agagccttca ataaggaga aagaaagac acatgcacac aggaatgttc
2101 ctattttaac attaccaagg tagaaagtcg ggacaaatta ccccagccgg tccaacctga
2161 tcctgtgtcc cattgtaagg agaaggatgt tgacgactgt tggttctatt ttacgtattc
2221 agtgaatggg aacaacgagg tcatggttca tgttgtggag aatccagagt gtcccactgg
2281 tccagacatc attccaattg tagctggtgt ggttgctgga attgttctta ttggccttgc
2341 attactgctg atatggaagc tttttaatgat aattcatgac agaagggagt tgctaaatt
2401 tgaaaaggag aaaatgaatg ccaaatggga cacgggtgaa aatcctattt ataagagtgc
```

Fig. 10B

```
2461 cgtaacaact gtggtcaatc cgaagtatga gggaaaatga gtactgcccg tgcaaatccc
2521 acaacactga atgcaaagta gcaatttcca tagtcacagt taggtagctt tagggcaata
2581 ttgccatggt tttactcatg tgcaggtttt gaaaatgtac aatatgtata atttttaaaa
2641 tgttttatta ttttgaaaat aatgttgtaa ttcatgccag ggactgacaa aagacttgag
2701 acaggatggt tattcttgtc agctaaggtc acattgtgcc ttttgacct tttcttcctg
2761 gactattgaa atcaagctta ttggattaag tgatatttct atagcgattg aaagggcaat
2821 agttaaagta atgagcatga tgagagtttc tgttaatcat gtattaaaac tgattttag
2881 ctttacatat gtcagtttgc agttatgcag aatccaaagt aaatgtcctg ctagctagtt
2941 aaggattgtt ttaaatctgt tattttgcta tttgcctgtt agacatgact gatgacatat
3001 ctgaaagaca agtatgttga gagttgctgg tgtaaaatac gtttgaaata gttgatctac
3061 aaaggccatg ggaaaaattc agagagttag gaaggaaaaa ccaatagctt taaaacctgt
3121 gtgccatttt aagagtttact taatgtttgg taactttttat gccttcactt tacaaattca
3181 agccttagat aaaagaaccg agcaattttc tgctaaaaag tccttgattt agcactattt
3241 acatacaggc catactttac aaagtatttg ctgaatgggg acctttgag ttgaatttat
3301 tttattattt ttattttgtt taatgtctgg tgctttctat cacctcttct aatctttaa
3361 tgtatttgtt tgcaattttg gggtaagact tttttatgag tacttttct ttgaagtttt
3421 agcggtcaat ttgcctttt aatgaacatg tgaagttata ctgtggctat gcaacagctc
3481 tcacctacgc gagtcttact ttgagttagt gccataacag accactgtat gtttacttct
3541 caccatttga gttgcccatc ttgtttcaca ctagtcacat tcttgtttta agtgccttta
3601 gttttaacag ttca
```

Fig. 11

```
   1 atgcctggga agatggtcgt gatccttgga gcctcaaata tactttggat aatgtttgca
  61 gcttctcaag cttttaaaat cgagaccacc ccagaatcta gatatcttgc tcagattggt
 121 gactccgtct cattgacttg cagcaccaca ggctgtgagt ccccattttt ctcttggaga
 181 acccagatag atagtccact gaatgggaag gtgacgaatg aggggaccac atctacgctg
 241 acaatgaatc ctgttagttt tgggaacgaa cactcttacc tgtgcacagc aacttgtgaa
 301 tctaggaaat tggaaaaagg aatccaggtg gagatctact cttttcctaa ggatccagag
 361 attcatttga gtggccctct ggaggctggg aagccgatca cagtcaagtg ttcagttgct
 421 gatgtatacc catttgacag gctggagata gacttactga aaggagatca tctcatgaag
 481 agtcaggaat tctggagga tgcagacagg aagtccctgg aaaccaagag tttggaagta
 541 acctttactc ctgtcattga ggatattgga aaagttcttg tttgccgagc taaattacac
 601 attgatgaaa tggattctgt gcccacagta aggcaggctg taaagaatt gcaagtctac
 661 atatcaccca agaatacagt tatttctgtg aatccatcca caaagctgca agaaggtggc
 721 tctgtgacca tgacctgttc cagcgagggt ctaccagctc cagagatttt ctggagtaag
 781 aaattagata tgggaatct acagcacctt tctggaaatg caactctcac cttaattgct
 841 atgaggatgg aagattctgg aatttatgtg tgtgaaggag ttaatttgat tgggaaaaac
 901 agaaaagagg tggaattaat tgttcaagag aaaccattta ctgttgagat ctcccctgga
 961 ccccggattg ctgctcagat tggagactca gtcatgttga catgtagtgt catgggctgt
1021 gaatccccat ctttctcctg gagaacccag atagacagcc ctctgagcgg gaaggtgagg
1081 agtgagggga ccaattccac gctgaccctg agccctgtga gttttgagaa cgaacactct
1141 tatctgtgca cagtgacttg tggacataag aaactggaaa agggaatcca ggtggagctc
1201 tactcattcc ctagagatcc agaaatcgag atgagtggtg gcctcgtgaa tgggagctct
1261 gtcactgtaa gctgcaaggt tcctagcgtg tacccccttg acggctgga gattgaatta
1321 cttaaggggg agactattct ggagaatata gagttttgg aggatacgga tatgaaatct
1381 ctagagaaca aagtttggga aatgaccttc atccctacca ttgaagatac tggaaaagct
1441 cttgtttgtc aggctaagtt acatattgat gacatggaat tgaacccaa acaaaggcag
1501 agtacgcaaa cactttatgt caatgttgcc cccagagata caaccgtctt ggtcagccct
1561 tcctccatcc tggaggaagg cagttctgtg aatatgacat gcttgagcca gggctttcct
1621 gctccgaaaa tcctgtggag caggcagctc cctaacgggg agctacagcc tctttctgag
1681 aatgcaactc tcaccttaat ttctacaaaa atggaagatt ctggggttta tttatgtgaa
1741 ggaattaacc aggctggaag aagcagaaag gaagtggaat taattatcca agttactcca
1801 aaagacataa aacttacagc ttttccttct gagagtgtca aagaaggaga cactgtcatc
1861 atctcttgta catgtggaaa tgttccagaa acatggataa tcctgaagaa aaaagcggag
1921 acaggagaca cagtactaaa atctatagat ggcgcctata ccatccgaaa ggcccagttg
1981 aaggatgcgg gagtatatga atgtgaatct aaaaacaaag ttggctcaca attaagaagt
2041 ttaacacttg atgttcaagg aagagaaaac aacaaagact attttctcc tgagcttctc
2101 gtgctctatt ttgcatcctc cttaataata cctgccattg gaatgataat ttactttgca
2161 agaaaagcca acatgaaggg gtcatatagt cttgtagaag cacagaaatc aaaagtgtag
```

Fig. 12A

```
   1 gaagagcaag aggcaggctc agcaaatggt tcagccccag tccccggtgg ctgtcagtca
  61 aagcaagccc ggttgttatg acaatggaaa acactatcag ataaatcaac agtgggagcg
 121 gacctaccta ggtaatgtgt tggtttgtac ttgttatgga ggaagccgag gttttaactg
 181 cgaaagtaaa cctgaagctg aagagacttg ctttgacaag tacactggga acacttaccg
 241 agtgggtgac acttatgagc gtcctaaaga ctccatgatc tgggactgta cctgcatcgg
 301 ggctgggcga gggagaataa gctgtaccat cgcaaaccgc tgccatgaag ggggtcagtc
 361 ctacaagatt ggtgacacct ggaggagacc acatgagact ggtggttaca tgttagagtg
 421 tgtgtgtctt ggtaatggaa aaggagaatg gacctgcaag cccatagctg agaagtgttt
 481 tgatcatgct gctgggactt cctatgtggt cggagaaacg tgggagaagc cctaccaagg
 541 ctggatgatg gtagattgta cttgcctggg agaaggcagc ggacgcatca cttgcacttc
 601 tagaaataga tgcaacgatc aggacacaag gacatcctat agaattggag acacctggag
 661 caagaaggat aatcgaggaa acctgctcca gtgcatctgc acaggcaacg gcgaggaga
 721 gtggaagtgt gagaggcaca cctctgtgca gaccacatcg agcggatctg gcccttcac
 781 cgatgttcgt gcagctgttt accaaccgca gcctcacccc cagcctcctc cctatggcca
 841 ctgtgtcaca gacagtggtg tggtctactc tgtggggatg cagtggttga agacacaagg
 901 aaataagcaa atgctttgca cgtgcctggg caacggagtc agctgccaag agacagctgt
 961 aacccagact tacggtggca acttaaatgg agagccatgt gtcttaccat tcacctacaa
1021 tggcaggacg ttctactcct gcaccacgga agggcgacag gacggacatc tttggtgcag
1081 cacaacttcg aattatgagc aggaccagaa atactctttc tgcacagacc acactgtttt
1141 ggttcagact caaggaggaa attccaatgg tgccttgtgc acttcccct tctatacaa
1201 caaccacaat tacactgatt gcacttctga gggcagaaga gacaacatga agtggtgtgg
1261 gaccacacag aactatgatg ccgaccagaa gtttgggttc tgccccatgg ctgcccacga
1321 ggaaatctgc acaaccaatg aagggggtcat gtaccgcatt ggagatcagt gggataagca
1381 gcatgacatg ggtcacatga tgaggtgcac gtgtgttggg aatggtcgtg gggaatggac
1441 atgcattgcc tactcgcaac ttcgagatca gtgcattgtt gatgacatca cttacaatgt
1501 gaacgacaca ttccacaagc gtcatgaaga ggggcacatg ctgaactgta catgcttcgg
1561 tcagggtcgg ggcaggtgga agtgtgatcc cgtcgaccaa tgccaggatt cagagactgg
1621 gacgttttat caaattggag attcatggga gaagtatgtg catggtgtca gataccagtg
1681 ctactgctat ggccgtgtca ttggggagtg gcattgccaa cctttacaga cctatccaag
1741 ctcaagtggt cctgtcgaag tatttatcac tgagactccg agtcagccca ctcccaccc
1801 catccagtgg aatgcaccac agccatctca catttccaag tacattctca ggtggagacc
1861 taaaaattct gtaggccgtt ggaaggaagc taccatacca ggccacttaa actcctacac
1921 catcaaaggc ctgaagcctg gtgtggtata cgagggccag ctcatcagca tccagcagta
1981 cggccaccaa gaagtgactc gctttgactt caccaccacc agcaccagca cctgtgac
2041 cagcaacacc gtgacaggag agacgactcc cttttctcct cttgtggcca cttctgaatc
2101 tgtgaccgaa atcacagcca gtagctttgt ggtctcctgg gtctcagctt ccgacaccgt
2161 gtcgggattc cgggtggaat atgagctgag tgaggaggga gatgagccac agtacctgga
2221 tcttccaagc acagccactc tgtgaacat ccctgacctg cttcctggcc gaaaatacat
2281 tgtaaatgtc tatcagatat ctgaggatgg ggagcagagt ttgatcctgt ctacttcaca
2341 aacaacagcg cctgatgccc ctcctgaccc gactgtggac caagttgatg acacctcaat
2401 tgttgttcgc tggagcagac cccaggctcc catcacaggg tacagaatag tctattcgcc
2461 atcagtagaa ggtagcagca cagaactcaa ccttcctgaa actgcaaact ccgtcaccct
2521 cagtgacttg caacctggtg ttcagtataa catcactatc tatgctgtgg aagaaaatca
```

Fig. 12B

```
2581 agaaagtaca cctgttgtca ttcaacaaga aaccactggc accccacgct cagatacagt
2641 gccctctccc agggacctgc agtttgtgga agtgacagac gtgaaggtca ccatcatgtg
2701 gacaccgcct gagagtgcag tgaccggcta ccgtgtggat gtgatcccg tcaacctgcc
2761 tggcgagcac gggcagaggc tgcccatcag caggaacacc tttgcagaag tcaccgggct
2821 gtcccctggg gtcacctatt acttcaaagt ctttgcagtg agccatggga gggagagcaa
2881 gcctctgact gctcaacaga caaccaaact ggatgctccc actaacctcc agtttgtcaa
2941 tgaaactgat tctactgtcc tggtgagatg gactccacct cgggcccaga taacaggata
3001 ccgactgacc gtgggcctta cccgaagagg ccagcccagg cagtacaatg tgggtccctc
3061 tgtctccaag tacccctga ggaatctgca gcctgcatct gagtacaccg tatccctcgt
3121 ggccataaag ggcaaccaag agagccccaa agccactgga gtctttacca cactgcagcc
3181 tgggagctct attccaccttt acaacaccga ggtgactgag accaccatcg tgatcacatg
3241 gacgcctgct ccaagaattg gttttaagct gggtgtacga ccaagccagg gaggagaggc
3301 accacgagaa gtgacttcag actcaggaag catcgttgtg tccggcttga ctccaggagt
3361 agaatacgtc tacaccatcc aagtcctgag agatggacag gaaagagatg cgccaattgt
3421 aaacaaagtg gtgacaccat tgtctccacc aacaaacttg catctggagg caaaccctga
3481 cactggagtg ctcacagtct cctgggagag gagcaccacc ccagacatta ctggttatag
3541 aattaccaca accccctacaa acggccagca gggaaattct ttggaagaag tggtccatgc
3601 tgatcagagc tcctgcactt ttgataacct gagtccggc ctggagtaca atgtcagtgt
3661 ttacactgtc aaggatgaca aggaaagtgt ccctatctct gataccatca tcccagctgt
3721 tcctcctccc actgacctgc gatcaccaa cattggtcca gacaccatgc gtgtcacctg
3781 ggctccaccc ccatccattg atttaaccaa cttcctggtg cgttactcac ctgtgaaaaa
3841 tgaggaagat gttgcagagt tgtcaatttc tccttcagac aatgcagtgg tcttaacaaa
3901 tctcctgcct ggtacagaat atgtagtgag tgtctccagt gtctacgaac aacatgagag
3961 cacacctctt agaggaagac agaaaacagg tcttgattcc ccaactggca ttgacttttc
4021 tgatattact gccaactctt ttactgtgca ctggattgct cctcgagcca ccatcactgg
4081 ctacaggatc cgccatcatc ccgagcactt cagtgggaga cctcgagaag atcgggtgcc
4141 ccactctcgg aattccatca ccctcaccaa cctcactcca ggcacagagt atgtggtcag
4201 catcgttgct cttaatggca gagaggaaag tccttattg attggccaac aatcaacagt
4261 ttctgatgtt ccgagggacc tggaagttgt tgctgcgacc cccaccagcc tactgatcag
4321 ctggatgct cctgctgtca cagtgagata ttacaggatc acttacggag aaacaggagg
4381 aaatagccct gtccaggagt tcactgtgcc tgggagcaag tctacagcta ccatcagcgg
4441 ccttaaacct ggagttgatt ataccatcac tgtgtatgct gtcactggcc gtggagacag
4501 ccccgcaagc agcaagccaa tttccattaa ttaccgaaca gaaattgaca aaccatccca
4561 gatgcaagtg accgatgttc aggacaacag cattagtgtc aagtggctgc cttcaagttc
4621 ccctgttact ggttacagag taaccaccac tccaaaaaat ggaccaggac caacaaaaac
4681 taaaactgca ggtccagatc aaacagaaat gactattgaa ggcttgcagc ccacagtgga
4741 gtatgtggtt agtgtctatg ctcagaatcc aagcggagag agtcagcctc tggttcagac
4801 tgcagtaacc aacattgatc gccctaaagg actggcattc actgatgtgg atgtcgattc
4861 catcaaaatt gcttgggaaa gcccacaggg gcaagtttcc aggtacaggg tgacctactc
4921 gagccctgag gatggaatcc atgagctatt ccctgcacct gatggtgaag aagacactgc
4981 agagctgcaa ggcctcagac cgggttctga gtacacagtc agtgtggttg ccttgcacga
5041 tgatatggag agccagcccc tgattggaac ccagtccaca gctattcctg caccaactga
```

Fig. 12C

```
5101 cctgaagttc actcaggtca cacccacaag cctgagcgcc cagtggacac cacccaatgt
5161 tcagctcact ggatatcgag tgcgggtgac ccccaaggag aagaccggac caatgaaaga
5221 aatcaaccit gctcctgaca gctcatccgt ggttgtatca ggacttatgg tggccaccaa
5281 atatgaagtg agtgtctatg ctcttaagga cactttgaca agcagaccag ctcagggtgt
5341 tgtcaccact ctggagaatg tcagcccacc aagaagggct cgtgtgacag atgctactga
5401 gaccaccatc accattagct ggagaaccaa gactgagacg atcactggct tccaagttga
5461 tgccgttcca gccaatggcc agactccaat ccagagaacc atcaagccag atgtcagaag
5521 ctacaccatc acaggtttac aaccaggcac tgactacaag atctacctgt acaccttgaa
5581 tgacaatgct cggagctccc ctgtggtcat cgacgcctcc actgccattg atgcaccatc
5641 caacctgcgt ttcctggcca ccacacccaa ttccttgctg gtatcatggc agccgccacg
5701 tgccaggatt accggctaca tcatcaagta tgagaagcct gggtctcctc ccagagaagt
5761 ggtccctcgg ccccgcccctg gtgtcacaga ggctactatt actggcctgg aaccgggaac
5821 cgaatataca atttatgtca ttgccctgaa gaataatcag aagagcgagc ccctgattgg
5881 aaggaaaaag acagacgagc ttccccaact ggtaacccit ccacacccca atcttcatgg
5941 accagagatc ttggatgttc cttccacagt tcaaaagacc cctttcgtca cccaccctgg
6001 gtatgacact ggaaatggta ttcagcttcc tggcacttct ggtcagcaac ccagtgttgg
6061 gcaacaaatg atctttgagg aacatggttt taggcggacc acaccgccca caacggccac
6121 ccccataagg cataggccaa gaccataccc gccgaatgta ggacaagaag ctctctctca
6181 gacaaccatc tcatgggccc cattccagga cacttctgag tacatcattt catgtcatcc
6241 tgttggcact gatgaagaac ccttacagtt cagggttcct ggaacttcta ccagtgccac
6301 tctgacaggc ctcaccagag gtgccaccta caacatcata gtggaggcac tgaaagacca
6361 gcagaggcat aaggttcggg aagaggttgt taccgtgggc aactctgtca acgaaggctt
6421 gaaccaacct acggatgact cgtgctttga ccctacaca gttcccatt atgccgttgg
6481 agatgagtgg gaacgaatgt ctgaatcagg ctttaaactg ttgtgccagt gcttaggctt
6541 tggaagtggt catttcagat gtgattcatc tagatggtgc catgacaatg gtgtgaacta
6601 caagattgga gagaagtggg accgtcaggg agaaaatggc cagatgatga gctgcacatg
6661 tcttgggaac ggaaaaggag aattcaagtg tgaccctcat gaggcaacgt gttacgatga
6721 tgggaagaca taccacgtag gagaacagtg gcagaaggaa tatctcggtg ccatttgctc
6781 ctgcacatgc tttggaggcc agcggggctg gcgctgtgac aactgccgca gacctggggg
6841 tgaacccagt cccgaaggca ctactggcca gtcctacaac cagtattctc agagatacca
6901 tcagagaaca aacactaatg ttaattgccc aattgagtgc ttcatgcctt agatgtaca
6961 ggctgacaga gaagattccc gagagtaaat catctttcca atccagagga acaagcatgt
7021 ctctctgcca agatccatct aaactggagt gatgttagca gacccagctt agagttcttc
7081 tttctttctt aagcccttg ctctggagga agttctccag cttcagctca actcacagct
7141 tctccaagca tcaccctggg agtttcctga gggttttctc ataaatgagg gctgcacatt
7201 gcctgttctg cttcgaagta ttcaataccg ctcagtattt taaatgaagt gattctaaga
7261 tttggtttgg gatcaatagg aaagcatatg cagccaacca agatgcaaat gttttgaaat
7321 gatatgacca aaatttaag taggaaagtc acccaaacac ttctgcttc acttaagtgt
7381 ctggcccgca atactgtagg aacaagcatg atcttgttac tgtgatattt taaatatcca
7441 cagtactcac tttttccaaa tgatcctagt aattgcctag aaatatcttt ctcttacctg
7501 ttatttatca atttttccca gtattttat acggaaaaa ttgtattgaa aacacttagt
7561 atgcagttga taagaggaat ttggtataat tatggtgggt gattatttt tatactgtat
7621 gtgccaaagc tttactactg tggaaagaca actgttttaa taaagattt acattccaca
```

Fig. 20
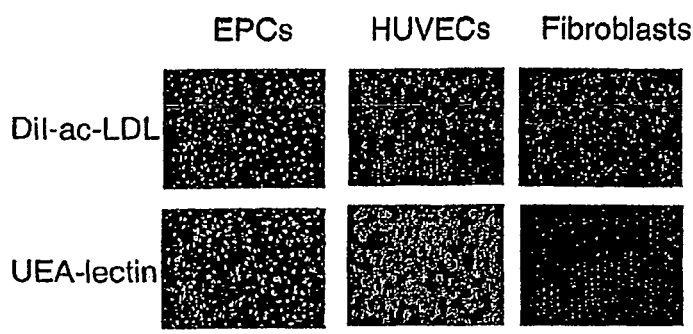
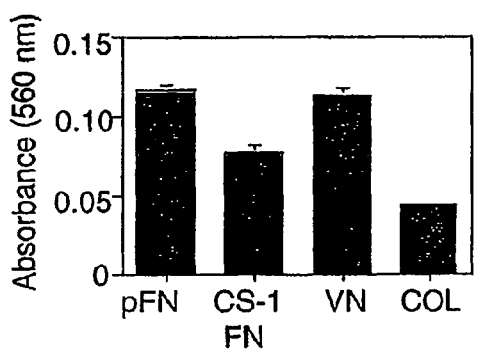
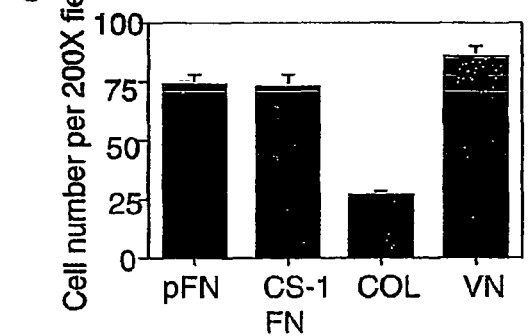
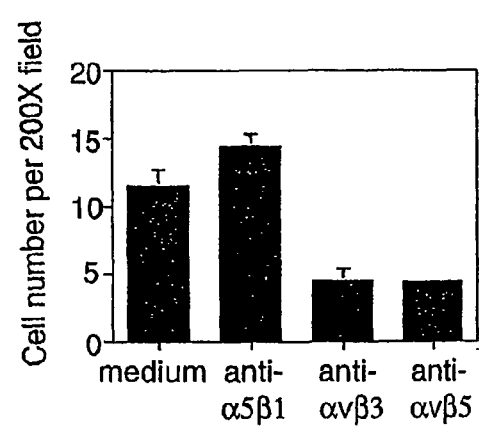
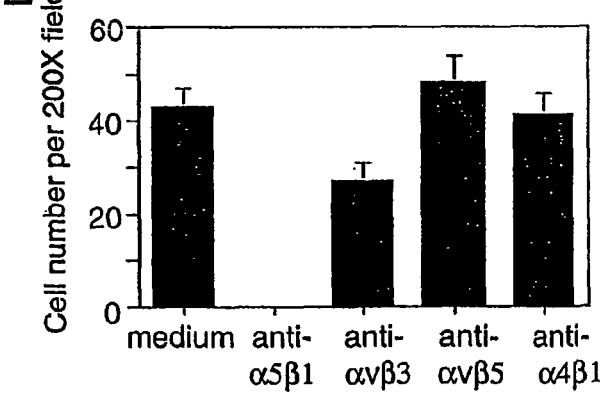

Endothelial progenitor cells

Bone marrow derived cells that can differentiate into ECs

Integrin α4β1 appears to be an early marker of EPCs

Fig. 24 EPC maturation

α4β1 mediates EPC adhesion to CS-1 fibronectin

α4β1 mediates EPC adhesion to rsVCAM

EPCs adhere to endothelial monolayers via α4β1

EPCs adhere to endothelial monolayers in a VCAM-dependent manner

Tie2 BMT model of stem cell role in neovascularization

Integrin α4β1 promotes EPC contributions to angiogenesis *in vivo*

α4β1 promotes EPC extravasation and participation in vessel formation

```
                        SEQUENCE LISTING

<160> NUMBER OF SEQ ID NOS: 97

<210> SEQ ID NO 1
<211> LENGTH: 1032
<212> TYPE: PRT
<213> ORGANISM: Homo sapiens

<400> SEQUENCE: 1

Met Ala Trp Glu Ala Arg Arg Glu Pro Gly Pro Arg Arg Ala Ala Val
1               5                   10                  15

Arg Glu Thr Val Met Leu Leu Leu Cys Leu Gly Val Pro Thr Gly Arg
            20                  25                  30

Pro Tyr Asn Val Asp Thr Glu Ser Ala Leu Leu Tyr Gln Gly Pro His
            35                  40                  45

Asn Thr Leu Phe Gly Tyr Ser Val Val Leu His Ser His Gly Ala Asn
        50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
        115                 120                 125

Val Thr Leu Ser Arg Gln Pro Gly Glu Asn Gly Ser Ile Val Thr Cys
    130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Asp Tyr Val Lys Lys Phe Gly
            180                 185                 190

Glu Asn Phe Ala Ser Cys Gln Ala Gly Ile Ser Ser Phe Tyr Thr Lys
        195                 200                 205

Asp Leu Ile Val Met Gly Ala Pro Gly Ser Ser Tyr Trp Thr Gly Ser
    210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255

Ala Gly His Phe Arg Ser Gln His Thr Thr Glu Val Val Gly Gly Ala
            260                 265                 270

Pro Gln His Glu Gln Ile Gly Lys Ala Tyr Ile Phe Ser Ile Asp Glu
        275                 280                 285

Lys Glu Leu Asn Ile Leu His Glu Met Lys Gly Lys Lys Leu Gly Ser
    290                 295                 300

Tyr Phe Gly Ala Ser Val Cys Ala Val Asp Leu Asn Ala Asp Gly Phe
305                 310                 315                 320

Ser Asp Leu Leu Val Gly Ala Pro Met Gln Ser Thr Ile Arg Glu Glu
                325                 330                 335
```

-continued

```
Gly Arg Val Phe Val Tyr Ile Asn Ser Gly Ser Ala Val Met Asn
                340                 345                 350
Ala Met Glu Thr Asn Leu Val Gly Ser Asp Lys Tyr Ala Ala Arg Phe
            355                 360                 365
Gly Glu Ser Ile Val Asn Leu Gly Asp Ile Asp Asn Asp Gly Phe Glu
        370                 375                 380
Asp Val Ala Ile Gly Ala Pro Gln Glu Asp Asp Leu Gln Gly Ala Ile
385                 390                 395                 400
Tyr Ile Tyr Asn Gly Arg Ala Asp Gly Ile Ser Ser Thr Phe Ser Gln
                405                 410                 415
Arg Ile Glu Gly Leu Gln Ile Ser Lys Ser Leu Ser Met Phe Gly Gln
            420                 425                 430
Ser Ile Ser Gly Gln Ile Asp Ala Asp Asn Asn Gly Tyr Val Asp Val
        435                 440                 445
Ala Val Gly Ala Phe Arg Ser Asp Ser Ala Val Leu Leu Arg Thr Arg
450                 455                 460
Pro Val Val Ile Val Asp Ala Ser Leu Ser His Pro Glu Ser Val Asn
465                 470                 475                 480
Arg Thr Lys Phe Asp Cys Val Glu Asn Gly Trp Pro Ser Val Cys Ile
                485                 490                 495
Asp Leu Thr Leu Cys Phe Ser Tyr Lys Gly Lys Glu Val Pro Gly Tyr
            500                 505                 510
Ile Val Leu Phe Tyr Asn Met Ser Leu Asp Val Asn Arg Lys Ala Glu
        515                 520                 525
Ser Pro Pro Arg Phe Tyr Phe Ser Ser Asn Gly Thr Ser Asp Val Ile
530                 535                 540
Thr Gly Ser Ile Gln Val Ser Ser Arg Glu Ala Asn Cys Arg Thr His
545                 550                 555                 560
Gln Ala Phe Met Arg Lys Asp Val Arg Asp Ile Leu Thr Pro Ile Gln
                565                 570                 575
Ile Glu Ala Ala Tyr His Leu Gly Pro His Val Ile Ser Lys Arg Ser
            580                 585                 590
Thr Glu Glu Phe Pro Pro Leu Gln Pro Ile Leu Gln Gln Lys Lys Glu
        595                 600                 605
Lys Asp Ile Met Lys Lys Thr Ile Asn Phe Ala Arg Phe Cys Ala His
610                 615                 620
Glu Asn Cys Ser Ala Asp Leu Gln Val Ser Ala Lys Ile Gly Phe Leu
625                 630                 635                 640
Lys Pro His Glu Asn Lys Thr Tyr Leu Ala Val Gly Ser Met Lys Thr
                645                 650                 655
Leu Met Leu Asn Val Ser Leu Phe Asn Ala Gly Asp Asp Ala Tyr Glu
            660                 665                 670
Thr Thr Leu His Val Lys Leu Pro Val Gly Leu Tyr Phe Ile Lys Ile
        675                 680                 685
Leu Glu Leu Glu Glu Lys Gln Ile Asn Cys Glu Val Thr Asp Asn Ser
        690                 695                 700
Gly Val Val Gln Leu Asp Cys Ser Ile Gly Tyr Ile Tyr Val Asp His
705                 710                 715                 720
Leu Ser Arg Ile Asp Ile Ser Phe Leu Leu Asp Val Ser Ser Leu Ser
                725                 730                 735
Arg Ala Glu Glu Asp Leu Ser Ile Thr Val His Ala Thr Cys Glu Asn
            740                 745                 750
```

-continued

```
Glu Glu Glu Met Asp Asn Leu Lys His Ser Arg Val Thr Val Ala Ile
            755                 760                 765

Pro Leu Lys Tyr Glu Val Lys Leu Thr Val His Gly Phe Val Asn Pro
770                 775                 780

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
            805                 810                 815

Ser Met Ala Pro Asn Val Ser Val Glu Ile Met Val Pro Asn Ser Phe
                820                 825                 830

Ser Pro Gln Thr Asp Lys Leu Phe Asn Ile Leu Asp Val Gln Thr Thr
            835                 840                 845

Thr Gly Glu Cys His Phe Glu Asn Tyr Gln Arg Val Cys Ala Leu Glu
        850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
                885                 890                 895

Cys Leu Asn Phe Leu Cys Asn Phe Gly Lys Met Glu Ser Gly Lys Glu
            900                 905                 910

Ala Ser Val His Ile Gln Leu Glu Gly Arg Pro Ser Ile Leu Glu Met
        915                 920                 925

Asp Glu Thr Ser Ala Leu Lys Phe Glu Ile Arg Ala Thr Gly Phe Pro
930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
                965                 970                 975

Thr Ile Val Ile Ile Ser Ser Leu Leu Leu Gly Leu Ile Val Leu
            980                 985                 990

Leu Leu Ile Ser Tyr Val Met Trp  Lys Ala Gly Phe Phe  Lys Arg Gln
        995                 1000                1005

Tyr Lys  Ser Ile Leu Gln Glu  Glu Asn Arg Arg Asp  Ser Trp Ser
    1010                1015                1020

Tyr Ile  Asn Ser Lys Ser Asn  Asp Asp
    1025                1030

<210> SEQ ID NO 2
<211> LENGTH: 798
<212> TYPE: PRT
<213> ORGANISM: Homo sapiens

<400> SEQUENCE: 2

Met Asn Leu Gln Pro Ile Phe Trp Ile Gly Leu Ile Ser Ser Val Cys
1               5                   10                  15

Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
            35                  40                  45

Thr Asn Ser Thr Phe Leu Gln Glu Gly Met Pro Thr Ser Ala Arg Cys
        50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Lys Asn Lys Asn Val Thr
                85                  90                  95
```

-continued

```
Asn Arg Ser Lys Gly Thr Ala Glu Lys Leu Lys Pro Glu Asp Ile His
            100                 105                 110

Gln Ile Gln Pro Gln Gln Leu Val Leu Arg Leu Arg Ser Gly Glu Pro
            115                 120                 125

Gln Thr Phe Thr Leu Lys Phe Lys Arg Ala Glu Asp Tyr Pro Ile Asp
            130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
            180                 185                 190

Met Pro Tyr Ile Ser Thr Thr Pro Ala Lys Leu Arg Asn Pro Cys Thr
            195                 200                 205

Ser Glu Gln Asn Cys Thr Thr Pro Phe Ser Tyr Lys Asn Val Leu Ser
210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
            260                 265                 270

Leu Leu Val Phe Ser Thr Asp Ala Gly Phe His Phe Ala Gly Asp Gly
            275                 280                 285

Lys Leu Gly Gly Ile Val Leu Pro Asn Asp Gly Gln Cys His Leu Glu
            290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
            340                 345                 350

Pro Lys Ser Ala Val Gly Thr Leu Ser Ala Asn Ser Ser Asn Val Ile
            355                 360                 365

Gln Leu Ile Ile Asp Ala Tyr Asn Ser Leu Ser Ser Glu Val Ile Leu
            370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
            420                 425                 430

Asn Lys Cys Pro Lys Lys Asp Ser Asp Ser Phe Lys Ile Arg Pro Leu
            435                 440                 445

Gly Phe Thr Glu Glu Val Glu Val Ile Leu Gln Tyr Ile Cys Glu Cys
            450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
            500                 505                 510
```

```
Asp Ala Tyr Cys Arg Lys Glu Asn Ser Ser Glu Ile Cys Ser Asn Asn
            515                 520                 525

Gly Glu Cys Val Cys Gly Gln Cys Val Cys Arg Lys Arg Asp Asn Thr
    530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
            580                 585                 590

Ser Leu Asp Thr Ser Thr Cys Glu Ala Ser Asn Gly Gln Ile Cys Asn
        595                 600                 605

Gly Arg Gly Ile Cys Glu Cys Gly Val Cys Lys Cys Thr Asp Pro Lys
    610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
            660                 665                 670

Val Glu Ser Arg Asp Lys Leu Pro Gln Pro Val Gln Pro Asp Pro Val
        675                 680                 685

Ser His Cys Lys Glu Lys Asp Val Asp Asp Cys Trp Phe Tyr Phe Thr
    690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
            740                 745                 750

Leu Leu Met Ile Ile His Asp Arg Arg Glu Phe Ala Lys Phe Glu Lys
        755                 760                 765

Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795

<210> SEQ ID NO 3
<211> LENGTH: 739
<212> TYPE: PRT
<213> ORGANISM: Homo sapiens

<400> SEQUENCE: 3

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
                20                  25                  30

Ser Arg Tyr Leu Ala Gln Ile Gly Asp Ser Val Ser Leu Thr Cys Ser
            35                  40                  45

Thr Thr Gly Cys Glu Ser Pro Phe Phe Ser Trp Arg Thr Gln Ile Asp
        50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95
```

-continued

```
Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
            115                 120                 125

Ala Gly Lys Pro Ile Thr Val Lys Cys Ser Val Ala Asp Val Tyr Pro
        130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
                195                 200                 205

Thr Val Arg Gln Ala Val Lys Glu Leu Gln Val Tyr Ile Ser Pro Lys
        210                 215                 220

Asn Thr Val Ile Ser Val Asn Pro Ser Thr Lys Leu Gln Glu Gly Gly
225                 230                 235                 240

Ser Val Thr Met Thr Cys Ser Ser Glu Gly Leu Pro Ala Pro Glu Ile
                245                 250                 255

Phe Trp Ser Lys Lys Leu Asp Asn Gly Asn Leu Gln His Leu Ser Gly
            260                 265                 270

Asn Ala Thr Leu Thr Leu Ile Ala Met Arg Met Glu Asp Ser Gly Ile
                275                 280                 285

Tyr Val Cys Glu Gly Val Asn Leu Ile Gly Lys Asn Arg Lys Glu Val
        290                 295                 300

Glu Leu Ile Val Gln Glu Lys Pro Phe Thr Val Glu Ile Ser Pro Gly
305                 310                 315                 320

Pro Arg Ile Ala Ala Gln Ile Gly Asp Ser Val Met Leu Thr Cys Ser
                325                 330                 335

Val Met Gly Cys Glu Ser Pro Ser Phe Ser Trp Arg Thr Gln Ile Asp
            340                 345                 350

Ser Pro Leu Ser Gly Lys Val Arg Ser Glu Gly Thr Asn Ser Thr Leu
        355                 360                 365

Thr Leu Ser Pro Val Ser Phe Glu Asn Glu His Ser Tyr Leu Cys Thr
        370                 375                 380

Val Thr Cys Gly His Lys Lys Leu Glu Lys Gly Ile Gln Val Glu Leu
385                 390                 395                 400

Tyr Ser Phe Pro Arg Asp Pro Glu Ile Glu Met Ser Gly Gly Leu Val
                405                 410                 415

Asn Gly Ser Ser Val Thr Val Ser Cys Lys Val Pro Ser Val Tyr Pro
            420                 425                 430

Leu Asp Arg Leu Glu Ile Glu Leu Leu Lys Gly Glu Thr Ile Leu Glu
        435                 440                 445

Asn Ile Glu Phe Leu Glu Asp Thr Asp Met Lys Ser Leu Glu Asn Lys
        450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510
```

```
Asp Thr Thr Val Leu Val Ser Pro Ser Ser Ile Leu Glu Glu Gly Ser
            515                 520                 525

Ser Val Asn Met Thr Cys Leu Ser Gln Gly Phe Pro Ala Pro Lys Ile
        530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
        595                 600                 605

Pro Ser Glu Ser Val Lys Glu Gly Asp Thr Val Ile Ile Ser Cys Thr
    610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
        675                 680                 685

Glu Asn Asn Lys Asp Tyr Phe Ser Pro Glu Leu Leu Val Leu Tyr Phe
    690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 4
<211> LENGTH: 2386
<212> TYPE: PRT
<213> ORGANISM: Homo sapiens

<400> SEQUENCE: 4

Met Leu Arg Gly Pro Gly Pro Gly Leu Leu Leu Leu Ala Val Gln Cys
1               5                   10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140
```

-continued

Gly Gln Ser Tyr Lys Ile Gly Asp Thr Trp Arg Pro His Glu Thr
145                 150                 155                 160

Gly Gly Tyr Met Leu Glu Cys Val Cys Leu Gly Asn Gly Lys Gly Glu
            165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
            195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
            245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
            275                 280                 285

Val Arg Ala Ala Val Tyr Gln Pro Gln Pro His Pro Gln Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
            325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
            370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Gln Gly Gly Asn Ser Asn
            405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
            485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
            530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp

-continued

```
            565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
            595                 600                 605
Ser Gly Pro Val Glu Val Phe Ile Thr Glu Thr Pro Ser Gln Pro Asn
            610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
            645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
            675                 680                 685
His Gln Glu Val Thr Arg Phe Asp Phe Thr Thr Thr Ser Thr Ser Thr
            690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
            725                 730                 735
Val Val Ser Trp Val Ser Ala Ser Asp Thr Val Ser Gly Phe Arg Val
            740                 745                 750
Glu Tyr Glu Leu Ser Glu Glu Gly Asp Glu Pro Gln Tyr Leu Asp Leu
            755                 760                 765
Pro Ser Thr Ala Thr Ser Val Asn Ile Pro Asp Leu Leu Pro Gly Arg
770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
            805                 810                 815
Pro Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
            835                 840                 845
Val Glu Gly Ser Ser Thr Glu Leu Asn Leu Pro Glu Thr Ala Asn Ser
            850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                        885                 890                 895
Glu Thr Thr Gly Thr Pro Arg Ser Asp Thr Val Pro Ser Pro Arg Asp
            900                 905                 910
Leu Gln Phe Val Glu Val Thr Asp Val Lys Val Thr Ile Met Trp Thr
            915                 920                 925
Pro Pro Glu Ser Ala Val Thr Gly Tyr Arg Val Asp Val Ile Pro Val
            930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
            965                 970                 975
Val Phe Ala Val Ser His Gly Arg Glu Ser Lys Pro Leu Thr Ala Gln
            980                 985                 990
```

```
Gln Thr Thr Lys Leu Asp Ala Pro   Thr Asn Leu Gln Phe  Val Asn Glu
        995                 1000                  1005

Thr Asp  Ser Thr Val Leu Val  Arg Trp Thr Pro Pro  Arg Ala Gln
    1010             1015                 1020

Ile Thr  Gly Tyr Arg Leu Thr  Val Gly Leu Thr Arg  Arg Gly Gln
    1025             1030                 1035

Pro Arg  Gln Tyr Asn Val Gly  Pro Ser Val Ser Lys  Tyr Pro Leu
    1040             1045                 1050

Arg Asn  Leu Gln Pro Ala Ser  Glu Tyr Thr Val Ser  Leu Val Ala
    1055             1060                 1065

Ile Lys  Gly Asn Gln Glu Ser  Pro Lys Ala Thr Gly  Val Phe Thr
    1070             1075                 1080

Thr Leu  Gln Pro Gly Ser Ser  Ile Pro Pro Tyr Asn  Thr Glu Val
    1085             1090                 1095

Thr Glu  Thr Thr Ile Val Ile  Thr Trp Thr Pro Ala  Pro Arg Ile
    1100             1105                 1110

Gly Phe  Lys Leu Gly Val Arg  Pro Ser Gln Gly Gly  Glu Ala Pro
    1115             1120                 1125

Arg Glu  Val Thr Ser Asp Ser  Gly Ser Ile Val Val  Ser Gly Leu
    1130             1135                 1140

Thr Pro  Gly Val Glu Tyr Val  Tyr Thr Ile Gln Val  Leu Arg Asp
    1145             1150                 1155

Gly Gln  Glu Arg Asp Ala Pro  Ile Val Asn Lys Val  Val Thr Pro
    1160             1165                 1170

Leu Ser  Pro Pro Thr Asn Leu  His Leu Glu Ala Asn  Pro Asp Thr
    1175             1180                 1185

Gly Val  Leu Thr Val Ser Trp  Glu Arg Ser Thr Thr  Pro Asp Ile
    1190             1195                 1200

Thr Gly  Tyr Arg Ile Thr Thr  Thr Pro Thr Asn Gly  Gln Gln Gly
    1205             1210                 1215

Asn Ser  Leu Glu Glu Val Val  His Ala Asp Gln Ser  Ser Cys Thr
    1220             1225                 1230

Phe Asp  Asn Leu Ser Pro Gly  Leu Glu Tyr Asn Val  Ser Val Tyr
    1235             1240                 1245

Thr Val  Lys Asp Asp Lys Glu  Ser Val Pro Ile Ser  Asp Thr Ile
    1250             1255                 1260

Ile Pro  Ala Val Pro Pro Pro  Thr Asp Leu Arg Phe  Thr Asn Ile
    1265             1270                 1275

Gly Pro  Asp Thr Met Arg Val  Thr Trp Ala Pro Pro  Pro Ser Ile
    1280             1285                 1290

Asp Leu  Thr Asn Phe Leu Val  Arg Tyr Ser Pro Val  Lys Asn Glu
    1295             1300                 1305

Glu Asp  Val Ala Glu Leu Ser  Ile Ser Pro Ser Asp  Asn Ala Val
    1310             1315                 1320

Val Leu  Thr Asn Leu Leu Pro  Gly Thr Glu Tyr Val  Val Ser Val
    1325             1330                 1335

Ser Ser  Val Tyr Glu Gln His  Glu Ser Thr Pro Leu  Arg Gly Arg
    1340             1345                 1350

Gln Lys  Thr Gly Leu Asp Ser  Pro Thr Gly Ile Asp  Phe Ser Asp
    1355             1360                 1365

Ile Thr  Ala Asn Ser Phe Thr  Val His Trp Ile Ala  Pro Arg Ala
    1370             1375                 1380
```

```
Thr Ile Thr Gly Tyr Arg Ile Arg His His Pro Glu His Phe Ser
1385                1390                1395

Gly Arg Pro Arg Glu Asp Arg Val Pro His Ser Arg Asn Ser Ile
1400                1405                1410

Thr Leu Thr Asn Leu Thr Pro Gly Thr Glu Tyr Val Val Ser Ile
1415                1420                1425

Val Ala Leu Asn Gly Arg Glu Glu Ser Pro Leu Leu Ile Gly Gln
1430                1435                1440

Gln Ser Thr Val Ser Asp Val Pro Arg Asp Leu Glu Val Val Ala
1445                1450                1455

Ala Thr Pro Thr Ser Leu Leu Ile Ser Trp Asp Ala Pro Ala Val
1460                1465                1470

Thr Val Arg Tyr Tyr Arg Ile Thr Tyr Gly Glu Thr Gly Gly Asn
1475                1480                1485

Ser Pro Val Gln Glu Phe Thr Val Pro Gly Ser Lys Ser Thr Ala
1490                1495                1500

Thr Ile Ser Gly Leu Lys Pro Gly Val Asp Tyr Thr Ile Thr Val
1505                1510                1515

Tyr Ala Val Thr Gly Arg Gly Asp Ser Pro Ala Ser Ser Lys Pro
1520                1525                1530

Ile Ser Ile Asn Tyr Arg Thr Glu Ile Asp Lys Pro Ser Gln Met
1535                1540                1545

Gln Val Thr Asp Val Gln Asp Asn Ser Ile Ser Val Lys Trp Leu
1550                1555                1560

Pro Ser Ser Ser Pro Val Thr Gly Tyr Arg Val Thr Thr Thr Pro
1565                1570                1575

Lys Asn Gly Pro Gly Pro Thr Lys Thr Lys Thr Ala Gly Pro Asp
1580                1585                1590

Gln Thr Glu Met Thr Ile Glu Gly Leu Gln Pro Thr Val Glu Tyr
1595                1600                1605

Val Val Ser Val Tyr Ala Gln Asn Pro Ser Gly Glu Ser Gln Pro
1610                1615                1620

Leu Val Gln Thr Ala Val Thr Asn Ile Asp Arg Pro Lys Gly Leu
1625                1630                1635

Ala Phe Thr Asp Val Asp Val Asp Ser Ile Lys Ile Ala Trp Glu
1640                1645                1650

Ser Pro Gln Gly Gln Val Ser Arg Tyr Arg Val Thr Tyr Ser Ser
1655                1660                1665

Pro Glu Asp Gly Ile His Glu Leu Phe Pro Ala Pro Asp Gly Glu
1670                1675                1680

Glu Asp Thr Ala Glu Leu Gln Gly Leu Arg Pro Gly Ser Glu Tyr
1685                1690                1695

Thr Val Ser Val Val Ala Leu His Asp Asp Met Glu Ser Gln Pro
1700                1705                1710

Leu Ile Gly Thr Gln Ser Thr Ala Ile Pro Ala Pro Thr Asp Leu
1715                1720                1725

Lys Phe Thr Gln Val Thr Pro Thr Ser Leu Ser Ala Gln Trp Thr
1730                1735                1740

Pro Pro Asn Val Gln Leu Thr Gly Tyr Arg Val Arg Val Thr Pro
1745                1750                1755

Lys Glu Lys Thr Gly Pro Met Lys Glu Ile Asn Leu Ala Pro Asp
1760                1765                1770

Ser Ser Ser Val Val Val Ser Gly Leu Met Val Ala Thr Lys Tyr
```

-continued

```
            1775                1780                1785

Glu Val Ser Val Tyr Ala Leu Lys Asp Thr Leu Thr Ser Arg Pro
    1790                1795                1800

Ala Gln Gly Val Val Thr Thr Leu Glu Asn Val Ser Pro Pro Arg
    1805                1810                1815

Arg Ala Arg Val Thr Asp Ala Thr Glu Thr Thr Ile Thr Ile Ser
    1820                1825                1830

Trp Arg Thr Lys Thr Glu Thr Ile Thr Gly Phe Gln Val Asp Ala
    1835                1840                1845

Val Pro Ala Asn Gly Gln Thr Pro Ile Gln Arg Thr Ile Lys Pro
    1850                1855                1860

Asp Val Arg Ser Tyr Thr Ile Thr Gly Leu Gln Pro Gly Thr Asp
    1865                1870                1875

Tyr Lys Ile Tyr Leu Tyr Thr Leu Asn Asp Asn Ala Arg Ser Ser
    1880                1885                1890

Pro Val Val Ile Asp Ala Ser Thr Ala Ile Asp Ala Pro Ser Asn
    1895                1900                1905

Leu Arg Phe Leu Ala Thr Thr Pro Asn Ser Leu Leu Val Ser Trp
    1910                1915                1920

Gln Pro Pro Arg Ala Arg Ile Thr Gly Tyr Ile Ile Lys Tyr Glu
    1925                1930                1935

Lys Pro Gly Ser Pro Pro Arg Glu Val Val Pro Arg Pro Arg Pro
    1940                1945                1950

Gly Val Thr Glu Ala Thr Ile Thr Gly Leu Glu Pro Gly Thr Glu
    1955                1960                1965

Tyr Thr Ile Tyr Val Ile Ala Leu Lys Asn Asn Gln Lys Ser Glu
    1970                1975                1980

Pro Leu Ile Gly Arg Lys Lys Thr Asp Glu Leu Pro Gln Leu Val
    1985                1990                1995

Thr Leu Pro His Pro Asn Leu His Gly Pro Glu Ile Leu Asp Val
    2000                2005                2010

Pro Ser Thr Val Gln Lys Thr Pro Phe Val Thr His Pro Gly Tyr
    2015                2020                2025

Asp Thr Gly Asn Gly Ile Gln Leu Pro Gly Thr Ser Gly Gln Gln
    2030                2035                2040

Pro Ser Val Gly Gln Gln Met Ile Phe Glu Glu His Gly Phe Arg
    2045                2050                2055

Arg Thr Thr Pro Pro Thr Thr Ala Thr Pro Ile Arg His Arg Pro
    2060                2065                2070

Arg Pro Tyr Pro Pro Asn Val Gly Glu Glu Ile Gln Ile Gly His
    2075                2080                2085

Ile Pro Arg Glu Asp Val Asp Tyr His Leu Tyr Pro His Gly Pro
    2090                2095                2100

Gly Leu Asn Pro Asn Ala Ser Thr Gly Gln Glu Ala Leu Ser Gln
    2105                2110                2115

Thr Thr Ile Ser Trp Ala Pro Phe Gln Asp Thr Ser Glu Tyr Ile
    2120                2125                2130

Ile Ser Cys His Pro Val Gly Thr Asp Glu Glu Pro Leu Gln Phe
    2135                2140                2145

Arg Val Pro Gly Thr Ser Thr Ser Ala Thr Leu Thr Gly Leu Thr
    2150                2155                2160

Arg Gly Ala Thr Tyr Asn Ile Ile Val Glu Ala Leu Lys Asp Gln
    2165                2170                2175
```

| | | | | | | | | | | |
|---|---|---|---|---|---|---|---|---|---|---|
| Gln | Arg | His | Lys | Val | Arg | Glu | Glu | Val | Thr | Val | Gly | Asn | Ser |
| | 2180 | | | | 2185 | | | | 2190 | |

Gln Arg His Lys Val Arg Glu Glu Val Thr Val Gly Asn Ser
    2180                2185                2190

Val Asn Glu Gly Leu Asn Gln Pro Thr Asp Asp Ser Cys Phe Asp
    2195                2200                2205

Pro Tyr Thr Val Ser His Tyr Ala Val Gly Asp Glu Trp Glu Arg
    2210                2215                2220

Met Ser Glu Ser Gly Phe Lys Leu Leu Cys Gln Cys Leu Gly Phe
    2225                2230                2235

Gly Ser Gly His Phe Arg Cys Asp Ser Ser Arg Trp Cys His Asp
    2240                2245                2250

Asn Gly Val Asn Tyr Lys Ile Gly Glu Lys Trp Asp Arg Gln Gly
    2255                2260                2265

Glu Asn Gly Gln Met Met Ser Cys Thr Cys Leu Gly Asn Gly Lys
    2270                2275                2280

Gly Glu Phe Lys Cys Asp Pro His Glu Ala Thr Cys Tyr Asp Asp
    2285                2290                2295

Gly Lys Thr Tyr His Val Gly Glu Gln Trp Gln Lys Glu Tyr Leu
    2300                2305                2310

Gly Ala Ile Cys Ser Cys Thr Cys Phe Gly Gly Gln Arg Gly Trp
    2315                2320                2325

Arg Cys Asp Asn Cys Arg Arg Pro Gly Gly Glu Pro Ser Pro Glu
    2330                2335                2340

Gly Thr Thr Gly Gln Ser Tyr Asn Gln Tyr Ser Gln Arg Tyr His
    2345                2350                2355

Gln Arg Thr Asn Thr Asn Val Asn Cys Pro Ile Glu Cys Phe Met
    2360                2365                2370

Pro Leu Asp Val Gln Ala Asp Arg Glu Asp Ser Arg Glu
    2375                2380                2385

<210> SEQ ID NO 5
<211> LENGTH: 3562
<212> TYPE: DNA
<213> ORGANISM: Homo sapiens

<400> SEQUENCE: 5

```
gccatcccgc gctctgcggg ctgggaggcc cgggccagga cgcgagtcct gcgcagccga      60
ggttccccag cgcccctgc agccgcgcgt aggcagagac ggagcccggc cctgcgcctc     120
cgcaccacgc ccgggacccc acccagcggc ccgtacccgg agaagcagcg cgagcacccg     180
aagctcccgg ctggcggcag aaaccgggag tggggccggg cgagtgcgcg catcccagg     240
ccggcccgaa cgctccgccc gcggtgggcc gacttcccct cctcttccct ctctccttcc     300
tttagcccgc tggcgccgga cacgctgcgc ctcatctctt ggggcgttct tccccgttgg     360
ccaaccgtcg catcccgtgc aactttgggg tagtggccgt ttagtgttga atgttcccca     420
ccgagagcgc atggcttggg aagcgaggcg cgaacccggc ccccgaaggg ccgccgtccg     480
ggagacggtg atgctgttgc tgtgcctggg ggtcccgacc ggccgcccct acaacgtgga     540
cactgagagc gcgctgcttt accagggccc ccacaacacg ctgttcggct actcggtcgt     600
gctgcacaga cacggggcga accgatggct cctagtgggt gcgcccactg ccaactggct     660
cgccaacgct tcagtgatca atcccggggc gatttacaga tgcaggatcg aaagaatcc     720
cggccagacg tgcgaacagc tccagctggg tagcccctaat ggagaacctt gtggaaagac     780
ttgtttggaa gagagagaca atcagtggtt gggggtcaca ctttccagac agccaggaga     840
```

```
aaatggatcc atcgtgactt gtgggcatag atggaaaaat atattttaca taaagaatga    900
aaataagctc cccactggtg gttgctatgg agtgccccct gatttacgaa cagaactgag    960
taaaagaata gctccgtgtt atcaagatta tgtgaaaaaa tttggagaaa attttgcatc   1020
atgtcaagct ggaatatcca gttttttacac aaaggattta attgtgatgg gggccccagg   1080
atcatcttac tggactggct ctcttttttgt ctacaatata actacaaata aatacaaggc   1140
ttttttagac aaacaaaatc aagtaaaatt tggaagttat ttaggatatt cagtcggagc   1200
tggtcatttt cggagccagc atactaccga agtagtcgga ggagctcctc aacatgagca   1260
gattggtaag gcatatatat tcagcattga tgaaaaagaa ctaaatatct acatgaaat    1320
gaaaggtaaa aagcttggat cgtactttgg agcttctgtc tgtgctgtgg acctcaatgc   1380
agatggcttc tcagatctgc tcgtgggagc acccatgcag agcaccatca gagaggaagg   1440
aagagtgttt gtgtacatca actctggctc gggagcagta atgaatgcaa tggaaacaaa   1500
cctcgttgga agtgacaaat atgctgcaag atttggggaa tctatagtta atcttggcga   1560
cattgacaat gatggctttg aagatgttgc tatcggagct ccacaagaag atgacttgca   1620
aggtgctatt tatatttaca atggccgtgc agatgggatc tcgtcaacct tctcacagag   1680
aattgaagga cttcagatca gcaaatcgtt aagtatgttt ggacagtcta tcaggaca    1740
aattgatgca gataataatg gctatgtaga tgtagcagtt ggtgcttttc ggtctgattc   1800
tgctgtcttg ctaaggacaa gacctgtagt aattgttgac gcttctttaa gccaccctga   1860
gtcagtaaat agaacgaaat ttgactgtgt tgaaatgga tggccttctg tgtgcataga    1920
tctaacactt tgtttctcat ataagggcaa ggaagttcca ggttacattg ttttgttta    1980
taacatgagt ttggatgtga acagaaaggc agagtctcca ccaagattct atttctcttc   2040
taatggaact tctgacgtga ttacaggaag catacaggtg tccagcagag aagctaactg   2100
tagaacacat caagcattta tgcggaaaga tgtgcgggac atcctcaccc caattcagat   2160
tgaagctgct taccaccttg gtcctcatgt catcagtaaa cgaagtacag aggaattccc   2220
accacttcag ccaattcttc agcagaagaa agaaaaagac ataatgaaaa aacaataaa    2280
ctttgcaagg ttttgtgccc atgaaaattg ttctgctgat ttacaggttt ctgcaaagat   2340
tgggttttg aagccccatg aaaataaaac atatcttgct gttgggagta tgaagacatt   2400
gatgttgaat gtgtccttgt ttaatgctgg agatgatgca tatgaaacga ctctacatgt   2460
caaactaccc gtgggtcttt atttcattaa gattttagag ctggaagaga agcaaataaa   2520
ctgtgaagtc acagataact ctggcgtggt acaacttgac tgcagtattg ctatatata    2580
tgtagatcat ctctcaagga tagatattag cttttctcctg gatgtgagct cactcagcag   2640
agcggaagag gacctcagta tcacagtgca tgctacctgt gaaaatgaag aggaaatgga   2700
caatctaaag cacagcagag tgactgtagc aatacccttta aaatatgagg ttaagctgac   2760
tgttcatggg tttgtaaacc caacttcatt tgtgtatgga tcaaatgatg aaaatgagcc   2820
tgaaacgtgc atggtggaga aaatgaactt aactttccat gttatcaaca ctggcaatag   2880
tatggctccc aatgttagtg tggaaataat ggtaccaaat tcttttagcc cccaaactga   2940
taagctgttc aacatttttgg atgtccagac tactactgga gaatgccact ttgaaaatta   3000
tcaaagagtg tgtgcattag agcagcaaaa gagtgcaatg cagaccttga aaggcatagt   3060
ccggttcttg tccaagactg ataagaggct attgtactgc ataaaagctg atccacattg   3120
tttaaatttc ttgtgtaatt ttgggaaaat ggaaagtgga aagaagcca gtgttcatat    3180
ccaactggaa ggccggccat ccattttaga aatggatgag acttcagcac tcaagtttga   3240
```

| aataagagca acaggttttc cagagccaaa tccaagagta attgaactaa acaaggatga | 3300 |
| gaatgttgcg catgttctac tggaaggact acatcatcaa agacccaaac gttatttcac | 3360 |
| catagtgatt atttcaagta gcttgctact tggacttatt gtacttctat tgatctcata | 3420 |
| tgttatgtgg aaggctggct tcttaaaag acaatacaaa tctatcctac aagaagaaaa | 3480 |
| cagaagagac agttggagtt atatcaacag taaaagcaat gatgattaag gacttctttc | 3540 |
| aaattgagag aatggaaaac ag | 3562 |

<210> SEQ ID NO 6
<211> LENGTH: 3562
<212> TYPE: DNA
<213> ORGANISM: Homo sapiens

<400> SEQUENCE: 6

| gccatcccgc gctctgcggg ctgggaggcc cgggccagga cgcgagtcct gcgcagccga | 60 |
| ggttccccag cgcccctgc agccgcgcgt aggcagagac ggagcccggc cctgcgcctc | 120 |
| cgcaccacgc ccgggacccc acccagcggc ccgtacccgg agaagcagcg cgagcacccg | 180 |
| aagctcccgg ctggcggcag aaaccgggag tgggccgggg cgagtgcgcg gcatcccagg | 240 |
| ccggcccgaa cgctccgccc gcggtgggcc gacttcccct cctcttccct ctctccttcc | 300 |
| tttagcccgc tggcgccgga cacgctgcgc ctcatctctt ggggcgttct tccccgttgg | 360 |
| ccaaccgtcg catcccgtgc aactttgggg tagtggccgt ttagtgttga atgttcccca | 420 |
| ccgagagcgc atggcttggg aagcgaggcg cgaacccggc ccccgaaggg ccgccgtccg | 480 |
| ggagacggtg atgctgttgc tgtgcctggg ggtcccgacc ggccgcccct acaacgtgga | 540 |
| cactgagagc gcgctgcttt accagggccc ccacaacacg ctgttcggct actcggtcgt | 600 |
| gctgcacagc cacggggcga accgatggct cctagtgggt gcgcccactg ccaactggct | 660 |
| cgccaacgct tcagtgatca atcccggggc gatttacaga tgcaggatcg aaagaatcc | 720 |
| cggccagacg tgcgaacagc tccagctggg tagccctaat ggagaacctt gtggaaagac | 780 |
| ttgtttggaa gagagagaca tcagtggtt gggggtcaca cttccagac agccaggaga | 840 |
| aaatggatcc atcgtgactt gtgggcatag atggaaaaat atattttaca taagaatga | 900 |
| aaataagctc cccactggtg gttgctatgg agtgccccct gatttacgaa cagaactgag | 960 |
| taaagaata gctccgtgtt atcaagatta tgtgaaaaaa tttggagaaa attttgcatc | 1020 |
| atgtcaagct ggaatatcca gttttacac aaaggattta attgtgatgg gggccccagg | 1080 |
| atcatcttac tggactggct ctctttttgt ctacaatata actacaaata aatacaaggc | 1140 |
| tttttagac aaacaaaatc aagtaaaatt tggaagttat ttaggatatt cagtcggagc | 1200 |
| tggtcatttt cggagccagc atactaccga agtagtcgga ggagctcctc aacatgagca | 1260 |
| gattggtaag gcatatatat tcagcattga tgaaaagaa ctaaatatct tacatgaaat | 1320 |
| gaaaggtaaa aagcttggat cgtactttgg agcttctgtc tgtgctgtgg acctcaatgc | 1380 |
| agatggcttc tcagatctgc tcgtgggagc acccatgcag agcaccatca gagaggaagg | 1440 |
| aagagtgttt gtgtacatca actctggctc gggagcagta atgaatgcaa tggaaacaaa | 1500 |
| cctcgttgga agtgacaaat atgctgcaag atttggggaa tctatagtta atcttggcga | 1560 |
| cattgacaat gatggctttg aagatgttgc tatcggagct ccacaagaag atgacttgca | 1620 |
| aggtgctatt tatatttaca atggccgtgc agatgggatc tcgtcaacct tctcacagag | 1680 |
| aattgaagga cttcagatca gcaaatcgtt aagtatgttt ggacagtcta tatcaggaca | 1740 |

```
aattgatgca gataataatg gctatgtaga tgtagcagtt ggtgcttttc ggtctgattc    1800
tgctgtcttg ctaaggacaa gacctgtagt aattgttgac gcttctttaa gccaccctga    1860
gtcagtaaat agaacgaaat ttgactgtgt tgaaaatgga tggccttctg tgtgcataga    1920
tctaacactt tgtttctcat ataagggcaa ggaagttcca ggttacattg ttttgtttta    1980
taacatgagt ttggatgtga acagaaaggc agagtctcca ccaagattct atttctcttc    2040
taatggaact tctgacgtga ttacaggaag catacaggtg tccagcagag aagctaactg    2100
tagaacacat caagcattta tgcggaaaga tgtgcgggac atcctcaccc caattcagat    2160
tgaagctgct taccaccttg gtcctcatgt catcagtaaa cgaagtacag aggaattccc    2220
accacttcag ccaattcttc agcagaagaa agaaaaagac ataatgaaaa aacaataaa    2280 ctttgcaagg ttttgtgccc atgaaaattg ttctgctgat ttacaggttt ctgcaaagat    2340 tgggttttg aagccccatg aaaataaaac atatcttgct gttgggagta tgaagacatt    2400
gatgttgaat gtgtccttgt ttaatgctgg agatgatgca tatgaaacga ctctacatgt    2460
caaactaccc gtgggtcttt atttcattaa gattttagag ctggaagaga agcaaataaa    2520
ctgtgaagtc acagataact ctggcgtggt acaacttgac tgcagtattg ctatatata    2580 tgtagatcat ctctcaagga tagatattag ctttctcctg gatgtgagct cactcagcag    2640
agcggaagag gacctcagta tcacagtgca tgctacctgt gaaaatgaag aggaaatgga    2700
caatctaaag cacagcagag tgactgtagc aatacctta aaatatgagg ttaagctgac    2760
tgttcatggg tttgtaaacc caacttcatt tgtgtatgga tcaaatgatg aaaatgagcc    2820
tgaaacgtgc atggtggaga aaatgaactt aactttccat gttatcaaca ctggcaaatag    2880 tatggctccc aatgttagtg tggaaataat ggtaccaaat tctttagcc cccaaactga    2940 taagctgttc aacattttgg atgtccagac tactactgga gaatgccact ttgaaaatta    3000
tcaaagagtg tgtgcattag agcagcaaaa gagtgcaatg cagaccttga aaggcatagt    3060
ccggttcttg tccaagactg ataagaggct attgtactgc ataaaagctg atccacattg    3120
tttaaatttc ttgtgtaatt ttgggaaaat ggaaagtgga aaagaagcca gtgttcatat    3180
ccaactggaa ggccggccat ccattttaga aatggatgag acttcagcac tcaagtttga    3240
aataagagca acaggttttc cagagccaaa tccaagagta attgaactaa caaggatga    3300 gaatgttgcg catgttctac tggaaggact acatcatcaa agacccaaac gttatttcac    3360
catagtgatt atttcaagta gcttgctact tggacttatt gtacttctat tgatctcata    3420
tgttatgtgg aaggctggct tctttaaaag acaatacaaa tctatcctac aagaagaaaa    3480
cagaagagac agttggagtt atatcaacag taaaagcaat gatgattaag gacttctttc    3540
aaattgagag aatggaaaac ag                                             3562

<210> SEQ ID NO 7
<211> LENGTH: 3614
<212> TYPE: DNA
<213> ORGANISM: Homo sapiens

<400> SEQUENCE: 7
gtccgccaaa acctgcgcgg ataggggaaga acagcacccc ggcgccgatt gccgtaccaa      60
acaagcctaa cgtccgctgg gccccggacg ccgcgcggaa aagatgaatt tacaaccaat    120
tttctggatt ggactgatca gttcagtttg ctgtgtgttt gctcaaacag atgaaaatag    180
atgtttaaaa gcaaatgcca aatcatgtgg agaatgtata caagcagggc caaattgtgg    240
gtggtgcaca aattcaacat ttttacagga aggaatgcct acttctgcac gatgtgatga    300
```

```
tttagaagcc ttaaaaaaga agggttgccc tccagatgac atagaaaatc ccagaggctc    360
caaagatata aagaaaaata aaatgtaac caaccgtagc aaaggaacag cagagaagct      420
caagccagag gatattcatc agatccaacc acagcagttg gttttgcgat taagatcagg    480
ggagccacag acatttacat taaaattcaa gagagctgaa gactatccca ttgacctcta    540
ctaccttatg gacctgtctt attcaatgaa agacgatttg gagaatgtaa aaagtcttgg    600
aacagatctg atgaatgaaa tgaggaggat tacttcggac ttcagaattg gatttggctc    660
atttgtggaa aagactgtga tgccttacat tagcacaaca ccagctaagc tcaggaaccc    720
ttgcacaagt gaacagaact gcaccacccc atttagctac aaaaatgtgc tcagtcttac    780
taataaagga gaagtattta atgaacttgt tggaaaacag cgcatatctg gaaatttgga    840
ttctccagaa ggtggtttcg atgccatcat gcaagttgca gtttgtggat cactgattgg    900
ctggaggaat gttacacggc tgctggtgtt ttccacagat gccgggtttc actttgctgg    960
agatgggaaa cttggtggca ttgttttacc aaatgatgga caatgtcacc tggaaaataa   1020
tatgtacaca atgagccatt attatgatta tccttctatt gctcaccttg tccagaaact   1080
gagtgaaaat aatattcaga caattttttgc agttactgaa gaatttcagc ctgtttacaa   1140
ggagctgaaa aacttgatcc ctaagtcagc agtaggaaca ttatctgcaa attctagcaa   1200
tgtaattcag ttgatcattg atgcatacaa ttccctttcc tcagaagtca ttttggaaaa   1260
cggcaaattg tcagaaggag taacaataag ttacaaatct tactgcaaga acggggtgaa   1320
tggaacaggg gaaaatggaa gaaaatgttc caatatttcc attggagatg aggttcaatt   1380
tgaaattagc ataacttcaa ataagtgtcc aaaaaaggat tctgacagct ttaaaattag   1440
gcctctgggc tttacggagg aagtagaggt tattcttcag tacatctgtg aatgtgaatg   1500
ccaaagcgaa ggcatccctg aaagtcccaa gtgtcatgaa ggaaatggga catttgagtg   1560
tggcgcgtgc aggtgcaatg aagggcgtgt tggtagacat tgtgaatgca gcacagatga   1620
agttaacagt gaagacatgg atgcttactg caggaaagaa aacagttcag aaatctgcag   1680
taacaatgga gagtgcgtct gcggacagtg tgtttgtagg aagagggata atacaaatga   1740
aatttattct ggcaaattct gcgagtgtga taatttcaac tgtgatagat ccaatggctt   1800
aatttgtgga ggaaatggtg tttgcaagtg tcgtgtgtgt gagtgcaacc ccaactacac   1860
tggcagtgca tgtgactgtt cttttggatac tagtacttgt gaagccagca acggacagat   1920
ctgcaatggc cgggggcatct gcgagtgtgg tgtctgtaag tgtacagatc cgaagtttca   1980
agggcaaacg tgtgagatgt gtcagacctg ccttggtgtc tgtgctgagc ataaagaatg   2040
tgttcagtgc agagccttca taaaggaga aagaaagac acatgcacac aggaatgttc   2100 ctatttaac attaccaagg tagaaagtcg ggacaaatta ccccagccgg tccaacctga   2160
tcctgtgtcc cattgtaagg agaaggatgt tgacgactgt tggttctatt ttacgtattc   2220
agtgaatggg aacaacgagg tcatggttca tgttgtggag aatccagagt gtcccactgg   2280
tccagacatc attccaattg tagctggtgt ggttgctgga attgttctta ttggccttgc   2340
attactgctg atatggaagc ttttaatgat aattcatgac agaagggagt ttgctaaatt   2400
tgaaaaggag aaaatgaatg ccaaatggga cacgggtgaa atcctatttt ataagagtgc   2460
cgtaacaact gtggtcaatc cgaagtatga gggaaaatga gtactgcccg tgcaaatccc   2520
acaacactga atgcaaagta gcaatttcca tagtcacagt taggtagctt tagggcaata   2580
ttgccatggt tttactcatg tgcaggtttt gaaaatgtac aatatgtata atttttaaaa   2640
```

-continued

| | |
|---|---|
| tgtttattta ttttgaaaat aatgttgtaa ttcatgccag ggactgacaa aagacttgag | 2700 |
| acaggatggt tattcttgtc agctaaggtc acattgtgcc tttttgacct tttcttcctg | 2760 |
| gactattgaa atcaagctta ttggattaag tgatatttct atagcgattg aaagggcaat | 2820 |
| agttaaagta atgagcatga tgagagtttc tgttaatcat gtattaaaac tgattttttag | 2880 |
| ctttacatat gtcagtttgc agttatgcag aatccaaagt aaatgtcctg ctagctagtt | 2940 |
| aaggattgtt ttaaatctgt tattttgcta tttgcctgtt agacatgact gatgacatat | 3000 |
| ctgaaagaca agtatgttga gagttgctgg tgtaaaatac gtttgaaata gttgatctac | 3060 |
| aaaggccatg ggaaaaattc agagagttag gaaggaaaaa ccaatagctt taaaacctgt | 3120 |
| gtgccatttt aagagttact taatgtttgg taacttttat gccttcactt tacaaattca | 3180 |
| agccttagat aaaagaaccg agcaattttc tgctaaaaag tccttgattt agcactattt | 3240 |
| acatacaggc catactttac aaagtatttg ctgaatgggg accttttgag ttgaatttat | 3300 |
| tttattattt ttattttgtt taatgtctgg tgcttctat cacctcttct aatctttaa | 3360 |
| tgtatttgtt tgcaattttg gggtaagact ttttatgag tacttttct ttgaagtttt | 3420 |
| agcggtcaat ttgcctttt aatgaacatg tgaagttata ctgtggctat gcaacagctc | 3480 |
| tcacctacgc gagtcttact ttgagttagt gccataacag accactgtat gtttacttct | 3540 |
| caccatttga gttgcccatc ttgtttcaca ctagtcacat tcttgtttta agtgccttta | 3600 |
| gttttaacag ttca | 3614 |

<210> SEQ ID NO 8
<211> LENGTH: 2220
<212> TYPE: DNA
<213> ORGANISM: Homo sapiens

<400> SEQUENCE: 8

| | |
|---|---|
| atgcctggga agatggtcgt gatccttgga gcctcaaata tactttggat aatgtttgca | 60 |
| gcttctcaag cttttaaaat cgagaccacc ccagaatcta gatatcttgc tcagattggt | 120 |
| gactccgtct cattgacttg cagcaccaca ggctgtgagt ccccattttt ctcttggaga | 180 |
| acccagatag atagtccact gaatgggaag gtgacgaatg aggggaccac atctacgctg | 240 |
| acaatgaatc ctgttagttt tgggaacgaa cactcttacc tgtgcacagc aacttgtgaa | 300 |
| tctaggaaat tggaaaaagg aatccaggtg gagatctact cttttcctaa ggatccagag | 360 |
| attcatttga gtggccctct ggaggctggg aagccgatca cagtcaagtg ttcagttgct | 420 |
| gatgtatacc catttgacag gctggagata gacttactga aggagatca tctcatgaag | 480 |
| agtcaggaat ttctggagga tgcagacagg aagtccctgg aaaccaagag tttggaagta | 540 |
| acctttactc ctgtcattga ggatattgga aaagttcttg tttgccgagc taaattacac | 600 |
| attgatgaaa tggattctgt gcccacagta aggcaggctg taaaagaatt gcaagtctac | 660 |
| atatcaccca agaatacagt tatttctgtg aatccatcca caaagctgca agaaggtggc | 720 |
| tctgtgacca tgacctgttc cagcgagggt ctaccagctc cagagatttt ctggagtaag | 780 |
| aaattagata atgggaatct acagcacctt ctggaaatg caactctcac cttaattgct | 840 |
| atgaggatgg aagattctgg aatttatgtg tgtgaaggag ttaatttgat tgggaaaaac | 900 |
| agaaaagagg tggaattaat tgttcaagag aaaccattta ctgttgagat ctcccctgga | 960 |
| ccccggattg ctgctcagat tggagactca gtcatgttga catgtagtgt catgggctgt | 1020 |
| gaatccccat ctttctcctg gagaaccag atagacagcc tctgagcgg gaaggtgagg | 1080 |
| agtgagggga ccaattccac gctgacccctg agccctgtga gttttgagaa cgaacactct | 1140 |

```
tatctgtgca cagtgacttg tggacataag aaactggaaa agggaatcca ggtggagctc      1200
tactcattcc ctagagatcc agaaatcgag atgagtggtg gcctcgtgaa tgggagctct      1260
gtcactgtaa gctgcaaggt tcctagcgtg taccccttg accggctgga gattgaatta       1320
cttaaggggg agactattct ggagaatata gagtttttgg aggatacgga tatgaaatct      1380
ctagagaaca aaagtttgga aatgaccttc atccctacca ttgaagatac tggaaaagct      1440
cttgtttgtc aggctaagtt acatattgat gacatggaat tcgacccaa acaaaggcag       1500 agtacgcaaa cactttatgt caatgttgcc cccagagata caaccgtctt ggtcagccct      1560
tcctccatcc tggaggaagg cagttctgtg aatatgacat gcttgagcca gggctttcct      1620
gctccgaaaa tcctgtggag caggcagctc cctaacgggg agctacagcc tctttctgag      1680
aatgcaactc tcaccttaat ttctacaaaa atggaagatt ctggggttta tttatgtgaa      1740
ggaattaacc aggctggaag aagcagaaag gaagtggaat taattatcca agttactcca      1800
aaagacataa aacttacagc ttttccttct gagagtgtca aagaaggaga cactgtcatc      1860
atctcttgta catgtggaaa tgttccagaa acatggataa tcctgaagaa aaaagcggag      1920
acaggagaca cagtactaaa atctatagat ggcgcctata ccatccgaaa ggcccagttg      1980
aaggatgcgg gagtatatga atgtgaatct aaaaacaaag ttggctcaca attaagaagt      2040
ttaacacttg atgttcaagg aagagaaaac aacaaagact attttctcc tgagcttctc       2100 gtgctctatt ttgcatcctc cttaataata cctgccattg gaatgataat ttactttgca      2160
agaaaagcca acatgaaggg gtcatatagt cttgtagaag cacagaaatc aaaagtgtag      2220

<210> SEQ ID NO 9
<211> LENGTH: 7680
<212> TYPE: DNA
<213> ORGANISM: Homo sapiens

<400> SEQUENCE: 9
gaagagcaag aggcaggctc agcaaatggt tcagccccag tccccggtgg ctgtcagtca        60
aagcaagccc ggttgttatg acaatggaaa acactatcag ataaatcaac agtgggagcg       120
gacctaccta ggtaatgtgt tggtttgtac ttgttatgga ggaagccgag gttttaactg       180
cgaaagtaaa cctgaagctg aagagacttg ctttgacaag tacactggga acacttaccg       240
agtgggtgac acttatgagc gtcctaaaga ctccatgatc tgggactgta cctgcatcgg       300
ggctgggcga gggagaataa gctgtaccat cgcaaaccgc tgccatgaag ggggtcagtc       360
ctacaagatt ggtgacacct ggaggagacc acatgagact ggtggttaca tgttagagtg       420
tgtgtgtctt ggtaatggaa aaggagaatg gacctgcaag cccatagctg agaagtgttt       480
tgatcatgct gctgggactt cctatgtggt cggagaaacg tgggagaagc ctaccaagg       540 ctggatgatg gtagattgta cttgcctggg agaaggcagc ggacgcatca cttgcacttc      600
tagaaataga tgcaacgatc aggacacaag gacatcctat agaattggag cacctggag       660 caagaaggat aatcgaggaa acctgctcca gtgcatctgc acaggcaacg gccgaggaga      720
gtggaagtgt gagaggcaca cctctgtgca gaccacatcg agcggatctg gccccttcac      780
cgatgttcgt gcagctgttt accaaccgca gcctcacccc cagcctcctc cctatggcca      840
ctgtgtcaca gacagtggtg tggtctactc tgtggggatg cagtggttga agacacaagg      900
aaataagcaa atgctttgca cgtgcctggg caacggagtc agctgccaag agacagctgt      960
aacccagact tacggtggca acttaaatgg agagccatgt gtcttaccat tcacctacaa     1020
```

```
tggcaggacg ttctactcct gcaccacgga agggcgacag gacggacatc tttggtgcag    1080
cacaacttcg aattatgagc aggaccagaa atactctttc tgcacagacc acactgtttt    1140
ggttcagact caaggaggaa attccaatgg tgccttgtgc cacttcccct tcctatacaa    1200
caaccacaat tacactgatt gcacttctga gggcagaaga acaacatga agtggtgtgg     1260 gaccacacag aactatgatg ccgaccagaa gtttgggttc tgccccatgg ctgcccacga    1320
ggaaatctgc acaaccaatg aagggtcat gtaccgcatt ggagatcagt gggataagca     1380
gcatgacatg ggtcacatga tgaggtgcac gtgtgttggg aatggtcgtg gggaatggac    1440
atgcattgcc tactcgcaac ttcgagatca gtgcattgtt gatgacatca cttacaatgt    1500
gaacgacaca ttccacaagc gtcatgaaga ggggcacatg ctgaactgta catgcttcgg    1560
tcagggtcgg ggcaggtgga agtgtgatcc cgtcgaccaa tgccaggatt cagagactgg    1620
gacgttttat caaattggag attcatggga gaagtatgtg catggtgtca gataccagtg    1680
ctactgctat ggccgtggca ttggggagtg gcattgccaa cctttacaga cctatccaag    1740
ctcaagtggt cctgtcgaag tatttatcac tgagactccg agtcagccca actcccaccc    1800
catccagtgg aatgcaccac agccatctca catttccaag tacattctca ggtggagacc    1860
taaaaattct gtaggccgtt ggaaggaagc taccatacca ggccacttaa actcctacac    1920
catcaaaggc ctgaagcctg gtgtggtata cgagggccag ctcatcagca tccagcagta    1980
cggccaccaa gaagtgactc gctttgactt caccaccacc agcaccagca cacctgtgac    2040
cagcaacacc gtgacaggag agacgactcc cttttctcct cttgtggcca cttctgaatc    2100
tgtgaccgaa atcacagcca gtagctttgt ggtctcctgg gtctcagctt ccgacaccgt    2160
gtcgggattc cgggtggaat atgagctgag tgaggaggga gatgagccac agtacctgga    2220
tcttccaagc acagccactt ctgtgaacat ccctgacctg cttcctggcc gaaaatacat    2280
tgtaaatgtc tatcagatat ctgaggatgg ggagcagagt ttgatcctgt ctacttcaca    2340
aacaacagcg cctgatgccc ctcctgaccc gactgtggac caagttgatg acacctcaat    2400
tgttgttcgc tggagcagac cccaggctcc catcacaggg tacagaatag tctattcgcc    2460
atcagtagaa ggtagcagca cagaactcaa ccttcctgaa actgcaaact ccgtcaccct    2520
cagtgacttg caacctggtg ttcagtataa catcactatc tatgctgtgg aagaaaatca    2580
agaaagtaca cctgttgtca ttcaacaaga aaccactggc acccacgct cagatacagt    2640 gccctctccc agggacctgc agtttgtgga agtgacagac gtgaaggtca ccatcatgtg    2700
gacaccgcct gagagtgcag tgaccggcta ccgtgtggat gtgatccccg tcaacctgcc    2760
tggcgagcac gggcagaggc tgcccatcag caggaacacc tttgcagaag tcaccgggct    2820
gtcccctggg gtcacctatt acttcaaagt ctttgcagtg agccatggga gggagagcaa    2880
gcctctgact gctcaacaga caaccaaact ggatgctccc actaacctcc agtttgtcaa    2940
tgaaactgat tctactgtcc tggtgagatg gactccacct cgggcccaga taacaggata    3000
ccgactgacc gtgggcctta cccgaagagg ccagcccagg cagtacaatg tgggtcccct    3060
tgtctccaag tacccctga ggaatctgca gcctgcatct gagtacaccg tatccctcgt    3120
ggccataaag gcaaccaag agagcccaa agccactgga gtctttacca cactgcagcc    3180
tgggagctct attccacctt acaacaccga ggtgactgag accaccatcg tgatcacatg    3240
gacgcctgct ccaagaattg gttttaagct gggtgtacga ccaagccagg aggagaggc    3300 accacgagaa gtgacttcag actcaggaag catcgttgtg tccggcttga ctccaggagt    3360
agaatacgtc tacaccatcc aagtcctgag agatggacag gaaagagatg cgccaattgt    3420
```

-continued

```
aaacaaagtg gtgacaccat tgtctccacc aacaaacttg catctggagg caaaccctga   3480
cactggagtg ctcacagtct cctgggagag gagcaccacc ccagacatta ctggttatag   3540
aattaccaca acccctacaa acggccagca gggaaattct ttggaagaag tggtccatgc   3600
tgatcagagc tcctgcactt ttgataacct gagtcccggc ctggagtaca atgtcagtgt   3660
ttacactgtc aaggatgaca aggaaagtgt ccctatctct gataccatca tcccagctgt   3720
tcctcctccc actgacctgc gattcaccaa cattggtcca gacaccatgc gtgtcacctg   3780
ggctccaccc ccatccattg atttaaccaa cttcctggtg cgttactcac ctgtgaaaaa   3840
tgaggaagat gttgcagagt tgtcaatttc tccttcagac aatgcagtgg tcttaacaaa   3900
tctcctgcct ggtacagaat atgtagtgag tgtctccagt gtctacgaac aacatgagag   3960
cacacctctt agaggaagac agaaaacagg tcttgattcc ccaactggca ttgactttc    4020
tgatattact gccaactctt ttactgtgca ctggattgct cctcgagcca ccatcactgg   4080
ctacaggatc cgccatcatc ccgagcactt cagtgggaga cctcgagaag atcgggtgcc   4140
ccactctcgg aattccatca ccctccaccaa cctcactcca ggcacagagt atgtggtcag   4200
catcgttgct cttaatggca gagaggaaag tcccttattg attggccaac aatcaacagt   4260
ttctgatgtt ccgagggacc tggaagttgt tgctgcgacc cccaccagcc tactgatcag   4320
ctgggatgcc cctgctgtca cagtgagata ttacaggatc acttacggag aaacaggagg   4380
aaatagccct gtccaggagt tcactgtgcc tgggagcaag tctacagcta ccatcagcgg   4440
ccttaaacct ggagttgatt ataccatcac tgtgtatgct gtcactggcc gtggagacag   4500
ccccgcaagc agcaagccaa tttccattaa ttaccgaaca gaaattgaca aaccatccca   4560
gatgcaagtg accgatgttc aggacaacag cattagtgtc aagtggctgc cttcaagttc   4620
ccctgttact ggttacagag taaccaccac tcccaaaaat ggaccaggac caacaaaaac   4680
taaaactgca ggtccagatc aaacagaaat gactattgaa ggcttgcagc ccacagtgga   4740
gtatgtggtt agtgtctatg ctcagaatcc aagcggagag agtcagcctc tggttcagac   4800
tgcagtaacc aacattgatc gccctaaagg actggcattc actgatgtgg atgtcgattc   4860
catcaaaatt gcttgggaaa gcccacaggg gcaagtttcc aggtacaggg tgacctactc   4920
gagccctgag gatggaatcc atgagctatt ccctgcacct gatggtgaag aagacactgc   4980
agagctgcaa ggcctcagac cgggttctga gtacacagtc agtgtggttg ccttgcacga   5040
tgatatggag agccagcccc tgattggaac ccagtccaca gctattcctg caccaactga   5100
cctgaagttc actcaggtca cacccacaag cctgagcgcc cagtggacac cacccaatgt   5160
tcagctcact ggatatcgag tgcgggtgac ccccaaggag aagaccggac caatgaaaga   5220
aatcaacctt gctcctgaca gctcatccgt ggttgtatca ggacttatgg tggccaccaa   5280
atatgaagtg agtgtctatg ctcttaagga cactttgaca agcagaccag ctcagggtgt   5340
tgtcaccact ctggagaatg tcagcccacc aagaagggct cgtgtgacag atgctactga   5400
gaccaccatc accattagct ggagaaccaa gactgagacg atcactggct tccaagttga   5460
tgccgttcca gccaatggcc agactccaat ccagagaacc atcaagccag atgtcagaag   5520
ctacaccatc acaggtttac aaccaggcac tgactacaag atctacctgt acaccttgaa   5580
tgacaatgct cggagctccc ctgtggtcat cgacgcctcc actgccattg atgcaccatc   5640
caacctgcgt ttcctggcca ccacacccaa ttccttgctg gtatcatggc agccgccacg   5700
tgccaggatt accggctaca tcatcaagta tgagaagcct gggtctcctc ccagagaagt   5760
```

| | |
|---|---|
| ggtccctcgg ccccgccctg gtgtcacaga ggctactatt actggcctgg aaccgggaac | 5820 |
| cgaatataca atttatgtca ttgccctgaa gaataatcag aagagcgagc ccctgattgg | 5880 |
| aaggaaaaag acagacgagc ttccccaact ggtaacccct ccacacccca atcttcatgg | 5940 |
| accagagatc ttggatgttc cttccacagt tcaaaagacc cctttcgtca cccaccctgg | 6000 |
| gtatgacact ggaaatggta ttcagcttcc tggcacttct ggtcagcaac ccagtgttgg | 6060 |
| gcaacaaatg atctttgagg aacatggttt taggcggacc acaccgccca aacggccac | 6120 |
| ccccataagg cataggccaa gaccataccc gccgaatgta ggacaagaag ctctctctca | 6180 |
| gacaaccatc tcatgggccc cattccagga cacttctgag tacatcattt catgtcatcc | 6240 |
| tgttggcact gatgaagaac ccttacagtt cagggttcct ggaacttcta ccagtgccac | 6300 |
| tctgacaggc ctcaccagag gtgccaccta acatcata gtggaggcac tgaaagacca | 6360 |
| gcagaggcat aaggttcggg aagaggttgt taccgtgggc aactctgtca acgaaggctt | 6420 |
| gaaccaacct acgatgact cgtgctttga ccctacaca gtttcccatt atgccgttgg | 6480 |
| agatgagtgg gaacgaatgt ctgaatcagg ctttaaactg ttgtgccagt gcttaggctt | 6540 |
| tggaagtggt catttcagat gtgattcatc tagatggtgc catgacaatg gtgtgaacta | 6600 |
| caagattgga gagaagtggg accgtcaggg agaaaatggc cagatgatga gctgcacatg | 6660 |
| tcttgggaac ggaaaaggag aattcaagtg tgaccctcat gaggcaacgt gttacgatga | 6720 |
| tgggaagaca taccacgtag gagaacagtg gcagaaggaa tatctcggtg ccatttgctc | 6780 |
| ctgcacatgc tttggaggcc agcggggctg gcgctgtgac aactgccgca gacctggggg | 6840 |
| tgaacccagt cccgaaggca ctactggcca gtcctacaac cagtattctc agagatacca | 6900 |
| tcagagaaca aacactaatg ttaattgccc aattgagtgc ttcatgcctt tagatgtaca | 6960 |
| ggctgacaga gaagattccc gagagtaaat catctttcca atccagagga acaagcatgt | 7020 |
| ctctctgcca agatccatct aaactggagt gatgttagca gacccagctt agagttcttc | 7080 |
| tttctttctt aagcccttg ctctggagga agttctccag cttcagctca actcacagct | 7140 |
| tctccaagca tcaccctggg agtttcctga gggttttctc ataaatgagg gctgcacatt | 7200 |
| gcctgttctg cttcgaagta ttcaataccg ctcagtattt taaatgaagt gattctaaga | 7260 |
| tttggtttgg gatcaatagg aaagcatatg cagccaacca agatgcaaat gttttgaaat | 7320 |
| gatatgacca aaattttaag taggaaagtc acccaaacac ttctgctttc acttaagtgt | 7380 |
| ctggcccgca atactgtagg aacaagcatg atcttgttac tgtgatattt taaatatcca | 7440 |
| cagtactcac tttttccaaa tgatcctagt aattgcctag aaatatcttt ctcttacctg | 7500 |
| ttatttatca attttttccca gtatttttat acggaaaaaa ttgtattgaa aacacttagt | 7560 |
| atgcagttga taagaggaat ttggtataat tatggtgggt gattattttt tatactgtat | 7620 |
| gtgccaaagc tttactactg tggaaagaca actgttttaa taaaagattt acattccaca | 7680 |

<210> SEQ ID NO 10
<211> LENGTH: 161
<212> TYPE: PRT
<213> ORGANISM: Homo sapiens

<400> SEQUENCE: 10

Ile Val Thr Cys Gly His Arg Trp Lys Asn Ile Phe Tyr Ile Lys Asn
1               5                   10                  15

Glu Asn Lys Leu Pro Thr Gly Gly Cys Tyr Gly Val Pro Pro Asp Leu
            20                  25                  30

Arg Thr Glu Leu Ser Lys Arg Ile Ala Pro Cys Tyr Gln Asp Tyr Val

```
                35                  40                  45
Lys Lys Phe Gly Glu Asn Phe Ala Ser Cys Gln Ala Gly Ile Ser Ser
         50                  55                  60

Phe Tyr Thr Lys Asp Leu Ile Val Met Gly Ala Pro Gly Ser Ser Tyr
 65                  70                  75                  80

Trp Thr Gly Ser Leu Phe Val Tyr Asn Ile Thr Thr Asn Lys Tyr Lys
                 85                  90                  95

Ala Phe Leu Asp Lys Gln Asn Gln Val Lys Phe Gly Ser Tyr Leu Gly
            100                 105                 110

Tyr Ser Val Gly Ala Gly His Phe Arg Ser Gln His Thr Thr Glu Val
                115                 120                 125

Val Gly Gly Ala Pro Gln His Glu Gln Ile Gly Lys Ala Tyr Ile Phe
            130                 135                 140

Ser Ile Asp Glu Lys Glu Leu Asn Ile Leu His Glu Met Lys Gly Lys
145                 150                 155                 160

Lys

<210> SEQ ID NO 11
<211> LENGTH: 20
<212> TYPE: PRT
<213> ORGANISM: Homo sapiens

<400> SEQUENCE: 11

Gly His Arg Trp Lys Asn Ile Phe Tyr Ile Lys Asn Glu Asn Lys Leu
 1               5                  10                  15

Pro Thr Gly Gly
             20

<210> SEQ ID NO 12
<211> LENGTH: 14
<212> TYPE: PRT
<213> ORGANISM: Homo sapiens

<400> SEQUENCE: 12

Tyr Gln Asp Tyr Val Lys Lys Phe Gly Glu Asn Phe Ala Ser
 1               5                  10

<210> SEQ ID NO 13
<211> LENGTH: 6
<212> TYPE: PRT
<213> ORGANISM: Homo sapiens

<400> SEQUENCE: 13

Ser Tyr Trp Thr Gly Ser
 1               5

<210> SEQ ID NO 14
<211> LENGTH: 11
<212> TYPE: PRT
<213> ORGANISM: Homo sapiens

<400> SEQUENCE: 14

Gly Gly Ala Pro Gln His Glu Gln Ile Gly Lys
 1               5                  10

<210> SEQ ID NO 15
<211> LENGTH: 10
<212> TYPE: PRT
<213> ORGANISM: Homo sapiens

<400> SEQUENCE: 15
```

```
Arg Thr Gln Ile Asp Ser Pro Leu Asn Gly
1               5                   10

<210> SEQ ID NO 16
<211> LENGTH: 10
<212> TYPE: PRT
<213> ORGANISM: Homo sapiens

<400> SEQUENCE: 16

Arg Thr Gln Ile Asp Ser Pro Leu Ser Gly
1               5                   10

<210> SEQ ID NO 17
<211> LENGTH: 4
<212> TYPE: PRT
<213> ORGANISM: Homo sapiens

<400> SEQUENCE: 17

Lys Leu Glu Lys
1

<210> SEQ ID NO 18
<211> LENGTH: 130
<212> TYPE: PRT
<213> ORGANISM: Homo sapiens

<400> SEQUENCE: 18

Ser Glu Pro Leu Ile Gly Arg Lys Lys Thr Asp Glu Leu Pro Gln Leu
1               5                   10                  15

Val Thr Leu Pro His Pro Asn Leu His Gly Pro Glu Ile Leu Asp Val
            20                  25                  30

Pro Ser Thr Val Gln Lys Thr Pro Phe Val Thr His Pro Gly Tyr Asp
        35                  40                  45

Thr Gly Asn Gly Ile Gln Leu Pro Gly Thr Ser Gly Gln Gln Pro Ser
    50                  55                  60

Val Gly Gln Gln Met Ile Phe Glu Glu His Gly Phe Arg Arg Thr Thr
65                  70                  75                  80

Pro Pro Thr Thr Ala Thr Pro Ile Arg His Arg Pro Arg Pro Tyr Pro
                85                  90                  95

Pro Asn Val Gly Glu Glu Ile Gln Ile Gly His Ile Pro Arg Glu Asp
            100                 105                 110

Val Asp Tyr His Leu Tyr Pro His Gly Pro Gly Leu Asn Pro Asn Ala
            115                 120                 125

Ser Thr
    130

<210> SEQ ID NO 19
<211> LENGTH: 3
<212> TYPE: PRT
<213> ORGANISM: Homo sapiens

<400> SEQUENCE: 19

Leu Asp Val
1

<210> SEQ ID NO 20
<211> LENGTH: 4
<212> TYPE: PRT
<213> ORGANISM: Homo sapiens

<400> SEQUENCE: 20
```

```
Arg Glu Asp Val
1

<210> SEQ ID NO 21
<211> LENGTH: 5
<212> TYPE: PRT
<213> ORGANISM: Homo sapiens

<400> SEQUENCE: 21

Ile Asp Ala Pro Ser
1               5

<210> SEQ ID NO 22
<211> LENGTH: 8
<212> TYPE: PRT
<213> ORGANISM: Homo sapiens

<400> SEQUENCE: 22

Glu Ile Leu Asp Val Pro Ser Thr
1               5

<210> SEQ ID NO 23
<211> LENGTH: 25
<212> TYPE: PRT
<213> ORGANISM: Homo sapiens

<400> SEQUENCE: 23

Asp Glu Leu Pro Gln Leu Val Thr Leu Pro His Pro Asn Leu His Gly
1               5                  10                  15

Pro Glu Ile Leu Asp Val Pro Ser Thr
            20                  25

<210> SEQ ID NO 24
<211> LENGTH: 11
<212> TYPE: PRT
<213> ORGANISM: Homo sapiens

<400> SEQUENCE: 24

His Gly Pro Glu Ile Leu Asp Val Pro Ser Thr
1               5                   10

<210> SEQ ID NO 25
<211> LENGTH: 5
<212> TYPE: PRT
<213> ORGANISM: Homo sapiens

<400> SEQUENCE: 25

Glu Ile Leu Asp Val
1               5

<210> SEQ ID NO 26
<211> LENGTH: 4
<212> TYPE: PRT
<213> ORGANISM: Homo sapiens

<400> SEQUENCE: 26

Leu Asp Val Pro
1

<210> SEQ ID NO 27
<211> LENGTH: 3
<212> TYPE: PRT
<213> ORGANISM: Homo sapiens
```

```
<400> SEQUENCE: 27

Leu Asp Val
1

<210> SEQ ID NO 28
<211> LENGTH: 4
<212> TYPE: PRT
<213> ORGANISM: Homo sapiens

<400> SEQUENCE: 28

Ile Asp Ala Pro
1

<210> SEQ ID NO 29
<211> LENGTH: 3
<212> TYPE: PRT
<213> ORGANISM: Homo sapiens

<400> SEQUENCE: 29

Arg Asp Val
1

<210> SEQ ID NO 30
<211> LENGTH: 8
<212> TYPE: PRT
<213> ORGANISM: Homo sapiens

<400> SEQUENCE: 30

Gly Pro Glu Tyr Leu Asp Val Pro
1               5

<210> SEQ ID NO 31
<211> LENGTH: 5
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 31

Xaa Cys Xaa Pro Cys
1               5

<210> SEQ ID NO 32
<211> LENGTH: 5
<212> TYPE: PRT
<213> ORGANISM: Homo sapiens

<400> SEQUENCE: 32

Arg Cys Asp Pro Cys
1               5

<210> SEQ ID NO 33
<211> LENGTH: 6
<212> TYPE: PRT
<213> ORGANISM: Homo sapiens

<400> SEQUENCE: 33

Cys Trp Leu Asp Val Cys
1               5
```

```
<210> SEQ ID NO 34
<211> LENGTH: 5
<212> TYPE: PRT
<213> ORGANISM: Homo sapiens

<400> SEQUENCE: 34

Tyr Cys Ala Pro Cys
1               5

<210> SEQ ID NO 35
<211> LENGTH: 5
<212> TYPE: PRT
<213> ORGANISM: Homo sapiens

<400> SEQUENCE: 35

Tyr Cys Asp Pro Cys
1               5

<210> SEQ ID NO 36
<211> LENGTH: 4
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: D-Phe

<400> SEQUENCE: 36

Cys Asp Phe Cys
1

<210> SEQ ID NO 37
<211> LENGTH: 5
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: ThioP

<400> SEQUENCE: 37

Arg Cys Asp Pro Cys
1               5

<210> SEQ ID NO 38
<211> LENGTH: 5
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: ThioP

<400> SEQUENCE: 38

Arg Cys Asp Pro Cys
1               5

<210> SEQ ID NO 39
<211> LENGTH: 11
<212> TYPE: PRT
<213> ORGANISM: Homo sapiens

<400> SEQUENCE: 39

Glu Gly Tyr Tyr Gly Asn Tyr Gly Val Tyr Ala
1               5                   10
```

```
<210> SEQ ID NO 40
<211> LENGTH: 5
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid

<400> SEQUENCE: 40

Xaa Cys Asp Pro Cys
1               5

<210> SEQ ID NO 41
<211> LENGTH: 8
<212> TYPE: PRT
<213> ORGANISM: Homo sapiens

<400> SEQUENCE: 41

Cys Gly Arg Gly Asp Ser Pro Cys
1               5

<210> SEQ ID NO 42
<211> LENGTH: 67
<212> TYPE: PRT
<213> ORGANISM: Homo sapiens

<400> SEQUENCE: 42

Asn Ser Val His Pro Cys Cys Asp Pro Val Thr Cys Glu Pro Arg Glu
1               5                   10                  15

Gly Glu His Cys Ile Ser Gly Pro Cys Cys Arg Asn Cys Lys Phe Leu
            20                  25                  30

Asn Ala Gly Thr Ile Cys Lys Arg Ala Met Leu Asp Gly Leu Asn Asp
        35                  40                  45

Tyr Cys Thr Gly Lys Ser Ser Asp Cys Pro Arg Asn Arg Tyr Lys Gly
    50                  55                  60

Lys Glu Asp
65

<210> SEQ ID NO 43
<211> LENGTH: 4
<212> TYPE: PRT
<213> ORGANISM: Homo sapiens

<400> SEQUENCE: 43

Met Leu Asp Gly
1

<210> SEQ ID NO 44
<211> LENGTH: 9
<212> TYPE: PRT
<213> ORGANISM: Homo sapiens

<400> SEQUENCE: 44

Arg Thr Gln Ile Asp Ser Pro Leu Asn
1               5

<210> SEQ ID NO 45
<211> LENGTH: 6
<212> TYPE: PRT
<213> ORGANISM: Homo sapiens

<400> SEQUENCE: 45

Thr Gln Ile Asp Ser Pro
```

```
1               5

<210> SEQ ID NO 46
<211> LENGTH: 4
<212> TYPE: PRT
<213> ORGANISM: Homo sapiens

<400> SEQUENCE: 46

Gln Ile Asp Ser
1

<210> SEQ ID NO 47
<211> LENGTH: 4
<212> TYPE: PRT
<213> ORGANISM: Homo sapiens

<400> SEQUENCE: 47

Ile Asp Ser Pro
1

<210> SEQ ID NO 48
<211> LENGTH: 4
<212> TYPE: PRT
<213> ORGANISM: Homo sapiens

<400> SEQUENCE: 48

Lys Leu Glu Lys
1

<210> SEQ ID NO 49
<211> LENGTH: 8
<212> TYPE: PRT
<213> ORGANISM: Homo sapiens

<400> SEQUENCE: 49

Gly Pro Glu Tyr Leu Asp Val Pro
1               5

<210> SEQ ID NO 50
<211> LENGTH: 4
<212> TYPE: PRT
<213> ORGANISM: Homo sapiens

<400> SEQUENCE: 50

Leu Asp Val Pro
1

<210> SEQ ID NO 51
<211> LENGTH: 4
<212> TYPE: PRT
<213> ORGANISM: Homo sapiens

<400> SEQUENCE: 51

Ile Leu Asp Val
1

<210> SEQ ID NO 52

<400> SEQUENCE: 52

000

<210> SEQ ID NO 53

<400> SEQUENCE: 53
```

000

<210> SEQ ID NO 54
<211> LENGTH: 52
<212> TYPE: PRT
<213> ORGANISM: Homo sapiens

<400> SEQUENCE: 54

Tyr Asn Val Asp Thr Glu Ser Ala Leu Leu Tyr Gln Gly Pro His Asn
1               5                   10                  15

Thr Ile Phe Gly Tyr Ser Val Val Leu His Ser His Gly Ala Asn Arg
            20                  25                  30

Trp Leu Leu Val Gly Ala Pro Thr Ala Asn Trp Leu Ala Asn Ala Ser
        35                  40                  45

Val Ile Asn Pro
    50

<210> SEQ ID NO 55
<211> LENGTH: 60
<212> TYPE: PRT
<213> ORGANISM: Homo sapiens

<400> SEQUENCE: 55

Gly Arg Pro Tyr Asn Val Asp Thr Glu Ser Ala Leu Leu Tyr Gln Gly
1               5                   10                  15

Pro His Asn Thr Leu Phe Gly Tyr Ser Val Val Leu His Ser His Gly
            20                  25                  30

Ala Asn Arg Trp Leu Leu Val Gly Ala Pro Thr Ala Asn Trp Leu Ala
        35                  40                  45

Asn Ala Ser Val Ile Asn Pro Gly Ala Ile Tyr Arg
    50                  55                  60

<210> SEQ ID NO 56
<211> LENGTH: 74
<212> TYPE: PRT
<213> ORGANISM: Homo sapiens

<400> SEQUENCE: 56

Gly Val Pro Thr Gly Arg Pro Tyr Asn Val Asp Thr Glu Ser Ala Leu
1               5                   10                  15

Leu Tyr Gln Gly Pro His Asn Thr Leu Phe Gly Tyr Ser Val Val Leu
            20                  25                  30

His Ser His Gly Ala Asn Arg Trp Leu Leu Val Gly Ala Pro Thr Ala
        35                  40                  45

Asn Trp Leu Ala Asn Ala Ser Val Ile Asn Pro Gly Ala Ile Tyr Arg
    50                  55                  60

Cys Arg Ile Gly Lys Asn Pro Gly Gln Thr
65                  70

<210> SEQ ID NO 57
<211> LENGTH: 27
<212> TYPE: PRT
<213> ORGANISM: Homo sapiens

<400> SEQUENCE: 57

Ile Val Thr Cys Gly His Arg Trp Lys Asn Ile Phe Tyr Ile Lys Asn
1               5                   10                  15

Glu Asn Lys Leu Pro Thr Gly Gly Cys Tyr Gly
            20                  25

<210> SEQ ID NO 58
<211> LENGTH: 34
<212> TYPE: PRT
<213> ORGANISM: Homo sapiens

<400> SEQUENCE: 58

Gly His Arg Trp Lys Asn Ile Phe Tyr Ile Lys Asn Glu Asn Lys Leu
1               5                   10                  15

Pro Thr Gly Gly Cys Tyr Gly Val Pro Pro Asp Leu Arg Thr Glu Leu
            20                  25                  30

Ser Lys

<210> SEQ ID NO 59
<211> LENGTH: 17
<212> TYPE: PRT
<213> ORGANISM: Homo sapiens

<400> SEQUENCE: 59

Ala Pro Cys Tyr Gln Asp Tyr Val Lys Lys Phe Gly Glu Asn Phe Ala
1               5                   10                  15

Ser

<210> SEQ ID NO 60
<211> LENGTH: 28
<212> TYPE: PRT
<213> ORGANISM: Homo sapiens

<400> SEQUENCE: 60

Cys Tyr Gln Asp Tyr Val Lys Lys Phe Gly Glu Asn Phe Ala Ser Cys
1               5                   10                  15

Gln Ala Gly Ile Ser Ser Phe Tyr Thr Lys Asp Leu
            20                  25

<210> SEQ ID NO 61
<211> LENGTH: 14
<212> TYPE: PRT
<213> ORGANISM: Homo sapiens

<400> SEQUENCE: 61

Gly Ser Ser Tyr Trp Thr Gly Ser Leu Phe Val Tyr Asn Ile
1               5                   10

<210> SEQ ID NO 62
<211> LENGTH: 20
<212> TYPE: PRT
<213> ORGANISM: Homo sapiens

<400> SEQUENCE: 62

Arg Ser Gln His Thr Thr Glu Val Val Gly Gly Ala Pro Gln His Glu
1               5                   10                  15

Gln Ile Gly Lys
            20

<210> SEQ ID NO 63
<211> LENGTH: 22
<212> TYPE: PRT
<213> ORGANISM: Homo sapiens

<400> SEQUENCE: 63

Gly Gly Ala Pro Gln His Glu Gln Ile Gly Lys Ala Tyr Ile Phe Ser
1               5                   10                  15

```
Ile Asp Glu Lys Glu Leu
            20

<210> SEQ ID NO 64
<211> LENGTH: 12
<212> TYPE: PRT
<213> ORGANISM: Homo sapiens

<400> SEQUENCE: 64

Gly Gly Ala Pro Gln His Glu Gln Ile Gly Lys Ala
1               5                   10

<210> SEQ ID NO 65
<211> LENGTH: 12
<212> TYPE: PRT
<213> ORGANISM: Homo sapiens

<400> SEQUENCE: 65

Trp Arg Thr Gln Ile Asp Ser Pro Leu Asn Gly Lys
1               5                   10

<210> SEQ ID NO 66
<211> LENGTH: 14
<212> TYPE: PRT
<213> ORGANISM: Homo sapiens

<400> SEQUENCE: 66

Ser Trp Arg Thr Gln Ile Asp Ser Pro Leu Asn Gly Lys Val
1               5                   10

<210> SEQ ID NO 67
<211> LENGTH: 15
<212> TYPE: PRT
<213> ORGANISM: Homo sapiens

<400> SEQUENCE: 67

Ser Trp Arg Thr Gln Ile Asp Ser Pro Leu Asn Gly Lys Val Thr
1               5                   10                  15

<210> SEQ ID NO 68
<211> LENGTH: 20
<212> TYPE: PRT
<213> ORGANISM: Homo sapiens

<400> SEQUENCE: 68

Pro Phe Phe Ser Trp Arg Thr Gln Ile Asp Ser Pro Leu Asn Gly Lys
1               5                   10                  15

Val Thr Asn Glu
            20

<210> SEQ ID NO 69
<211> LENGTH: 8
<212> TYPE: PRT
<213> ORGANISM: Homo sapiens

<400> SEQUENCE: 69

Ser Arg Lys Leu Glu Lys Gly Ile
1               5

<210> SEQ ID NO 70
<211> LENGTH: 12
<212> TYPE: PRT
<213> ORGANISM: Homo sapiens
```

```
<400> SEQUENCE: 70

Cys Glu Ser Arg Lys Leu Glu Lys Gly Ile Gln Val
1               5                   10

<210> SEQ ID NO 71
<211> LENGTH: 16
<212> TYPE: PRT
<213> ORGANISM: Homo sapiens

<400> SEQUENCE: 71

Ala Thr Cys Glu Ser Arg Lys Leu Glu Lys Gly Ile Gln Val Glu Ile
1               5                   10                  15

<210> SEQ ID NO 72
<211> LENGTH: 27
<212> TYPE: PRT
<213> ORGANISM: Homo sapiens

<400> SEQUENCE: 72

Leu Cys Thr Ala Thr Cys Glu Ser Arg Lys Leu Glu Lys Gly Ile Gln
1               5                   10                  15

Val Glu Ile Tyr Ser Phe Pro Lys Asp Pro Glu
            20                  25

<210> SEQ ID NO 73
<211> LENGTH: 13
<212> TYPE: PRT
<213> ORGANISM: Homo sapiens

<400> SEQUENCE: 73

Gly His Lys Lys Leu Glu Lys Gly Ile Gln Val Glu Leu
1               5                   10

<210> SEQ ID NO 74
<211> LENGTH: 12
<212> TYPE: PRT
<213> ORGANISM: Homo sapiens

<400> SEQUENCE: 74

Val Thr Cys Gly His Lys Lys Leu Glu Lys Gly Ile
1               5                   10

<210> SEQ ID NO 75
<211> LENGTH: 23
<212> TYPE: PRT
<213> ORGANISM: Homo sapiens

<400> SEQUENCE: 75

Thr Cys Gly His Lys Lys Leu Glu Lys Gly Ile Gln Val Glu Leu Tyr
1               5                   10                  15

Ser Phe Pro Arg Asp Pro Glu
            20

<210> SEQ ID NO 76
<211> LENGTH: 24
<212> TYPE: PRT
<213> ORGANISM: Homo sapiens

<400> SEQUENCE: 76

Pro Val Ser Phe Glu Asn Glu His Ser Tyr Leu Cys Thr Val Thr Cys
1               5                   10                  15

Gly His Lys Lys Leu Glu Lys Gly
            20
```

```
<210> SEQ ID NO 77
<211> LENGTH: 11
<212> TYPE: PRT
<213> ORGANISM: Homo sapiens

<400> SEQUENCE: 77

Arg Thr Gln Ile Asp Ser Pro Leu Ser Gly Lys
1               5                   10

<210> SEQ ID NO 78
<211> LENGTH: 16
<212> TYPE: PRT
<213> ORGANISM: Homo sapiens

<400> SEQUENCE: 78

Phe Ser Trp Arg Thr Gln Ile Asp Ser Pro Leu Ser Gly Lys Val Arg
1               5                   10                  15

<210> SEQ ID NO 79
<211> LENGTH: 18
<212> TYPE: PRT
<213> ORGANISM: Homo sapiens

<400> SEQUENCE: 79

Glu Ser Pro Ser Phe Trp Trp Arg Thr Gln Ile Asp Ser Pro Leu Ser
1               5                   10                  15

Gly Lys

<210> SEQ ID NO 80
<211> LENGTH: 13
<212> TYPE: PRT
<213> ORGANISM: Homo sapiens

<400> SEQUENCE: 80

Thr Ala Ile Asp Ala Pro Ser Asn Leu Arg Asp Ala Ser
1               5                   10

<210> SEQ ID NO 81
<211> LENGTH: 16
<212> TYPE: PRT
<213> ORGANISM: Homo sapiens

<400> SEQUENCE: 81

Thr Ala Ile Asp Ala Pro Ser Asn Leu Arg Phe Leu Ala Thr Thr Pro
1               5                   10                  15

<210> SEQ ID NO 82
<211> LENGTH: 17
<212> TYPE: PRT
<213> ORGANISM: Homo sapiens

<400> SEQUENCE: 82

Arg Ser Ser Pro Val Val Ile Asp Ala Ser Thr Ala Ile Asp Ala Pro
1               5                   10                  15

Ser

<210> SEQ ID NO 83
<211> LENGTH: 19
<212> TYPE: PRT
<213> ORGANISM: Homo sapiens
```

<400> SEQUENCE: 83

Ile Asp Ala Pro Ser Asn Leu Arg Phe Leu Ala Thr Thr Pro Asn Ser
1               5                   10                  15

Leu Leu Val

<210> SEQ ID NO 84
<211> LENGTH: 36
<212> TYPE: PRT
<213> ORGANISM: Homo sapiens

<400> SEQUENCE: 84

Ile Asp Ala Pro Ser Asn Leu Arg Phe Leu Ala Thr Thr Pro Asn Ser
1               5                   10                  15

Leu Leu Val Ser Trp Gln Pro Pro Arg Ala Arg Ile Thr Gly Tyr Ile
            20                  25                  30

Ile Lys Tyr Glu
            35

<210> SEQ ID NO 85
<211> LENGTH: 7
<212> TYPE: PRT
<213> ORGANISM: Homo sapiens

<400> SEQUENCE: 85

Ile Asp Asp Val Pro Ser Thr
1               5

<210> SEQ ID NO 86
<211> LENGTH: 16
<212> TYPE: PRT
<213> ORGANISM: Homo sapiens

<400> SEQUENCE: 86

Asn Leu His Gly Pro Glu Ile Leu Asp Val Pro Ser Thr Val Gln Lys
1               5                   10                  15

<210> SEQ ID NO 87
<211> LENGTH: 13
<212> TYPE: PRT
<213> ORGANISM: Homo sapiens

<400> SEQUENCE: 87

Pro His Pro Asn Leu His Gly Pro Glu Ile Leu Asp Val
1               5                   10

<210> SEQ ID NO 88
<211> LENGTH: 20
<212> TYPE: PRT
<213> ORGANISM: Homo sapiens

<400> SEQUENCE: 88

Ile Leu Asp Val Pro Ser Thr Val Gln Lys Thr Pro Phe Val Thr His
1               5                   10                  15

Pro Gly Tyr Asp
            20

<210> SEQ ID NO 89
<211> LENGTH: 17
<212> TYPE: PRT
<213> ORGANISM: Homo sapiens

```
<400> SEQUENCE: 89

Val Thr Leu Pro His Pro Asn Leu His Gly Pro Glu Ile Leu Asp Val
1               5                   10                  15

Pro

<210> SEQ ID NO 90
<211> LENGTH: 5
<212> TYPE: PRT
<213> ORGANISM: Homo sapiens

<400> SEQUENCE: 90

Glu Ile Leu Asp Val
1               5

<210> SEQ ID NO 91
<211> LENGTH: 8
<212> TYPE: PRT
<213> ORGANISM: Homo sapiens

<400> SEQUENCE: 91

Ile Pro Arg Glu Asp Val Asp Tyr
1               5

<210> SEQ ID NO 92
<211> LENGTH: 9
<212> TYPE: PRT
<213> ORGANISM: Homo sapiens

<400> SEQUENCE: 92

Gly His Ile Pro Arg Asp Asp Val Asp
1               5

<210> SEQ ID NO 93
<211> LENGTH: 8
<212> TYPE: PRT
<213> ORGANISM: Homo sapiens

<400> SEQUENCE: 93

Gly His Ile Pro Arg Glu Asp Val
1               5

<210> SEQ ID NO 94
<211> LENGTH: 84
<212> TYPE: PRT
<213> ORGANISM: Homo sapiens

<400> SEQUENCE: 94

Leu Asp Val Pro Ser Thr Val Gln Lys Thr Pro Phe Val Thr His Pro
1               5                   10                  15

Gly Tyr Asp Thr Gly Asn Gly Ile Gln Leu Pro Gly Thr Ser Gly Gln
                20                  25                  30

Gln Pro Ser Val Gly Gln Gln Met Ile Phe Glu His Gly Phe Arg
            35                  40                  45

Arg Thr Thr Pro Pro Thr Thr Ala Thr Pro Ile Arg His Arg Pro Arg
        50                  55                  60

Pro Tyr Pro Pro Asn Val Gly Glu Glu Ile Gln Ile Gly His Ile Pro
65                  70                  75                  80

Arg Glu Asp Val
```

```
<210> SEQ ID NO 95
<211> LENGTH: 90
<212> TYPE: PRT
<213> ORGANISM: Homo sapiens

<400> SEQUENCE: 95

Pro Glu Ile Leu Asp Val Pro Ser Thr Val Gln Lys Thr Pro Phe Val
1               5                   10                  15

Thr His Pro Gly Tyr Asp Thr Gly Asn Gly Ile Gln Leu Pro Gly Thr
            20                  25                  30

Ser Gly Gln Gln Pro Ser Val Gly Gln Gln Met Ile Phe Glu Glu His
        35                  40                  45

Gly Phe Arg Arg Thr Thr Pro Pro Thr Thr Ala Thr Pro Ile Arg
    50                  55                  60

His Arg Pro Arg Pro Tyr Pro Pro Asn Val Gly Glu Glu Ile Gln Ile
65                  70                  75                  80

Gly His Ile Pro Arg Glu Asp Val Asp Tyr
                85                  90

<210> SEQ ID NO 96
<211> LENGTH: 647
<212> TYPE: PRT
<213> ORGANISM: Homo sapiens

<400> SEQUENCE: 96

Met Pro Gly Lys Met Val Val Ile Leu Gly Ala Ser Asn Ile Leu Trp
1               5                   10                  15

Ile Met Phe Ala Ala Ser Gln Ala Phe Lys Ile Glu Thr Thr Pro Glu
            20                  25                  30

Ser Arg Tyr Leu Ala Gln Ile Gly Asp Ser Val Ser Leu Thr Cys Ser
        35                  40                  45

Thr Thr Gly Cys Glu Ser Pro Phe Phe Ser Trp Arg Thr Gln Ile Asp
    50                  55                  60

Ser Pro Leu Asn Gly Lys Val Thr Asn Glu Gly Thr Thr Ser Thr Leu
65                  70                  75                  80

Thr Met Asn Pro Val Ser Phe Gly Asn Glu His Ser Tyr Leu Cys Thr
                85                  90                  95

Ala Thr Cys Glu Ser Arg Lys Leu Glu Lys Gly Ile Gln Val Glu Ile
            100                 105                 110

Tyr Ser Phe Pro Lys Asp Pro Glu Ile His Leu Ser Gly Pro Leu Glu
        115                 120                 125

Ala Gly Lys Pro Ile Thr Val Lys Cys Ser Val Ala Asp Val Tyr Pro
    130                 135                 140

Phe Asp Arg Leu Glu Ile Asp Leu Leu Lys Gly Asp His Leu Met Lys
145                 150                 155                 160

Ser Gln Glu Phe Leu Glu Asp Ala Asp Arg Lys Ser Leu Glu Thr Lys
                165                 170                 175

Ser Leu Glu Val Thr Phe Thr Pro Val Ile Glu Asp Ile Gly Lys Val
            180                 185                 190

Leu Val Cys Arg Ala Lys Leu His Ile Asp Glu Met Asp Ser Val Pro
        195                 200                 205

Thr Val Arg Gln Ala Val Lys Glu Leu Gln Val Tyr Ile Ser Pro Lys
    210                 215                 220

Asn Thr Val Ile Ser Val Asn Pro Ser Thr Lys Leu Gln Glu Gly Gly
225                 230                 235                 240
```

```
Ser Val Thr Met Thr Cys Ser Ser Glu Gly Leu Pro Ala Pro Glu Ile
            245                 250                 255
Phe Trp Ser Lys Lys Leu Asp Asn Gly Asn Leu Gln His Leu Ser Gly
        260                 265                 270
Asn Ala Thr Leu Thr Leu Ile Ala Met Arg Met Glu Asp Ser Gly Ile
        275                 280                 285
Tyr Val Cys Glu Gly Val Asn Leu Ile Gly Lys Asn Arg Lys Glu Val
        290                 295                 300
Glu Leu Ile Val Gln Ala Phe Pro Arg Asp Pro Glu Ile Glu Met Ser
305                 310                 315                 320
Gly Gly Leu Val Asn Gly Ser Ser Val Thr Val Ser Cys Lys Val Pro
            325                 330                 335
Ser Val Tyr Pro Leu Asp Arg Leu Glu Ile Glu Leu Leu Lys Gly Glu
            340                 345                 350
Thr Ile Leu Glu Asn Ile Glu Phe Leu Glu Asp Thr Asp Met Lys Ser
            355                 360                 365
Leu Glu Asn Lys Ser Leu Glu Met Thr Phe Ile Pro Thr Ile Glu Asp
        370                 375                 380
Thr Gly Lys Ala Leu Val Cys Gln Ala Lys Leu His Ile Asp Asp Met
385                 390                 395                 400
Glu Phe Glu Pro Lys Gln Arg Gln Ser Thr Gln Thr Leu Tyr Val Asn
                405                 410                 415
Val Ala Pro Arg Asp Thr Thr Val Leu Val Ser Pro Ser Ser Ile Leu
            420                 425                 430
Glu Glu Gly Ser Ser Val Asn Met Thr Cys Leu Ser Gln Gly Phe Pro
            435                 440                 445
Ala Pro Lys Ile Leu Trp Ser Arg Gln Leu Pro Asn Gly Glu Leu Gln
        450                 455                 460
Pro Leu Ser Glu Asn Ala Thr Leu Thr Leu Ile Ser Thr Lys Met Glu
465                 470                 475                 480
Asp Ser Gly Val Tyr Leu Cys Glu Gly Ile Asn Gln Ala Gly Arg Ser
                485                 490                 495
Arg Lys Glu Val Glu Leu Ile Ile Gln Val Thr Pro Lys Asp Ile Lys
            500                 505                 510
Leu Thr Ala Phe Pro Ser Glu Ser Val Lys Glu Gly Asp Thr Val Ile
        515                 520                 525
Ile Ser Cys Thr Cys Gly Asn Val Pro Glu Thr Trp Ile Ile Leu Lys
        530                 535                 540
Lys Lys Ala Glu Thr Gly Asp Thr Val Leu Lys Ser Ile Asp Gly Ala
545                 550                 555                 560
Tyr Thr Ile Arg Lys Ala Gln Leu Lys Asp Ala Gly Val Tyr Glu Cys
                565                 570                 575
Glu Ser Lys Asn Lys Val Gly Ser Gln Leu Arg Ser Leu Thr Leu Asp
            580                 585                 590
Val Gln Gly Arg Glu Asn Asn Lys Asp Tyr Phe Ser Pro Glu Leu Leu
        595                 600                 605
Val Leu Tyr Phe Ala Ser Ser Leu Ile Ile Pro Ala Ile Gly Met Ile
        610                 615                 620
Ile Tyr Phe Ala Arg Lys Ala Asn Met Lys Gly Ser Tyr Ser Leu Val
625                 630                 635                 640
Glu Ala Gln Lys Ser Lys Val
            645
```

```
<210> SEQ ID NO 97
<211> LENGTH: 6
<212> TYPE: PRT
<213> ORGANISM: Homo sapiens

<400> SEQUENCE: 97

Cys Tyr Tyr Gly Asn Cys
1               5
```

METHOD FOR ALTERING HEMATOPOIETIC PROGENITOR CELL ADHESION, DIFFERENTIATION, AND MIGRATION

This application claims priority to U.S. Provisional Application Ser. No. 60/507,202, filed Sep. 29, 2003, the contents of which are incorporated herein in their entirety.

This invention was made, in part, with government support under grant numbers CA71619, and CA 83133 awarded by the National Cancer Institute of the National Institutes of Health. The U.S. government has certain rights in the invention.

FIELD OF THE INVENTION

The invention relates to methods for altering hematopoietic progenitor cell (such as hematopoietic stem cell and endothelial progenitor cell) adhesion and/or migration to a target tissue, and for altering hematopoietic progenitor cell differentiation into a second cell. The invention also relates to methods for screening test compounds for altering the level of hematopoietic progenitor cell adhesion and/or migration to a target tissue, and for altering hematopoietic progenitor cell differentiation into a second cell. The invention further relates to methods for isolating hematopoietic progenitor cells.

BACKGROUND OF THE INVENTION

Hematopoietic progenitor cells (such as bone marrow derived, CD34+ stem cells) promote the repair of diseased and damaged tissues and offer promise for the treatment of hereditary and acquired human diseases (Asahara et al. (1997) Science 275, 964-967; Rafii et al. (2003) Nat. Med. 9, 702-12; Takahashi et al. (1999) Nat. Med. 5, 434-438; Kawamoto et al. (2001) Circulation 103, 634-637; Hattori et al. (2001) J. Exp. Med. 193, 1005-1014; Otani et al. (2002) Nat. Med. 8, 1004-1010 (2002); Priller (2001) et al. J. Cell Biol. 155, 733-738; LaBarge et al. (2002) Cell. 111, 589-601; and Torrente et al. (2003) J. Cell Biol. 162, 511-520). For example, bone marrow derived, CD34+ stem cells promote neovascularization by differentiating into endothelial cells (Asahara et al. (1997) supra; Rafii et al. (2003) Nat. Med. 9, 702-12; Takahashi et al. (1999) Nat. Med. 5, 434-438; Kawamoto et al. (2001) Circulation 103, 634-637; Hattori et al. (2001) J. Exp. Med. 193, 1005-1014; Otani et al. (2002) Nat. Med. 8, 1004-1010 (2002); Priller (2001) et al. J. Cell Biol. 155, 733-738; LaBarge et al. (2002) Cell. 111, 589-601; Torrente et al. (2003) J. Cell Biol. 162, 511-520); Lyden et al. (2001) Nat. Med. 7, 1194-201; Ruzinova et al. (2003) Cancer Cell. 4: 277-289; Jain et al. (2003) Cancer Cell 3, 515-516; Religa et al. (2002) Transplantation 74, 1310-1315; and Boehm et al. (2004) J. Clin. Invest. 114, 419-426). Although neovascularization stimulates healing of injured tissue (Asahara et al. (1997) supra; Rafii et al. (2003) Nat. Med. 9, 702-12; Takahashi et al. (1999) Nat. Med. 5, 434-438; Kawamoto et al. (2001) Circulation 103, 634-637; Hattori et al. (2001) J. Exp. Med. 193, 1005-1014; Otani et al. (2002) Nat. Med. 8, 1004-1010 (2002); and Carmeliet (2003) Nat. Med. 9, 653-660), it nonetheless also promotes undesirable consequences such as tumor growth and inflammatory disease (Lyden et al. (2001) Nat. Med. 7, 1194-201; Ruzinova et al. (2003) Cancer Cell. 4: 277-289; Jain et al. (2003) Cancer Cell 3, 515-516; Carmeliet (2003) Nat. Med. 9, 653-660; and Hanahan et al. (1996) Cell 86, 353-364).

While the art appreciates some of the advantages of using hematopoietic progenitor cells, it remains unclear how hematopoietic progenitor cell adhesion, differentiation, and migration may be modulated. Thus, there remains a need for methods for altering hematopoietic progenitor cell adhesion and/or migration to a target tissue, and for altering hematopoietic progenitor cell differentiation into a second cell.

SUMMARY OF THE INVENTION

The present invention satisfies the need in the art by providing methods for altering hematopoietic progenitor cell (HPC) adhesion and/or migration to a target tissue, and for altering hematopoietic progenitor cell differentiation into a second cell. The invention also provides methods for screening test compounds for altering the level of hematopoietic progenitor cell adhesion and/or migration to a target tissue, and for altering hematopoietic progenitor cell differentiation into a second cell. The invention further provides methods for isolating hematopoietic progenitor cells.

In particularly preferred embodiments, the invention provides a method for altering the level of hematopoietic progenitor cell adhesion to target tissue, comprising: a) providing: i) a population of cells comprising hematopoietic progenitor cells that express integrin $\alpha4\beta1$, ii) target tissue that is not bone marrow endothelial tissue, and iii) one or more agent that alters specific binding of integrin $\alpha4\beta1$ to an integrin $\alpha4\beta1$ ligand, and b) treating one or more of the population of cells and the target tissue with the agent under conditions for specific binding of the integrin $\alpha4\beta1$ with the integrin $\alpha4\beta1$ ligand, thereby altering the level of adhesion of the hematopoietic progenitor cells to the target tissue. In one embodiment, the treating further comprises altering the level of trans-endothelial migration of the hematopoietic progenitor cells. In another embodiment, the treating further comprises altering the level of differentiation of the hematopoietic progenitor cells into a second cell, such as when compared to adjacent normal tissues and/or to other normal organs (e.g., Examples 22-23, and FIG. 36a-b). In another embodiment, the treating does not comprise altering the level of angiogenesis in the target tissue.

While not intending to limit the type or source of HPCs, in one embodiment, the HPCs may be transgenic or wild type. In another embodiment, the HPCs comprise CD34+ non-endothelial cells and/or CD34+CD133+ cells which can differentiate into endothelium (FIG. 34a). In a further embodiment, the HPCs comprise one or more of hematopoietic stem cell, endothelial progenitor cell, lymph endothelial progenitor cell, mesenchymal precursor cell, myeloid progenitor cell, lymphoid progenitor cell, granulocyte progenitor cell, macrophage progenitor cell, megakaryocyte progenitor cell, erythroid progenitor cell, Pro-B cell and Pro T cell, bone marrow progenitor cell, peripheral blood progenitor cell, umbilical cord progenitor cell, CD34+ progenitor cell comprised in any tissue (such as lung tissue, breast tissue, prostate tissue, cervical tissue, pancreatic tissue, colon tissue, ovarian tissue, stomach tissue, esophageal tissue, mouth tissue, tongue tissue, gum tissue, skin tissue, muscle tissue, heart tissue, liver tissue, bronchial tissue, cartilage tissue, bone tissue, testis tissue, kidney tissue, endometrium tissue, uterus tissue, bladder tissue, bone marrow tissue, lymphoma tissue, spleen tissue, thymus tissue, thyroid tissue, brain tissue, neuron tissue, gall bladder tissue, ocular tissue (e.g., the cornea, uvea, choroids, macula, vitreous humor, etc.), and joint tissue (e.g., synovium tissue, etc.). In one embodiment, the bone marrow progenitor cells comprise one or more of CD31+ cells (Example 24, FIG. 36e-f), cKit+ cells, VEGFR1+ cells, VEGFP2+ cells, and CD34+ cells.

The invention is not intended to be limited to the type or source of target tissue. Nonetheless, in one embodiment, the target tissue comprises one or more of vascular endothelial, muscle, neuronal, tumor, inflammatory, peripheral blood, cord blood, heart, ocular, skin, synovial, tumor, lung, breast, prostate, cervical, pancreatic, colon, ovarian, stomach, esophageal, mouth, tongue, gum, skin, liver, bronchial, cartilage, testis, kidney, endometrium, uterus, bladder, spleen, thymus, thyroid, brain, neuron, gall bladder, ocular, and joint tissues. In a preferred embodiment, the tissue is injured, ischemic and/or malignant (such as metastatic malignant tumor tissue). In another embodiment, the target tissue comprises one or more of fibronectin and vascular tissue. In a preferred embodiment, the vascular tissue comprises one or more cell types such as endothelial cells, pericyte cells, vascular smooth muscle cells, angiogenic tissue, and tissue that is not angiogenic.

The invention is not intended to be limited to the source or type of second cell into which the HPC differentiates. In one embodiment, the second cell type comprises a mesenchymal cell precursor and/or mesenchymal cell, such as, without limitation, one or more of fibroblast cell, myofibroblast cell, stromal cell, pericyte cell, vascular smooth muscle cell, and endothelial cell. In another embodiment, the second cell type comprises an epithelial cell, such as one or more of epidermal cell, secretory cell, hair cell, cornea cell, hepatocyte cell, alveolar cell, pneumocyte cell, skin cell, intestinal cell, and renal cell. In a preferred embodiment, the secretory cell is chosen from one or more of mammary epithelial cell, intestinal cell, and sebaceous epithelial cell, and the hair cells is chosen from one or more of ear hair cell and skin hair cell. In a further embodiment, the second cell type comprises a muscle cell precursor and/or muscle cell such as, without limitation, one or more of skeletal muscle myocyte cell, cardiac myocyte cell, vascular smooth muscle cell, endocardium cell, and myocardium cell. In yet another embodiment, the second cell type comprises a neuronal cell precursor and/or neuronal cell such as, without limitation, one or more of astrocyte cell, Schwann cell, Purkinje cell, dendritic cell, and glial cell. In another embodiment, the second cell type comprises an immune cell precursor and/or immune cell such as one or more of B lymphocyte cell, T lymphocyte cell, monocyte/macrophage cell, granulocyte cell, eosinophil cell, neutrophil cell, natural killer cell, and megakaryocyte cell, wherein the monocyte cell is exemplified, but not limited to, one or more of macrophage cell, osteoclast cell and osteoblast cell. In yet a another embodiment, the second cell type comprises an embryonic cell precursor, an embryonic cell, a melanocyte cell precursor, melanocyte cell, myoepithelial cell precursor and/or a myoepithelial cell such as those found in glandular tissues.

The invention is not limited to the location of treatment of the HPCs and target tissue with the agent. In one embodiment, the treating may be in vitro (Examples 19, 20), ex vivo, and in vivo in a mammalian subject (Example 21). In a preferred embodiment, the mammalian subject is chosen from one or more of a subject that has a disease, is susceptible to having a disease, is suspected of having a disease, and is suspected of being susceptible to having a disease. More preferably, the treating is chosen from one or more of before, during, and after manifestation of one or more symptoms of the disease. In one preferred embodiment, the mammalian subject is human.

In one embodiment, the disease is angiogenic, such as, without limitation, one or more of neoplasm, diabetic retinopathy, macular degeneration associated with neovascularization, psoriasis hemangiomas, gingivitis, rheumatoid arthritis, osteoarthritis, inflammation, and inflammatory bowel diseases. While not intending to limit the target tissue in the subject, in one embodiment, the tissue comprises one or more of ocular tissue, skin tissue, bone tissue, and synovial tissue, wherein the ocular tissue is exemplified by retina, macula, cornea, choroids, and vitreous humor. In another embodiment, the tissue comprises a tumor, such as a malignant tumor, and more preferably a metastatic malignant tumor.

In another embodiment, the disease is not angiogenic. In some embodiments, it may be desirable to reduce adhesion of HPCs to a target tissue in non-angiogenic diseases such as in diseases that are exemplified by, but not limited to, fibrosis (wherein hematopoietic progenitor cells differentiate into fibroblasts or other cells in the exemplary tissues of lung, liver cardiac, skin, and/or cornea cells), atherosclerosis (wherein hematopoietic progenitor cells differentiate into the exemplary macrophages/monocytes, vascular smooth muscle cells, and/or endothelial cells in a blood vessel wall), restenosis (wherein hematopoietic progenitor cells differentiate into vascular smooth muscle cells, immune cells such as monocytes/macrophages, eosinophils, granulocytes and/or to other immune cells in a blood vessel wall), chronic inflammatory diseases such as rheumatoid arthritis (wherein hematopoietic progenitor cells differentiate into endothelial cells, pericytes, and/or synoviocytes, which digest cartilage, monocytes/macrophages which secrete angiogenic and inflammatory factors), asthma (wherein hematopoietic progenitor cells differentiate into eosinophils and their immune cells, endothelial cells, pericytes, and/or fibroblasts), cancer (wherein hematopoietic progenitor cells differentiate into malignant cells and/or stromal cells such as fibroblasts, endothelial cells, smooth muscle cells, and/or monocytes, etc.), whether or not the cancer is metastatic, myocardial infarction (wherein hematopoietic progenitor cells differentiate into inflammatory cells arising from hematopoietic stem cells and/or fibroblasts arising from hematopoietic stem cells), and ischemic disease, such as hemorrhagic stroke (brain), acute respiratory disorder, myocardial infarction, peripheral artery disease (inhibit inflammatory cells that arise from hematopoietic stem cells).

In another embodiment, it may be desirable to increase adhesion of HPCs to a target tissue in non-angiogenic diseases such as in a subject that has undergone bone marrow transplantation and a subject that will undergo bone marrow transplantation, wherein the treating is chosen from one or more of before, during, and after the bone marrow transplantation. In another embodiment, the mammalian subject is chosen from a subject that has undergone hematopoietic progenitor cell transplantation and a subject that will undergo hematopoietic progenitor cell transplantation, wherein the treating is chosen from one or more of before, during, and after the hematopoietic progenitor cell transplantation. In yet a further embodiment, the mammalian subject has and/or is susceptible to developing a wound to a tissue (wound healing of all types including, but not limited to, burns, skin wounds, surgical wounds to any tissue and organ including cosmetic surgery and internal surgery, scar replacement, myocardial infarction (the invention is useful to repair tissues by stimulating blood vessel growth, epithelial tissue repair by regrowth, and cardiac myocytes development), severed nerves (e.g., involving neuronal cells and endothelial cells of any type), injured brain (e.g., involving neuronal cells and endothelial cells), injured muscle (e.g., involving myocytes and endothelial cells), congenitally damaged muscle as in muscular dystrophy—Duchenne and other diseases involving skeletal myocytes, peripheral artery ischemia disease (PAD) (the invention is useful for stimulating homing by, adhesion by, and differentiation of hematopoietic progenitor cells to muscle cells, neuronal cells, endothelial cells, pericytes, and/ or vascular smooth muscle), stroke (the invention is useful for stimulating homing by, adhesion by, and differentiation of hematopoietic progenitor cells to neuronal cells and/or vascular cells), Parkinson's disease (the invention is useful for stimulating homing by, adhesion by, and differentiation of hematopoietic progenitor cells into cells that produce serotonin). In another embodiment, the mammalian subject has diabetes and/or is susceptible to developing diabetes (the invention is useful for stimulating homing by, adhesion by, and differentiation of hematopoietic progenitor cells into pancreatic islet cells, which are the source of insulin). In a further embodiment, the mammalian subject has and/or is susceptible to developing AIDS (the invention is useful for stimulating homing by, adhesion by, and differentiation of hematopoietic progenitor cells to T-cells to stimulate T-cell repopulation of tissues). In another embodiment, the mammalian subject has and/or is susceptible to developing cancer (the invention is useful for stimulating homing by, adhesion by, and differentiation of hematopoietic progenitor cells to cancer fighting immune cells such as T cells and natural killer cells.

The invention is not intended to be limited to a particular type or source of agent that alters HPC adhesion and/or migration to a target tissue, and that alters HPC differentiation into a second cell type. In one embodiment, the agent comprises a peptide, such as an antibody as exemplified by, but not limited to, an antibody that comprises an anti-integrin $\alpha4\beta1$ antibody (e.g., Examples 19-21, FIGS. 34*b*, *d-e*, and 35*b-d*). In one embodiment, the specificity of binding of the anti-integrin $\alpha4\beta1$ antibody may be compared to a control antibody such as anti-$\beta2$ integrin antibody (Example 24), cIgG antibody (Example 24), anti-$\alpha v\beta5$ (P1F6), and anti-$\alpha5\beta1$ (P1F6) (FIGS. 17-20 and 34) and anti-$\alpha v\beta3$ (LM609) (FIG. 20). In another embodiment, the comprises one or more of an anti-vascular cell adhesion molecule antibody, and an anti-fibronectin antibody. In another embodiment, the agent comprises an antisense sequence, such as, without limitation, an antisense sequence that comprises one or more of an integrin $\alpha4\beta1$ antisense sequence, a vascular cell adhesion molecule antisense sequence, and a fibronectin antisense sequence. In yet another embodiment, the agent comprises a ribozyme such as, without limitation, a ribozyme that comprises an integrin $\alpha4\beta1$ ribozyme, a vascular cell adhesion molecule ribozyme, and a fibronectin ribozyme. While the invention is not limited to the mechanism of action of the agent, in one embodiment, the agent may function by one or more of a) inducing expression of $\alpha4\beta1$ on HPCs; b) activating $\alpha4\beta1$ on HPCS such as by increasing the level of specific binding of integrin $\alpha4\beta1$ to one or more of its ligands, and c) inducing expression of one or more $\alpha4\beta1$ ligand by the one or more cell type.

It is also not intended that the invention be limited to any particular type or source of integrin $\alpha4\beta1$ ligand. In one preferred embodiment, the ligand comprises one or more of vascular cell adhesion molecule (VCAM) and fibronectin.

The invention additionally provides a method for altering the level of hematopoietic progenitor cell trans-endothelial migration to target tissue, comprising: a) providing: i) a population of cells comprising hematopoietic progenitor cells that express integrin $\alpha4\beta1$, ii) target tissue that is not bone marrow endcothelial tissue, and iii) one or more agent that alters specific binding of integrin $\alpha4\beta1$ to an integrin $\alpha4\beta1$ ligand, and b) treating one or more of the population of cells and the target tissue with the agent under conditions for specific binding of the integrin $\alpha4\beta1$ with the integrin $\alpha4\beta1$ ligand, thereby altering the level of trans-endothelial migration of the hematopoietic progenitor cells to the target tissue. In one embodiment, the treating does not comprise altering the level of angiogenesis in the tissue to which the hematopoietic progenitor cells migrate.

Additionally provided herein is a method for altering the level of hematopoietic progenitor cell differentiation into a second cell type that is not a bone marrow endothelial cell, comprising: a) providing: i) a population of cells comprising hematopoietic progenitor cells that express integrin $\alpha4\beta1$, and ii) one or more agent that alters specific binding of integrin $\alpha4\beta1$ to an integrin $\alpha4\beta1$ ligand, and b) treating the population of cells with the agent under conditions for specific binding of the integrin $\alpha4\beta1$ with the integrin $\alpha4\beta1$ ligand, thereby altering the level of differentiation of the hematopoietic progenitor cell into the second cell type. In one embodiment, the treating does not comprise altering the level of angiogenesis in the tissue in which the hematopoietic progenitor cells differentiate.

The invention also provides a method for screening a test compound for altering the level of hematopoietic progenitor cell adhesion to target tissue that is not bone marrow endothelial tissue, comprising: a) providing: i) a first composition comprising integrin $\alpha4\beta1$, ii) a second composition comprising one or more integrin $\alpha4\beta1$ ligand, and iii) a test compound, b) contacting the test compound with one or more of the first composition and the second composition under conditions for specific binding of the integrin $\alpha4\beta1$ with the integrin $\alpha4\beta1$ ligand, and c) detecting an altered level of specific binding of the integrin $\alpha4\beta1$ with the integrin $\alpha4\beta1$ ligand in the presence of the test compound compared to in the absence of the test compound, thereby identifying the test compound as alerting the level of hematopoietic progenitor cell adhesion to the target tissue. In one embodiment, the method further comprises identifying the test compound as altering the level of one or more of migration of the hematopoietic progenitor cells, and of differentiation of the hematopoietic progenitor cells into a second cell type. Changes in the levels of migration and differentiation may be compared to control adjacent normal tissues or to other normal organs (e.g., Example 22 such as inhibition of HPC differentiation as exemplified in Example 23, FIG. 36*a-b*). The contacting is not limited to any particular location, but may be in vitro (Examples 19, 20), ex vivo, and in vivo in a non-human mammal (Example 21).

The invention additionally provides a method for screening a test compound for altering the level of hematopoietic progenitor cell trans-endothelial migration to a tissue that is not bone marrow endothelial tissue, comprising: a) providing: i) a first composition comprising integrin $\alpha4\beta1$, ii) a second composition comprising one or more integrin $\alpha4\beta1$ ligand, and iii) a test compound, b) contacting the test compound with one or more of the first composition and the second composition under conditions for specific binding of the integrin $\alpha4\beta1$ with the integrin $\alpha4\beta1$ ligand, and c) detecting an altered level of specific binding of the integrin $\alpha4\beta1$ with the integrin $\alpha4\beta1$ ligand in the presence of the test compound compared to in the absence of the test compound, thereby identifying the test compound as alerting the level of hematopoietic progenitor cell trans-endothelial migration to the tissue.

Also provided by the invention is a method for screening a test compound for altering the level of hematopoietic progenitor cell differentiation into a second cell type that is not a bone marrow endothelial cell, comprising: a) providing: i) a first composition comprising integrin $\alpha4\beta1$, ii) a second composition comprising one or more integrin $\alpha4\beta1$ ligand, and iii) a test compound, b) contacting the test compound with one or more of the first composition and the second composition under conditions for specific binding of the integrin α4β1 with the integrin α4β1 ligand, and c) detecting an altered level of specific binding of the integrin α4β1 with the integrin α4β1 ligand in the presence of the test compound compared to in the absence of the test compound, thereby identifying the test compound as alerting the level of hematopoietic progenitor cell differentiation into the second cell type.

The invention additionally provides a method for isolating hematopoietic progenitor cells from a tissue, comprising: a) providing: i) a tissue comprising hematopoietic progenitor cells, ii) an antibody that specifically binds to integrin α4β1 polypeptide, b) treating the tissue with the agent under conditions such that the antibody binds to the hematopoietic progenitor cells, and c) isolating the hematopoietic progenitor cells that bind to the antibody.

BRIEF DESCRIPTION OF THE DRAWINGS

FIG. 1 shows the polypeptide sequence (SEQ ID NO:1) of the human α4 subunit, GenBank Accession No. XP_039012.1.

FIG. 2 shows the polypeptide sequence (SEQ ID NO:2) of the human β1 subunit, GenBank Accession No. P05556.

FIG. 3 shows the polypeptide sequence of the human vascular cell adhesion molecule (VCAM), GenBank Accession Nos. P19320 (SEQ ID NO:3) (A) and XP_035774 (SEQ ID NO:96) (B).

FIG. 4 shows the polypeptide sequence (SEQ ID NO:4) of human fibronectin, GenBank Accession No. P02751.

FIG. 8 shows the cDNA sequence (SEQ ID NO:5) of the human integrin α4 subunit cDNA, GenBank Accession No. XM_039012.

FIG. 9 shows the cDNA sequence (SEQ ID NO:6) of the human integrin α4 subunit, GenBank Accession No. XM_039012.

FIG. 10 shows the cDNA sequence (SEQ ID NO:7) of the human integrin β1 subunit, GenBank Accession No. X07979.

FIG. 11 shows the human VCAM cDNA sequence (SEQ ID NO:8), GenBank Accession No. X53051.

FIG. 12 shows the sequence of human fibronectin cDNA (SEQ ID NO:9), GenBank Accession No. X02761.

and for CD31 (red) expression at 200×. Vessels positive for both are yellow (arrows). (F) Mean+/−S.E.M. LacZ+ CD31+ vessels (n=8). Statistical significance was determined using Student's t-test.

Figure 19:
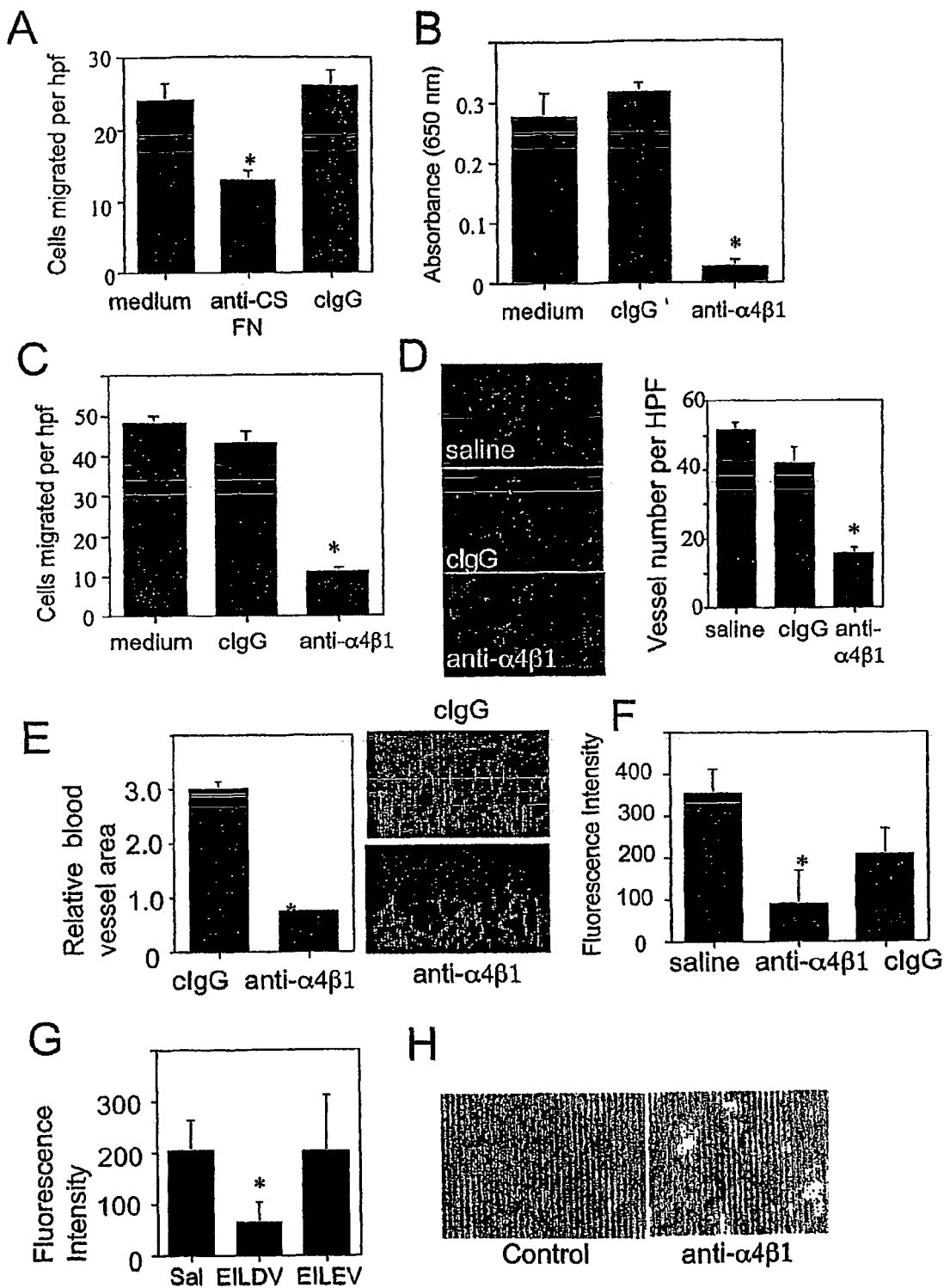

FIG. 19 shows (A) Migration of endothelial cells on 8 μm pore transwells coated with 5 μg/ml CS-1 fibronectin in the presence of medium, anti-CS-1 fibronectin or control antibodies (W6/32, anti-MHC). (B, C) Adhesion of endothelial cells to plastic plates coated with 5 μg/ml CS-1 fibronectin, in the presence of medium, anti-α4β1 (HP1/2) or control antibodies (P1F6). (D) Cryosections from bFGF stimulated, saline or antibody-treated CAMs were immunostained to detect blood vessel expression of von Willebrand Factor. (E) Angiogenesis was initiated in FVB/N mice by corneal transplantation of polymerized pellets containing 400 ng/ml of VEGF. Animals (n=5) were treated on day 0 and day 3 with anti-α4β1 (PS/2) or control IgG (cIgG). Fifteen minutes prior to sacrifice on day 5, mice were injected intravenously with endothelial specific lectin, Bandeira simplifolia-FITC and tissues were cryopreserved. Angiogenic response to VEGF was quantified as the percent green fluorescent area visible under high power magnification (100×). (F-G) Angiogenesis was initiated in nude mice by subcutaneous injection of 400 μl growth factor reduced matrigel supplemented with 400 ng/ml of bFGF containing (F) 200 μg function blocking rat anti-integrin α4β1 (PS/2) or isotype-matched control antibodies (rat anti-integrin β2) and (G) 50 μM EILDV or EILEV peptides. Fifteen minutes prior to sacrifice on day 5, mice were injected intravenously with endothelial specific lectin, Bandeira simplifolia-FITC. Matrigel plugs were homogenized in RIPA buffer and fluorescence intensity determined.

FIG. 20 shows (A) Cytofluorescence analysis of ECs, EPCs, and fibroblasts for UEA-1 lectin binding and uptake of DiI-acetylated LDL. (1) Adhesion of purified EPCs to plastic plates coated with 5 μg/ml fibronectin, CS-1 fibronectin, vitronectin and collagen. (C) Migration of purified EPCs on 8 μm pore transwells coated with 5 μg/ml fibronectin, CS-1 fibronectin, vitronectin and collagen. (D,E) Adhesion of purified EPCs on plastic plates coated with 5 μg/ml vitronectin in the presence of medium, anti-α4β1 (HP1/2), anti-α1β3 (LM609), anti-αvβ5 (P1F6), or anti-α5β1 (P1F6).

Figure 21:
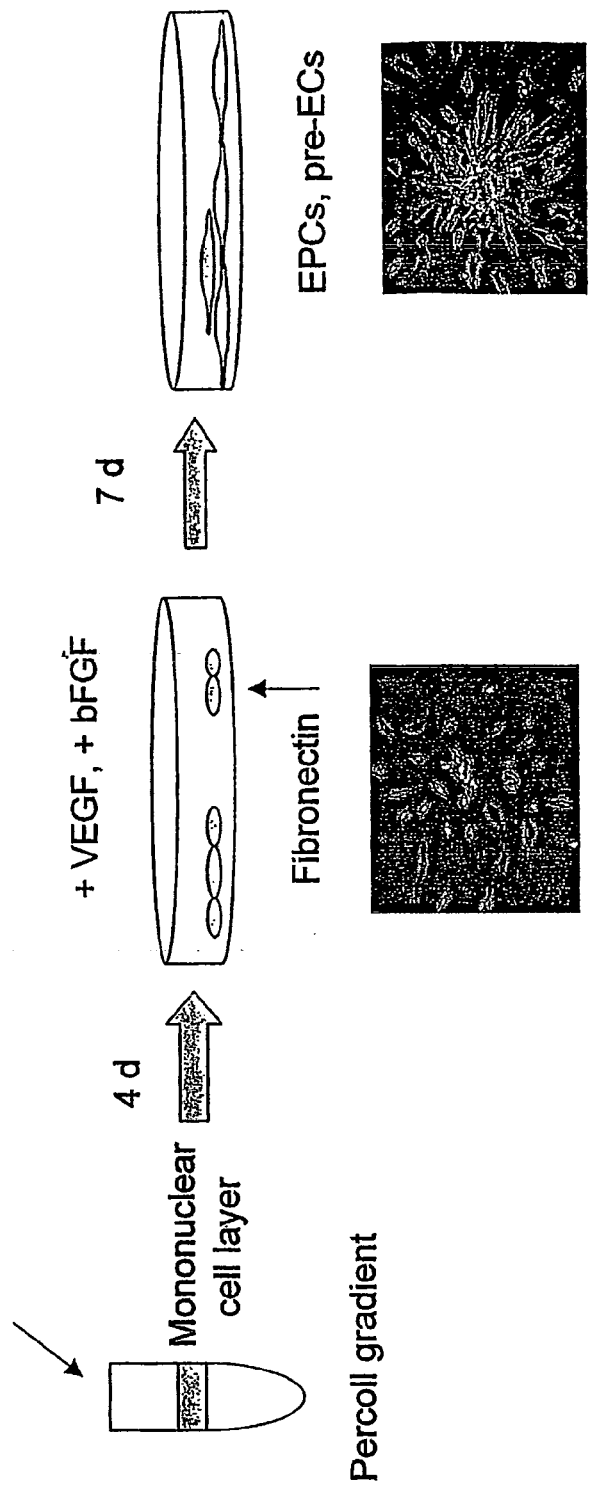

FIG. 21 shows that bone marrow derived cells can differentiate into endothelial cells (Ecs).

Figure 22:
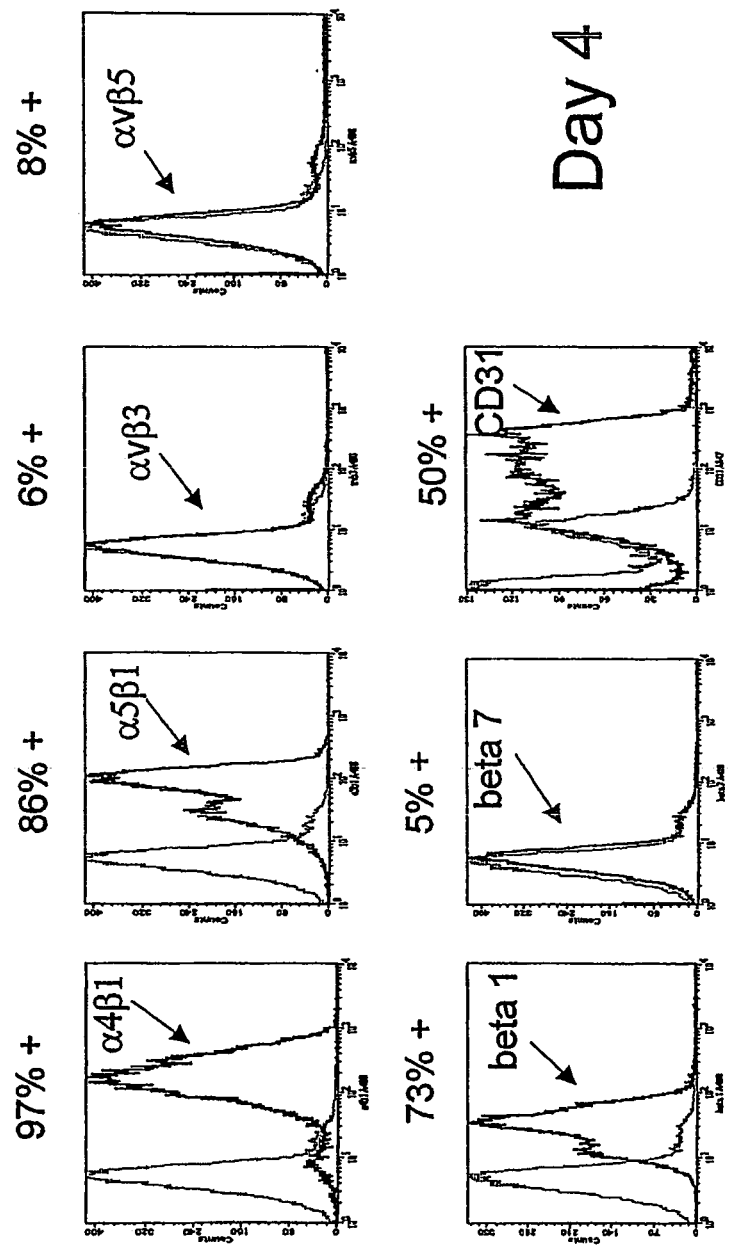

FIG. 22 shows that integrin α4β1 is an early marker of endothelial progenitor cells EPCs).

Figure 23:
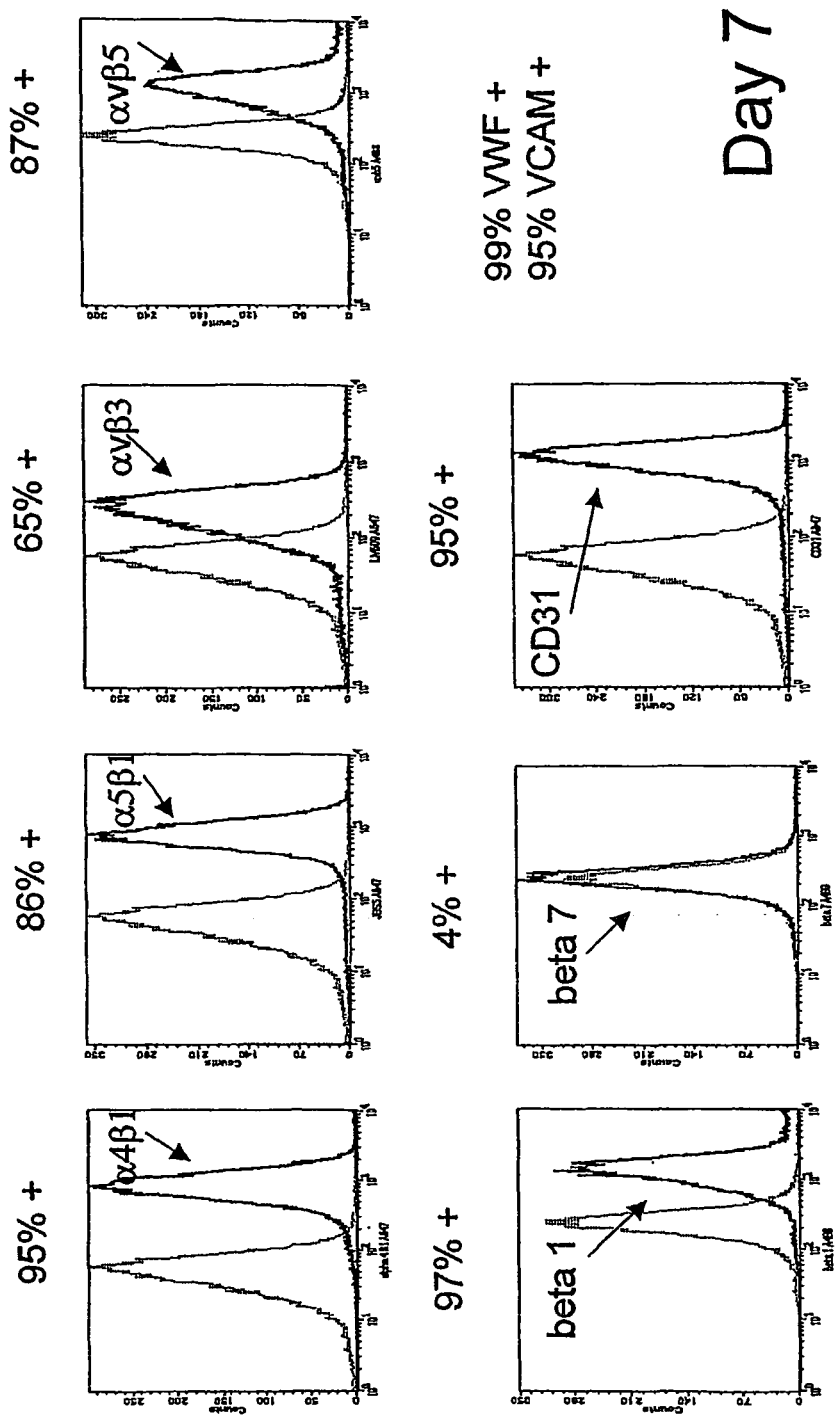

FIG. 23 shows that endothelial progenitor cells remain integrin α4β1-positive and acquire αv integrin expression.

Figure 24:
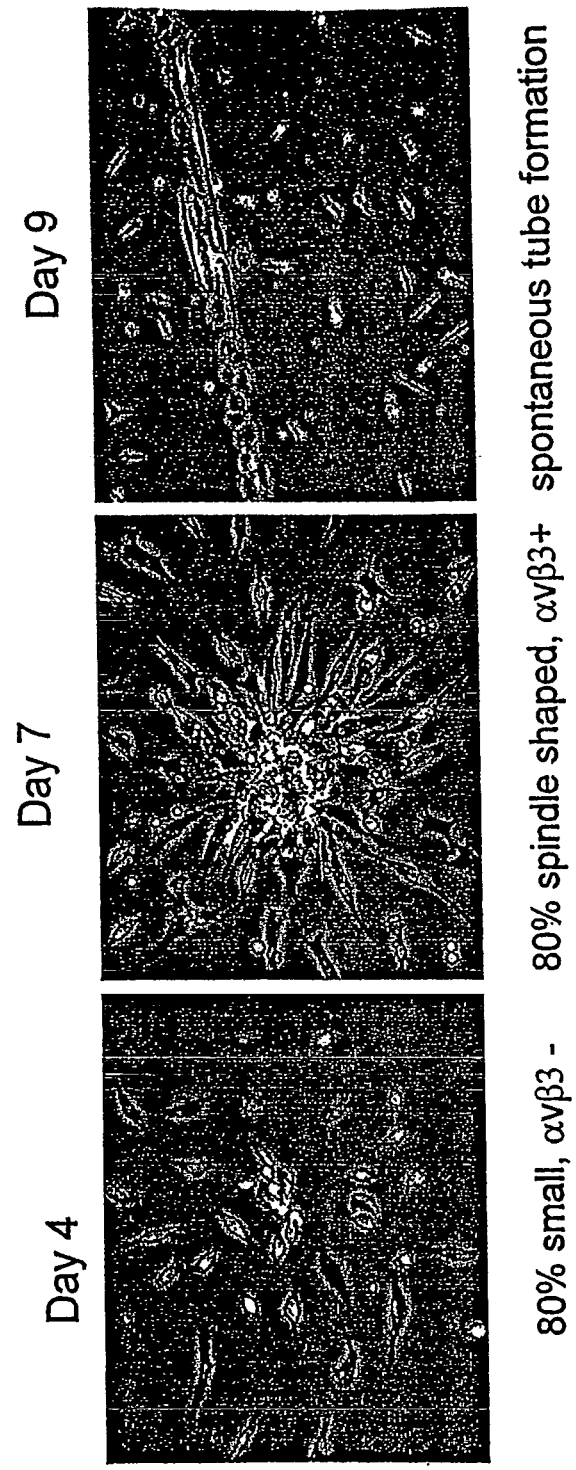

FIG. 24 shows endothelial progenitor cell maturation on days 4, 7, and 9.

Figure 25:
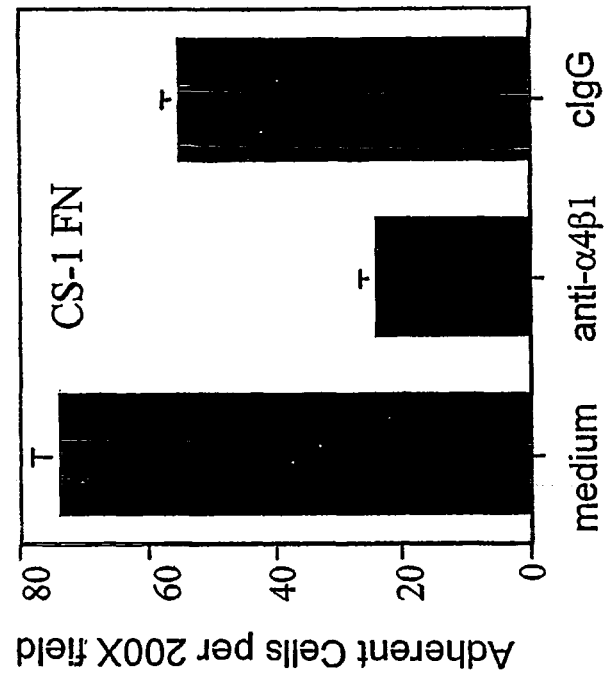

FIG. 25 shows that integrin α4β1 mediates endothelial progenitor cell adhesion to fibronectin.

Figure 26:
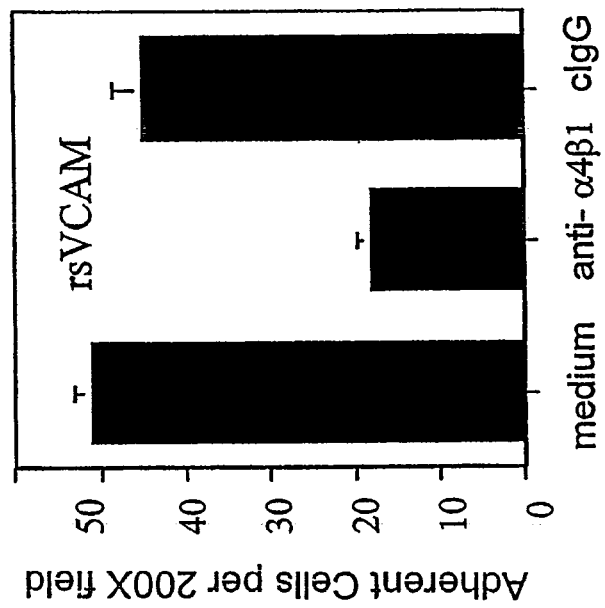

FIG. 26 shows that integrin α4β1 mediates endothelial progenitor cell adhesion to rsVCAM.

Figure 27:
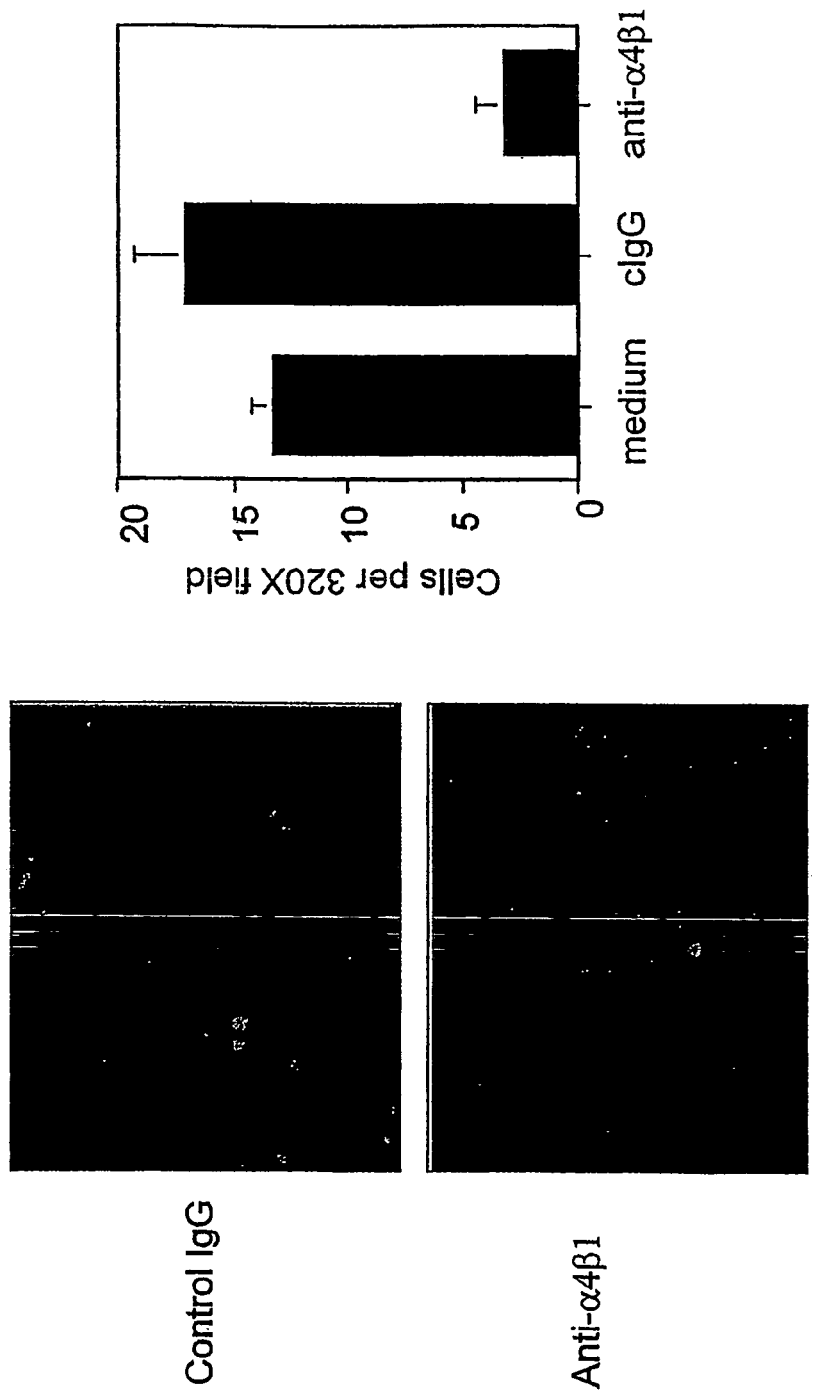

FIG. 27 shows that endothelial progenitor cells adhere to endothelial monolayers via integrin α4β1.

Figure 28:
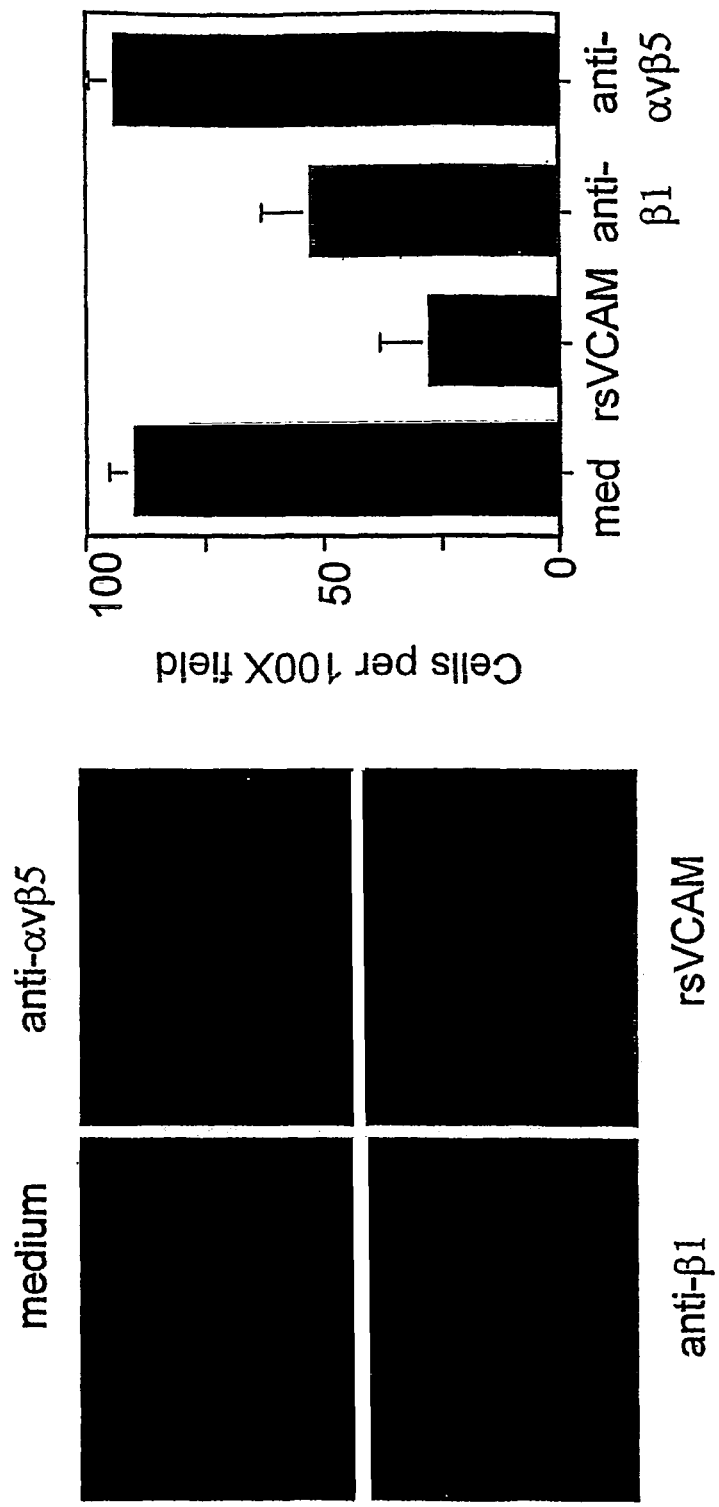

FIG. 28 shows that endothelial progenitor cells adhere to endothelial monolayers in a VCAM-dependent manner.

Figure 29:
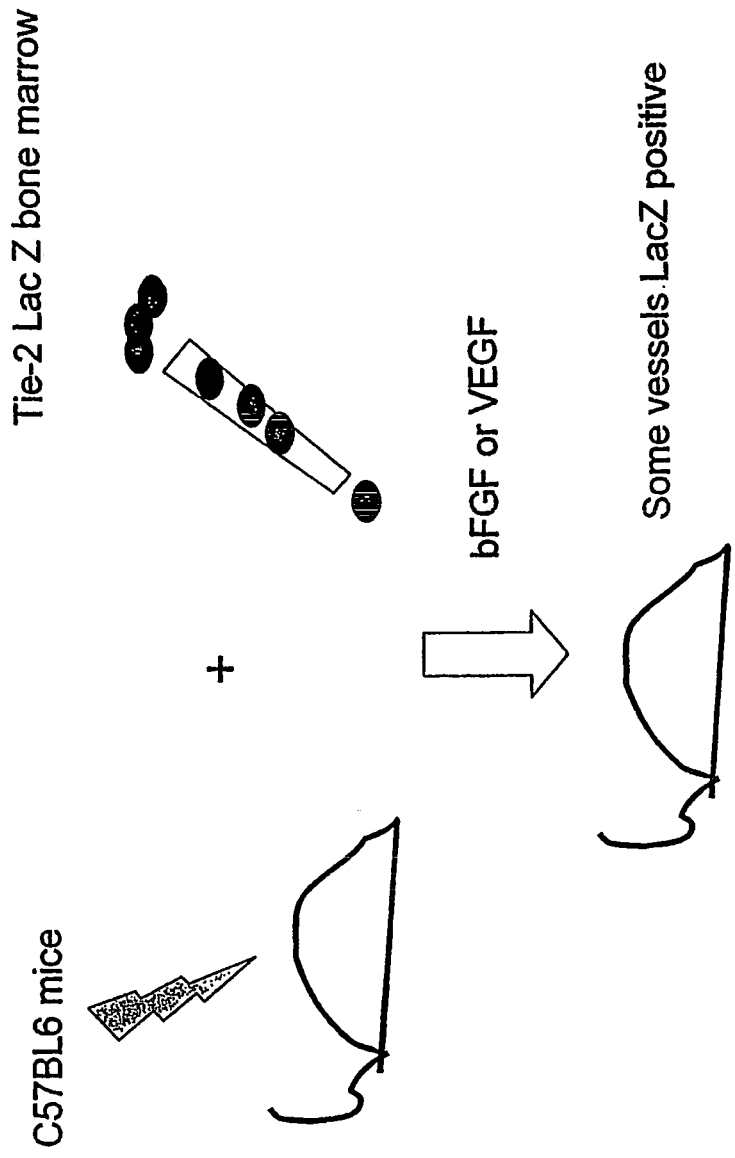

FIG. 29 shows the exemplary Tie2BMT model of hematopoietic stem cell role in neovascularization.

Figure 30:
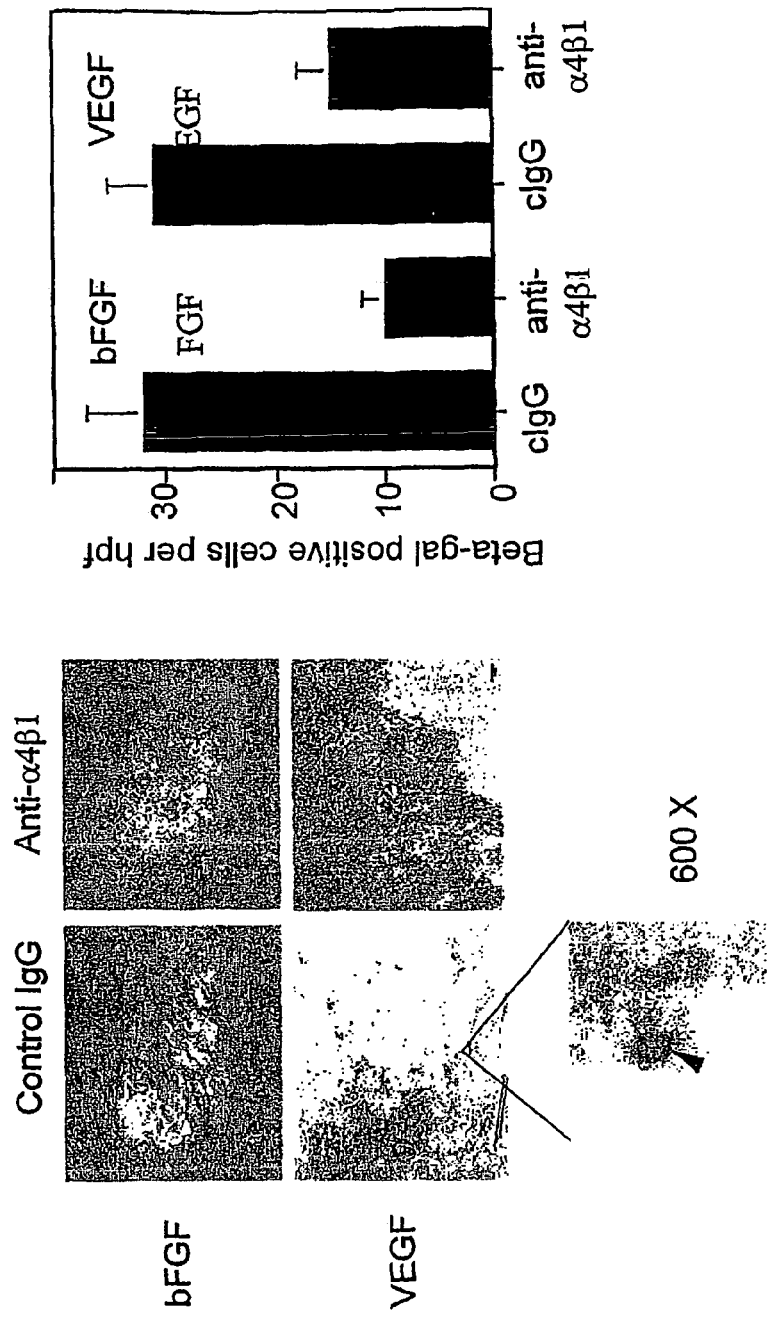

FIG. 30 shows that antagonists of integrin α4β1 block endothelial progenitor cell entry into neovascular beds.

Figure 31:
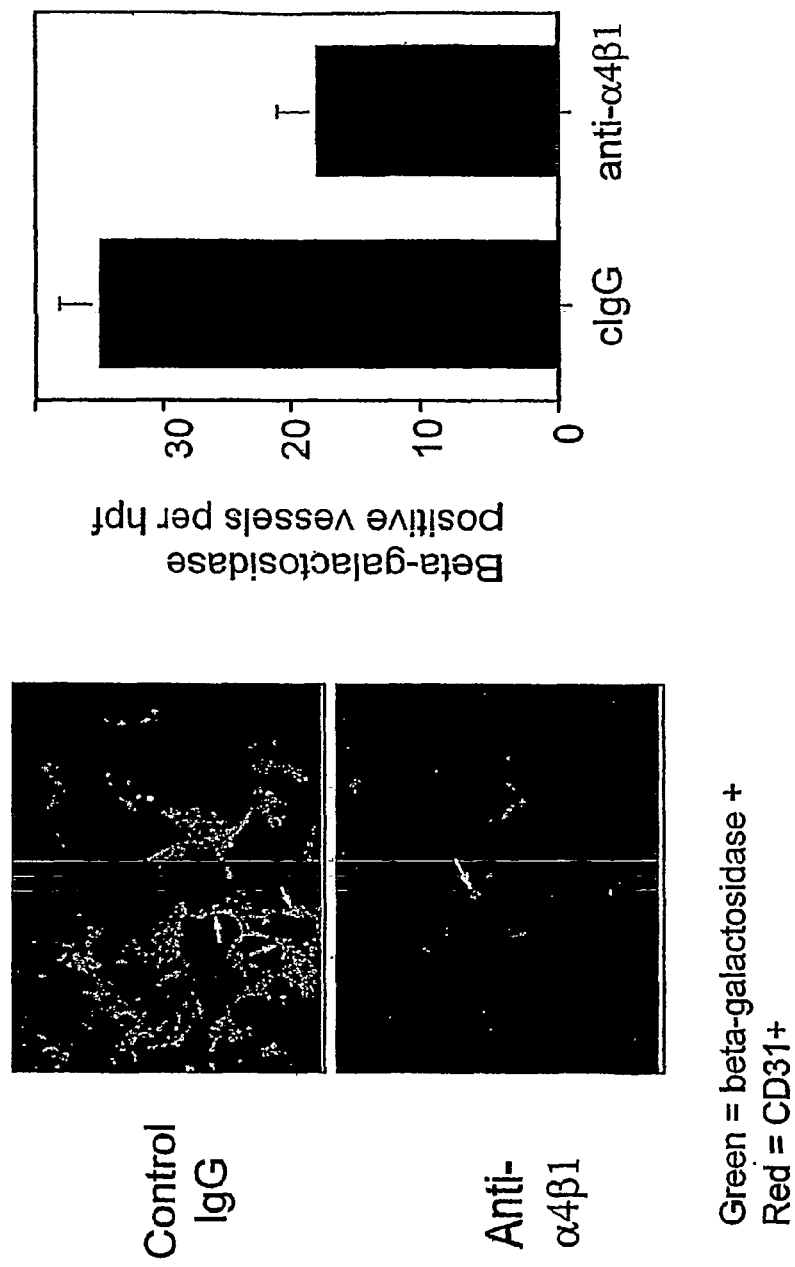

FIG. 31 shows that integrin α4β1 promotes endothelial progenitor cell contributions to angiogenesis in vivo.

Figure 32:
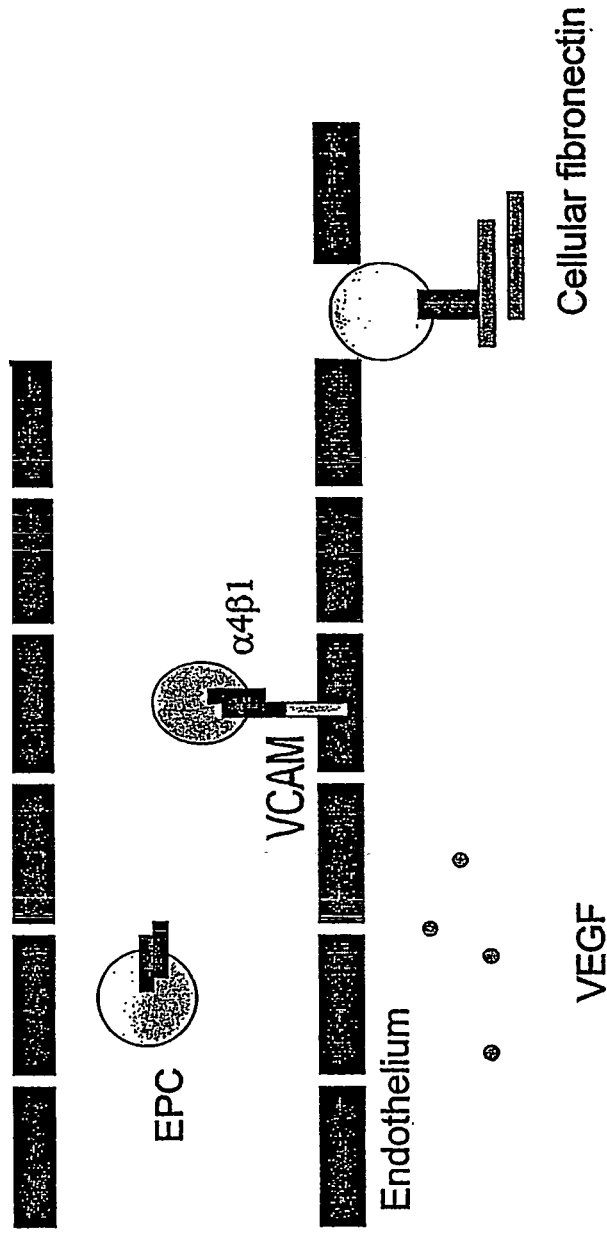

FIG. 32 shows that integrin α4β1 promotes endothelial progenitor cell extravasation and participation in vessel formation.

Figure 33:
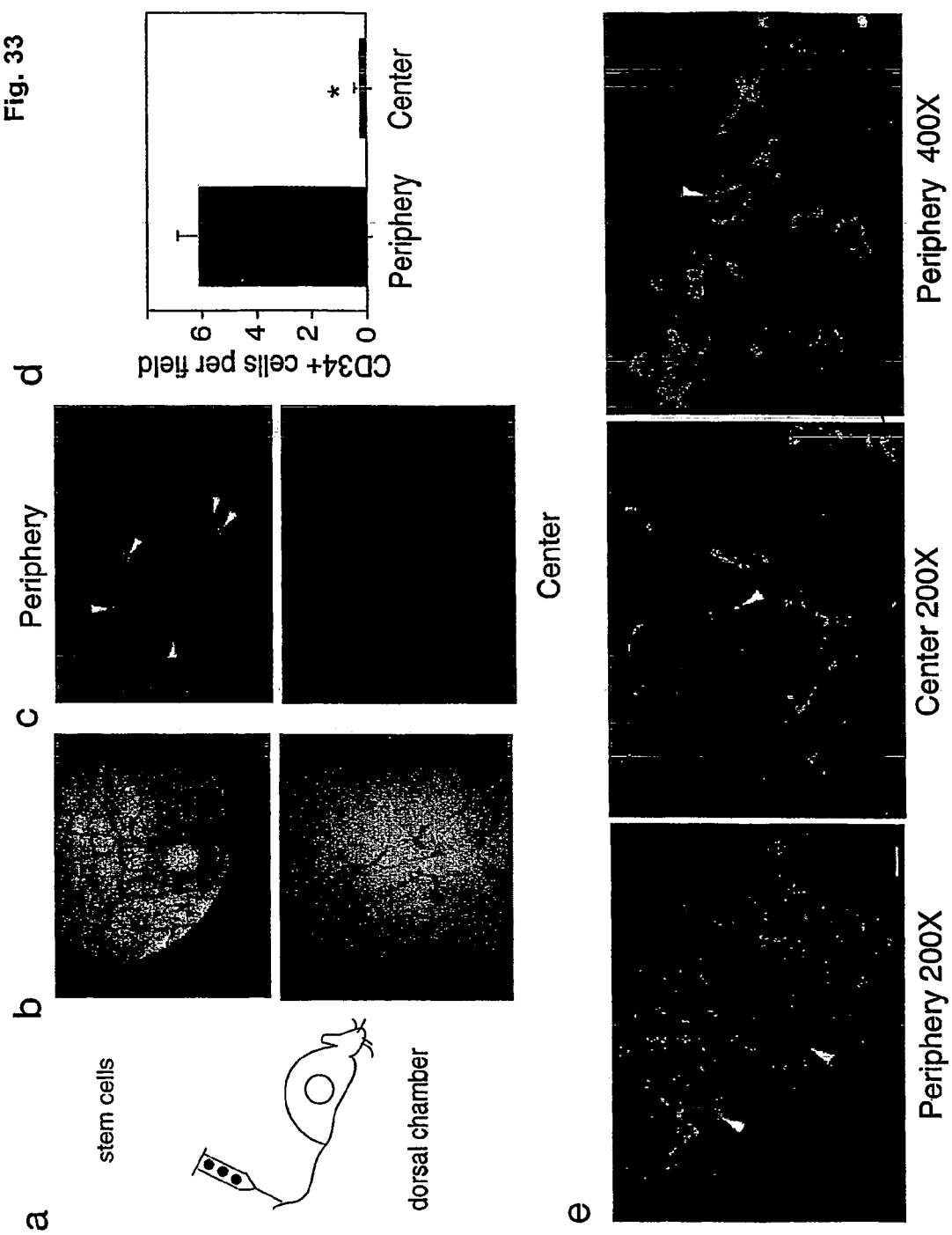

FIG. 33 shows that human CD34+ stem cells home to peripheral tumor vasculature (a) CMTMR labeled stem cells were injected into nude mice with breast carcinomas under dorsal skinfold transparent chambers. (b) Upper, Tumor and vasculature in transparent chambers. Lower, Peripheral and central tumor vessels are clearly visible. (C) Fluorescence video microscopy of peripheral and central tumor vascular beds. Arrowheads indicate hematopoietic stein cells (200× magnification). (d) Average number of hematopoietic stem cells per 200× microscopic field+/−SEM from (C). (e) Cryosections of tumors immunostained with anti-murine CD31 (green) at 200× and 400× magnification. Hematopoietic stem cells (arrowheads) are in or near blood vessels (arrows). Asterisks indicate P<0.05. Bar-50 μm.

Figure 34:
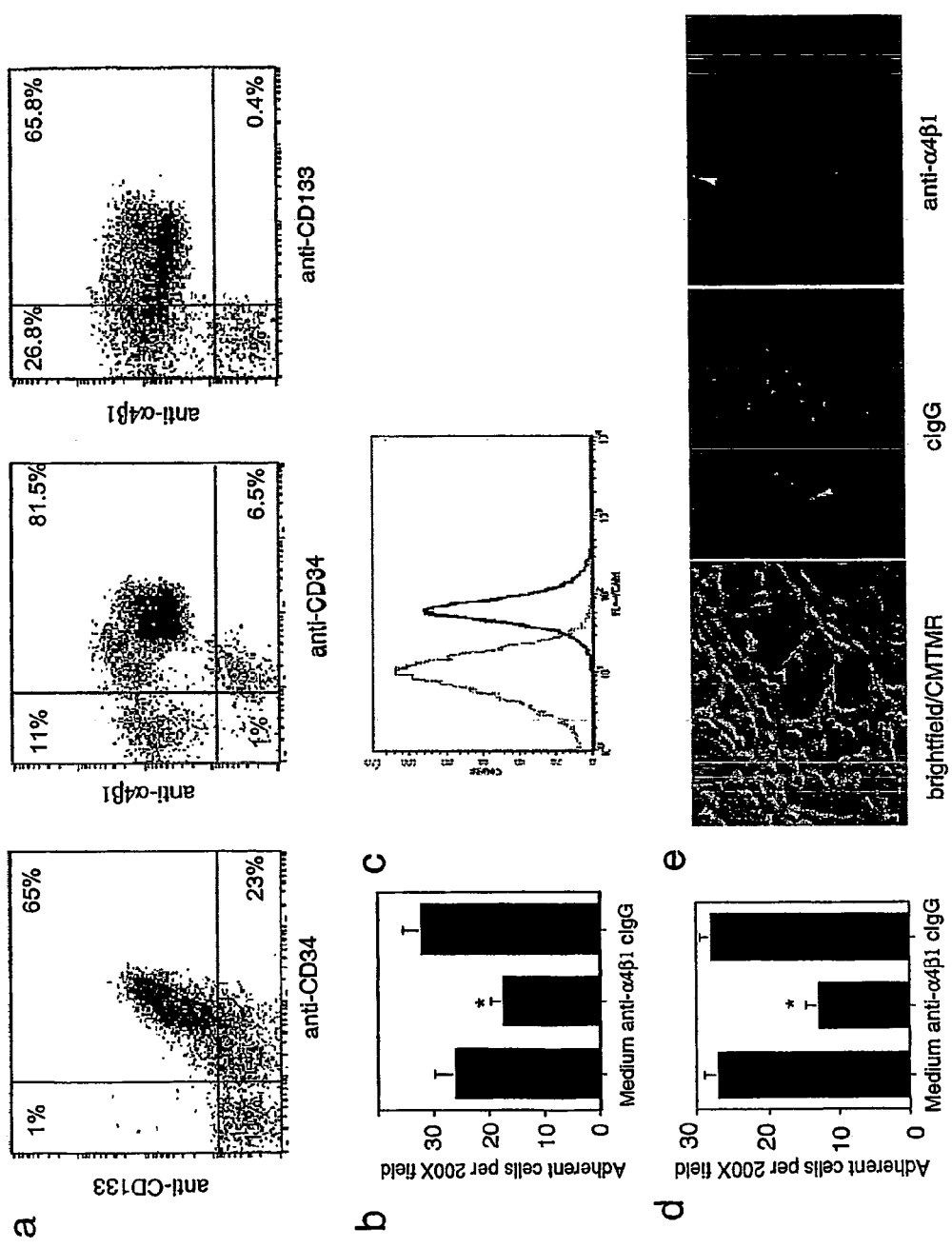

FIG. 34 shows that integrin α4β1 on human CD34+ stem cells (a) FACs profiles for CD34, CD133 and integrin α4β1 on stem cells. (b) Stem cell adhesion to CS-1 fibronectin in the presence of culture medium, anti-α4β1 (HP2/1) or control antibodies (P1F6)+/−SEM. (c) FACS profiles for VCAM (black) and nonspecific IgG control (grey) on ECs. (d) Stem cells adhesion to HUVECs in the presence of medium, anti-α4β1 (HP2/1) or control antibodies (P1F6)+/−SEM. (e) Left, Brightfield/red fluorescence images of stem cells on ECs. Right, red fluorescence images of stem cells on ECs in the presence of anti-α4β1 (HP2/1) or control antibodies (cIgG, P1F6). Asterisks indicate P<0.05.

Figure 35:
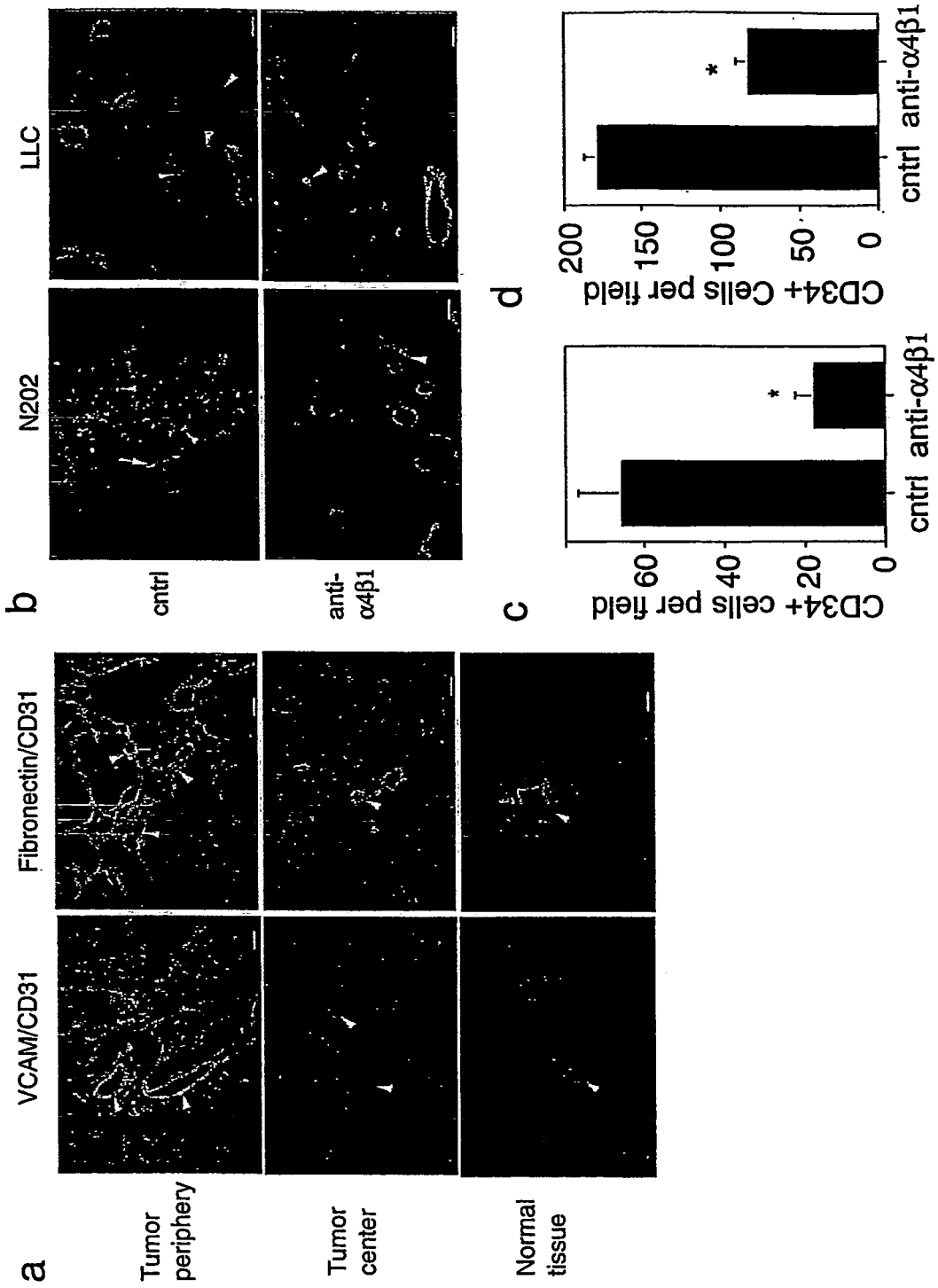

FIG. 35 shows that integrin α4β1 and ligands in hematopoietic stem cell homing (a) Cryosections of murine breast carcinomas or normal tissue (colon, left; heart, right) immunostained for CD31 (red) and VCAM or fibronectin (green). Arrowheads indicate blood vessels. Yellow indicates EC expression of VCAM/fibronectin. (b) Cryosections of breast carcinomas N202) or Lewis lung carcinomas (LLC) from mice injected with hematopoietic stem cells (red, arrowheads) in the presence of anti-human α4β1_antibody or negative controls (Cntrl) immunostained with anti-murine CD31 (green, arrows). (c-d) Average number of hematopoietic stem cells per 200× microscopic field for ©) N202 and (d) LLC tumors+/−SEM. Asterisks indicate P<0.05. Bar=50 μm.

Figure 36:
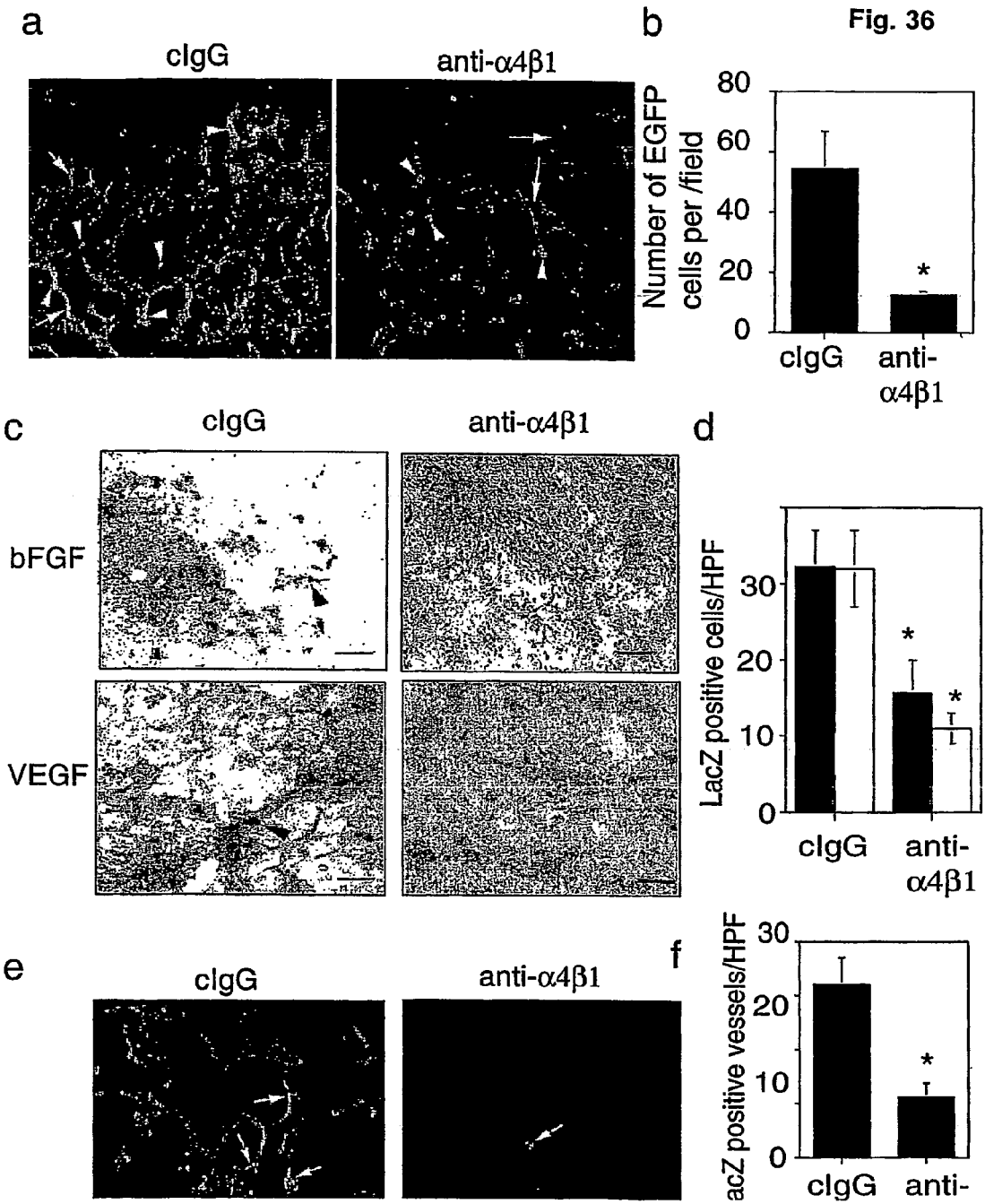

FIG. 36 shows that integrin α4β1 promotes hematopoietic stem cell homing from the bone marrow (a) Cryosections of LLC tumors from mice injected with EGFP+Lin− cells (green, arrowheads) and control antibody (cIgG) or anti-α4β1 immunostained with anti-CD31 (red, arrows). EGFP+ vessels are yellow. (b) Average number of EGFP cells per 200× microscopic field+/−SEM. (C) Cryosections of bFGF or VEGF saturated Matrigel from mice transplanted with Tie2LacZ bone marrow and treated with anti-α4β1 or control antibody (cIgG) stained to detect beta-galactosidase (200×). (d) Average numbers of LacZ+ cells per 200× field+/−SEM from (C): VEGF (black bars). FGF (white bars). (e) Cryosections from (d) immunostained for beta-galactosidase (green) and CD31 (red). LacZ+/CD31+ vessels are yellow (arrows). (f) Average number of LacZ+/CD31+ vessels per 200× field+/−SEM. Asterisks indicate P<0.05. Bar=50 μm.

DEFINITIONS

To facilitate understanding of the invention, a number of terms are defined below.

As used in this specification and the appended claims, the singular forms "a," "an" and "the" includes both singular and plural references unless the content clearly dictates otherwise.

As used herein, the term "or" when used in the expression "A or B," where A and B refer to a composition, disease, product, etc., means one, or the other, or both.

The term "on" when in reference to the location of a first article with respect to a second article means that the first article is on top and/or into the second article, including, for example, where the first article permeates into the second article after initially being placed on it.

As used herein, the term "comprising" when placed before the recitation of steps in a method means that the method encompasses one 4 or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the content clearly dictates otherwise. For example, a method comprising steps a, b, and c encompasses, for example, a method of performing steps in the order of steps a, c, and b, the order of steps c, b, and a, and the order of steps c, a, and b, etc.

Unless otherwise indicated, all numbers expressing quantities of ingredients, properties such as molecular weight, reaction conditions, and so forth as used in the specification and claims are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximation, the numerical values in the specific examples are reported as precisely as possible. Any numerical value, however, inherently contains standard deviations that necessarily result from the errors found in the numerical value's testing measurements.

The term "not" when preceding, and made in reference to, any particularly named molecule (such as a protein, nucleotide sequence, etc.) or phenomenon (such as cell adhesion, cell migration, cell differentiation, angiogenesis, biological activity, biochemical activity, etc.) means that only the particularly named molecule or phenomenon is excluded.

The term "altering" and grammatical equivalents as used herein in reference to the level of any molecule (such as a protein, nucleotide sequence, etc.) or phenomenon (such as cell adhesion, cell migration, cell differentiation, angiogenesis, biological activity, biochemical activity, etc.) refers to an increase and/or decrease in the quantity of the substance and/or phenomenon, regardless of whether the quantity is determined objectively and/or subjectively.

The term "increase," "elevate," "raise," and grammatical equivalents when in reference to the level of a molecule (such as a protein, nucleotide sequence, etc.) or phenomenon (such as cell adhesion, cell migration, cell differentiation, angiogenesis, biological activity, biochemical activity, etc.) in a first sample relative to a second sample, mean that the quantity of the substance and/or phenomenon in the first sample is higher than in the second sample by any amount that is statistically significant using any art-accepted statistical method of analysis such as the Student's t-test. In one embodiment, the increase may be determined subjectively, for example when a patient refers to their subjective perception of disease symptoms, such as pain, clarity of vision, etc. In another embodiment, the quantity of the substance and/or phenomenon in the first sample is at least 10% greater than, preferably at least 25% greater than, more preferably at least 50% greater than, yet more preferably at least 75% greater than, and most preferably at least 90% greater than the quantity of the same substance and/or phenomenon in a second sample.

The terms "reduce," "inhibit," "diminish," "suppress," "decrease," and grammatical equivalents when in reference to the level of a molecule (such as a protein, nucleotide sequence, etc.) or phenomenon (such as cell adhesion, cell migration, cell differentiation, angiogenesis, biological activity, biochemical activity, etc.) in a first sample relative to a second sample, mean that the quantity of substance and/or phenomenon in the first sample is lower than in the second sample by any amount that is statistically significant using any art-accepted statistical method of analysis. In one embodiment, the reduction may be determined subjectively, for example when a patient refers to their subjective perception of disease symptoms, such as pain, clarity of vision, etc. In another embodiment, the quantity of substance and/or phenomenon in the first sample is at least 10% lower than, preferably, at least 25% lower than, more preferably at least 50% lower than, yet more preferably at least 75% lower than, and most preferably at least 90% lower than the quantity of the same substance and/or phenomenon in a second sample. A reduced level of a molecule and/or phenomenon need not, although it may, mean an absolute absence of the molecule and/or phenomenon.

Reference herein to any specifically named protein (such as "integrin $\alpha 4\beta 1$," "vascular cell adhesion molecule, fibronectin, etc.) refers to a polypeptide having at least one of the biological activities (such as those disclosed herein and/or known in the art) of the specifically named protein, wherein the biological activity is detectably by any method. In a preferred embodiment, the amino acid sequence of the polypeptide has at least 95% homology (i.e., identity) with the amino acid sequence of the specifically named protein. Reference herein to any specifically named protein (such as "integrin $\alpha 4\beta 1$," "vascular cell adhesion molecule, fibronectin, etc.) also includes within its scope fragments, fusion proteins, and variants of the specifically named protein that have at least 95% homology with the amino acid sequence of the specifically named protein.

The term "fragment" when in reference to a protein refers to a portion of that protein that may range in size from four (4) contiguous amino acid residues to the entire amino acid sequence minus one amino acid residue. Thus, a polypeptide sequence comprising "at least a portion of an amino acid sequence" comprises from four (4) contiguous amino acid residues of the amino acid sequence to the entire amino acid sequence.

The term "variant" of a protein as used herein is defined as an amino acid sequence which differs by insertion, deletion, and/or conservative substitution of one or more amino acids from the protein. The term "conservative substitution" of an amino acid refers to the replacement of that amino acid with another amino acid which has a similar hydrophobicity, polarity, and/or structure. For example, the following aliphatic amino acids with neutral side chains may be conservatively substituted one for the other: glycine, alanine, valine, leucine, isoleucine, serine, and threonine. Aromatic amino acids with neutral side chains which may be conservatively substituted one for the other include phenylalanine, tyrosine, and tryptophan. Cysteine and methionine are sulphur-containing amino acids which may be conservatively substituted one for the other. Also, asparagine may be conservatively substituted for glutamine, and vice versa, since both amino acids are amides of dicarboxylic amino acids. In addition, aspartic acid (aspartate) my be conservatively substituted for glutamic acid (glutamate) as both are acidic, charged (hydrophilic) amino acids. Also, lysine, arginine, and histidine my be conservatively substituted one for the other since each is a basic, charged (hydrophilic) amino acid. Guidance in determining which and how many amino acid residues may be substituted, inserted or deleted without abolishing biological and/or immunological activity may be found using computer programs well known in the art, for example, DNAStar™ software. In one embodiment, the sequence of the variant has at least 95% identity, preferably at least 90% identity, more preferably at least 85% identity, yet more preferably at least 75% identity, even more preferably at least 70% identity, and also more preferably at least 65% identity with the sequence of the protein in issue.

Reference herein to any specifically named nucleotide sequence (such as a sequence encoding integrin α4β1 etc.) includes within its scope fragments, homologs, and sequences that hybridize under high and/or medium stringnet conditions to the specifically named nucleotide sequence, and that have at least one of the biological activities (such as those disclosed herein and/or known in the art) of the specifically named nucleotide sequence, wherein the biological activity is detectable by any method.

The nucleotide "fragment" may range in size from an exemplary 10, 20, 50, 100 contiguous nucleotide residues to the entire nucleic acid sequence minus one nucleic acid residue. Thus, a nucleic acid sequence comprising "at least a portion of" a nucleotide sequence comprises from ten (10) contiguous nucleotide residues of the nucleotide sequence to the entire nucleotide sequence.

The term "homolog" of a specifically named nucleotide sequence refers to an oligonucleotide sequence which has at least 95% identity, more preferably at least 90% identity, yet more preferably at least 85% identity, yet more preferably at least 80% identity, also more preferably at least 75% identity, yet more preferably at least 70% identity, and most preferably at least 65% identity with the sequence of the nucleotide sequence in issue.

With respect to sequences that hybridize under stringent condition to the specifically named nucleotide sequence, high stringency conditions comprise conditions equivalent to binding or hybridization at 68° C. in a solution containing 5×SSPE, 1% SDS, 5×Denhardt's reagent and 100 µg/ml denatured salmon sperm DNA followed by washing in a solution containing 0.1×SSPE, and 0.1% SDS at 68° C. when a probe of about 100 to about 1000 nucleotides in length is employed. "Medium stringency conditions" when used in reference to nucleic acid hybridization comprise conditions equivalent to binding or hybridization at 42° C. in a solution of 5×SSPE (43.8 g/l NaCl, 6.9 g/l NaH2PO4-H2O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 85% to 95% homology to the first nucleic acid sequence, then another hybridization condition is said to be equivalent to the hybridization condition of interest if this other hybridization condition also results in hybridization of the first nucleic acid sequence with the other nucleic acid sequences that have from 85% to 95% homology to the first nucleic acid sequence.

As will be understood by those of skill in the art, it may be advantageous to produce a nucleotide sequence encoding a protein of interest, wherein the nucleotide sequence possesses non-naturally occurring codons. Therefore, in some preferred embodiments, codons preferred by a particular prokaryotic or eukaryotic host (Murray et al., Nucl. Acids Res., 17 (1989)) are selected, for example, to increase the rate of expression or to produce recombinant RNA transcripts having desirable properties, such as a longer half-life, than transcripts produced from naturally occurring sequence.

The term "naturally occurring" as used herein when applied to an object (such as cell, etc.) and/or chemical (such as amino acid, amino acid sequence, nucleic acid, nucleic acid sequence, codon, etc.) means that the object and/or compound can be found in nature. For example, a naturally occurring polypeptide sequence refers to a polypeptide sequence that is present in an organism (including viruses) that can be isolated from a source in nature, wherein the polypeptide sequence has not been intentionally modified by man in the laboratory.

The terms nucleotide sequence "comprising a particular nucleic acid sequence" and protein "comprising a particular amino acid sequence" and equivalents of these terms, refer to any nucleotide sequence of interest and to any protein of interest that contains the particularly named nucleic acid sequence and the particularly named amino acid sequence, respectively. The invention does not limit on the source (e.g., cell type, tissue, animal, etc.), nature (e.g., synthetic, recombinant, purified from cell extract, etc.), and/or sequence of the nucleotide sequence of interest and/or protein of interest. In one embodiment, the nucleotide sequence of interest and protein of interest include coding sequences of structural genes (e.g., probe genes, reporter genes, selection marker genes, oncogenes, drug resistance genes, growth factors, etc.).

The term "chosen from A, B and C" means selecting one or more of A, B, and C.

A "composition comprising a particular polynucleotide sequence" as used herein refers broadly to any composition containing the recited polynucleotide sequence. The composition may comprise an aqueous solution containing, for example, salts (e.g., NaCl), detergents (e.g., SDS), and other components (e.g., Denhardt's solution, dry milk, salmon sperm DNA, etc.).

The terms "hematopoietic progenitor cell" and "TPC" refer to an uncommitted (i.e., undifferentiated) and/or partially committed (i.e., partially differentiated) cell. Hematopoietic progenitor cells are oligopotent, that is, they have the ability to differentiate into more than one cell type, comprising, without limitation, granulocytes (e.g., promyelocytes, neutrophils, eosinophils, basophils), erythrocytes (e.g., reticulocytes, erythrocytes), thrombocyte (e.g., megakaryoblasts, platelet producing megakaryocytes, platelets), and monocytes (e.g., monocytes, macrophages).

Hematopoietic progenitor cells usually, but not necessarily, reside in the bone marrow. They are also found in the blood circulation and are also resident within other tissues. Hematopoietic progenitor cells are identified by surface markers. For example, human progenitor cells are identified by the surface marker CD34 (CD34+ cells). 0.1% of circulating cells in the blood are CD34+ while 2.1% of bone marrow cells are CD34+. Hematopoietic stem cells resident in tissues have also been found to be CD34+. Bone marrow derived (i.e., isolated from bone marrow or from the circulation) and tissue derived CD34+ cells can differentiate into muscle, neuronal tissues, epithelial tissues, vascular cells, immune cells and others and may be used to repopulate target tissues. Hematopoietic progenitor cells have been used therapeutically to repopulate damaged and disease tissues and spontaneously participate in tissues repair processes and pathologies in vivo (Belicci et. al. (2004) J. Neurosci Res. 77, 475-86; Otani et al., 2002, Nature Med. 8, 1004-1010; Otani et. al., (2004) J. Clin. Invest. 114, 765-774; Tamaki et. al. (2002) J. Cell Biol. 157, 571-577; Torrente et al. (2004) J. Clin. Invest. 114, 182-195; Hashimoto et. al. (2004) J. Clin. Invest. 113, 243-252)

The term "hematopoietic progenitor cell" expressly includes hematopoietic stem cells, endothelial progenitor cells, lymphendothelial progenitor cells, mesenchymal precursor cells, myeloid progenitor cells, lymphoid progenitor cells, granulocyte progenitor cell, macrophage progenitor cells, megakaryocyte progenitor cells, erythroid progenitor cells, Pro-B cells and Pro T cells (Terskikh (2003) Blood 102, 94-101).

Hematopoietic progenitor cells may be isolated and cultured using methods disclosed herein as well as those known in the art, such as from blood products (e.g., U.S. Pat. Nos. 5,061,620 and 6,645,489 incorporated by reference). A "blood product" as used in the present invention defines a product obtained from the body or an organ of the body containing cells of hematopoietic origin. Such sources include unfractionated bone marrow, umbilical cord, peripheral blood, liver, thymus, lymph and spleen. It will be apparent to those of ordinary skill in the art that all of the aforementioned crude or unfractionated blood products can be enriched for cells having "hematopoietic progenitor cell" characteristics in a number of ways. For example, the blood product can be depleted from the more differentiated progeny. The more mature, differentiated cells can be selected against, via cell surface molecules they express. Additionally, the blood product can be fractionated selecting for CD34.sup.+ cells. Such selection can be accomplished using methods disclosed herein, as well as commercially available magnetic anti-CD34 beads (Dynal, Lake Success, N.Y.). Unfractionated blood products can be obtained directly from a donor or retrieved from cryopreservative storage.

The terms "hematopoietic stem cell" and "HSC" refer to an oligopotent cell type that gives rise to more differentiated "precursor cells" such as, without limitation, endothelial progenitor cells, lymphendothelial progenitor cells, mesenchymal precursor cells, myeloid progenitor cells, lymphoid progenitor cells, granulocyte progenitor cell, macrophage progenitor cells, megakaryocyte progenitor cells, erythroid progenitor cells, Pro-B cells and Pro T cells (Terskikh et. al. (2003) supra). HSCs reside in the bone marrow, often attached to bone, but are also found in the circulation and also resident within other tissues. Hematopoietic stem cells have the capacity for self-renewal while more committee progenitors do not (Terskikh et. al. (2003) supra). HSCs and HPCs share common cell surface markers, in particular, for human cells by the marker CD34. HSCs are Lineage negative (lacking specific markers for any differentiated cells, such as B220 on B cells, CD3 on T-cells, CD11b on myeloid cells, etc.), CD34+, c-kit+ (Belicci et. al. (2004) supra). In mice these cells are c-kit+, Thy1.1lo, Sca-1+ and Lin− (Rafii et al. 2003, supra). Additionally, some progenitors, including endothelial progenitors, express CD133.

The terms "endothelial progenitor cells," "EPCs," "endothelial cell progenitors," and "lymphendothelial progenitor cells" refer to cells that arise from HSCs and that give rise to differentiated endothelial and lymphendothelial cells, respectively. EPCs are CD34+, CD133+, c-kit+ and Lin− (Rafii et al. 2003, supra). Furthermore they may be VEGFR2+ and/or VEGFR3+ (Rafii et al. 2003, supra). Human endothelial progenitor cells express the surface molecules CD34, flk-1, and/or tie-2 (Isner et al., U.S. Pat. No. 5,980,887, the entire contents of which are herein incorporated by reference). Mouse endothelial cell progenitors express the TM gene, tie-2 gene, and/or fgf3 gene, and/or stain with the GSL I B4 lectin (Hatzopoulos et al. (1998) Development 125:1457-1468).

The term "mesenchymal progenitor cells" refers to cells arising from HSCs and that give rise to fibroblasts and other stromal cells such as bone, adipose tissues and cartilage (Gronthos et. al., 2003. J. Cell Sci. 116, 1827-1835).

The term "myeloid progenitor cells" refers to cells arising from HSCs and that are precursors that give rise to granulocytes, macrophages, erythrocytes, megakaryocytes (and thus platelets) and possibly endothelial cells, muscle cells and other tissues (Terskikh, et. al. (2003) supra).

The term "lymphoid progenitor cells" refers to cells arising from HSCs and that give rise to T and B cells (Otani et. al. (2002) supra).

As used herein, the term "tissue exhibiting angiogenesis" refers to a tissue in which new blood vessels are developing from pre-existing blood vessels.

As used herein, the term "inhibiting angiogenesis," "diminishing angiogenesis," "reducing angiogenesis," and grammatical equivalents thereof refer to reducing the level of angiogenesis in a tissue to a quantity which is preferably 10% less than, more preferably 50% less than, yet more preferably 75% than, even more preferably 90% less than, the quantity in a control tissue, and most preferably is at the same level which is observed in a control tissue. A reduced level of angiogenesis need not, although it may, mean an absolute absence of angiogenesis. The invention does not require, and is not limited to, methods that wholly eliminate angiogenesis.

The level of angiogenesis may be determined using methods well known in the art, including, without limitation, counting the number of blood vessels and/or the number of blood vessel branch points, as discussed herein. An alternative assay involves an in vitro cell adhesion assay that shows whether a compound inhibits the ability of α4β1-expressing cells (e.g. M21 melanoma cells) to adhere to VCAM or fibronectin. Another in vitro assay contemplated includes the tubular cord formation assay that shows growth of new blood vessels at the cellular level (D). S. Grant et al., Cell, 58: 933-943 (1989)). Art-accepted in vivo assays are also known, and involve the use of various test animals such as chickens, rats, mice, rabbits and the like. These in vivo assays include the chicken chorioallantoic membrane (CAM) assay, which is suitable for showing anti-angiogenic activity in both normal and neoplastic tissues (D. H. Ausprunk, Amer. J. Path., 79, No. 3: 597-610 (1975) and L. Ossonowski and E. Reich, Cancer Res., 30: 2300-2309 (1980)). Other in vivo assays include the mouse metastasis assay, which shows the ability of a compound to reduce the rate of growth of transplanted tumors in certain mice, or to inhibit the formation of tumors or pre-neoplastic cells in mice which are predisposed to cancer or which express chemically-induced cancer (M. J. Humphries et al., Science, 233: 467-470 (1986) and M. J. Humphries et al., J. Clin. Invest., 81: 782-790 (1988)).

The term "integrin α4β1" is interchangeably used with the terms "CD49d/CD29," "very late antigen 4," and "VLA4" to refer to a member of the family of integrins. An "integrin" is an extracellular receptor that is expressed in a wide variety of cells and binds to specific ligands in the extracellular matrix. The specific ligands bound by integrins can contain an arginine-glycine-aspartic acid tripeptide (Arg-Gly-Asp; RGD) or a leucine-aspartic acid-valine (Leu-Asp-Val) tripeptide, and include, for example, fibronectin, vitronectin, osteopontin, tenascin, and von Willebrands's factor. Integrin α4β1 is a heterodimeric cell surface adhesion receptor composed of an α4 and β1 subunits that bind to ligands which are present in the extracellular matrix (ECM) as well as on the cell surface. An exemplary α4 polypeptide sequence is shown in FIG. 1, and an exemplary β1 polypeptide sequence is shown in FIG. 2.

The term "integrin α4β1" is contemplated also to include a portion of α4β1. The term "portion," when used in reference to a protein (as in a "portion of α4β1") refers to a fragment of that protein. The fragments may range in size from three (3) contiguous amino acid residues to the entire amino acid sequence minus one amino acid residue. Thus, a polypeptide sequence comprising "at least a portion of an amino acid sequence" comprises from three (3) contiguous amino acid residues of the amino acid sequence to the entire amino acid sequence.

In one preferred embodiment, the portion of integrin α4β1 comprises a portion of the α4 polypeptide sequence. In a more preferred embodiment, the portion of the α4 polypeptide sequence shown in FIG. 1 comprises the sequence IVTCGHRWKNIPYIKNENKLPTG-GCYGVPPDLRTELSKRIAPCYQDYVKKFGENFAS CQAGISSFYTKDLIVMGAPGSSY-WTGSLFVYNITTNFYKAFLDKQNQVKFGSYLGY SVGAGHFRSQHTTEVVGGAPQHE-QIGKAYIFSIDEKELNILHEMKGKK (SEQ ID NO:10) (from amino acid 141 to amino acid 301). In a more preferred embodiment, the portion of integrin α4β1 comprises the sequence GHRWKN IFYIKNENKLPTGG (SEQ ID NO:11) (from amino acid 145 to amino acid 164), the sequence YQDYVKKFGENFAS (SEQ ID NO:12) (from amino acid 184 to amino acid 197), the sequence SYWTGS (SEQ ID NO:13) (from amino acid 219 to amino acid 224), the sequence GGAPQHEQIGK (SEQ ID NO:14) (from amino acid 270 to amino acid 280), and the sequence YNVDTES ALLYQGPHNT IFGYSVVLHS HGANRWLLVG APTAN-WLANA SVINP (SEQ ID NO:54) (from amino acid 34 to amino acid 85). In an alternative embodiment, the invention expressly includes portions of the α4 polypeptide sequence (which is exemplified by the sequence of FIG. 1) that contain the fore-mentioned portions. Such sequences include, for example, GRPYNVDTESALLYQGPHNTLFGYSVV-LHSHGANRWLLVG APTANWLANASVINGAIYR (SEQ ID NO:55), GVPTGRPYNVDTESAL LYQGPHNT LFGYSWLHSHGANRWLLVGAPTANWLANASVI NPGAIYRCRIGKNPGQT (SEQ ID NO:56), IVTCGHR-WKYNNKLPTGGCYG (SEQ ID NO:57), GHRWKNIFY-IKNENKLPTGGCYGVPPDLRTELSK (SEQ ID NO:58), APCYQDYVKKFGENFAS (SEQ ID NO:59), CYQDYVKKFGENFASCQA GISSFYTKDL (SEQ ID NO:60), GSSYWTGSLFVYNI (SEQ ID NO:61), RSQHT-TEVVGGAPQHEQIGK (SEQ ID NO:62), GGAPQHE-QIGKAYIFSIDEKEL (SEQ ID NO:63), and/or GGAPQHE-QIGKA (SEQ ID NO:64).

The terms "isolated," "purified," and grammatical equivalents thereof when used in reference to a molecule (e.g., protein, DNA, RNA, etc.) or article (e.g., hematopoietic progenitor cell) in a sample refer to the reduction (by at least 10%, preferably by at least 25%, more preferably by at least 50%, even more preferably by at least 75%, and most preferably by at least 90%) in the amount of at least one contaminant molecule and/or article from the sample. Thus, purification results in an "enrichment," i.e., an increase, in the amount of the desirable molecule and/or article relative to one or more other molecules and/or articles in the sample.

A "non-endothelial cell" is any cell type other than an endothelial cell (i.e., is not an endothelial cell) such as, without limitation, stem cell, lymph cell, mesenchymal cell, myeloid cell, lymphoid cell, granulocyte cell, macrophage cell, megakaryocyte cell, erythroid cell, B cell, T cell, bone marrow cell, muscle cell, neural cell, etc.

The terms "disease" and "pathological condition" are used interchangeably to refer to a state, signs, and/or symptoms that are associated with any impairment, interruption, cessation, or disorder of the normal state of a living animal or of any of its organs or tissues that interrupts or modifies the performance of normal functions, and may be a response to environmental factors (such as malnutrition, industrial hazards, or climate), to specific infective agents (such as worms, bacteria, or viruses), to inherent defect of the organism (such as various genetic anomalies, or to combinations of these and other factors. The term "disease" includes responses to injuries, especially if such responses are excessive, produce symptoms that excessively interfere with normal activities of an individual, and/or the tissue does not heal normally (where excessive is characterized as the degree of interference, or the length of the interference).

DESCRIPTION OF THE INVENTION

The present invention satisfies the need in the art by providing methods for altering hematopoietic progenitor cell adhesion and/or migration to a target tissue, and for altering hematopoietic progenitor cell differentiation into a second cell type. The invention also provides methods for screening test compounds for altering the level of hematopoietic cell adhesion and/or migration to a target tissue, and for altering hematopoietic progenitor cell differentiation into a second cell type. The invention further provides methods for isolating hematopoietic progenitor cells. The methods of the invention are useful in, for example, diagnosis, prophylaxis, and reduction of symptoms of diseases and conditions that are associated with HPC adhesion, migration and differentiation. The methods of the present invention are also useful in isolating HPCs cells, and in determining the mechanisms that underlie development and wound healing. The methods of the invention are based, in part, on the inventor's fortuitous discovery that integrin α4β1 plays a role in HPC adhesion, migration, and differentiation.

Hematopoietic stem cells provide up to 15% of new vessels in tumors by differentiating into endothelial cells (ECs) (Ruzinova et al. Cancer Cell 4:277-289 (2003)), but some hematopoietic stem cells may also promote angiogenesis by differentiating into cells such as monocytes, which secrete angiogenic factors (Cursiefen et al. (2004) J. Clin. Invest. 113:1040-1050). As most CD34+ cells express integrin α4β1 and α4β1 antagonists nearly completely blocked hematopoietic stem cell homing, data herein (Examples 17-24) indicate that α4β1 regulates both roles for hematopoietic stem cells in neovascularization. It is also not clear whether hematopoietic stem cells, partially committed precursors cells or a combination of the two participate in angiogenesis. Our data shows that endothelial progenitor cells also home to tumors in an α4β1 dependent manner. Data herein thus show that inhibition of α4β1 blocks the homing of the exemplary hematopoietic stem cells to the neovasculature and subsequent outgrowth into endothelium.

It is the inventor's consideration that the exemplary circulating hematopoietic stem cells home to sites of neovascularization (Asahara et al. (1997) supra; Rafii et al. (2003) Nat.

Med. 9, 702-12; Takahashi et al. (1999) Nat. Med. 5, 434-438; Kawamoto et al. (2001) Circulation 103, 634-637; Hattori et al. (2001) J. Exp. Med. 193, 1005-1014; Lyden et al. (2001) Nat. Med. 7, 1194-201; Ruzinova et al. (2003) Cancer Cell. 4:277-289; Jain et al. (2003) Cancer Cell 3, 515-516; Religa et al. (2002) Transplantation 74, 1310-1315; and Boehm et al. (2004) J. Clin. Invest. 114, 419-426)), where they give rise to approximately 15% of the vasculature (Ruzinova et al. (2003) Cancer Cell. 4: 277-289). They also home to muscle, brain and other tissues, where they participate in tissue regeneration or pathogenesis by differentiating into muscle, nerve and other cell types (Priller (2001) et al. J. Cell Biol. 155, 733-738; LaBarge et al. (2002) Cell. 111, 589-601; Torrente et al. (2003) J. Cell Biol. 162, 511-520; 13. Religa et al. (2002) Transplantation 74, 1310-1315; and Boehm et al. (2004) J. Clin. Invest. 114, 419-426)).

Integrin α4β1-VCAM interactions promote heterotypic cell adhesion during many processes in vivo. α4β1-VCAM interactions are involved in normal embryonic development, as embryonic loss of either molecule inhibits fusion of the chorion with the allantois (Yang et al. (1995) Development 121, 549-560; and Kwee et al. (1995) Development 121, 489-503) and of endocardium with myocardium (Yang et al. (1995) Development 121, 549-560; and Kwee et al. (1995) Development 121, 489-503). Integrin α4β1 interactions with fibronectin and/or VCAM are also involved in immune cell trafficking in inflammation (Guan et al. (2990) Cell 60, 53-61; and Elices et al. (1990) Cell 60, 577-584) and cancer (Melder et al. (1996) Nat Med. 2:992-997), for adhesion of immune cell precursors to bone marrow EC and for the homing of these cells back to the bone marrow (Simmons et al. (1992) Blood. 80, 388-395; Papayannopoulou et al. (2001) Blood 98, 2403-2411; Craddock et al. (1997) Blood 90, 4779-4788; and Miyake et al. (1991) J. Cell Biol. 114, 557-565). In one embodiment, our data demonstrate a novel function of the interaction of α4β1 with the exemplary ligands VCAM and fibronectin, that is, to promote the association of the exemplary hematopoietic stem cells with endothelial cells during neovascularization and tissue remodeling.

Data herein (e.g., Examples 17-24, FIGS. 21-36) show that integrin α4β1 plays a central role in the homing of the exemplary hematopoietic stem cells to tumors, inflammatory tissues and injured tissue, and that manipulation of the expression and/or function of integrin α4β1 and its ligands offers a means for modulating pathological processes that involve hematopoietic progenitor cells, such as hematopoietic stem cells.

The invention is further discussed below under the headings: A) Integrin α4β1 Ligands, B) Agents Which Alter Binding Of Integrin α4β1 To Its Ligands, C) Integrin α4β1 Mediates Trafficking of Endothelial Progenitor Cells, As Exemplified By Endothelial Stem Cells, During Neovascularization, D) Altering Hematopoietic Progenitor Cell Adhesion, Migration and Differentiation, E) Altering Hematopoietic Progenitor Cell Adhesion, Migration, and Differentiation, F) Detecting Hematopoietic Progenitor Cells That Express Integrin α4β1, G) Screening Compounds, and H) Isolating Hematopoietic Progenitor Cells.

A. Integrin α4β1 Ligands

The methods of the invention employ agents which inhibit the specific binding of integrin α4β1 with one or more of its ligands. The term "ligand" as used herein in reference to a ligand for the integrin α4β1 receptor, refers to a molecule and/or portion thereof, to which α4β1 specifically binds. In one embodiment, binding of the ligand initiates a specific biological response (e.g., hematopoietic progenitor cell adhesion, migration, and/or differentiation) and/or the transduction of a signal in a cell. Integrin α4β1 ligands may be present on the cell surface or present in the extracellular matrix (ECM).

In one preferred embodiment, an integrin α4β1 ligand that is present on the cell surface is exemplified by the vascular cell adhesion molecule (VCAM). An example of the polypeptide sequence of VCAM is shown in FIG. 3. In another preferred embodiment, the integrin α4β1 ligand is a portion of VCAM. Preferred portions of VCAM (FIG. 3A, GenBank Accession Nos. P19320) comprise the amino acid sequence RTQIDSPLNG (SEQ ID NO:15) (from amino acid 60 to amino acid 69); the amino acid sequence RTQIDSPLSG (SEQ ID NO:16) (from amino acid 348 to amino acid 357); and the amino acid sequence KLEK (SEQ ID NO:17) (from amino acid 103 to amino acid 106, and from amino acid 391 to amino acid 394). Other portions of VCAM are also contemplated, which preferably contain one of more of the RTQIDSPLNG (SEQ ID NO:15), RTQIDSPLSG (SEQ ID NO:16), or KLEK (SEQ ID NO:17) sequences. These are exemplified by, but not limited to, WRTQIDSPLNGK (SEQ ID NO:65), SWRTQIDSPLNGKV (SEQ ID NO:66), SWRTQIDSPLNGKVT (SEQ ID NO:67), PFFSWRTQIDSPLNGKVTNE (SEQ ID NO:68), SRKLEKGI (SEQ ID NO:69), CESRKLEKGIQV (SEQ ID NO:70), ATCESRKLEKGIQVEI (SEQ ID NO:71), LCTATCESRKLEKGIQVEIYSFPKDPE (SEQ ID NO:72), GHKKLEKGIQVEL (SEQ ID NO:73), VTCGHKKLEKGI (SEQ ID NO:74), TCGHKKLEKGIQVELYSFPRDPE (SEQ ID NO:75), PVSFENEHSYLCTVTCGHKKLEKG (SEQ ID NO:76), RTQIDSPLSGK (SEQ ID NO:77), FSWRTQIDSPLSGKVR (SEQ ID NO:78), and/or ESPSFWWRTQIDSPLSGK (SEQ ID NO:79).

In another preferred embodiment, an integrin α4β1 ligand that is present in the ECM is exemplified by fibronectin. An exemplary polypeptide sequence of fibronectin is shown in FIG. 4. In another preferred embodiment, the integrin α4β1 ligand is a portion of fibronectin. Preferred portions of fibronectin as exemplified in FIG. 4 include the IIICS sequence (SEPLIGRKKTDELPQLVTLPHPNLHGPE ILDVPSTVQKTPFVTBPGYDTGNGIQLPGTS-GQQPSVGQQMIFEEHGFRRTTPPTTAT PIRHRPRPYP-PNVGEEIQIGHIPREDVDYHLYPHGPGLNPNAST) (SEQ ID NO:18) from amino acid 1982 to amino acid 2111, which encodes two α4β1 binding sites. In one more preferred embodiment, the portion comprises the CS-1 sequence which contains the amino acid sequence LDV (SEQ ID NO:19) (from amino acid 2011 to amino acid 2013). In an alternative embodiment, the portion comprises the CS-5 sequence which contains the amino acid sequence REDV (SEQ ID NO:20) (from amino acid 2091 to amino acid 2094). In yet another preferred embodiment, the portion comprises the amino acid sequence IDAPS (SEQ ID NO:21) (from amino acid 1903 to amino acid 1907). The invention further includes portions of fibronectin that contain the fore-mentioned sequences, as exemplified by, but not limited to, the sequences TAIDAPSNLRDAS (SEQ ID NO:80), TAIDAPSNLRFLATTP (SEQ ID NO:81), RSSPVVIDASTAIDAPS (SEQ ID NO:82), IDAPSNLRFLATTPNSLLV (SEQ ID NO:83), IDAPSNLR-FLATTPNSLLVSWQPPRARITGYIIKYE (SEQ ID NO:84), IDDVPST (SEQ ID NO:85), NLHGPEILDVPSTVQK (SEQ ID NO:86), PHPNLHGPEILDV (SEQ ID NO:87), ILDVPSTVQKTPFVTHPGYD (SEQ ID NO:88), VTLPHPNLHGPEILDVP (SEQ ID NO:89), EILDV (SEQ ID NO:90), IPREDVDY (SEQ ID NO:91), GHIPRDDVD (SEQ ID NO:92), GHIPREDV (SEQ ID NO:93), LDVPSTVQKTPFVTHPGYDTGNGIQLPGTS-GQQPSVGQQMIFEEHG FRRTTPPTTATPIRHRPRPYP- PNVGEEIQIGHIPREDV (SEQ ID NO:94), and/or PEIDVQSTVQKTPFVTHPGYDT-GNGIQLPGTSGQQPSVGQQMIFEEHGFRRTTPPTT TATPIRHRRRPYPPNVGEEIQIGHIPREDVDY (SEQ ID NO:95).

Integrin α4β1 ligands other than VCAM, fibronectin, and portions thereof are also contemplated to be within the scope of the invention. These ligands may be determined using routine methods available to those skilled in the art. For example, the existence of antibodies against VCAM, fibronectin, and integrin α4β1 makes possible methods for isolating other integrin α4β1 and integrin α4β1 ligands. One method takes advantage of an antibody characteristic known as idiotypy. Each antibody contains a unique region that is specific for an antigen. This region is called the idiotype. Antibodies themselves contain antigenic determinants; the idiotype of an antibody is an antigenic determinant unique to that molecule. By immunizing an organism with antibodies, one can raise "anti-antibodies" that recognize antibodies, including antibodies that recognize the idiotype. Antibodies that recognize the idiotype of another antibody are called anti-idiotypic antibodies. Some anti-idiotypic antibodies mimic the shape of the original antigen that the antibody recognizes and are said to bear the "internal image" of the antigen (Kennedy (1986) Sci. Am. 255:48-56). For example, anti-idiotypic antibodies have been successfully generated against anti-ELAM1 antibodies and were found to recognize the ELAM1 ligand, which (similarly to integrin α4β1) is a molecule expressed on the surface of endothelial cells (U.S. Pat. No. 6,252,043, incorporated in its entirety by reference).

When the antigen is a ligand, certain anti-idiotypes can bind to that ligand's receptor. Several of these have been identified, including anti-idiotypes that bind to receptors for insulin, angiotensin II, adenosine I, adrenalin, and rat brain nicotine and opiate receptors (Carlsson and Glad (1989) Bio/Technology 7:567-73).

B. Agents which Alter Binding of Integrin α4β1 to its Ligands

Some preferred methods of the present invention include the step of utilizing an agent that alters (i.e., increases or decreases) the specific binding of α4β1 to one or more of its ligands. The term "specific binding," as used herein in reference to the binding of an agent to either integrin α4β1 or an integrin α4β1 ligand, means that the interaction is dependent upon the presence of a particular structure on integrin α4β1 or its ligand, respectively. For example, if an agent is specific for epitope "A," the presence of a protein containing epitope A (or free, unlabelled A) in a reaction containing labeled "A" and the agent will reduce the amount of labeled A bound to the agent.

The terms "inhibit the specific binding" and "reduce the specific binding" when used in reference to the effect of an agent on the specific binding of integrin α4β1 with an integrin α4β1 ligand, mean that the agent reduces the level of specific binding of integrin α4β1 with its ligand to a quantity which is preferably 10% less than, more preferably 50% less than, yet more preferably 75% less than, even more preferably 90% less than, the quantity of specific binding in a control sample, and most preferably is at the same level which is observed in a control sample, as detected by (for example) an Enzyme Linked Immunosorbant Assay (ELISA). A reduced level of specific binding need not, although it may, mean an absolute absence of specific binding. The invention does not require, and is not limited to, methods that wholly eliminate specific binding of integrin α4β1 with its ligand.

The term "antagonist" is used herein to mean a molecule, (e.g. antibody) which can inhibit the specific binding of a receptor and its ligand. An anti-α4β1 integrin antibody, which inhibits the specific binding of α4β1 with fibronectin, is an example of an α4β1 antagonist. An antagonist can act as a competitive inhibitor or a noncompetitive inhibitor of α4β1 binding to its ligand.

The terms "agent," "test agent," "test compound," "compound," "molecule," and "test molecule," refer to any type of molecule (for example, a peptide, nucleic acid, carbohydrate, lipid, organic, and inorganic molecule, etc.) obtained from any source (for example, plant, animal, and environmental source, etc.), or prepared by any method (for example, purification of naturally occurring molecules, chemical synthesis, genetic engineering methods, etc.). Agents comprise both known and potential compounds. Agents are exemplified by, but not limited to, antibodies, nucleic acid sequences such as antisense and ribozyme sequences, and compounds produced by chemical libraries, phage libraries, etc. as further described below.

Without intending to limit the invention to any mechanism, and recognizing that an understanding of a mechanism is not required, it is contemplated that an agent can inhibit the specific binding of an integrin α4β1 receptor with its ligand by various mechanisms, including, for example, by binding to the binding site which is located on the ligand (e.g., VCAM) thereby inhibiting the binding of the integrin α4β1 receptor to its binding site on the ligand, or by binding to a site other than the binding site on the ligand and sterically hindering the binding of the integrin α4β1 receptor to the binding site on the ligand. Alternatively, the agent may bind to integrin α4β1 (rather than to the integrin α4β1 ligand) thereby causing a conformational or other change in the receptor that inhibits binding of integrin α4β1 to the ligand.

1. Antibodies

In one embodiment, the agent that inhibits the specific binding of α4β1 to one or more of its ligands is an antibody. The terms "antibody" and "immunoglobulin" are interchangeably used to refer to a glycoprotein or a portion thereof (including single chain antibodies), which is evoked in an animal by an immunogen and which demonstrates specificity to the immunogen, or, more specifically, to one or more epitopes contained in the immunogen. The term "antibody" expressly includes within its scope antigen binding fragments of such antibodies, including, for example, Fab, F(ab')$_2$, Fd or Fv fragments of an antibody. The antibodies of the invention also include chimeric and humanized antibodies. Antibodies may be polyclonal or monoclonal. The term "polyclonal antibody" refers to an immunoglobulin produced from more than a single clone of plasma cells; in contrast "monoclonal antibody" refers to an immunoglobulin produced from a single clone of plasma cells.

Antibodies contemplated to be within the scope of the invention include naturally occurring antibodies as well as non-naturally occurring antibodies, including, for example, single chain antibodies, chimeric, bifunctional and humanized antibodies, as well as antigen-binding fragments thereof. Naturally occurring antibodies may be generated in any species including murine, rat, rabbit, hamster, human, and simian species using methods known in the art. Non-naturally occurring antibodies can be constructed using solid phase peptide synthesis, can be produced recombinantly or can be obtained, for example, by screening combinatorial libraries consisting of variable heavy chains and variable light chains as previously described (Huse et al., Science 246:1275-1281 (1989)). These and other methods of making, for example, chimeric, humanized, CDR-grafted, single chain, and bifunctional antibodies are well known to those skilled in the art (Winter and Harris, Immunol. Today 14:243-246 (1993); Ward et al., Nature 341:544-546 (1989); Hilyard et al., Protein Engineering: A practical approach (IRL Press 1992); and Borrabeck, Antibody Engineering, 2d ed. (Oxford University Press 1995).

As used herein, the term "antibody" when used in reference to an anti-integrin antibody, particularly an anti-integrin α4β1 antibody, refers to an antibody which specifically binds to one or more epitopes on an integrin α4β1 polypeptide or peptide portion thereof, and which may or may not include some or all of an RGD binding domain. In one embodiment, an anti-integrin α4β1 antibody, or antigen binding fragment thereof, is characterized by having specific binding activity for integrin α4β1 of at least about $1\times10^5 M^{-1}$, more preferably at least about $1\times10^6 M^{-1}$, and yet more preferably at least about $1\times10^7 M^{-1}$.

Those skilled in the art know how to make polyclonal and monoclonal antibodies that are specific to a desirable polypeptide. For example, monoclonal antibodies may be generated by immunizing an animal (e.g., mouse, rabbit, etc.) with a desired antigen and the spleen cells from the immunized animal are immortalized, commonly by fusion with a myeloma cell.

Immunization with antigen may be accomplished in the presence or absence of an adjuvant (e.g., Freund's adjuvant). Typically, for a mouse, 10 µg antigen in 50-200 µl adjuvant or aqueous solution is administered per mouse by subcutaneous, intraperitoneal or intramuscular routes. Booster immunization may be given at intervals (e.g., 2-8 weeks). The final boost is given approximately 24 days prior to fusion and is generally given in aqueous form rather than in adjuvant.

Spleen cells from the immunized animals may be prepared by teasing the spleen through a sterile sieve into culture medium at room temperature, or by gently releasing the spleen cells into medium by pressure between the frosted ends of two sterile glass microscope slides. The cells are harvested by centrifugation (400×g for 5 min.), washed and counted.

Spleen cells are fused with myeloma cells to generate hybridoma cell lines. Several mouse myeloma cell lines which have been selected for sensitivity to hypoxanthine-aminopterin-thymidine (HAT) are commercially available and may be grown in, for example, Dulbecco's modified Eagle's medium (DMEM) (Gibco BRL) containing 10-15% fetal calf serum. Fusion of myeloma cells and spleen cells may be accomplished using polyethylene glycol (PEG) or by electrofusion using protocols that are routine in the art. Fused cells are distributed into 96-well plates followed by selection of fused cells by culture for 1-2 weeks in 0.1 ml DMEM containing 10-15% fetal calf serum and HAT. The supernatants are screened for antibody production using methods well known in the art. Hybridoma clones from wells containing cells that produce antibody are obtained (e.g., by limiting dilution). Cloned hybridoma cells ($4-5\times10^6$) are implanted intraperitoneally in recipient mice, preferably of a BALB/c genetic background. Sera and ascites fluids are typically collected from mice after 10-14 days.

The invention also contemplates humanized antibodies that are specific for at least a portion of integrin α4β1 and/or its ligands. Humanized antibodies may be generated using methods known in the art, including those described in U.S. Pat. Nos. 5,545,806; 5,569,825 and 5,625,126, the entire contents of which are incorporated by reference. Such methods include, for example, generation of transgenic non-human animals which contain human immunoglobulin chain genes and which are capable of expressing these genes to produce a repertoire of antibodies of various isotypes encoded by the human immunoglobulin genes.

In a preferred embodiment, the antibody is specific for (i.e., specifically binds to) integrin α4β1 and/or a portion thereof. While the invention is illustrated using antibodies to the C-terminus of fibronectin and to integrin α4β1, and using exemplary peptide antagonists to integrin α4β1, the invention is not limited to the use of these particular agents. Rather, the invention expressly includes any agent which inhibits the specific binding of integrin α4β1 to one or more integrin α4β1 ligands. In one preferred embodiment, the anti-integrin α4β1 antibody binds integrin α4β1 with at least 2 times greater, preferably at least 5 times greater, more preferably at least 10 times greater, and yet more preferably at least 100 times greater, affinity than it binds another integrin, for example, αVβ3 and/or αVβ5. Anti-integrin α4β1 antibodies include, without limitation, mouse anti-human integrin α4β1 antibodies such as HP2/1, HP1/3, HP 1/1, HP1/7, HP2/4 (Sanchez-Madrid et al. (1986) Eur. J. Immunol. 16, 1342-1349), ALC1/4.1, ALC 1/5.1 (Munoz et al. (1997) Biochem J., 327, 27-733), 44H6 (Quackenbush et al. (1985) J. Immunol. 134: 1276-1285), P1H4, P4C2, P4G9 (Wayner et al. (1998) J. Cell Biol. 109:1321), 9C10 (Kinashi et al. (1994) Blood Cells 20: 25-44)), 9F10 (Hemler et al. (1987) J. Biol. Chem. 262:11478), B5G10 (Hemler et al. (1987) J. Biol. Chem. 262, 3300-3309), 15/7 (Yednock et al. (1995) J. Biol. Chem. 270:28740-28750), SG/73 (Miyake et al. (1992) J. Cell Biol., 119, 653-662). Also included within the scope of this invention are humanized anti-human integrin α4β1 antibodies, such as "ANTEGREN™" (also known as natalizumab) (Tubridy et al. (1999) Neurology 53(3):466-72, Sheremata et al. (1999) Neurology 52: No. 5, Mar. 23, 1999, and Lin et al. (1998) Current Opinion in Chemical Biology 2:453-457) and the chimeric antibodies disclosed by Newman et al., U.S. Pat. No. 5,750,105, the contents of which are incorporated by reference; rat anti-mouse integrin α4β1 antibodies such as PS/2 (Chisholm et al. (1993) European J. Immunol 23: 682-688); mouse anti-rat α4β1 antibodies such as TA-2 (Issekutz (1991) J. Immunol 147:4178-4184); and rat anti-mouse α4β1 antibodies such as R1-2 (Holzmann et al. (1989) Cell 56: 37-46).

In another preferred embodiment, the antibody is specific for VCAM and/or a portion thereof. In a more preferred embodiment, the anti-VCAM antibody inhibits the binding of VCAM to α4β1 integrin but not to other integrins. Exemplary antibodies include, for example, 4B2 and 1E10, P1B8, and P3C4 (Needham et al. (1994) Cell Adhes. Commun. 2:87-99; Dittel et al. (1993) Blood 81:2272-2282), and the chimeric antibodies disclosed by Newman et al., U.S. Pat. No. 5,750, 105, the contents of which are incorporated by reference.

In yet another preferred embodiment, the antibody is specific for fibronectin and/or a portion thereof. In a more preferred embodiment, the anti-VCAM antibody inhibits the binding of VCAM to α4β1 integrin but not to other integrins. Such antibodies include, without restriction, antibodies against the major and minor integrin α4β1-binding sites in the C-terminal region of fibronectin, and antibodies against neighboring hepanin binding sites that interfere with binding of integrin α4β1 to fibronectin. Exemplary antibodies include P1F11 and P3D4 (Garcia-Pardo et al. (1992) Biochemical and Biophysical Research Communications 186(1):135-42); and the antibodies 20E10, 21E5, 9E9, 16E6, 19B7, 26G10, 30B6, 36C9, and 39B6 (Mostafavi-Pour et al. (2001) Matrix Biology 20(1):63-73).

2. Peptides

In an alternative embodiment, the agent which inhibits the specific binding of integrin α4β1 to one or more of its ligands is a peptide, such as the exemplary peptide EILDVPST (SEQ ID NO:22) which inhibits integrin α4β1 binding to its ligand (WO 03/019136 A3 to Varner). The term "peptide" as used herein is used broadly to refer to at least two amino acids and/or amino acid analogs that are covalently linked by a peptide bond and/or an analog of a peptide bond. The term peptide includes oligomers and polymers of amino acids and/or amino acid analogs. The term peptide also includes molecules which are commonly referred to as peptides, which generally contain from about two to about twenty amino acids. The term peptide also includes molecules which are commonly referred to as polypeptides, which generally contain from about twenty to about fifty amino acids. The term peptide also includes molecules which are commonly referred to as proteins, which generally contain from about fifty to about 3000 amino acids. The amino acids of the peptide antagonists may be L-amino acids and/or D-amino acids.

The terms "derivative" or "modified" when in reference to a peptide mean that the peptide contains at least one derivative amino acid. A "derivative" of an amino acid and a "modified" amino acid are chemically modified amino acids. Derivative amino acids can be "biological" or "non-biological" amino acids. Chemical derivatives of one or more amino acid members may be achieved by reaction with a functional side group. Illustrative derivatized molecules include for example those molecules in which free amino groups have been derivatized to form amine hydrochlorides, p-toluene sulfonyl groups, carboxybenzoxy groups, t-butyloxycarbonyl groups, chloroacetyl groups and/or formyl groups. Free carboxyl groups may be derivatized to form salts, methyl and ethyl esters and/or other types of esters and hydrazides. Free hydroxyl groups may be derivatized to form O-acyl and/or O-alkyl derivatives. The imidazole nitrogen of histidine may be derivatized to form N-im-benzylhistidine. Also included as chemical derivatives are those peptides that contain naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine for lysine. Other included modifications are amino terminal acylation (e.g., acetylation or thioglycolic acid amidation), terminal carboxylamidation (e.g., with ammonia or methylamine), and similar terminal modifications. Terminal modifications are useful, as is well known, to reduce susceptibility by proteinase digestion and therefore to prolong the half-life of the peptides in solutions, particularly in biological fluids where proteases may be present. Exemplary modified amino acids include, without limitation, 2-Aminoadipic acid, 3-Aminoadipic acid, beta-Alanine, beta-Aminopropionic acid, 2-Aminobutyric acid, 4-Aminobutyric acid, piperidinic acid, 6-Aminocaproic acid, 2-Aminoheptanoic acid, 2-Aminoisobutyric acid, 3-Aminoisobutyric acid, 2-Aminopimelic acid, 2,4-Diaminobutyric acid, Desmosine, 2,2'-Diaminopimelic acid, 2,3-Diaminopropionic acid, N-Ethylgilycine, N-Ethylasparagine, Hydroxylysine, allo-Hydroxylysine, 3-Hydroxyproline, 4-Hydroxyproline, Isodesmosine, allo-Isoleucine, N-Methylglycine, sarcosine, N-Methylisoleucine, N-Methylavaline, Norvaline, Norleucine, and Ornithine. Derivatives also include peptides containing one or more additions or deletions, as long as the requisite activity is maintained.

The amino acids of the peptides are contemplated to include biological amino acids as well as non-biological amino acids. The term "biological amino acid" refers to any one of the known 20 coded amino acids that a cell is capable of introducing into a polypeptide translated from an mRNA. The term "non-biological amino acid" refers to an amino acid that is not a biological amino acid. Non-biological amino acids are useful, for example, because of their stereochemistry or their chemical properties. The non-biological amino acid norleucine, for example, has a side chain similar in shape to that of methionine. However, because it lacks a side chain sulfur atom, norleucine is less susceptible to oxidation than methionine. Other examples of non-biological amino acids include aminobutyric acids, norvaline and allo-isoleucine, that contain hydrophobic side chains with different steric properties as compared to biological amino acids.

Peptides that are useful in the instant invention may be synthesized by several methods, including chemical synthesis and recombinant DNA techniques. Synthetic chemistry techniques, such as solid phase Merrifield synthesis are preferred for reasons of purity, freedom from undesired side products, ease of production, etc. A summary of the techniques available are found in several references, including Steward et. al., Solid Phase Peptide Synthesis, W. H. Freeman, Co., San Francisco (1969); Bodanszky, et. al., Peptide Synthesis, John Wiley and Sons, Second Edition (1976); J. Meienhofer, Hormonal Proteins and Peptides, 2: 46, Academic Press (1983); Merrifield, Adv. Enzymol. 32: 221-96 (1969); Fields et. al., Intl. Peptide Protein Res., 35: 161-214 (1990), and U.S. Pat. No. 4,244,946 for solid phase peptide synthesis; and Schroder et al., The Peptides, Vol 1, Academic Press (New York) (1965) for classical solution synthesis. Protecting groups usable in synthesis are described as well in Protective Groups in Organic Chemistry, Plenum Press, New York (1973). Solid phase synthesis methods consist of the sequential addition of one or more amino acid residues or suitably protected amino acid residues to a growing peptide chain. Either the amino or carboxyl group of the first amino acid residue is protected by a suitable selectively removable protecting group. A different, selectively removable protecting group is utilized for amino acids containing a reactive side group such as lysine.

The resultant linear peptides may then be reacted to form their corresponding cyclic peptides. A method for cyclizing peptides is described in Zimmer et. al., Peptides, 393-394 (1992), ESCOM Science Publishers, B.V., 1993. To cyclize peptides containing two or more cysteines through the formation of disulfide bonds, the methods described by Tam et al., J. Am. Chem. Soc., 113: 6657-6662 (1991); Plaue, Int. J. Peptide Protein Res., 35: 510-517 (1990); Atherton, J. Chem. Soc. Trans. 1: 2065 (1985); and B. Kamber et. al., Helv. Chim. Acta 63: 899 (1980) are useful. Polypeptide cyclization is a useful modification to generate modified peptides (e.g., peptidomimetics) because of the stable structures formed by cyclization and in view of the biological activities observed for cyclic peptides.

Alternatively, selected compounds of the present invention are produced by expression of recombinant DNA constructs prepared in accordance with well-known methods once the peptides are known. Such production can be desirable to provide large quantities or alternative embodiments of such compounds. Production by recombinant means may be more desirable than standard solid phase peptide synthesis for peptides of at least 8 amino acid residues. The DNA encoding the desired peptide sequence is preferably prepared using commercially available nucleic acid synthesis methods. Following these nucleic acid synthesis methods, DNA is isolated in a purified form that encodes the peptides. Methods to construct expression systems for production of peptides in recombinant hosts are also generally known in the art. Preferred recombinant expression systems, when transformed into compatible hosts, are capable of expressing the DNA encoding the peptides. Other preferred methods used to produce peptides comprise culturing the recombinant host under conditions that are effective to bring about expression of the encoding DNA to produce the peptide of the invention and ultimately to recover the peptide from the culture.

Expression can be effected in prokaryotic and eukaryotic hosts. The prokaryotes are most frequently represented by various strains of E. coli. However, other microbial strains may also be used, such as bacilli, for example Bacillus subtilis, various species of Pseudomonas, or other bacterial strains. In such prokaryotic systems, plasmid vectors that contain replication sites and control sequences derived from a species compatible with the host are used. For example, a workhorse vector for E. coli is pBR322 and its derivatives. Commonly used prokaryotic control sequences, which contain promoters for transcription initiation, optionally with an operator, along with ribosome binding-site sequences, include such commonly used promoters as the beta-lactamase (penicillinase) and lactose (lac) promoter systems, the tryptophan (trp) promoter system, and the lambda-derived $P_L$ promoter and N-gene ribosome binding site. However, any available promoter system compatible with prokaryote expression is suitable for use.

Expression systems useful in eukaryotic hosts comprise promoters derived from appropriate eukaryotic genes. A class of promoters useful in yeast, for example, includes promoters for synthesis of glycolytic enzymes (e.g., those for 3-phosphoglycerate kinase). Other yeast promoters include those from the enolase gene or the Leu2 gene obtained from YEp13. Suitable mammalian promoters include the early and late promoters from SV40 or other viral promoters such as those derived from polyoma, adenovirus II, bovine papilloma virus or avian sarcoma viruses. Suitable viral and mammalian enhancers may also be used. In the event plant cells are used as an expression system, the nopaline synthesis promoter, for example, is appropriate.

Once the expression systems are constructed using wellknown restriction and ligation techniques, transformation of appropriate host cells is done using standard techniques appropriate to such cells. The cells containing the expression systems are cultured under conditions appropriate for production of the peptides, and the peptides are then recovered and purified.

In a preferred embodiment, the agent that specifically binds integrin α4β1 finds use in methods of the invention where the peptide binds to integrin α4β1 with at least about a two-fold greater, more preferably at least about five-fold greater, even more preferably at least about ten-fold greater, and most preferably at least about one hundred-fold greater, specificity for integrin α4β1 than for another integrin such as αVβ3. As such, the various RGD and RLD containing peptides that have been identified based on their relatively high binding affinity for integrin αVβ3 or for integrin αVβ5 (PCT/US94/13542) are not considered peptide antagonists of integrin α4β1 binding to its ligand, as defined herein.

Exemplary peptides which inhibit the specific binding of integrin α4β1 to one or more of its ligands include, without limitation, CS-1 fibronectin and fragments of CS-1 fibronectin, such as DELPQLVTLPHPNLHGPEILDVPST (SEQ ID NO:23), HGPEILDVPST (SEQ ID NO:24), and EILDV (SEQ ID NO:25) (Wayner et al., J. Cell Biol. (1989) 109(3): 1321-30); LDVP (SEQ ID NO:26) (Clements et al., J. Cell Sci. (1994) 107 (Pt 8):2127-35), LDV (SEQ ID NO:27) (Wayner et al., J. Cell Biol. (1992) 116(2):489-97); IDAP (SEQ ID NO:28) and RDV (SEQ ID NO:29) (Clements et al., J. Cell Sci. (1994) 107 (Pt 8):2127-35); GPEYLDVP (SEQ ID NO:30) (Bochner et al., J. Exp. Med. (1991) 173(6):1553-7); (X) C*DPC* (SEQ ID NO:40) where X is any amino acid or modified amino acid, (X) C*(X)PC* (SEQ ID NO:31) where X is any amino acid, RC*DPC* (SEQ ID NO:32), C*WLDVC* (SEQ ID NO:33), YC*APC* (SEQ ID NO:34) and YC*DPC* (SEQ ID NO:35), and phenyacyl-C*DfC* (SEQ ID NO:36) (where "f" is D-Phe) (Jackson et al., J. Med. Chem. (1997) 40(21):3359-68); RC*D(ThioP)C* (SEQ ID NO:37) (Nowlin et al., J. Biol. Chem. (1993) September 25, 268(27):20352-9); 9-fluorenecarboxylRC*D(ThioP)C* (SEQ ID NO:38) (Cardarelli et al., J. Biol. Chem. (1994) 269(28):18668-73); EGYYGNYGVYA (SEQ ID NO:39) and C*YYGNC* (SEQ ID NO:97) where * indicates cyclization points; and modifications thereof (Thorsett et al., inhibitors of leukocyte adhesion (1996) WO9602644); 1-adamantaneacetyl-Cys-Gly-Arg-Gly-Asp-Ser-Pro-Cys (SEQ ID NO:41) (Cardarelli et al., J. Biol. Chem. (1994) 269(28): 18668-73). Other exemplary peptides include snake disintegrins, which are exemplified by, but not limited to, EC3 from Echis carinatus, EC3B which is a subunit of EC3 and which has the sequence NSVHPCCDPVTCEPREGEHCISGPC-CRNCKFLNAGTICKRAMLDGLNDYCTGKSSD CPRN-RYKGKED (SEQ ID NO:42), MLDG (SEQ ID NO:43), a peptide fragment of EC3; and modifications thereof (Brando et al., Biochem. Biophys. Res. Commun. (2000) 267(1):413-417, and Marcinkiewicz et al., J. Biol. Chem. (1999) 274 (18):1 2468-73); soluble VCAM (Rose et al. (2000) Blood 95:602-609); soluble VCAM fragments (Dudgeon et al., Eur. J. Biochem. (1994) 226(2):517-23); VCAM peptide sequences RTQIDSPLN (SEQ ID NO:44), TQIDSP (SEQ ID NO:45), QIDS (SEQ ID NO:46), IDSP (SEQ ID NO:47) and KLEK (SEQ ID NO:48) (Clements et al., J. Cell Sci. (1994) 107 (Pt 8): 2127-35).

Figure 5:
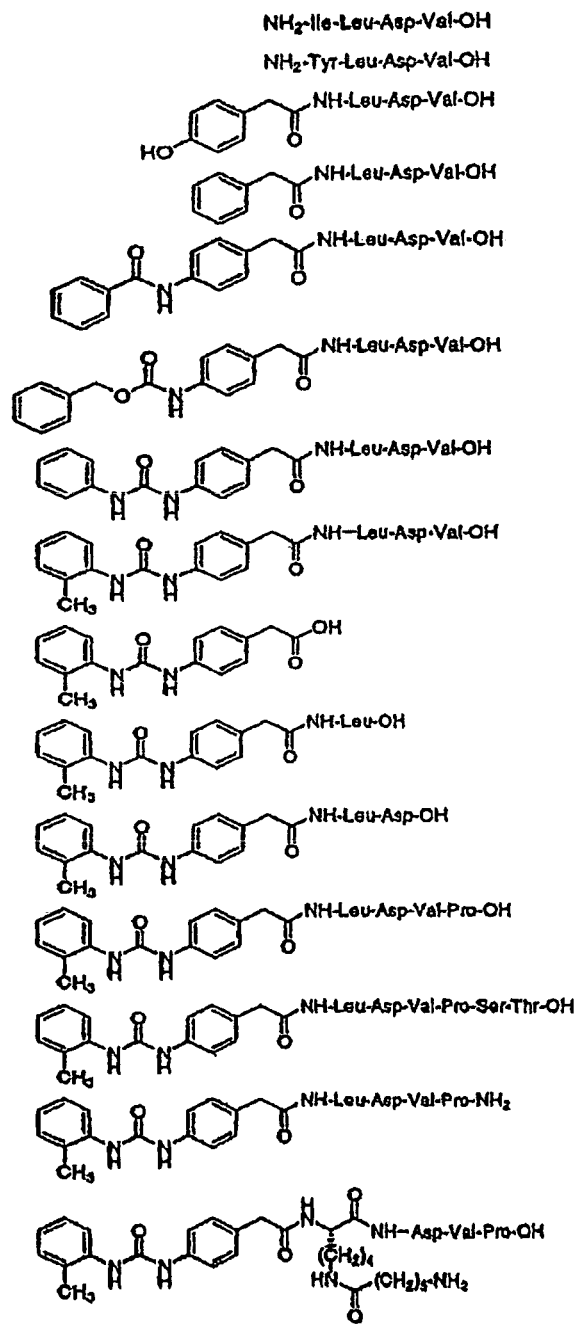
FIG. 5 shows exemplary agents which inhibit binding of integrin α4β1 to VCAM.
Figure 6:
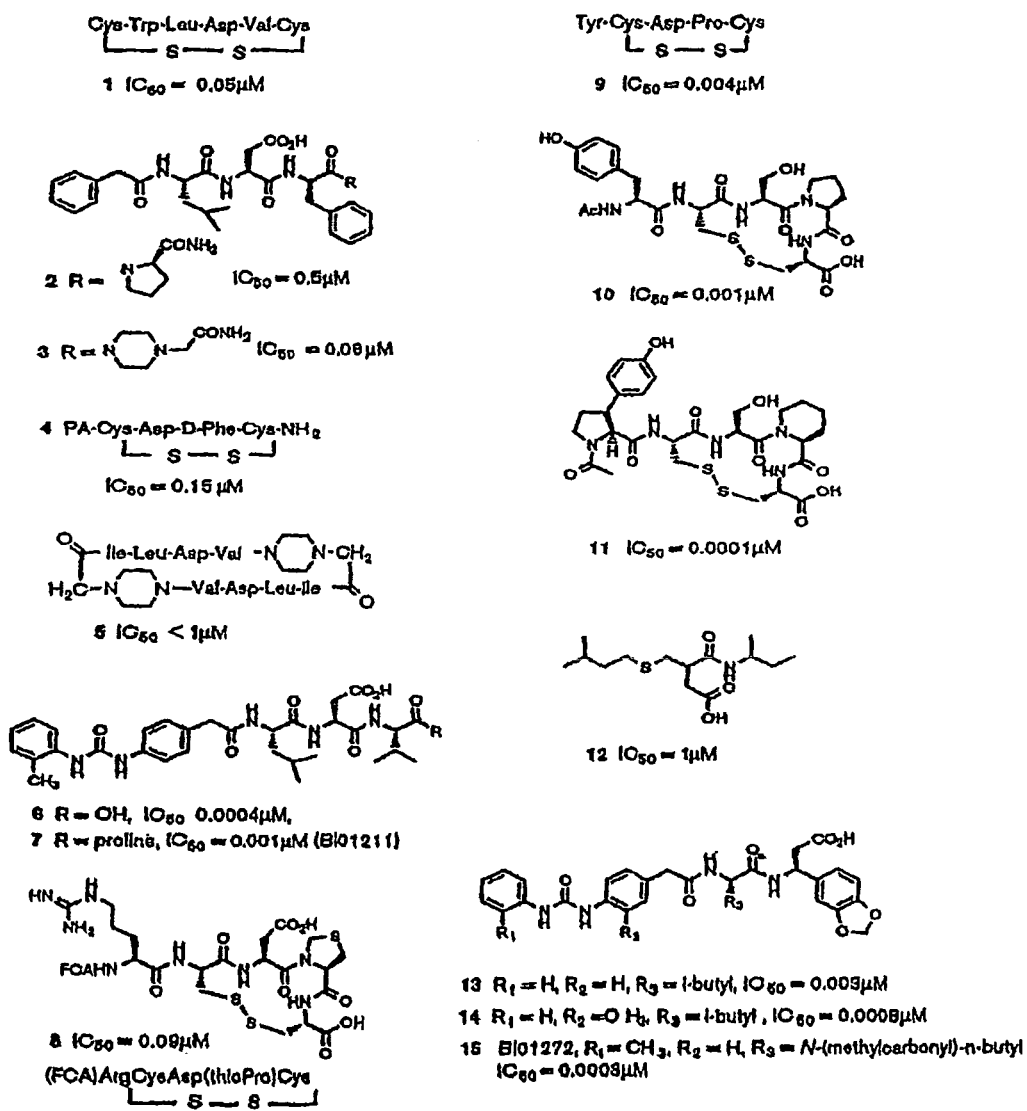
FIG. 6 shows exemplary agents which inhibit binding of integrin α4β1 to its ligands, with IC50 values based on direct binding assays. In this Figure, the abbreviations are as follows: FCA, 9-fluorenecarboxyl; IC, inhibition concentration; PA, phenylacetyl.
Figure 7:
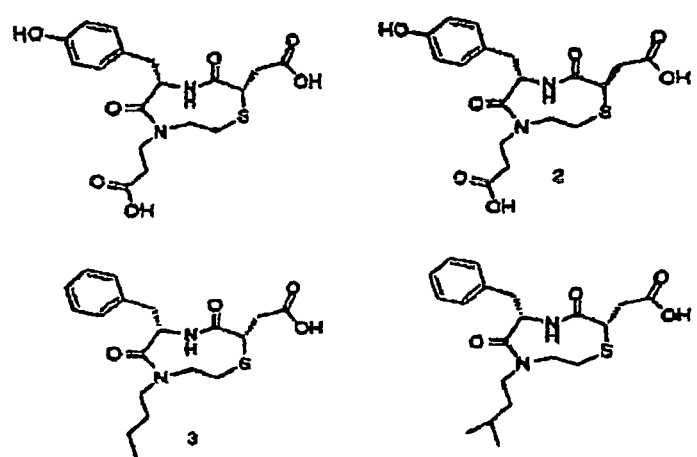
FIG. 7 shows exemplary β-turn mimetics which inhibit binding of integrin α4β1 to fibronectin.

Further exemplary modified peptides which inhibit the specific binding of integrin α4β1 to one or more of its ligands include a peptidomimetic (i.e., an organic molecules that mimics the structure of a peptide); or a peptoid such as a vinylogous peptoid. Examples of cyclic peptides and peptidomimetics which are within the scope of the invention include, without limitation, those which are based on the peptide structure GPEYLDVP (SEQ ID NO:49), such as the compound named TBC722 (Kogan et al., WO9600581), based on the peptide structure LDVP (SEQ ID NO:50) including phenylacetyl LDFp (Arrhenius et al., WO9515973; Arrhenius et al., WO9606108), based on the peptide structure ILDV (SEQ ID NO:51) (Dutta, WO9702289); BIO1211 (4-(2-methylphenylluriedo)phenylacetyl LDVP) BIO1272 (Lin et al., WO9200995; Lin et al., WO9622966), CY9652 a CS-1 peptidomimetic, TBC3342, ZD-7349 (Curley et al. (1999) Cell. Mol. Life Sci., 56:427-441); and others (EP-842943-A2, WO9842656-A1, WO9620216-A1, WO9600581-A1, Souers et al. (1998) Bioorg. Med. Chem. Lett., 8:2297-2302). Exemplary peptides and modified peptides are illustrated in FIG. 5 (see, Lin et al. (1999) J. Med. Chem., 42:920-934), FIG. 6 (See, Lin et al. (1998) Curr. Opin. Chem. Biol., 2:453-457), and FIG. 7 (See, Souers et al. (1998) Bioorg. Med. Chem. Lett., 8:2297-2302). Methods for generating libraries of mimetics and for evaluating the library of mimetics for inhibiting the binding of receptors to their ligands are known in the art (Souers et al. (1998) supra).

Other peptides useful as α4β1 antagonists that reduce angiogenesis can be purchased from commercial sources, and can be identified by screening libraries of peptides, which can be prepared using well known methods of chemical synthesis (Koivunen et al. J. Cell Biol., 124: 373-380 (1994)). For example, peptide agonists of integrin α4β1 other than those specifically disclosed herein may be identified using methods known in the art, such as by panning phage-display peptide libraries as described in U.S. Pat. No. 5,780,426 to Palladino et al., the entire contents of which are herein incorporated by reference. For example, phage-display peptide libraries are panned with the integrin α4β1 receptor attached to a solid support, such as small diameter (1 μm) polystyrene latex beads. Phage selected by this method can then be tested for specific binding to integrin α4β1 via ELISA or other immunologically-based assays. Individual peptide sequences are then determined via sequencing of phage DNA. Further analysis of the minimal peptide sequence required for binding can be assessed via deletion and site-directed mutagenesis, followed by testing of the phage for binding to integrin α4β1 via ELISA. Since the identified peptide candidates are fused to the major phage coat protein, soluble peptides are then chemically synthesized and the activity of these free peptides are tested in various in vitro and in vivo assays for the ability to act as antagonists of the integrin α4β1 receptor.

3. Nucleic Acid Sequences

In an alternative embodiment, the agent that inhibits the specific binding of α4β1 to one or more of its ligands is a nucleic acid sequence. The terms "nucleic acid sequence" and "nucleotide sequence" as used herein refer to two or more nucleotides that are covalently linked to each other. Included within this definition are oligonucleotides, polynucleotide, and fragments and/or portions thereof, DNA and/or RNA of genomic and/or synthetic origin which may be single- or double-stranded, and represent the sense or antisense strand. Nucleic acid sequences that are particularly useful in the instant invention include, without limitation, antisense sequences and ribozymes. The nucleic acid sequences are contemplated to bind to genomic DNA sequences or RNA sequences that encode integrin α4β1 or one or more of its ligands, thereby inhibiting the binding of integrin α4β1 with one or more of its ligands. Antisense and ribozyme sequences may be delivered to cells by transfecting the cell with a vector that expresses the antisense nucleic acid or the ribozyme as an mRNA molecule. Alternatively, delivery may be accomplished by entrapping ribozymes and antisense sequences in liposomes.

a. Antisense Sequences

Antisense sequences have been successfully used to inhibit the expression of several genes (Markus-Sekura (1988) Anal. Biochem. 172:289-295; Hambor et al. (1988) J. Exp. Med. 168:1237-1245; and patent EP 140 308), including the gene encoding VCAM1, one of the integrin α4β1 ligands (U.S. Pat. No. 6,252,043, incorporated in its entirety by reference). The terms "antisense DNA sequence" and "antisense sequence" as used herein interchangeably refer to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Sense mRNA generally is ultimately translated into a polypeptide. Thus, an "antisense DNA sequence" is a sequence which has the same sequence as the non-coding strand in a DNA duplex, and which encodes an "antisense RNA" (i.e., a ribonucleotide sequence whose sequence is complementary to a "sense mRNA" sequence). The designation (−) (i.e., "negative") is sometimes used in reference to the antisense strand, with the designation (+) sometimes used in reference to the sense (i.e., "positive") strand. Antisense RNA may be produced by any method, including synthesis by splicing an antisense DNA sequence to a promoter that permits the synthesis of antisense RNA. The transcribed antisense RNA strand combines with natural mRNA produced by the cell to form duplexes. These duplexes then block either the further transcription of the mRNA or its translation, or promote its degradation.

Any antisense sequence is contemplated to be within the scope of this invention if it is capable of reducing the level of expression of integrin α4β1 and/or one or more of its ligands (e.g., VCAM and fibronectin) to a quantity which is less than the quantity of integrin α4β1 or integrin α4β1 ligand expression in a control tissue which is (a) not treated with the antisense integrin α4β1 or integrin α4β1 ligand sequence, (b) treated with a sense integrin α4β1 or integrin α4β1 ligand sequence, or (c) treated with a nonsense sequence.

The terms "reducing the level of expression of integrin α4β1 or integrin α4β1 ligand," "diminishing integrin α4β1 or integrin α4β1 ligand expression" and grammatical equivalents thereof, refer to reducing the level of integrin α4β1 or integrin α4β1 ligand expression to a quantity which is preferably 20% less than the quantity in a control tissue, more preferably is 50% less than the quantity in a control tissue, yet more preferably is 90% less than the quantity in a control tissue, and most preferably is at the background level of, or is undetectable by, a Western blot analysis of integrin α4β1 or integrin α4β1 ligand, by immunofluorescence for detection of integrin α4β1 or integrin α4β1 ligand, by reverse transcription polymerase chain (RT-PCR) reaction for detection of integrin α4β1 or integrin α4β1 ligand mRNA, or by in situ hybridization for detection of integrin α4β1 or integrin α4β1 ligand mRNA. When a background level or undetectable level of integrin α4β1 or integrin α4β1 ligand peptide or mRNA is measured, this may indicate that integrin α4β1 or integrin α4β1 ligand is not expressed. A reduced level of integrin α4β1 or integrin α4β1 ligand need not, although it may, mean an absolute absence of expression of integrin α4β1 or integrin α4β1 ligand. The invention does not require, and is not limited to, antisense integrin α4β1 or integrin α4β1 ligand sequences that eliminate expression of integrin α4β1 or integrin α4β1 ligand.

Antisense integrin α4β1 or integrin α4β1 ligand sequences capable of reducing the level of integrin α4β1 expression include, for example, sequences which are capable of hybridizing with at least a portion of integrin α4β1 cDNA or integrin α4β1 ligand cDNA under high stringency or medium stringency conditions. Antisense integrin α4β1 sequences and antisense integrin α4β1 ligand sequences within the scope of this invention may be designed using approaches known in the art. In a preferred embodiment, the antisense integrin α4β1 sequences and antisense integrin α4β1 ligand sequences are designed to be hybridizable to integrin α4β1 mRNA or to integrin α4β1 ligand mRNA which is encoded by the coding region of the integrin α4β1 gene and the integrin α4β1 ligand gene, respectively. Alternatively, antisense integrin α4β1 or integrin α4β1 ligand sequences may be designed to reduce transcription by hybridizing to upstream nontranslated sequences, thereby preventing promoter binding to transcription factors.

In a preferred embodiment, the antisense oligonucleotide sequences of the invention range in size from about 8 to about 100 nucleotide residues. In yet a more preferred embodiment, the oligonucleotide sequences range in size from about 8 to about 30 nucleotide residues. In a most preferred embodiment, the antisense sequences have 20 nucleotide residues.

However, the invention is not intended to be limited to the number of nucleotide residues in the oligonucleotide sequence disclosed herein. Any oligonucleotide sequence that is capable of reducing the expression of integrin α4β1 or of integrin α4β1 ligand is contemplated to be within the scope of this invention. For example, oligonucleotide sequences may range in size from about 3 nucleotide residues to the entire integrin α4β1 or integrin α4β1 ligand cDNA sequence. The art skilled know that the degree of sequence uniqueness decreases with decreasing length, thereby reducing the specificity of the oligonucleotide for the integrin α4β1 mRNA, or integrin α4β1 ligand mRNA.

The antisense oligonucleotide sequences that are useful in the methods of the instant invention may comprise naturally occurring nucleotide residues as well as nucleotide analogs. Nucleotide analogs may include, for example, nucleotide residues that contain altered sugar moieties, altered inter-sugar linkages (e.g., substitution of the phosphodiester bonds of the oligonucleotide with sulfur-containing bonds, phosphorothioate bonds, alkyl phosphorothioate bonds, N-alkyl phosphoramidates, phosphorodithioates, alkyl phosphonates and short chain alkyl or cycloalkyl structures), or altered base units. Oligonucleotide analogs are desirable, for example, to increase the stability of the antisense oligonucleotide compositions under biologic conditions since natural phosphodiester bonds are not resistant to nuclease hydrolysis. Oligonucleotide analogs may also be desirable to improve incorporation efficiency of the oligonucleotides into liposomes, to enhance the ability of the compositions to penetrate into the cells where the nucleic acid sequence whose activity is to be modulated is located, in order to reduce the amount of antisense oligonucleotide needed for a therapeutic effect thereby also reducing the cost and possible side effects of treatment.

Antisense oligonucleotide sequences may be synthesized using any of a number of methods known in the art, as well as using commercially available services (e.g., Genta, Inc.). Synthesis of antisense oligonucleotides may be performed, for example, using a solid support and commercially available DNA synthesizers. Alternatively, antisense oligonucleotides may also be synthesized using standard phosphoramidate chemistry techniques. For example, it is known in the art that for the generation of phosphodiester linkages, the oxidation is mediated via iodine, while for the synthesis of phosphorothioates, the oxidation is mediated with 3H-1,2-benzodithiole-3-one,1,-dioxide in acetonitrile for the step-wise thioation of the phosphite linkages. The thioation step is followed by a capping step, cleavage from the solid support, and purification on HPLC, e.g., on a PRP-1 column and gradient of acetonitrile in triethylammonium acetate, pH 7.0.

In one embodiment, the antisense DNA sequence is an "integrin α4β1 antisense DNA sequence" (i.e., an antisense DNA sequence which is designed to bind with at least a portion of the integrin α4β1 genomic sequence or with integrin α4β1 mRNA). The design of integrin α4β1 antisense DNA sequences is facilitated by the availability of the sequences for the integrin α4 subunit cDNA (FIGS. 8 and 9), and integrin β1 cDNA (FIG. 10). Particularly preferred antisense sequences are those which hybridize with genomic DNA or with RNA encoding a portion of integrin α4β1 which is involved in the specific binding with one or more of its ligands. Such integrin α4β1 portions are exemplified by, but not limited to, the sequences (see FIG. 1) which comprises the sequence IVTCGHRWKNIFYIKYNENKLPTGGCY-CVPPDLRTELSKRIAPCYQDYVKKFGENFAA SCQAG-ISSFYTKDLIVMGAPGSSY-WTGSLFVYNITTNKYKAFLDKQNQVKFGSYLG YSVGAGHFRSQHTTEVVGGAPQHE-QIGKAYIFSIDEKELNILHEMKGKK (SEQ ID NO:10) (from amino acid 141 to amino acid 301), GHRWKN IFY-IKNENKLPTGG (SEQ ID NO:11) (from amino acid 145 to amino acid 164), YQDYVKKFGENFAS (SEQ ID NO:12) (from amino acid 184 to amino acid 197), SYWTGS (SEQ ID NO:13) (from amino acid 186 to amino acid 224), GGAPQHEQIGK (SEQ ID NO:14) (from amino acid 270 to amino acid 280), YNVDTES ALLYQGPHNT IFGYSVV-LHS HGANRWLLVG APTANWLANA SVINP (SEQ ID NO:54) (from amino acid 34 to amino acid 85), GRPYN-VDTESALLYQGPHNTLFGYSVVLHSHGANRWLLVG APTANWLANASVINPGAIYR (SEQ ID NO:55), GVPT-GRPYNVDTESAL LYQGPHNT LFGYSVVLHSHGANR-WLLVGAPTANWLANASVI NPGAIYRCRIGKNPGQT (SEQ ID NO:56), IVTCGHRWKNIFYIKNENKLPTG-GCYG (SEQ ID NO:57), GHRWKNIFYIKNENKLPTG-GCYGVPPDLRTELSK (SEQ ID NO:58), APCYQDYVKKFGENFAS (SEQ ID NO:59), CYQDYVKKFGENFASCQA GISSFYTKDL (SEQ ID NO:60), GSSYWTGSLFVYNI (SEQ ID NO:61), RSQHT-TEVVGGAPQHEQIGK (SEQ ID NO:62), GGAPQHE-QIGKAYIFSIDEKEL (SEQ ID NO:63), and/or GGAPQHE-QIGKA (SEQ ID NO:64).

In another embodiment, the antisense DNA sequence is a "vascular cell adhesion molecule antisense DNA sequence," i.e., and antisense DNA sequence which is designed to bind with at least a portion of the VCAM genomic sequence or with VCAM mRNA. The selection and design of these antisense sequences is made possible by the availability of VCAM cDNA sequences (FIG. 11). Exemplary preferred antisense sequences are those which hybridize with genomic DNA or with RNA encoding a portion of VCAM (FIG. 3A, GenBank Accession Nos. P19320) which is involved in the specific binding of VCAM with integrin α4β1. Examples of at least a portion of VCAM comprise the amino acid sequence RTQIDSPLNG (SEQ ID NO:15) (from amino acid 60 to amino acid 69); RTQIDSPLSG (SEQ ID NO:16) (from amino acid 348 to amino acid 357), KLEK (SEQ ID NO:17) (from amino acid 103 to amino acid 106, and from amino acid 391 to amino acid 394), RTQIDSPLNG (SEQ ID NO:15), RTQIDSPLSG (SEQ ID NO:16), KLEK (SEQ ID NO:17), WRTQIDSPLNGK (SEQ ID NO:65), SWRTQID-SPLNGKV (SEQ ID NO:66), SWRTQIDSPLNGKVT (SEQ ID NO:67), PFFSWRTQIDSPLNGKVTNE (SEQ ID NO:68), SRKLEKGI (SEQ ID NO:69), CESRKLEKGIQV (SEQ ID NO:70), ATCESRKLEKGIQVEI (SEQ ID NO:71), LCTATCESRKLEKGIQVEIYSFPKDPE (SEQ ID NO:72), GHKKLEKGIQVEL (SEQ ID NO:73), VTCGHKKLEKGI (SEQ ID NO:74), TCGHKKLEKGIQVELYSFPRDPE (SEQ ID NO:75), PVSFENEHSYLCTVTCGHKKLEKG (SEQ ID NO:76), RTQIDSPLSGK (SEQ ID NO:77), FSWRTQIDSPLSGKVR (SEQ ID NO:78), and/or ESPSF-WWRTQIDSPLSGK (SEQ ID NO:79).

In yet another embodiment, the antisense DNA sequence is a "fibronectin α4β1 antisense DNA sequence" (i.e., an antisense DNA sequence which is designed to bind with at least a portion of the fibronectin genomic sequence or with fibronectin α4β1 mRNA). The selection and design of these antisense sequences is made possible by the availability of the sequence for fibronectin cDNA (FIG. 12). Exemplary nucleic acid sequences which may be targeted are those which encode the following sequences shown in FIG. 4, the IIICS sequence (SEPLIGRKKTDELPQLVTLPHPNLHGPE ILDVP-STVQKTPFVTHPGYDTGNGIQLPGGTS-GQQPSVGQQMIFEEHGFRRTTPPTT ATPIRHRPRPYP-PNVGEEIQIGHIPREDVVDYHLYPHGPGLNPNAST) (SEQ ID NO:18) from amino acid 1982 to amino acid 2111, the CS-1 sequence which contains the amino acid sequence LDV (SEQ ID NO:19) (from amino acid 2011 to amino acid 2013), the CS-5 sequence which contains the amino acid sequence REDV (SEQ ID NO:20) (from amino acid 2091 to amino acid 2093), IDAPS (SEQ ID NO:21) (from amino acid 1903 to amino acid 1907), TAIDAPSNLRDAS (SEQ ID NO:80), TAIDAPSNLRFLATTP (SEQ ID NO:81), RSSPV-VIDASTAIDAPS (SEQ ID NO:82), IDAPSNLRFLATTP-NSLLV (SEQ ID NO:83), IDAPSNLRFLATIT-NSLLVSWQPPRARITGYIIKYE (SEQ ID NO:84), IDDVPST (SEQ ID NO:85), NLHGPEILDVPSTVQK (SEQ ID NO:86), PHPNLHGPEILDV (SEQ ID NO:87), ILDVP-STVQKTPFVTHPGYD (SEQ ID NO:88), VTLPHPNLHG-PEILDVP (SEQ ID NO:89), EILDV (SEQ ID NO:90), IPREDVDY (SEQ ID NO:91), GHIPRDDVD (SEQ ID NO:92), GHIPREDV (SEQ ID NO:93), LDVPSTVQKT-PFVTHPGYDTGNGIQLPGTSGQQPSVGQQMIFEEHG FRRTTPPTTATPIRHRPRPYPPNVGEEIQIGHIPREDV (SEQ ID NO:94), and/or PEILDVPSTVQKTPFVTIIPGY-DTGNGIQLPGTSGQQPSVGQQMIFEEHGFRRTTPPTT TATPIRHRPRPYPPNVGEEIQIGHIPREDVDY (SEQ ID NO:95).

b. Ribozyme

In some alternative embodiments, the agent that inhibits the specific binding of integrin α4β1 to its ligand is a ribozyme. Ribozyme sequences have been successfully used to inhibit the expression of several genes including the gene encoding VCAM1, which is one of the integrin α4β1 ligands (U.S. Pat. No. 6,252,043, incorporated in its entirety by reference).

The term "ribozyme" refers to an RNA sequence that hybridizes to a complementary sequence in a substrate RNA and cleaves the substrate RNA in a sequence specific manner at a substrate cleavage site. Typically, a ribozyme contains a "catalytic region" flanked by two "binding regions." The ribozyme binding regions hybridize to the substrate RNA, while the catalytic region cleaves the substrate RNA at a "substrate cleavage site" to yield a "cleaved RNA product." The nucleotide sequence of the ribozyme binding regions may be completely complementary or partially complementary to the substrate RNA sequence with which the ribozyme binding regions hybridize. Complete complementarity is preferred, in order to increase the specificity, as well as the turnover rate (i.e., the rate of release of the ribozyme from the cleaved RNA product), of the ribozyme. Partial complementarity, while less preferred, may be used to design a ribozyme binding region containing more than about 10 nucleotides. While contemplated to be within the scope of the claimed invention, partial complementarity is generally less preferred than complete complementarity since a binding region having partial complementarity to a substrate RNA exhibits reduced specificity and turnover rate of the ribozyme when compared to the specificity and turnover rate of a ribozyme which contains a binding region having complete complementarity to the substrate RNA. A ribozyme may hybridize to a partially or completely complementary DNA sequence but cannot cleave the hybridized DNA sequence since ribozyme cleavage requires a 2'-OH on the target molecule, which is not available on DNA sequences.

The ability of a ribozyme to cleave at a substrate cleavage site may readily be determined using methods known in the art. These methods include, but are not limited to, the detection (e.g., by Northern blot analysis as described herein, reverse-transcription polymerase chain reaction (RT-PCR), in situ hybridization and the like) of reduced in vitro or in vivo levels of RNA which contains a ribozyme substrate cleavage site for which the ribozyme is specific, compared to the level of RNA in controls (e.g., in the absence of ribozyme, or in the presence of a ribozyme sequence which contains a mutation in one or both unpaired nucleotide sequences which renders the ribozyme incapable of cleaving a substrate RNA).

Ribozymes contemplated to be within the scope of this invention include, but are not restricted to, hammerhead ribozymes (See e.g., Reddy et al., U.S. Pat. No. 5,246,921; Taira et al., U.S. Pat. No. 5,500,357, Goldberg et al., U.S. Pat. No. 5,225,347, the contents of each of which are herein incorporated by reference), Group I intron ribozyme (Kruger et al. (1982) Cell 31: 147-157), ribonuclease P (Guerrier-Takada et al. (1983) Cell 35: 849-857), hairpin ribozyme (Hampel et al., U.S. Pat. No. 5,527,895 incorporated by reference), and hepatitis delta virus ribozyme (Wu et al. (1989) Science 243:652-655).

A ribozyme may be designed to cleave at a substrate cleavage site in any substrate RNA so long as the substrate RNA contains one or more substrate cleavage sequences, and the sequences flanking the substrate cleavage site are known. In effect, expression in vivo of such ribozymes and the resulting cleavage of RNA transcripts of a gene of interest reduces or ablates expression of the corresponding gene.

For example, where the ribozyme is a hammerhead ribozyme, the basic principle of a hammerhead ribozyme design involves selection of a region in the substrate RNA which contains a substrate cleavage sequence, creation of two stretches of antisense oligonucleotides (i.e., the binding regions) which hybridize to sequences flanking the substrate cleavage sequence, and placing a sequence which forms a hammerhead catalytic region between the two binding regions.

In order to select a region in the substrate RNA which contains candidate substrate cleavage sites, the sequence of the substrate RNA needs to be determined. The sequence of RNA encoded by a genomic sequence of interest is readily determined using methods known in the art. For example, the sequence of an RNA transcript may be arrived at either manually, or using available computer programs (e.g., GENE-WORKS, from IntelliGenetic Inc., or RNADRAW available from the internet at ole@mango.mef.ki.se), by changing the T in the DNA sequence encoding the RNA transcript to a U.

Substrate cleavage sequences in the target RNA may be located by searching the RNA sequence using available computer programs. For example, where the ribozyme is a hammerhead ribozyme, it is known in the art that the catalytic region of the hammerhead ribozyme cleaves only at a substrate cleavage site which contains a NUH, where N is any nucleotide, U is a uridine, and H is a cytosine (C), uridine (U), or adenine (A) but not a guanine (G). The U-H doublet in the NUH cleavage site does not include a U-G doublet since a G would pair with the adjacent C in the ribozyme and prevent ribozyme cleavage. Typically, N is a G and H is a C. Consequently, GUC has been found to be the most efficient substrate cleavage site for hammerhead ribozymes, although ribozyme cleavage at CUC is also efficient.

In a preferred embodiment, the substrate cleavage sequence is located in a loop structure or in an unpaired region of the substrate RNA. Computer programs for the prediction of RNA secondary structure formation are known in the art and include, for example, "RNADRAW", "RNAFOLD" (Hofacker et al. (1994) Monatshefte F. Chemie 125:167-188; McCaskill (1990) Biopolymers 29:1105-1119). "DNASIS" (Hitachi), and "THE VIENNA PACKAGE."

In addition to the desirability of selecting substrate cleavage sequences which are located in a loop structure or an unpaired region of the substrate RNA, it is also desirable, though not required, that the substrate cleavage sequence be located downstream (i.e., at the 3'-end) of the translation start codon (AUG or GUG) such that the translated truncated polypeptide is not biologically functional.

In a preferred embodiment, the ribozyme is an "integrin α4β1 ribozyme" (i.e., a ribozyme whose substrate cleavage sequence is designed to hybridize with a portion of integrin α4β1 that is involved in the specific binding of integrin α4β1 with one or more of its ligands). Such integrin α4β1 portions are exemplified by, but not limited to, the sequences (see FIG. 1) which comprises the sequence IVTCGHRWKNIFY-IKNENKLPTGGCYGVPPDLRTELSKRIAPCYQDYVK-KFGENFAASCQAGISSFYTKDLIVMGAPGSSYWTGS-LFVYNITTNKYKAFLDKQNQVKFGSYLGYSVGAGH-FRSQHTTEVVGGAPQHEQIGKAYIFSIDEKELNILHE-MKGKK (SEQ ID NO:10) (from amino acid 141 to amino acid 301), GHRWKN IFYIKNENKLPTGG (SEQ ID NO:11) (from amino acid 145 to amino acid 164), YQDYVKKFGENFAS (SEQ ID NO:12) (from amino acid 184 to amino acid 197), SYWTGS (SEQ ID NO:13) (from amino acid 186 to amino acid 224), GGAPQHEQIGK (SEQ ID NO:14) (from amino acid 270 to amino acid 280), YNVDTES ALLYQGPHNT IFGYSVVLHS HGANR-WLLVG APTANWLANA SVINP (SEQ ID NO:54) (from amino acid 34 to amino acid 85), GRPYNVDTESALLYQG-PHNTLFGYSVVLHSHGANRWLLVG APTANWLA-NASVINPGAIYR (SEQ ID NO:55), GVPTGRPYNVDTE-SAL LYQGPHNT LFGYSVVLHSHGANRWLLVGAPTANWLANASVI NPGAIYRCRIGKNPGQT (SEQ ID NO:56), IVTCGHR-WKNIFYIKNENKLPTGGCYG (SEQ ID NO:57), GHR-WKNIFYIKNENKLPTGGCYGVPPDLRTELSK (SEQ ID NO:58), APCYQDYVKKFGENFAS (SEQ ID NO:59), CYQDYVKKFGENFASCQA GISSFYTKDL (SEQ ID NO:60), GSSYWTGSLFVYNI (SEQ ID NO:61), RSQHT-TEVVGGAPQHEQIGK (SEQ ID NO:62), GGAPQHE-QIGKAYIFSIDEKEL (SEQ ID NO:63), and/or GGAPQHE-QIGKA (SEQ ID NO:64).

In an alternative embodiment, the substrate cleavage sequence is designed to hybridize with a portion of an integrin α4β1 ligand, wherein the portion is involved in the specific binding of the ligand with integrin α4β1.

In a more preferred embodiment, the ribozyme is a "vascular cell adhesion molecule ribozyme" (i.e., a ribozyme whose substrate cleavage sequence is designed to hybridize with a portion of VCAM that is involved in the specific binding of VCAM with integrin α4β1). Exemplary portions of the ligand VCAM (FIG. 3A In a preferred embodiment, the complementarity between the ribozyme binding regions and the substrate RNA is complete. However, the invention is not limited to ribozyme sequences in which the binding regions show complete complementarity with the substrate RNA. Complementarity may be partial, so long as the desired specificity of the ribozyme for a substrate cleavage site and the rate of cleavage of the substrate RNA are achieved. Thus, base changes may be made in one or both of the ribozyme binding regions as long as substantial base pairing with the substrate RNA in the regions flanking the substrate cleavage sequence is maintained and base pairing with the substrate cleavage sequence is minimized. The term "substantial base pairing" means that greater than about 65%, more preferably greater than about 75%, and yet more preferably greater than about 90% of the bases of the hybridized sequences are base-paired.

It may be desirable to increase the intracellular stability of ribozymes expressed by an expression vector. This is achieved by designing the expressed ribozyme such that it contains a secondary structure (e.g., stem-loop structures) within the ribozyme molecule. Secondary structures which are suitable for stabilizing ribozymes include, but are not limited to, stem-loop structures formed by intra-strand base pairs. An alternative to the use of a stem-loop structure to protect ribozymes against ribonuclease degradation is by the insertion of a stem loop at each end of the ribozyme sequence (Sioud and Drlica (1991) Proc. Natl. Acad. Sci. USA 88:7303-7307). Other secondary structures which are useful in reducing the susceptibility of a ribozyme to ribonuclease degradation include hairpin, bulge loop, interior loop, multi-branched loop, and pseudoknot structure as described in "Molecular and Cellular Biology," Stephen L. Wolfe (Ed.), Wadsworth Publishing Company (1993) p. 575. Additionally, circularization of the ribozyme molecule protects against ribonuclease degradation since exonuclease degradation is initiated at either the 5'-end or 3'-end of the RNA. Methods of expressing a circularized RNA are known in the art (see, e.g., Puttaraju et al. (1993) Nucl. Acids Res. 21:4253-4258).

Once a ribozyme with desirable binding regions, a catalytic region and nuclease stability has been designed, the ribozyme may be produced by any known means including chemical synthesis. Chemically synthesized ribozymes may be introduced into a cell by, for example, microinjection electroporation, lipofection, etc. In a preferred embodiment, ribozymes are produced by expression from an expression vector that contains a gene encoding the designed ribozyme sequence.

4. Other Agents

While the present invention is illustrated herein using antibody, peptide, and nucleic acid sequences that inhibit the specific binding of integrin $\alpha4\beta1$ to one or more of its ligands, the invention expressly contemplates within its scope other agents (e.g., organic molecules, inorganic molecules, etc.) so long as the agent is capable of inhibiting the specific binding of integrin $\alpha4\beta1$ to one or more of its ligands. Such agents may be identified by screening libraries of test compounds (made as described below) using a competitive binding assay or a cell adhesion assay. In a competitive binding assay, for example, integrin $\alpha4\beta1$ is coated on plastic microtiter plates and contacted with a labeled known integrin $\alpha4\beta1$ ligand (e.g., CS-1 fibronectin or VCAM). The test compounds are tested for their ability to inhibit binding of the labeled ligand to integrin $\alpha4\beta1$. Compounds that inhibit such binding are identified as agents that are capable of inhibiting the specific binding of integrin $\alpha4\beta1$ to the ligand.

Alternatively, in a cell adhesion assay, a labeled known integrin $\alpha4\beta1$ ligand (e.g., CS-1 fibronectin or VCAM) is coated on culture plates, and cells which express integrin $\alpha4\beta1$ are allowed to adhere to the ligand for 20-30 minutes in the presence of libraries of test compounds. Compounds that inhibit the binding of the integrin $\alpha4\beta1$-expressing cells to the coating of integrin $\alpha4\beta1$ ligand are identified as agents that inhibit the specific binding of integrin $\alpha4\beta1$ to the ligand.

C. Integrin $\alpha4\beta1$ Mediates Trafficking of Endothelial Progenitor Cells, as Exemplified by Endothelial Stem Cells, During Neovascularization Bone marrow derived stem cells contribute to the repopulation of tissues undergoing repair, including vascular endothelium, smooth muscle, neurons and muscle (Asahara et al., Science. 1997 Feb. 14; 275(5302):964-7; Jain et al., Cancer Cell. 2003 June; 3(6):515-6; Religa et al., Transplantation. 2002 Nov. 15; 74(9):1310-5; Priller et al., J Cell Biol. 2001 Nov. 26; 155(5):733-8; LaBarge et al., Cell, 2002 Nov. 15; 111(4):589-601). The mechanisms by which hematopoietic stem cells home to sites of ongoing tissue repair remain unclear. Here we show that integrin $\alpha4\beta1$ (VLA-4) promotes the emigration of endothelial precursor cells (EPCs) from the circulation to sites of angiogenesis. During angiogenesis, integrin $\alpha4\beta1$ promotes the attachment of EPCs to VCAM on activated endothelium and to alternatively spliced tissue (CS-1) fibronectin, which is found underlying this endothelium. Antagonists of $\alpha4\beta1$ block the efflux of EPCs from the circulation during angiogenesis, thereby suppressing growth factor and tumor induced angiogenesis in vivo. Thus, $\alpha4\beta1$ contributes to angiogenesis by regulating hematopoietic stem cell recruitment to the neovascular bed.

Neovascularization is a key component of tissue repair processes that contribute to wound healing, but when chronically stimulated, it also plays a role in pathologies such as tumor growth and inflammatory disease (Carmeliet et al., Nat Med. 2003 June; 9(6):653-60; Carmeliet et al., Nature. 2000 Sep. 14; 407(6801):249-57). Neovascularization is thought to arise by at two mechanisms. Activation of quiescent endothelial cells within tissue blood vessels by angiogenic growth factors promotes the development of new blood vessels by sprouting (Carmeliet et al., Nat Med. 2003 June; 9(6):653-60; Carmeliet et al., Nature. 2000 Sep. 14; 407(6801):249-57). A second mechanism involves the homing of bone marrow derived endothelial stem cells to sites of neovascularization such as ischemic limbs or tumors (Asahara et al., Science. 1997 February supra; Jain et al., Cancer Cell. 2003 June; 3(6):515-6; Lyden et al., Nat. Med. 2001 November; 7(11): 1194-201; Takahashi et al., Nat Med. 1999 April; 5(4):434-8; Kawamoto et al., Circulation. 2001 Feb. 6; 103(5):634-7; Hattori et al., J Exp Med. 2001 May 7; 193(9):1005-14; Kalka et al., Proc Natl Acad Sci USA. 2000 Mar. 28; 97(7):3422-7). These bone marrow derived stem cells can home to muscle, brain and other tissues undergoing repair whereupon they participate in tissue regeneration (Asahara et al., Science. 1997 February supra; Jain et al., Cancer Cell. 2003 June; 3(6):515-6; Religa et al., Transplantation. 2002 Nov. 15; 74(9):1310-5; Priller et al., J Cell Biol. 2001 Nov. 26; 155(5): 733-8; LaBarge et al., Cell. 2002 Nov. 15; 111(4):589-601; Lyden et al., Nat Med. 2001 November; 7(11): 1194-201; Takahashi et al., Nat Med. 1999 April; 5(4):434-8; Kawamoto et al., Circulation. 2001 Feb. 6; 103(5):634-7; Hattori et al., J Exp Med. 2001 May 7; 193(9):1005-14; Kalka et al., Proc Natl Acad Sci USA. 2000 Mar. 28; 97(7):3422-7; Torrente et al., J Cell Biol. 2003 Aug. 4; 162(3):511-20). However, the mechanisms by which bone marrow derived stem cells such as EPCs exit from the circulation and enter tissues to participate in tissue repair process remain unclear.

Antagonists of integrin $\alpha4\beta1$ (antibodies, peptides, etc.) inhibit bone marrow derived stem cells or precursor cells from entering tissues by blocking their association with the vascular endothelium and by blocking their migration on the extracellular matrix in tissues beneath the endothelium. These antagonists can be used to block hematopoietic stem cells from participating in angiogenesis, atherosclerosis, restenosis, inflammation, cancer, and other diseases in which hematopoietic stem cells play a role. Additionally, reagents that selectively bind to α4β1 such as high affinity antibodies, recombinant soluble VCAM or CS-1 fibronectin, can be used to purify hematopoietic stem cells from tissues, bone marrow, peripheral blood, cord blood, etc. so that they may be expanded and used further for therapeutic applications such as repair of damaged heart tissue, stimulation of angiogenesis in ischemic tissues and repair of congenital muscle defects. Finally, cytokines that upregulate VCAM on vascular endothelium may be used to encourage the entry of hematopoietic stem cells into tissues by providing a site for hematopoietic stem cells to adhere to the vascular endothelium.

Currently, bone marrow derived hematopoietic stem cells are under study for use in the repair of muscle, heart, ischemic tissues, nerves and a myriad of other imaginable applications. While researchers can show that purified or native bone marrow derived hematopoietic stem cells do enter into normal tissues and participate in tissue regeneration, generally the number of cells that make it into tissues is small. Additionally, bone marrow derived hematopoietic stem cells participate in pathological processes such as tumor growth and angiogenesis, atherosclerosis and restenosis. Data herein (such as Examples 4-15) shows identification of the molecular pathway through which these cells recognize the endothelium, adhere to it and enter into the tissue. Furthermore, we have determined several methods to inhibit or promote hematopoietic stem cell homing.

As integrin α4β1 is also an effector of immune cell trafficking in vivo, data herein (Examples 4-15) suggest that α4β1 may be expressed by "the hemangioblast," a putative precursor common to HSCs and EPC lineages. Data herein shows that integrin α4β1 plays an important and unique role in tissue repair processes, by mediating the interaction of endothelial precursor cells with more established endothelium. Integrin α4β1 may also play a key role in regulating endothelial sprouting from established vessels; its transient expression on neovessels may indicate a functional role early in the angiogenic process. As CD34 positive bone marrow derived stem cells are integrin α4β1 positive, it is possible that this integrin regulates the trafficking of other CD34 positive stem cells into tissues during tissues repair. These data indicate that antagonists of integrin α4β1 could be used to inhibit pathological angiogenesis and tumor growth as well as other pathological conditions in which hematopoietic stem cells play an important. These data also suggest that hematopoietic stem cell homing to tissues needing repair could be enhanced by stimulating the endothelium to express VCAM and by stimulating hematopoietic stem cells α4β1 activity.

Little is known about the mechanisms by which hematopoietic stem cells exit from the circulation and enter into tissues. Furthermore, methods to block or enhance this process are unknown. Thus, the invention provides the only known method to block or promote hematopoietic stem cell homing to tissues. The invention is useful in blocking homing by using inhibitors of integrin α4β1, which is the hematopoietic stem cell receptor for the vascular endothelium. The invention is also useful in stimulating homing by causing VCAM, the counter-receptor on endothelium, to be expressed (by applying growth factors or inflammatory cytokines to the regional vasculature).

Antibody, peptide or organic molecule inhibitors of integrin α4β1 may be used in vivo to inhibit hematopoietic stem cells from entering tissues and participating in aberrant tissue repair processes, such as pathological angiogenesis in cancer, arthritis and neovascular eye disease, atherosclerosis, restenosis and others. Stimulation of VCAM expression on the endothelium of tissues needing repair may be used to promote hematopoietic stem cell homing to tissues. Finally, reagents that bind α4β1 with high affinity may be used to purify or isolate hematopoietic stem cells for use in therapeutic applications.

Data herein (e.g., Examples 4-15) shows that inhibiting α4β1 blocks angiogenesis (growth factor and tumor induced), blocks endothelial stem cell growth in vitro, blocks endothelial stem cell attachment to endothelium in vitro and blocks endothelial stem cell recruitment to endothelium in vivo. Data herein (e.g., Examples 4-15) also shows that all bone marrow derived stem cells (which may be identified by expression of the CD34 positive marker) express α4β1 and are currently showing that blocking α4β1 blocks additional stem cell from adhering to endothelium and entering tissues. These studies show the feasibility of using α4β1 expression, in combination with additional markers of stem cells, to isolate stem cells.

The invention is useful by exploiting inhibition of integrin α4β1: Inhibition of tumor growth (by blocking angiogenesis and immune cell contributions to tumor growth), inhibition of other neovascular diseases such as arthritis, eye disease, and psoriasis, inhibition of atherosclerosis and restenosis by blocking hematopoietic stem cell contribution to these diseases.

The invention is also useful by exploiting enhancement of hematopoietic stem cell entry into tissues by inducing the expression of VCAM on endothelium, the counter receptor for α4β1: enhancement of angiogenesis in ischemic disease (heart attach, diabetes), enhancement of muscle repair and nerve repair in neuromuscular diseases, enhancing other types of tissue repair. The invention is also useful for isolating hematopoietic stem cells using integrin α4β1 selection.

D. Altering Hematopoietic Progenitor Cell Adhesion, Migration and Differentiation The invention further provides methods for altering HPC adhesion and/or migration to a target tissue, and for altering HPC differentiation into a second cell type, by employing an agent that alters the specific binding of integrin α4β1 to its ligand. The invention is premised at least in part on the surprising discovery that integrin (α4β1 (VLA-4) promotes the homing of the exemplary circulating hematopoietic stem cells to the α4β1 ligands, vascular cell adhesion molecule (VCAM) and cellular fibronectin, which are expressed on neovasculature (Examples 17-24). CD34+ stem cells, which express integrin α4β1, homed to sites of active neovascularization but not to normal tissues. Antagonists of integrin α4β1 blocked the adhesion of the exemplary hematopoietic stem cells to endothelium in vitro and in vivo and their outgrowth into neovessels (Examples 17-24).

The term "cell adhesion" as used herein refers to the physical contacting of the cell to one or more components of the extracellular matrix (e.g., fibronectin, collagens I-XVIII, laminin, vitronectin, fibrinogen, osteopontin, Del 1, tenascin, von Willebrands's factor, etc.), to a ligand which is expressed on the cell surface (e.g., VCAM, ICAM, LI-CAM, VE-cadherin, integrin a2, integrin a3, etc.) and/or to another cell of the same type (e.g., adhesion of an HPC to another HPC) or of a different type (e.g., adhesion of an HPC to an endothelial cell, endothelial stem cell, stem cell expressing CD34, fibroblast cell, stromal cell, tumor cell, etc.).

The term "reducing cell adhesion" refers to reducing the level of adhesion to a quantity which is preferably 10% less than, more preferably 50% less than, yet more preferably 75% than, even more preferably 90% less than, the quantity in a control cell, and most preferably is at the same level which is observed in a control cell. A reduced level of cell adhesion need not, although it may, mean an absolute absence of cell adhesion. The invention does not require, and is not limited to, methods that wholly eliminate cell adhesion. The level of cell adhesion may be determined using methods disclosed herein an others known in the art (e.g., WO 03/019136 A3 to Varner).

The term "cell migration" as used herein refers to the translocation of a cell across one or more components of the extracellular matrix (e.g., fibronectin, collagens I-XVIII, laminin, vitronectin, fibrinogen, osteopontin, Del 1, tenascin, von Willebrands's factor, etc.), and/or along the surface of another cell of the same type (e.g., migration of an HPC along another HPC) and/or of a different cell (e.g., migration of an HPC along an endothelial cell, endothelial stem cell, stem cell expressing CD34, fibroblast cell, stromal cell, tumor cell, etc.). Thus, "trans-endothelial migration" of a cell refers to the translocation of the cell across one or more components of the extracellular matrix and/or cells of endothelial tissue.

The term "reducing cell migration" refers to reducing the level of migration of a cell to a quantity which is preferably 10% less than, more preferably 50% less than, yet more preferably 75% less than, and even more preferably 90% less than, the quantity in a control cell, and most preferably is at the same level which is observed in a control cell. A reduced level of cell migration need not, although it may, mean an absolute absence of cell migration. The invention does not require, and is not limited to, methods that wholly eliminate cell migration. The level of cell migration may be determined using methods disclosed herein and known in the art, such as time lapse video microscopy, scratch type wound assay, and others (e.g., WO 03/019136 A3 to Varner).

The "level of differentiation" when in reference to a cell of interest in a sample is a relative term that refers to the quantity per cell of interest (e.g., hematopoietic progenitor cell) of expressed differentiation marker (e.g., B220, CD3, CD11b, etc.) compared to the quantity per cell of the same marker that is expressed by a differentiated cell (e.g., B cells that express the B220 marker, T-cells that express the CD3 marker, and myeloid cells that express the CD11b marker, respectively).

The term "reducing cell differentiation" refer to reducing the level of differentiation of a cell to a quantity which is preferably 10% less than, more preferably 50% less than, yet more preferably 75% less than, and even more preferably 90% less than, the quantity in a control cell, and most preferably is at the same level which is observed in a control cell. A reduced level of cell differentiation need not, although it may, mean an absolute absence of cell differentiation. The invention does not require, and is not limited to, methods that wholly eliminate cell migration. The level of cell differentiation may be determined using methods disclosed herein and known in the art.

E. Altering Hematopoietic Progenitor Cell Adhesion, Migration, and Differentiation The invention provides methods for altering HPC adhesion, migration and/or differentiation in a subject by altering the binding of $\alpha 4\beta 1$ to one or more of its ligands (e.g., fibronectin and VCAM) in a tissue in the subject. In one embodiment, the subject has a condition that is associated with undesirable HPC adhesion, migration, and/or differentiation, such as in angiogenic disease. The term "angiogenic disease" is used broadly herein to mean any condition characterized, at least in part, by neovascularization. In contrast, a "non-angiogenic disease" is a condition that is not associated with neovascularization. Angiogenesis includes normal angiogenesis processes (e.g., scar formation during wound healing or during fertility), and angiogenesis, which is associated with a pathological condition, such as that which occurs in ocular tissue (e.g., retina, macular or cornea), in skin such as occurs with psoriasis, in synovial tissue, in bone, in intestinal tissue, or in a tumor, including pathological conditions that are exemplified by, but not limited to, neoplasms, ocular diseases such as diabetic retinopathy and macular degeneration associated with neovascularization, skin diseases such as psoriasis and hemangiomas, gingivitis, arthritic conditions such as rheumatoid arthritis and osteoarthritis, and inflammatory bowel diseases.

In another embodiment, the subject has a neoplasm. The terms "neoplasm" and "tumor" refer to a tissue growth that is characterized, in part, by angiogenesis. Neoplasms may be benign and are exemplified, but not limited to, a hemangioma, glioma, teratoma, and the like. Neoplasms may alternatively be malignant, for example, a carcinoma, sarcoma, glioblastoma, astrocytoma, neuroblastoma, retinoblastoma, and the like.

The terms "malignant neoplasm" and "malignant tumor" refer to a neoplasm that contains at least one cancer cell. A "cancer cell" refers to a cell undergoing early, intermediate or advanced stages of multi-step neoplastic progression as previously described (H. C. Pitot (1978) in "Fundamentals of Oncology," Marcel Dekker (Ed.), New York pp 15-28). The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. A cell in the early stages of malignant progression is referred to as "hyperplastic cell" and is characterized by dividing without control and/or at a greater rate than a normal cell of the same cell type in the same tissue. Proliferation may be slow or rapid, but continues unabated. A cell in the intermediate stages of neoplastic progression is referred to as a "dysplastic cell." A dysplastic cell resembles an immature epithelial cell, is generally spatially disorganized within the tissue and loses its specialized structures and functions. During the intermediate stages of neoplastic progression, an increasing percentage of the epithelium becomes composed of dysplastic cells. "Hyperplastic" and "dysplastic" cells are referred to as "pre-neoplastic" cells. In the advanced stages of neoplastic progression a dysplastic cell become a "neoplastic" cell. Neoplastic cells are typically invasive (i.e., they either invade adjacent tissues, or are shed from the primary site and circulate through the blood and lymph) to other locations in the body where they initiate one or more secondary cancers (i.e., "metastases"). Thus, the term "cancer" is used herein to refer to a malignant neoplasm, which may or may not be metastatic. Malignant neoplasms that can be diagnosed using a method of the invention include, for example, carcinomas such as lung cancer, breast cancer, prostate cancer, cervical cancer, pancreatic cancer, colon cancer, ovarian cancer; stomach cancer, esophageal cancer, mouth cancer, tongue cancer, gum cancer, skin cancer (e.g., melanoma, basal cell carcinoma, Kaposi's sarcoma, etc.), muscle cancer, heart cancer, liver cancer, bronchial cancer, cartilage cancer, bone cancer, testis cancer, kidney cancer, endometrium cancer, uterus cancer, bladder cancer, bone marrow cancer, lymphoma cancer, spleen cancer, thymus cancer, thyroid cancer, brain cancer, neuron cancer, mesothelioma, gall bladder cancer, ocular cancer (e.g., cancer of the cornea, cancer of uvea, cancer of the choroids, cancer of the macula, vitreous humor cancer, etc.), joint cancer (e.g., synovium cancer), glioblastoma, lymphoma, and leukemia. Malignant neoplasms are further exemplified by sarcomas (such as osteosarcoma and Kaposi's sarcoma). The invention expressly contemplates within its scope any malignant neoplasm, so long as the neoplasm is characterized, at least in part, by angiogenesis associated with α4β1 expression by the newly forming blood vessels.

The terms "reducing the severity of a pathological condition," "diminishing the severity of a pathological condition, and "reducing symptoms associated with a pathological condition" mean that adverse clinical signs or symptoms associated with the pathological condition are reduced, delayed, or eliminated, as compared to the level of the pathological condition in the absence of treatment with the particular composition or method. The effects of diminishing the severity of a pathological condition may be determined by methods routine to those skilled in the art including, but not limited to, angiography, ultrasonic evaluation, fluoroscopic imaging, fiber optic endoscopic examination, biopsy and histology, blood tests, which can be used to determine relevant enzyme levels or circulating antigen or antibody, imaging tests which can be used to detect a decrease in the growth rate or size of a neoplasm, or an ophthalmic procedure which can be used to identify a reduction in the number of blood vessels in the retina of a diabetic patient. Such clinical tests are selected based on the particular pathological condition being treated. For example, it is contemplated that the methods of the invention result in a "reduction in tumor tissue" (e.g., a decrease in the size, weight, and/or volume of the tumor tissue) as compared to a control tumor tissue (e.g., the same tumor prior to treatment with the invention's methods, or a different tumor in a control subject). A reduction in the severity of a pathological condition also can be detected based on comments made by the patient being treated, for example, that a patient suffering from arthritis feels less pain or has greater joint mobility, or that a patient with diabetic retinopathy or with macular degeneration due to neovascularization can see more clearly, or the like.

Pathological conditions that are amenable to prevention and/or treatment with the invention's methods include any pathological condition whose development or progression in a tissue involves HPC adhesion, migration and/or differentiation. Exemplary pathological conditions include, for example, solid tumor cancers, solid tumor metastases, angiofibromas, skin cancer, retrolental fibroplasia, Kaposi's sarcoma, childhood hemangiomas, diabetic retinopathy, neovascular glaucoma, age related macular degeneration, psoriasis, gingivitis, rheumatoid arthritis, osteoarthritis, ulcerative colitis, Crohn's disease, inflammatory bowel disease, and atheroscrelotic plaques.

Other pathological conditions include those that entail injury to tissue. The term "injured" in reference to a tissue refers to tissue in which the cellular organization of the tissue has been altered as compared to the cellular organization in normal tissue. Such injury may result, for example, from a breaking of the skin tissue (e.g., a cut, slash, laceration) such as accidental cuts or cuts associated with burns, surgery, etc. Injured tissues include lung, breast, prostate, cervical, pancreatic, colon, ovarian, stomach, esophagus cancer, mouth cancer, tongue cancer, gum, muscle, etc. In particular, skin injury that is associated with undesirable formation of scar tissue is particularly amenable to the invention's therapeutic approaches.

An agent that is useful in altering binding of integrin α4β1 to a α4β1 ligand may be administered by various routes including, for example, orally, intranasally, or parenterally, including intravenously, intramuscularly, subcutaneously, intraorbitally, intracapsularly, intrasynovially, intraperitoneally, intracistemally or by passive or facilitated absorption through the skin using, for example, a skin patch or transdermal iontophoresis. Furthermore, the agent can be administered by injection, intubation, via a suppository, orally or topically, the latter of which can be passive, for example, by direct application of an ointment or powder containing the agent, or active, for example, using a nasal spray or inhalant. The agent can also be administered as a topical spray, if desired, in which case one component of the composition is an appropriate propellant. The pharmaceutical composition also can be incorporated, if desired, into liposomes, microspheres or other polymer matrices (Gregoriadis, "Liposome Technology," Vol. 1, CRC Press, Boca Raton, Fla. 1984). Liposomes, for example, which consist of phospholipids or other lipids, are nontoxic, physiologically acceptable and metabolizable carriers that are relatively simple to make and administer. Liposomes are lipid-containing vesicles having a lipid bilayer as well as other lipid carrier particles that can entrap chemical agents. Liposomes may be made of one or more phospholipids, optionally including other materials such as sterols. Suitable phospholipids include phosphatidyl cholines, phosphatidyl serines, and many others that are well known in the art. Liposomes can be unilamellar, multilamellar or have an undefined lamellar structure. For example, in an individual suffering from a metastatic carcinoma, the agent in a pharmaceutical composition can be administered intravenously, orally or by another method that distributes the agent systemically.

Agents that inhibit the specific binding of integrin α4β1 to one or more of its ligands may be administered in conjunction with other therapies. For example, in the case of cancer therapy, the agent may be administered in conjunction with conventional drug therapy and/or chemotherapy that is directed against solid tumors and for control of establishment of metastases. In one embodiment, the agent is administered during or after chemotherapy. In a more preferred embodiment, the agent is administered after chemotherapy, at a time when the tumor tissue will be responding to the toxic assault. The tumor will attempt to induce angiogenesis to recover by the provision of a blood supply and nutrients to the tumor tissue. Such recovery will be thwarted by the administration of agents which inhibit angiogenesis by inhibiting the specific binding of integrin α4β1 to one or more of its ligands. In an alternative embodiment, the agent may be administered after surgery in which solid tumors have been removed as a prophylaxis against future metastases.

In one embodiment, an agent is administered in a "therapeutic amount" (i.e., in an amount which is sufficient to achieve a desired result). In particular, a therapeutic amount is that amount which inhibits the specific binding of α4β1 integrin to its specific ligand in a tissue of a subject, and which results in the reduction, delay, or elimination of undesirable pathologic effects in the subject. One of ordinary skill recognizes that a "therapeutically effective" amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

A therapeutic amount may be determined using in vitro and in vivo assays known in the art, and is generally about 0.0001 to 100 mg/kg body weight.

The "subject" to whom the agents are administered includes any animal which is capable of developing angiogenesis in a tissue, including, without limitation, human and non-human animals such simians, rodents, ovines, bovines, ruminants, lagomorphs, porcines, caprines, equines, canines, felines, aves, etc. Preferred non-human animals are members of the Order Rodentia (e.g., mouse and rat). Thus, the compounds of the invention may be administered by human health professionals as well as veterinarians.

F. Detecting Hematopoietic Progenitor Cells that Express Integrin α4β1

The invention additionally provides methods for detecting HPCs that express integrin α4β1 by using an agent that specifically binds to integrin α4β1 polypeptides and/or to integrin α4β1 mRNA. These methods are useful for identifying the presence of HPCs whose adhesion, migration, and differentiation is amenable to modulation using the invention's methods, regardless of whether such HPCs are located in normal tissue or in tissue involved in a pathological condition. As such, the invention further provides methods of diagnosing a pathological condition characterized by involvement of HPCs that express integrin α4β1.

Integrin α4β1 polypeptide may be detected using Western blot analysis or immunofluorescence. Alternatively, the presence of integrin α4β1 mRNA using reverse transcription polymerase chain (RT-PCR), or in situ hybridization.

In one embodiment, the agent which is used in detecting the presence of integrin α4β1 polypeptide and/or mRNA can be detectably labeled, for example, by linking the agent to a moiety, which is selected based, for example, on whether specific binding of the agent is to be detected in vivo or whether a tissue to which the agent is suspected of binding is to be removed (e.g., by biopsy) and examined ex vivo.

A moiety useful for labeling an agent antagonist can be a radionuclide, a paramagnetic material, an X-ray attenuating material, a fluorescent, chemiluminescent or luminescent molecule, a molecule such as biotin, or a molecule that can be visualized upon reaction with a particular reagent, for example, a substrate for an enzyme or an epitope for an antibody. The moiety can be linked to an agent using well known methods, which are selected, in part, based on the chemical nature of the agent and the moiety. For example, where the moiety is an amino acid sequence such as a hexahistidine (His6) sequence, and the agent is a peptide, the His6 sequence can be synthesized as part of the peptide, and the His6-labeled agent can be identified by the binding of a nickel ion reagent to the His6 moiety.

Methods for chemically linking a moiety to an agent also can be utilized. For example, methods for conjugating polysaccharides to peptides are exemplified by, but not limited to coupling via alpha- or epsilon-amino groups to $NaIO_4$-activated oligosaccharide, using squaric acid diester (1,2-diethoxycyclobutene-3,4-dione) as a coupling reagent, coupling via a peptide linker wherein the polysaccharide has a reducing terminal and is free of carboxyl groups (U.S. Pat. No. 5,342,770), coupling with a synthetic peptide carrier derived from human heat shock protein hsp65 (U.S. Pat. No. 5,736,146), and using the methods of U.S. Pat. No. 4,639,512. Methods for conjugating proteins to proteins include coupling with a synthetic peptide carrier derived from human heat shock protein hsp65 (U.S. Pat. No. 5,736,146), the methods used to conjugate peptides to antibodies (U.S. Pat. Nos. 5,194,254; 4,950,480), the methods used to conjugate peptides to insulin fragments (U.S. Pat. No. 5,442,043), the methods of U.S. Pat. No. 4,639,512, and the method of conjugating the cyclic decapeptide polymyxin B antibiotic to and IgG carrier using EDAC (1-ethyl-3-(3-dimethylaminopropyl)carbodiimide)-mediated amide formation (Drabick et al. (1998) Antimicrob. Agents Chemother. 42:583-588). Approaches to conjugate nucleic acids to proteins are also known in the art, such as those described in U.S. Pat. Nos. 5,574,142; 6,117, 631; 6,110,687; each of is incorporated in its entirety by reference. Methods for conjugating lipids to peptides have been described in the art including, but not limited to, the use of reductive amination and an ether linkage which contains a secondary or tertiary amine (U.S. Pat. No. 6,071,532), the methods of U.S. Pat. No. 4,639,512, the methods used for covalently coupling peptides to unilamellar liposomes (Friede et al. (1994) Vaccine 12:791-797), of coupling human serum albumin to liposomes using the hetero-bifunctional reagent N-succinimidyl-5-acetylthioacetate (SATA) (Kamps et al. (1996) Biochim. Biophys. Acta 1278:183-190), of coupling antibody Fab' fragments to liposomes using a phospholipid-poly(ethylene glycol)-maleimide anchor (Shahinian et al. (1995) Biochim. Biophys. Acta 1239:157-167), and of coupling Plasmodiuin CTL epitope to palmitic acid via cysteine-serine spacer amino acids (Verheul et al. (1995) J. Immunol. Methods 182:219-226).

A specifically bound agent can be detected in an individual using an in vivo imaging method, such as a radionuclide imaging, positron emission tomography, computerized axial tomography, X-ray or magnetic resonance imaging method, or can be detected using an ex vivo method, wherein, following administration, a sample of the tissue is obtained from the individual, and specific binding of the agent in the sample is detected (e.g., by immunohistochemical analysis; see WO 03/019136 A3 to Varner).

An agent that is specifically bound to α4β1 integrin in a sample can be detected directly by detecting the agent, or indirectly by detecting the presence of a moiety such as by detecting radioactivity emitted by a radionuclide moiety. Specifically bound agent also can be detected indirectly by further contacting it with a reagent that specifically interacts with the agent, or with a moiety linked to the agent, and detecting interaction of the reagent with the agent or label. For example, the moiety can be detected by contacting it with an antibody that specifically binds the moiety, particularly when the moiety is linked to the agent. The moiety also can be, for example, a substrate, which is contacted by an enzyme that interacts with and changes the moiety such that its presence can be detected. Such indirect detection systems, which include the use of enzymes such as alkaline phosphatase, horseradish peroxidase, beta-galactosidase and the like, are well known in the art and commercially available, as are the methods for incorporating or, linking the particular moiety to a particular type of agent.

G. Screening Compounds

The invention also provides methods for screening test compounds for altering the level of hematopoietic cell adhesion and/or migration to a target tissue, and for altering hematopoietic progenitor cell differentiation into a second cell type, comprising: a) providing: i) a first composition comprising integrin α4β1, ii) a second composition comprising one or more integrin α4β1 ligand, iii) a test compound, b) contacting said test compound with one or more of said first composition and said second composition under conditions for specific binding of said integrin α4β1 with said integrin α4β1 ligand, and c) detecting an altered level of specific binding of said integrin α4β1 with said integrin α4β1 ligand in the presence of said test compound compared to in the absence of said test compound, thereby identifying said test compound as altering the level of hematopoietic cell adhesion and/or migration to a target tissue, and as altering hematopoietic progenitor cell differentiation into a second cell type.

The tissue can be contacted with the agent in vivo or ex vivo (see, for example, U.S. Pat. No. 5,622,699, incorporated by reference). Where a screening method of the invention is performed using an in vitro format, it can be adapted to automated procedure, thus allowing high throughput screening assays for examining libraries of molecules to identify potential α4β1 antagonists, which can alter HPC adhesion, migration, and/or differentiation.

Alternatively, a screening assays is carried out by contacting isolated HPCs with a test compound, and detecting an altered level of HPC adhesion, migration and/or differentiation, thereby identifying the compound as altering the level of HPC adhesion, migration and/or differentiation.

Test compounds may be made by art-known methods for preparing libraries of molecules, and are exemplified by methods for preparing oligonucleotide libraries (Gold et al., U.S. Pat. No. 5,270,163, incorporated by reference); peptide libraries (Koivunen et al., supra, 1993, 1994); peptidomimetic libraries (Blondelle et al., Trends Anal. Chem. 14:83-92 (1995)) oligosaccharide libraries (York et al., Carb. Res. 285: 99-128 (1996); Liang et al., Science 274:1520-1522 (1996); and Ding et al., Adv. Expt. Med. Biol. 376:261-269 (1995)); lipoprotein libraries (de Kruif et al., FEBS Lett., 399:232-236 (1996)); glycoprotein or glycolipid libraries (Karaoglu et al., J. Cell Biol. 130:567-577 (1995)); or chemical libraries containing, for example, drugs or other pharmaceutical agents (Gordon et al., J. Med. Chem. 37:1385-1401 (1994); Ecker and Crook, Bio/Technology 13:351-360 (1995), U.S. Pat. No. 5,760,029, incorporated by reference). Libraries of diverse molecules also can be obtained from commercial sources.

H. Isolating Hematopoietic Progenitor Cells

The invention further provides a method for isolating HPCs from a tissue by treating a tissue which contains HPCs with an agent (e.g. antibody) capable of specific binding to integrin α4β1, and isolating HPCs to which the agent binds. These methods are based, in part, on the inventor's discovery that HPCs express integrin α4β1.

In one embodiment, HPCs comprise endothelial progenitor cells (EPCs). EPCs useful in regulating angiogenesis (Isner et al., U.S. Pat. No. 5,980,887, incorporated by reference). Heterologous, homologous, and autologous endothelial cell progenitor grafts incorporate in vivo into sites of active angiogenesis or blood vessel injury (i.e., they selectively migrate to such locations (Isner et al., U.S. Pat. No. 5,980,887). Endothelial cell progenitors are present in a number of tissues including, for example, peripheral blood, bone marrow, and umbilical cord blood. Endothelial cell progenitors may be isolated in accordance with the invention's methods by treating a tissue (e.g., peripheral blood, bone marrow, umbilical cord blood, etc.) which contains endothelial cell progenitors with an antibody which is capable of specific binding to at least a portion of integrin α4β1 polypeptide, followed by isolating cells which bind to the antibody. The endothelial cell progenitor nature of the isolated cells may be confirmed by determining the presence of endothelial cell progenitor-specific antigens (e.g., CD34, flk-1, and/or tie-2) on the surface of the isolated cells using commercially available antibodies to these antigens. It may be desirable, but not necessary, to expand endothelial cell progenitors in vivo prior to treating the tissue that contains endothelial cell progenitors by administration of recruitment growth factors (e.g., GM-CSF and IL-3) to the patient.

Thus, in one embodiment, the isolated endothelial cell progenitors can be used to enhance angiogenesis or to deliver an angiogenesis modulator (e.g., anti- or pro-angiogenic agents, respectively), to sites of pathologic or utilitarian angiogenesis. Additionally, in another embodiment, endothelial cell progenitors can be used to induce re-endothelialization of an injured blood vessel, and thus reduce restenosis by indirectly inhibiting smooth muscle cell proliferation (Isner et al., U.S. Pat. No. 5,980,887).

In one preferred embodiment, the endothelial cell progenitors can be used alone to potentiate a patient for angiogenesis. Some patient populations, typically elderly patients, may have either a limited number of endothelial cells or a limited number of functional endothelial cells. Thus, if one desires to promote angiogenesis, for example, to stimulate vascularization by using a potent angiogenesis such as VEGF, such vascularization can be limited by the lack of endothelial cells. However, by administering the endothelial cell progenitors one can potentiate the vascularization in those patients.

Because endothelial cell progenitors home to foci of angiogenesis, these cells are also useful as autologous vectors for gene therapy and diagnosis of ischemia or vascular injury. For example, these cells can be utilized to inhibit as well as augment angiogenesis. For anti-neoplastic therapies, for example, endothelial cell progenitors can be transfected with or coupled to cytotoxic agents, cytokines or co-stimulatory molecules to stimulate an immune reaction, other anti-tumor drugs, or angiogenesis inhibitors. For treatment of regional ischemia, angiogenesis could be amplified by prior transfection of endothelial cell progenitors to achieve constitutive expression of angiogenic cytokines and/or selected matrix proteins. In addition, the endothelial cell progenitors may be labeled (e.g., radiolabeled), administered to a patient and used in the detection of ischemic tissue or vascular injury.

Autologous endothelial cell progenitor transplants have been successfully used, and endothelial cell progenitors have been shown to be easily manipulated and expanded ex vivo (U.S. Pat. Nos. 5,980,887; 5,199,942; and 5,541,103, the disclosures of which are incorporated by reference).

Once isolated, HPCs (such as endothelial progenitor cells) may optionally stored in cryogenic conditions before administering to a subject to treat a number of conditions. Administration to a subject may be by any suitable means, including, for example, intravenous infusion, bolus injection, and site directed delivery via a catheter. Preferably, the HPCs obtained from the subject are re-administered. Generally, from about $10^6$ to about $10^{18}$ HPCs are administered to the subject for transplantation.

In one embodiment, HPCs (such as endothelial progenitor cells) may be transgenic or wild type. A "transgenic" cell refers to a cell which contains a "transgene," i.e., any nucleic acid sequence which is introduced into the cell by experimental manipulations. A transgene may be an "endogenous DNA sequence" or a "heterologous DNA sequence" (i.e., "foreign DNA"). A transgenic cell is contrasted with a "wild-type cell" that does not contain a transgene. HPCs may be transgenic for genes that encode a variety of proteins including anticancer agents, as exemplified by genes encoding various hormones, growth factors, enzymes, cytokines, receptors, MHC molecules and the like. The term "genes" includes nucleic acid sequences both exogenous and endogenous to cells into which a virus vector, for example, a pox virus such as swine pox containing the human TNF gene may be introduced. Additionally, it is of interest to use genes encoding polypeptides for secretion from the HPCs so as to provide for a systemic effect by the protein encoded by the gene. Specific genes of interest include those encoding TNF, TGF-α, TGF-β, hemoglobin, interleukin-1, interleukin-2, interleukin-3, interleukin-4, interleukin-5, interleukin-6, interleukin-7, interleukin-8, interleukin-9, interleukin-10, interleukin-11, interleukin-12 etc., GM-CSF, G-CSF, M-CSF, human growth factor, co-stimulatory factor B7, insulin, factor VIII, factor IX, PDGF, EGF, NGF, EPO, β-globin, cell mitogens and the like, as well as biologically active modifications of these proteins. The gene may further encode a product that regulates expression of another gene product or blocks one or more steps in a biological pathway. In addition, the gene may encode a toxin fused to a polypeptide (e.g., a receptor ligand), or an antibody that directs the toxin to a target, such as a tumor cell. Similarly, the gene may encode a therapeutic protein fused to a targeting polypeptide, to deliver a therapeutic effect to a diseased tissue or organ.

In another embodiment, HPCs (such as endothelial progenitor cells) can also be used to deliver genes to enhance the ability of the immune system to fight a particular disease or tumor. For example, the cells can be used- to deliver one or more cytokines (e.g., IL-2) to boost the immune system and/or one or more antigens.

In yet another embodiment, HPCs (such as endothelial progenitor cells) may also be used to selectively administer drugs, such as an antiangiogenesis compound such as O-chloroacetyl carbamoyl fumagillol (TNP-470). Preferably, the drug would be incorporated into the cell in a vehicle such as a liposome, a timed released capsule, etc. The HPCs (such as endothelial progenitor cells) would then selectively target a site of active angiogenesis such as a rapidly growing tumor where the compound would be released. By this method, one can reduce undesired side effects at other locations.

In a further embodiment, HPCs (such as endothelial progenitor cells) may be used to enhance blood vessel formation in ischemic tissue (i.e., a tissue having a deficiency in blood as the result of an ischemic disease). Such tissues can include, for example, muscle, brain, kidney and lung. Ischemic diseases include, for example, cerebrovascular ischemia, renal ischemia, pulmonary ischemia, limb ischemia, ischemic cardiomyopathy and myocardial ischemia. Methods for inducing the formation of new blood vessels in ischemic tissue are disclosed in Isner et al., U.S. Pat. No. 5,980,887, herein incorporated by reference.

EXPERIMENTAL

The following examples serve to illustrate certain preferred embodiments and aspects of the present invention and are not to be construed as limiting the scope thereof.

Example 1

Inhibition of Endothelial Progenitor Cell Migration In Vivo in Mouse and Rat Animal Models Integrin $\alpha 4\beta 1$ inhibitors can be used to prevent endothelial cell precursors from exiting the blood stream and entering sites of neovascularization. Angiogenesis assay are performed in mouse or nude rats transplanted with murine Tie2-LacZ bone marrow by injecting matrigel, a viscous extracellular matrix that solidifies at body temperature, containing angiogenic growth factors. Mice are treated by intravenous injection with anti-murine $\alpha 4\beta 1$ and control antibodies or other inhibitors of $\alpha 4\beta 1$. $\alpha 4\beta 1$ inhibitors are anticipated to block LacZ staining cells from incorporating into blood vessels, indicating that $\alpha 4\beta 1$ regulates endothelial precursor cell egress from the circulation. Frozen sections of the matrigel are stained with antibodies directed CD31 and Factor VIII related antigen to obtain an indication of angiogenic index.

Example 2

Endothelial Progenitor Cells (EPC) Express Integrin $\alpha 4\beta 1$

Figure 13:
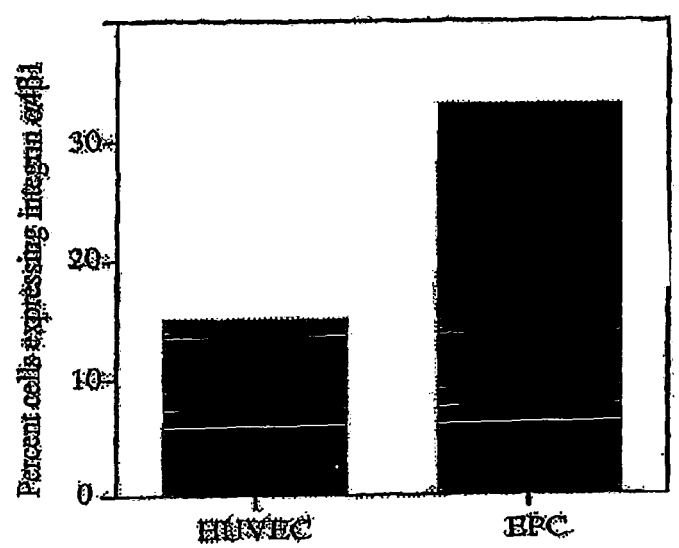
FIG. 13 shows a graph of percent cells expressing integrin α4β1 versus human umbilical vein endothelial cells (HUVEC) and endothelial progenitor cells (EPCs).

Purified human umbilical vein endothelial cells ("HUVECS") (Clonetics, San Diego, Calif.) and endothelial progenitor cells ("EPCs") cultured on fibronectin from circulating CD34+ stem cells (see Asahara et al., Science, 275:964-967, (1997)), were incubated with mouse anti-human integrin $\alpha 4\beta 1$ antibodies for 60 minutes on ice, washed twice with PBS and then incubated for 30 minutes on ice in rhodamine-labeled goat anti-mouse IgG. Cells were washed twice with cold PBS then analyzed on a FACSCAN analyzer for expression of integrin $\alpha 4\beta 1$. The percent cells expressing this integrin was determined and plotted according to cell type (FIG. 13).

Thirty-three percent of endothelial progenitor cells were positive for integrin $\alpha 4\beta 1$ expression while only 12% of HUVECS were positive. These results showed that the inhibitory effect of $\alpha 4\beta 1$ antagonists in angiogenesis result from an inhibition of the participation of endothelial progenitor cells in angiogenesis.

Example 3

Figure 14:
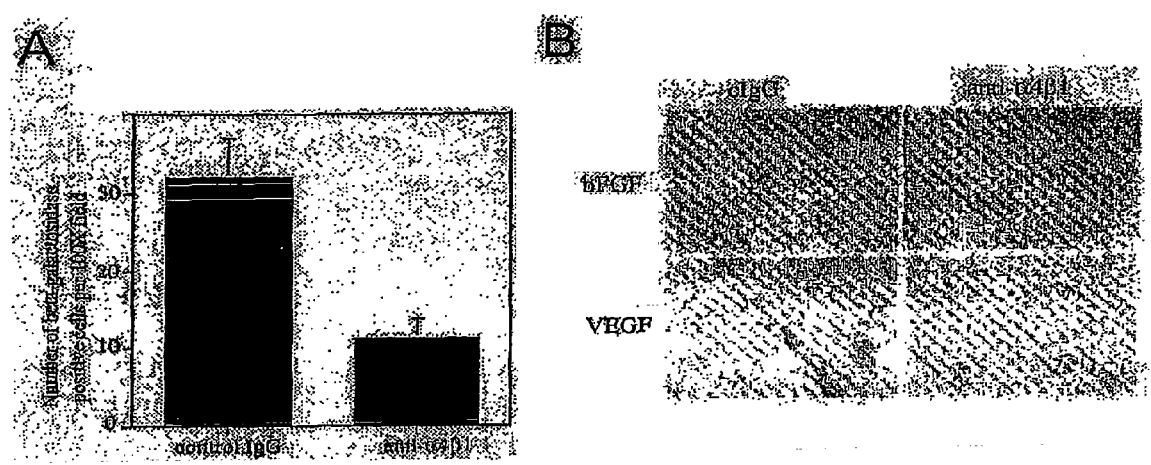
FIG. 14 shows a graph of number of beta-galactosidase positive cells per 100× field versus antibody treatments (Panel A) and photographs of immunostained cryosections of excised matrigel plugs (Panel B).
Figure 15:
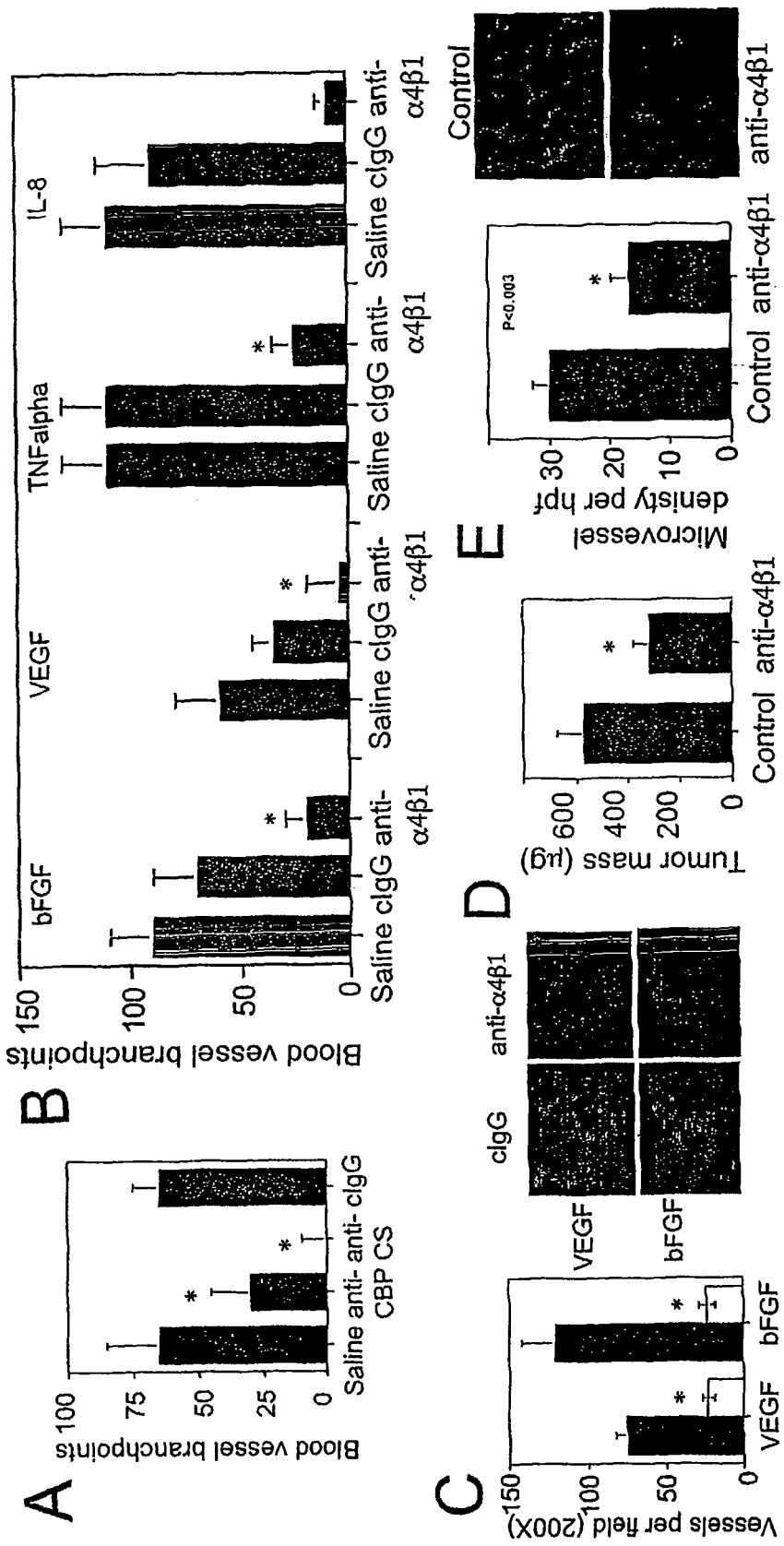
FIG. 15 shows that integrin α4β1 and CS-1 fibronectin regulate angiogenesis. (A) Blood vessel branchpoints at 30× magnification in CAMs stimulated with 1 µg/ml bFGF and treated with anti-fibronectin CBP or CS-1 function-blocking or control antibodies. (B) Blood vessel branchpoints in bFGF, VEGF, TNFα, or IL-8 stimulated CAMs treated saline, anti-integrin α4β1 (HP1/2) or control isotype matched antibodies. (C) Angiogenesis was initiated in FVB/N mice by subcutaneous injection growth factor reduced matrigel supplemented with bFGF or VEGF, and mice (n=8) were treated by i.v. injection of rat anti-integrin α4β1 (PS/2) (white bars) or isotype-matched control antibodies (rat anti-integrin β2) (black bars). Microvessel density was quantified at 200× by CD31 immunohistochemistry (right). (D-E) HT29 human α4β1 negative colon carcinoma cells were implanted subcutaneously in nude mice (n=10) and mice with palpable tumors (about 30 mm$^3$) were treated by i.v. injection of saline, rat-anti-mouse α4β1 or isotype matched control antibody, anti-CD11b integrin. (D) Mean tumor mass+/−SEM. (E) CD31 positive microvessels were detected by immunohistochemistry and quantified per 200× field.
Figure 16:
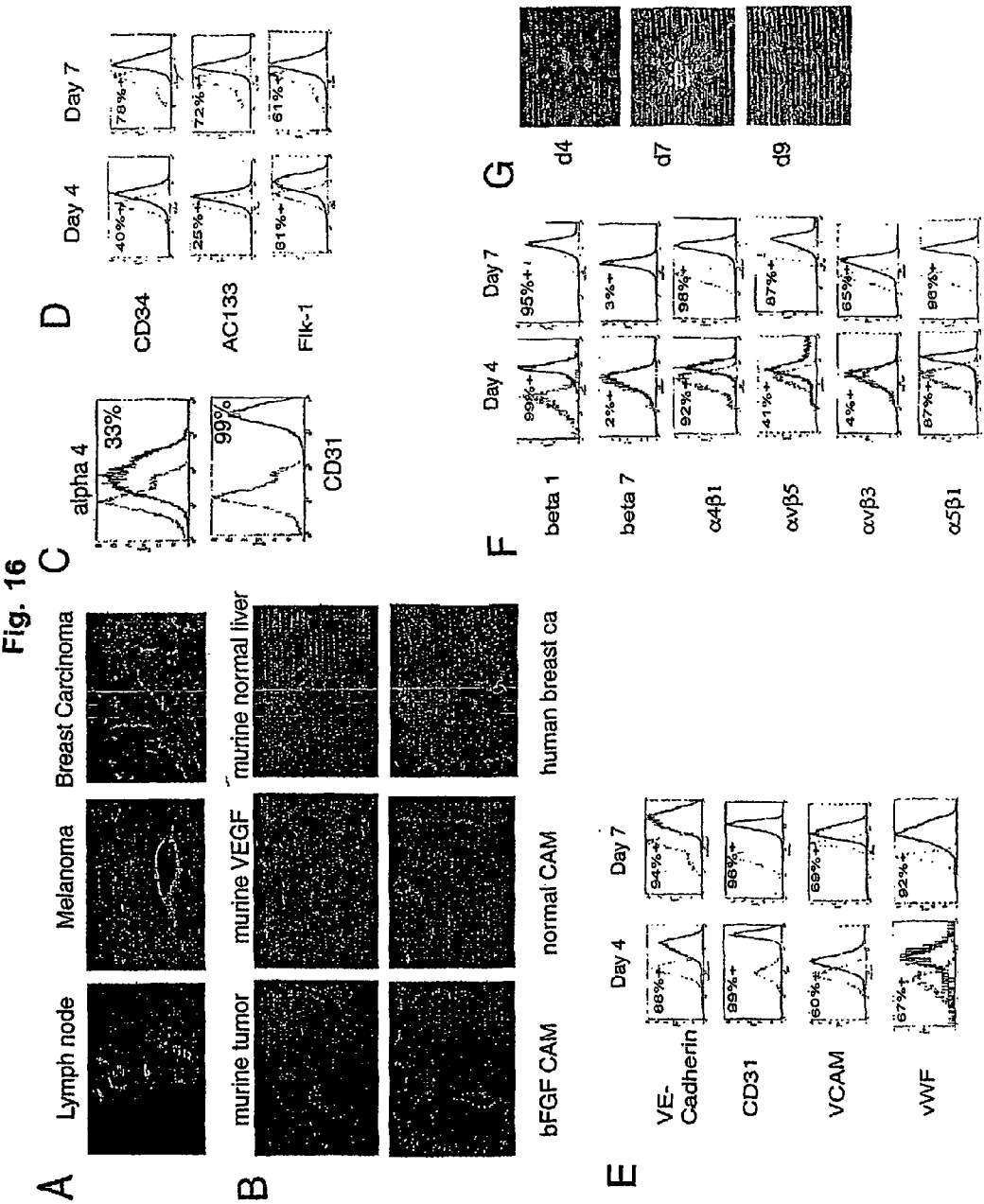
FIG. 16 shows expression of α4β1 on endothelial cells and endothelial precursor cells. (A) Five micron thick cryosections of human lymph node, melanoma and invasive ductal breast carcinoma were immunostained with anti-vWF (green) antibodies and P1H4, an anti-human α4β1 (red) antibody. (B) Five micron thick cryosections of human breast carcinoma, murine MTAG spontaneous breast carcinoma, murine VEGF matrigel, normal murine liver, bFGF stimulated CAM and normal CAM were immunostained with anti-vWF (red) antibodies and goat anti-alpha 4 cytoplasmic tail (green) antibody. Concordance of expression is indicated by yellow. C) FACs analysis of HMVECs for CD31 and α4β1 expression. (D) FACs analysis of expression levels in EPCs at day 4 and day 7 of CD34, AC133, and Flk-1. (E) FACs analysis of expression levels in EPCs at day 4 and day 7 of CD31, VE-Cadherin, VCAM, and vWF. (F) PACs analysis of expression levels in EPCs at day 4 and day 7 of beta 1, beta 7, beta 2, α4β1, αvβ3, αvβ5 and α5β1. (G) Micrographs under transmitted light of EPCs at 4, 7 or 9 days in culture.
Figure 17:
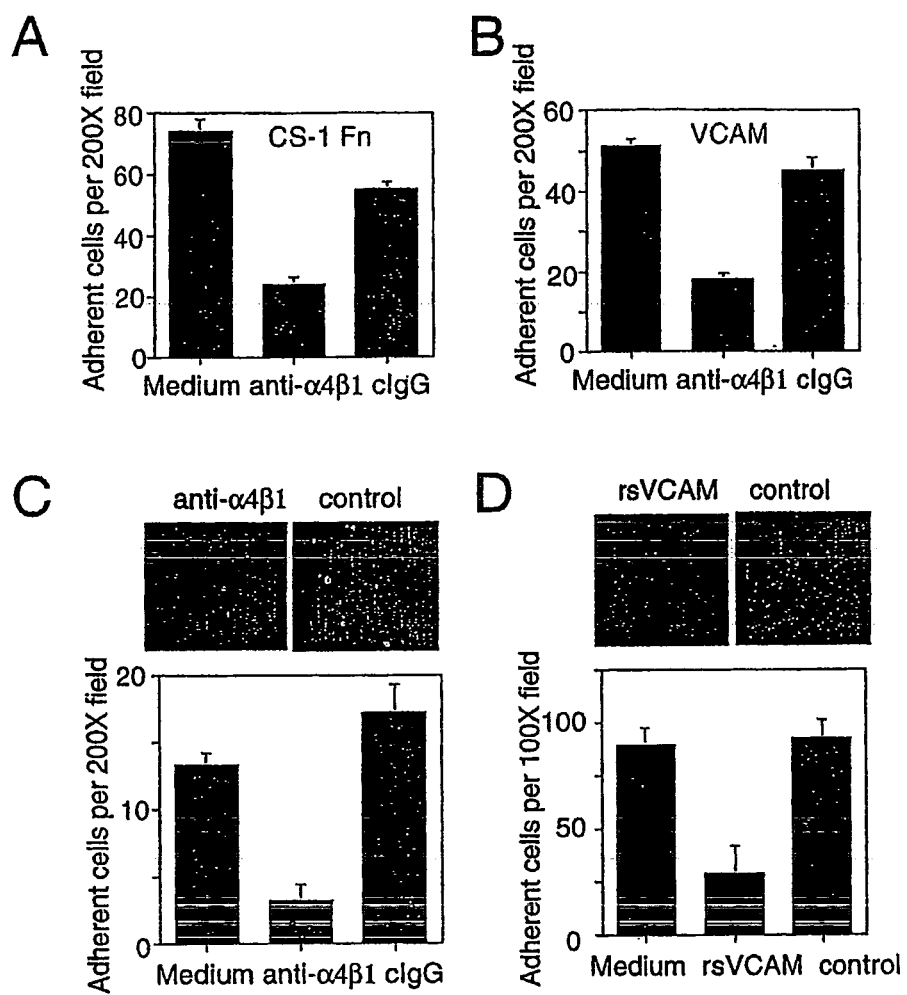
FIG. 17 shows functional roles of EPC expressed α4β1. (A-B) Adhesion of purified EPCs on plastic plates coated with (A) 5 µg/ml CS-1 fibronectin or (B) recombinant soluble VCAM in the presence of medium, anti-α4β1 (HP1/2) or control antibodies (P1F6). (C) Adhesion of DiI-labeled purified EPCs to HUVEC monolayers VCAM in the presence of medium, anti-α4β1 (HP1/2) or control antibodies (P1F6). Cells were quantified by counting adherent red fluorescent cells per 200× microscopic field. (D) Adhesion of DiI-labeled purified EPCs to HUVEC monolayers in the presence of medium, rsVCAM or control protein. Statistical significance was determined using Student's t-test.
Figure 18:
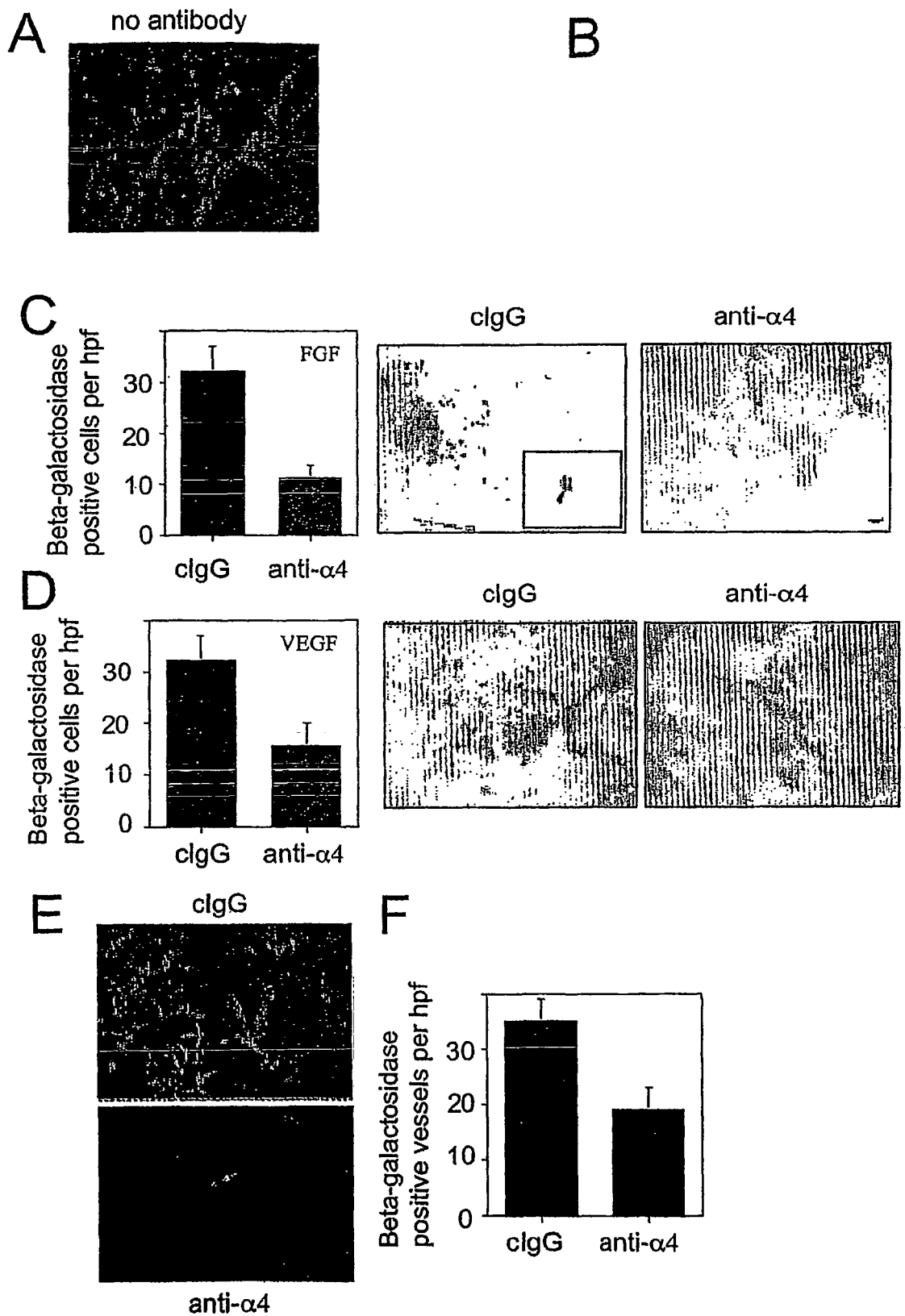
FIG. 18 shows integrin α4β1 controls endothelial precursor cell trafficking in vivo. (A) DiI acetylated-LDL (red) labeled endothelial progenitor cells were mixed in growth factor depleted matrigel with 400 ng/ml VEGF, no antibody, control antibody (P1F6) or anti-human α4β1 antibody (HP1/2). After 5 days, mice were injected with *Bandeira simplicifolia* lectin-FITC (green) and sacrificed. Cryosections were analyzed by fluorescence microscopy. (B) DiI acetylated-LDL labeled endothelial progenitor cells were injected i.v. into animals bearing 200 mm3 HT29 colon carcinoma tumors together with no antibody, control antibody (P1F6) or anti-human α4β1 antibody (HP1/2). After 5 days, mice were injected with *Bandeira simplicifolia* lectin-FITC and sacrificed. Cryosections were analyzed by fluorescence microscopy. (C-D) Tie2LacZpositive bone marrow was transplanted into irradiated FVB/N mice. After one month of recovery, angiogenesis was with bFGP (B) or VEGF (C) and mice were treated by i.v. injection with rat anti-mouse α4β1 (PS/2) or isotype matched control (anti-b2 integrin) antibody (n=8). Cryosections were treated to detect expression of beta galactosidase within the matrigel plugs (200×); inset, 600×. Mean+/−S.E.M. of Lac Z positive cells per 200× field was determined. (E) LacZ positive cells were detected within vessels by immunostaining for beta-galactosidase (green)

$\alpha 4\beta 1$ Antagonists Block Endothelial Stem Cell Contribution to Angiogenesis Murine angiogenesis was induced by subcutaneous injection 400 μl of growth factor depleted matrigel containing 400 ng/ml bFGF or VEGF into the rear dorsal flanks of inbred mice of the strain FVB/N or into FVB/N mice that had been irradiated and transplanted with bone marrow from Tie2LacZ mice. Animals were treated by intravenous injection on day 0 and day 3 with 200 μg of endotoxin free rat anti-murine $\alpha 4\beta 1$ antibody (PS-2) in 100l or control isotype matched rat anti-murine integrin beta 2 antibody on days 1 and 4 (n=10). After 5 days, matrigel plugs were excised, embedded in OCT, frozen and sectioned. Thin sections (5 μm) were immunostained with rat anti-murine CD31 followed by Alexa 565-conjugated goat anti-rat immunoglobulin. CD31 positive vessel density per 200x microscopic field was determined in 5 fields per matrigel plug. Mean vessel density per field+/− SEM was graphed versus treatment condition. Photographs were taken of representative fields of control IgG and anti-$\alpha 4\beta 1$ treated bFGF or VEGF containing plugs stained for beta galactosidase expression, with red indicating CD31 positive blood vessels and blue representing nuclei of all cells (FIG. 14B). Sections from Tie2/LacZ transplanted mice were analyzed for presence of bone marrow derived endothelial cells by staining sections for expression of beta galactosidase using a kit from Life Technologies. Blue cells in the plugs that arose from the transplanted bone marrow were counted (FIG. 14A) with bFGF stimulating angiogenesis.

Antagonists of integrin $\alpha 4\beta 1$ prevent the participation of endothelial progenitor cells in angiogenesis. Beta galactosidase expressing endothelial cells derive from bone marrow because these mice were irradiated to kill their own bone marrow prior to transplantation with bone marrow from mice that express LacZ under an endothelial specific promoter, the Tie2 promoter. Thus, endothelial cells that arise from bone marrow will turn blue in tissues incubated in a substrate for beta galactosidase. These data showed that fewer blue endothelial cells were induced by growth factors in mice treated with anti-$\alpha 4\beta 1$ than in mice treated with control antibodies. Therefore, anti-$\alpha 4\beta 1$ inhibited the participation in angiogenesis of endothelial progenitors derived from bone marrow.

Example 4

Exemplary Material and Methods

The following are some exemplary materials and methods that may be useful in the invention, particularly in Examples 5-13 and FIGS. 15-20.

A. Chick Chorioallantoic Membrane Angiogenesis Assays

Chick chorioallantoic membranes of 10 day old chicken embryos were stimulated with 1 µg/ml bFGF and function-blocking antibodies (25 µg/ml) directed against the RGD containing cell-binding domain (CBP) and the EILDV containing C-terminal CS-1 domain of fibronectin, as well as isotype matched control antibodies (anti-MHC) were applied. Three days later, blood vessel branchpoints were counted using 30× magnification. Angiogenesis was stimulated in CAMs with 1 µg/ml bFGF, VEGF, TNFα, or IL-8. Saline or antibodies directed against integrin α4β1 (mouse anti-human α4β1 antibodies HP1/2, P4G9, P1H4 and rat anti-mouse α4β1 PS2 were all tested were similar results) and control isotype matched antibodies were applied to CAMs and blood vessel branchpoints were counted 3 days later. Cryosections from bFGF stimulated, saline or antibody-treated CAMs were immunostained to detect blood vessel expression of von Willebrand Factor. VWF+ structures were quantified in five 200× microscopic fields. Each experiment was repeated 3-4 times and results from representative experiments are shown.

B. Murine Angiogenesis Assays

Angiogenesis was initiated in FVB/N mice by subcutaneous injection of 400 µl growth factor reduced matrigel supplemented with 400 ng/ml of bFGF or VEGF. Mice were treated on day 0 and 3 by intravenous injection of 200 µg function blocking rat anti-integrin α4β1 (PS/2) or isotype-matched control antibodies (rat anti-integrin β2, BD Pharmingen). Matrigel plugs were excised after 5 days and cryopreserved. Cryosections were immunostained to detect CD31 expression and counterstain with DAPI. Microvessel density was quantified in 10 randomly selected 200× microscopic fields for each plug in each treatment group (n=8). Alternatively, angiogenesis was initiated in FVB/N mice by corneal transplantation of polymerized pellets containing 400 ng/ml of VEGF. Animals (n=5) were treated on day 0 and day 3 with anti-α4β1 (PS/2) or control IgG. Fifteen minutes prior to sacrifice on day 5, mice were injected intravenously with endothelial specific lectin, $Bandeira\ simplifolia$-FITC and tissues were cryopreserved. Angiogenic response to VEGF was quantified as the percent green fluorescent area visible at 100× magnification. Additionally, five million HT29 human α4β1 negative colon carcinoma cells were implanted subcutaneously in nude mice. When tumors were palpable (about 30 $mm^3$), mice were treated twice weekly by i.v. injection of saline, rat-anti-mouse α4β1 or isotype matched control antibody, anti-CD11b integrin (M1/70, BD Pharmingen). Tumor dimensions were determined every other day and tumor mass was determined after four weeks of treatment. Mean tumor mass+/− SEM is presented. Cryosections of tumors were immunostained to detect CD31 (BD Pharmingen) and microvessel density was quantified for 5 randomly selected microscopic fields. Additionally, tumors were stained with hematoxylin and eosin (n=10). Three experiments were performed and selected representative data is shown. Statistical significance was determined using Student's t-test.

C. FACs Analysis

The expression profile of surface antigens of human microvascular endothelial cells, human umbilical vein endothelial cells and endothelial progenitor cells was analyzed by FACs analysis using mouse antibodies directed against human α4β1 (HP1/2), αvβ3 (LM609), αvβ5 (P1F6), α5β1 (JBS5), beta 1 (P4C10), beta 7 (FIB504, Beckton Dickinson Pharmingen) CD34 (8G12, Becton Dickinson), AC133 (AC133, Miltenyi Biotec), Flk-1 (A-3, Santa Cruz Biotechnology), CD45 (2D1, Beckton Dickinson) CD31 (HEC7, Endogen), VE-Cadherin (BV6, Chemicon International), and VCAM (P8B1, Chemicon International) and rabbit anti-VWF (Dako).

D. Isolation of Endothelial Progenitor Cells

Mononuclear cells from human peripheral blood were isolated using known methods. In some experiments, CD34 positive cells were purified from the mononuclear population using MACS magnetic bead systems. Cells were cultured up to 9 days in endothelial growth medium (EGM-2 containing 2% fetal bovine serum, bFGF, VEGF and). After 7 days, 80% of the cells are spindle shaped and express vascular cell markers as well as stem cell markers.

E. Adhesion and Migration Assays

Adhesion were performed essentially as described. For adhesion analysis, day 7 EPCs were allowed to adhere to triplicate well of 48 well plates coated with 5 µg/ml CS-1 fibronectin (recombinant H120 fragment, a kind gift from Martin J. Humphries), recombinant soluble VCAM, plasma fibronectin, vitronectin (purified as described) or collagen for 30 minutes. Plates were washed 5 times and adherent cells were quantified at 200× magnification. Alternatively, cells were stained with crystal violet, washed, air dried and extracted with acetic acid. Absorbance at 600 nm was then determined. In some experiments, 25 µg/ml function-blocking antibodies against integrins α4β1 (HP1/2), α5β1 (JBS5) beta 1 (P4C10), αvβ5 (P1F6), or αvβ3 (LM609) were added to the adhesion assay. Migration assays were performed as described. EPCs were added to triplicate 8 µm pore size transwell inserts coated with 5 µg/ml CS-1 fibronectin (recombinant H120 fragment from Martin J. Humphries), collagen, fibronectin or vitronectin. After 4 hours, cells were fixed with 3.7% paraformaldehyde, stained with crystal violet and cells on the underside of the transwell were quantified.

F. Bone Marrow Transplantation

Bone marrow from Tie2LacZ transgenic mice (n=8) was transplanted into irradiated FVB/N mice. After one month of recovery, angiogenesis was initiated by injection of growth factor reduced matrigel supplemented with 400 ng/ml of bFGF or VEGF. Mice were treated on day 0 and day 3 by i.v. injection of 200 µg rat anti-mouse α4β1 antibody (PS/2) or isotype matched control (anti-b2 integrin). Plugs were excised after 5-7 days and cryopreserved. Cryosections were treated to detect expression of beta galactosidase within the matrigel plugs. Micrographs were taken at 200× and at 600× magnification. Lac Z positive cells per 200× field were quantified in 10 microscopic fields. Cryosections were also immunostained with rabbit anti-beta galactosidase and rat anti-murine CD31. Micrographs are taken at 200×. LacZ, CD31 positive vessels were quantified in 10 microscopic fields. Statistical significance was determined using Student's t-test.

Example 5

In studies to analyze the roles of fibronectin and its receptors in angiogenesis, we found that antagonists of the RGD cell-binding domain of fibronectin and its receptor α5β1 potently block angiogenesis (Kim et al., Am J Pathol. 2000 April; 156(4):1345-62). To our surprise, antibodies that recognize the EILDV site in the alternatively spliced domain of tissue fibronectin, CS-1 fibronectin, potently blocked angiogenesis in the chick chorioallantoic membrane (CAM) model (FIG. 15A, $P<0.05$). These antagonists interfere with the binding of CS-1 fibronectin to its principle receptor, integrin α4β1 (Guan et al., Cell. 1990 Jan. 12; 60(1):53-61). Importantly, these antibodies inhibited the attachment and migration of cultured human endothelial cells on CS-1 fibronectin. These results suggest that CS-1 fibronectin and its receptor integrin α4β1 may play roles in angiogenesis. These findings are consistent with our previous observation that fibronectin expression is significantly upregulated during angiogenesis (Kim et al. 2000 supra) and the independent reports showing that CS-1 fibronectin expression is upregulated in association with vessels-during wound repair in skin, heart and other tissues, as well as during chronic inflammatory diseases such as rheumatoid arthritis (Elices et al., J Clin Invest. 1994 93(1):405-16; Morales-Ducret et al., J. Immunol. 1992 149 (4):1424-31). Based on these results, we considered whether α4β1 was involved in angiogenesis. To evaluate the role of α4β1 in angiogenesis, α4β1 function-blocking antibodies were applied to CAMs stimulated with bFGF, VEGF, TNFα or IL-8. Anti-α4β1 blocked angiogenesis induced by each of these growth factors (FIG. 15B, P<0.05). These studies indicate that integrin α4β1 plays a role in neovascularization in the chick CAM model.

Example 6

To assess the role of α4β1 in mammalian angiogenesis, we tested the effects of antagonists of integrin α4β1 in several murine models of neovascularization. We injected anti-integrin α4β1 antibody (PS/2) intravenously into mice that were stimulated to undergo angiogenesis by subcutaneous injection of either bFGF or VEGF saturated Matrigel. (FIG. 15C). We found that inhibition of α4β1 significantly blocked angiogenesis, whether assessed by microvascular density or total vessel content (P<0.05). Additionally, peptide antagonists of α4β1 (EILDV, derived from CS-1 fibronectin) also blocked neovascularization in this model, providing further support for a role of for α4β1 in this process. Anti-α4β1 antibodies also blocked corneal angiogenesis (P<0.05). Importantly, antagonists of integrin α4β1 significantly inhibited tumor angiogenesis and tumor growth (FIG. 15D-E). Thus, CS-1 fibronectin and its receptor integrin α4β1 play important roles in the control of neovascularization.

Example 7

We next reasoned that if α4β1 regulates angiogenesis, this integrin should be expressed on the vasculature of tumors and other neovascular tissues. To evaluate the expression pattern of integrin α4β1 on the neovascular beds of human tumors, we performed immunohistochemistry to detect expression of integrin α4β1 and von Willebrand Factor, a marker of vascular endothelium (Kim et al. 2000 supra). Using a variety of monoclonal anti-α4 antibodies, to our surprise we were rarely able to show expression of α4 on tumor endothelium, yet we detected integrin 4 expression in control tissues such as lymph node and human melanoma (refs; FIG. 16A). Occasionally, we detected α4β1 expression on a subset of blood vessels within tumors, such as invasive ductal breast carcinoma (FIG. 16A). Using an antibody that reacts with the cytoplasmic tail of alpha 4, we were able to detect high levels of alpha 4 expression on vascular endothelial cells in growth factor stimulated CAMs, growth factor stimulated murine tissue, murine tumors and human tumors (FIG. 16B). However, unlike neovascular integrins α5β1 and αvβ3 (Brooks et al., Science. 1994 264:569-71), integrin α4β1 is only weakly expressed on proliferating human microvascular or venous endothelial cells in vitro (FIG. 16C).

Example 8

As α4β1 is only weakly expressed on proliferating purified endothelial cells, we reasoned that this integrin might be transiently expressed by endothelial cells in vivo or expressed by endothelial precursors during neovascularization. Since new vessels can arise not only by sprouting but also by the seeding of bone marrow derived stem cells in tissues, we considered whether EPCs may express α4β1. To isolate EPCs, we cultured the mononuclear fraction of peripheral blood leukocytes or CD34 positive stem cells (isolated from the mononuclear fraction of peripheral blood leukocytes) on fibronectin cultured plates in the presence of the angiogenic cytokines bFGF and VEGF. The resulting EPCs not only express high levels of α4β1 but also co-express stem cell markers such as CD34, CD133, Flk-1 (Asahara et al., et al., 1997 February supra; Brooks et al., Science. 1994 supra), CD45 and CD18 as well as endothelial markers such as VE-cadherin, VCAM, CD31 and VWF (FIG. 16D-E). With increasing time in culture, these cells acquire additional characteristics of endothelial cells, expressing increasing amounts of CD34, VE-cadherin, VCAM, and VWF (FIG. 16D-E). These cells exhibit a larger, elongated, adherent morphology and spontaneously form tube-like structures (FIG. 16F). Importantly, while EPCs are strongly positive for integrin α4β1, they fail to express the closely related leukocyte integrin α4β7 (FIG. 16D). EPCs are also positive for other adhesion receptors, including integrin α59β1, the RGD-binding fibronectin receptor (Kim et al. 2000 supra). Strikingly, EPCs express little integrin αvβ5 and no αvβ3 during their early stages of in vitro development but high levels of these integrins are observed in later stages (FIG. 16E), suggesting that these integrins are upregulated as EPCs acquire increasingly greater endothelial characteristics. The EPCs are also positive for UEA lectin staining, a characteristic of cells of endothelial lineage and bind DiI acetylated LDL. Thus, in contrast to mature endothelial cells, EPCs are strongly positive for integrin α4β1 expression.

Example 9

Since integrins on circulating lymphocytes are often maintained in an inactive or low affinity state (Peichev et al., Blood. 2000 Feb. 1; 95(3):952-8), we next determined whether the integrin α4β1 expressed by EPCs is functional. In fact, EPCs attach to and migrate on CS-1 fibronectin, as well as collagen, plasma fibronectin, and vitronectin. Importantly, adhesion to CS-1 fibronectin is mediated by integrin α4β1 as function-blocking anti-α4β1 and β1 antibodies prevented EPC attachment to this matrix protein (FIG. 17A). Since α4β1 is also a receptor for the immunoglobulin superfamily molecule VCAM that is expressed by activated endothelium, we also examined the ability of EPCs to attach to plates coated with recombinant soluble VCAM (rsVCAM). Antagonists of α4β1 blocked EPC attachment to VCAM, indicating that integrin α4β1 is a functionally active receptor for both CS-1 fibronectin and VCAM on endothelial stem cells (FIG. 17B).

Example 10

To determine whether EPCs can attach to proliferating vascular endothelium that has been stimulated by angiogenic growth factors, we plated EPCs labeled with DiI-acetylated LDL onto proliferating endothelial monolayers. EPCs bound strongly to endothelium in a α4β1 dependent manner (FIG. 17C) and that rsVCAM blocked EPC attachment to endothelial monolayers (FIG. 17D). Similar results were obtained when α4β1 antibodies or rsVCAM were pre-incubated with EPCs, but not when they were pre-incubated with endothelial monolayers. Thus, α4β1 mediates the attachment of EPCs to VCAM on vascular endothelium. As VCAM is upregulated in endothelium undergoing angiogenesis in response to inflammatory cytokines and growth factors and recombinant soluble forms of VCAM can inhibit angiogenesis (Nakao et al. J. Immunol. 2003 Un 1; 170(11):5704-11), these results suggest that α4-VCAM interactions may facilitate the movement of bone marrow derived stem or precursor cells into tissues during angiogenesis and tissue repair. In fact, integrin α4β1-VCAM interactions play obligatory roles in facilitating heterotypic cell adhesion in vivo during embryonic development, (chorion-allantois, endocardium-myocardium, primary myoblast fushions), in immune cell trafficking (extravasation of lymphocytes, monocytes, and eosinophils in inflammation) and in retention of immune cell precursors in the bone marrow (Rosen et al., Cell. 1992 Jun. 26; 69(7): 1107-19). Thus α4-VCAM interactions may regulate stem cell entry into sites of tissues repair.

Example 11

To determine whether α4β1 regulates the formation of neovessels by EPCs, we subcutaneously implanted nude mice with DiI labeled human EPCs in matrigel containing VEGF and anti-human α4β1 or control antibodies. After five days, neovessels were visualized with an injection of *Bandeira simplifolia*. We observed that many EPCs formed vessels (FIG. 18A) and that anti-α4β1 but not control antibodies blocked vessels formation. These studies indicate that EPCs are competent to form neovessels and that α4β1 function is required for this process.

Example 12

To determine whether α4β1 mediates the attachment of EPCs to angiogenic endothelium in vivo, we adoptively transferred human EPCs into nude mice bearing subcutaneously implanted integrin α4β1 negative colon carcinoma tumors. Mice were systemically treated with anti-human α4β1 antibodies, control antibodies or saline. We found that EPCs incorporated into neovessels and that only antagonists of human α4β1 blocked this event (FIG. 18B). These finding demonstrate that integrin α4β1 mediates the extravasation of endothelial stem cells from the circulation into angiogenic tissue. As all CD34 positive stem cells must cross the endothelium to enter into tissues, these studies suggest that α4β1 mediates stem cell trafficking in vivo.

Example 13

To investigate the role of α4β1 in the regulation of bone marrow derived endothelial stem cell trafficking in vivo, we induced angiogenesis in mice transplanted with bone marrow from Tie2Lac Z mice and systemically treated the animals with anti-murine α4β1 antibodies (PS/2) and control antibodies (anti-murine β2 integrin). We determined that anti-α4β1 antibodies, but not anti-β2 antibodies, significantly blocked the incorporation of LacZ positive cells and vessels in matrigel whether angiogenesis was induced by bFGF or by VEGF (FIG. 18C-D). To further determine whether Lac Z positive cells incorporate into blood vessels and express endothelial markers, we immunostained cryosections with anti-beta-galactosidase (green) and anti-murine CD31 (red). We identified a significant number of the Lac Z positive bone marrow derived cells (>90%) within CD31 positive vessels and observed that antagonists of α4β1 blocked the incorporation of these cells into neovessels (FIG. 18E-F). These studies indicate that α4β1 promotes the entry of bone marrow derived endothelial stem cells into tissues where they participate in the formation of neovasculature.

Example 14

Additional data herein is shown in FIG. 19. FIG. 19A shows migration of endothelial cells on 8 µm pore transwells coated with 5 µg/ml CS-1 fibronectin in the presence of medium, anti-CS-1 fibronectin or control antibodies (W6/32, anti-MHC). FIG. 19B, C shows adhesion of endothelial cells to plastic plates coated with 5 µg/ml CS-1 fibronectin, in the presence of medium, anti-α4β1 (HP1/2) or control antibodies (P1F6). FIG. 19D shows cryosections from bFGF stimulated, saline or antibody-treated CAMs were immunostained to detect blood vessel expression of von Willebrand Factor. VWF+ structures were quantified in five 200× microscopic fields. FIG. 19E shows angiogenesis was initiated in FVB/N mice by corneal transplantation of polymerized pellets containing 400 ng/ml of VEGF. Animals (n=5) were treated on day 0 and day 3 with anti-α4β1 (PS/2) or control IgG (cIgG). Fifteen minutes prior to sacrifice on day 5, mice were injected intravenously with endothelial specific lectin, *Bandeira simplifolia*-FITC and tissues were cryopreserved. Angiogenic response to VEGF was quantified as the percent green fluorescent area visible under high power magnification (100×). FIG. 19F-G shows angiogenesis was initiated in nude mice by subcutaneous injection of 400 µl growth factor reduced matrigel supplemented with 400 ng/ml of bFGF containing (F) 200 µg function blocking rat anti-integrin α4β1 (PS/2) or isotype-matched control antibodies (rat anti-integrin β2) and FIG. 19G shows using 50 µM EILDV or EILEV peptides. Fifteen minutes prior to sacrifice on day 5, mice were injected intravenously with endothelial specific lectin, *Bandeira simplifolia*-FITC. Matrigel plugs were homogenized in RIPA buffer and fluorescence intensity determined.

Example 15

Additional data herein is shown in FIG. 20. FIG. 20A shows cytofluorescence analysis of ECs, EPCs, and fibroblasts for UEA-1 lectin binding and uptake of DiI-acetylated LDL. FIG. 20B shows adhesion of purified EPCs to plastic plates coated with 5 µg/ml fibronectin, CS-1 fibronectin, vitronectin and collagen. FIG. 20C shows migration of purified EPCs on 8 µm pore transwells coated with 5 µg/ml fibronectin, CS-1 fibronectin, vitronectin and collagen, and FIG. 20D shows adhesion of purified EPCs on plastic plates coated with 5 µg/ml vitronectin in the presence of medium, anti-α4β1 (HP1/2), anti-α3β1 (LM609), anti-αvβ5 (P1F6), or anti-α5β1 (P1F6).

Example 16

The following are some exemplary materials and methods that may be useful in the invention, particularly in Examples 17-24 and FIGS. 33-36. Statistical significance was determined using Student's t-test.

A. Stem Cell Isolation:

$3.7 \times 10^9$ mononuclear cells were purified by Histopaque gradient centrifugation from 6 units of human buffy coats from the San Diego Blood Bank. CD34 cell isolation was performed by positive selection over two anti-CD34 columns using kits from Miltenyi Biotech (Auburn, Calif.). The yield of CD34+ cells was $3 \times 10^6$ at a purity of 89% as assessed by FACs analysis.

B. Intravital Microscopy

Stem cells were labeled with 5-and-6-4-chloromethylbenzoylamino-tetramethyl-rhodamine (CMTMR, invitrogen, Carlsbad, Calif.) in culture medium for 15 minutes on ice and washed. $1 \times 10^6$ labeled stem cells were intravenously injected into mice with N202 syngeneic GFP expressing tumor spheroids grown on transplanted mammary fat pad under transparent dorsal skinfold chambers. Animals were sedated (15-20 minutes) while in vivo fluorescence microscopy was performed using a Mikron Instrument Microscope (Mikron Instrument, San Diego, Calif.) equipped with epi-illuminator and video-triggered stroboscopic illumination from a xenon arc IV-7600, EG&G, Salem, Mass.). A silicon intensified target camera (SIT68, Dage-MTI, Michigan City, Ind.) is attached to the microscope. A Hamamatsu image processor (Argus 20) with firmware version 2.50 (Hamamatsu Photonic System, USA) is used for image enhancement and to capture images to a computer. A Zeiss Achroplan 20×/0.5 W objective 10/0.22 was used to capture images.

C. FACs Analysis

FACs analysis was performed at the UCSD Cancer Center Core facility. Expression of integrin $\alpha 4\beta 1$, CD34 and CD133 on stem cells was analyzed by two color fluorescence using PE-conjugated mouse anti-human $\alpha 4\beta 1$ (HP2/1, Chemicon International, Temecula, Calif.), FITC- and PE-conjugated mouse anti-human CD34 (AC136, Miltenyi Biotech, Auburn, Calif.), and PE-conjugated CD133 (AC133/1, Miltenyi Biotech, Auburn, Calif.), CD31 (HEC7, Pierce). Expression of VCAM on ECs was determined with P8B1 (Chemicon International, Temecula, Calif.).

D. Immunohistochemistry

Cryosections were fixed in cold acetone for 2 minutes, air dried and rehydrated in phosphate buffered saline (PBS) for 5 minutes. Slides were washed in 0.05-0.1% Triton X-100 in PBS for 2 minutes, incubated in 5% Bovine Serum Albumin in PBS overnight at 4° C. and in primary antibody (5-10 µg/ml) for 2 hours RT, washed three times in PBS and incubated in secondary antibody at 1 µg/ml for 1 hour RT. Slides were washed three times in PBS, stained with DAPI and coverslips mounted. Primary antibodies were: fibronectin (TV-1, Chemicon), anti-mouse VCAM (M/K-2 from Chemicon), anti-pan species VCAM (H-276, sc-8304 from Santa Cruz), and anti-mouse CD31 (MEC 13.3 from Pharmingen).

E. Adhesion Assays

Adhesion assays were performed on plastic 48 well plates coated with 5 µg/ml of recombinant H120 CS-1 fibronectin (from Martin J. Humphries, University of Birmingham, UK) as described (Kim et al. (2000) Am. J. Pathol. 156, 1345-1362). Stem cells were incubated on coated plates for 30 minutes in the presence of 25 µg/ml anti-$\alpha 4\beta 1$_(HP2/1) or anti-$\alpha v\beta 5$ (P1F6, from Dr. David Cheresh, the Scripps Research Institute). CMTMR labeled stem cells were incubated in HEPES buffered serum free culture medium in the presence of 25 µg/ml HP2/1 or P1F6 on HUVEC monolayers for 60 minutes at 37° C. Unbound cells were removed by washing gently with PBS. Cells were fixed in 3.7% parafomaldeyde. Representative fields were photographed at 200× and the number of cells adhering per field was quantified in five representative fields per treatment condition.

F. Adoptive Transfer Tumor Studies $3 \times 10^6$ CMTMR labeled stem cells were incubated in saline, 50 µg/ml of control antibody (LM609, anti-human $\alpha v\beta 3$) or anti-human $\alpha 4\beta 1$ (HP2/1, a gift from Roy Lobb, Biogen or 9F10, Becton-Dickinson, San Diego, Calif.). The cells were incubated with antibodies on ice for 30 minutes before injecting into nude mice bearing N202 or Lewis lung carcinoma tumors. After one hour, animals were sacrificed. Tumors plus surrounding connective tissue were excised and cryopreserved (n=6).

Alternatively, lineage negative (Lin−) cells were isolated from the bone marrow of EGFP mice by negative immune selection as previously described (Otani et al. (2002) Nat. Med. 8, 1004-1010) Cells were injected into nude mice bearing 0.5 cm Lewis lung carcinoma tumors. Animals were treated for the following five days with saline, control antibody (anti-CD11b) or anti-murine $\alpha 4\beta 1$ antibody (PS/2). After five days, animals were sacrificed. Tumors plus surrounding connective tissue were excised and cryopreserved (n=6).

G. Bone Marrow Transplantation

Bone marrow from FVB/N-Tie2LacZ mice was transplanted into irradiated FVB/N mice. After 12 weeks, mice were injected with 400 µl growth factor reduced Matrigel supplemented with 400 ng/ml of bFGF or VEGF and treated on day 1 and 3 by i.v. injection of 200 µg/mouse rat antimouse of $\alpha 4\beta 1$ antibody (low endotoxin PS/2, a kind gift from Biogen) or rat-anti-mouse $\beta 2$ integrin (low endotoxin M1/70, Becton-Dickinson, San Diego, Calif.). Plugs were excised after 5 days (n=8). Studies were performed twice. Cryosections were incubated in X-gal or immunostained with rabbit anti-beta galactosidase and rat anti-murine CD31 (MEC13.3, Becton-Dickinson, San Diego, Calif.). Positive vessels were quantified at 200× in 10 randomly selected microscopic fields.

Example 17

Stem Cells Home Selectively to Neovasculature

To understand how stem cells home to the neovasculature, we employed real time-intravital microscopy to study the movement of stem cells transplanted into mice with breast carcinomas. Human CD34+ stem cells were labeled with a red fluorescent cell tracking dye and were injected into the circulation of nude mice that had been implanted with murine breast carcinoma spheroids on mammary fat pads under dorsal skinfold chambers (FIG. 33a). Intravital microscopy was performed immediately thereafter to track stem cell homing to the tumor. Tumors and associated non-fluorescent blood vessels were visible (FIG. 33b), enabling us to evaluate cell attachment within the vasculature. Circulating fluorescent cells were evident in both the central and peripheral tumor vasculature but they arrested only in blood vessels at the tumor periphery (FIG. 33c-d). In contrast, stem cells rarely arrested in the tumor center (FIG. 33c-d), or in other organs. Postmortem analysis of tumors by fluorescence microscopy confirmed that stem cells (red, arrowheads) arrested only in the tumor peripheral vasculature, identified by anti-CD31 immunostaining (green, arrows), or extravasated into the neighboring tissue (FIG. 33e). These studies indicate that stem cells home selectively to the growing peripheral tumor vasculature and suggest that specific cell attachment mechanisms may play a role in this homing response.

Example 18

Stem Cells Express Integrin $\alpha 4\beta 1$

To determine how stem cells arrest in peripheral vasculature, we examined the roles of cell adhesion molecules in stem cell homing. Circulating cells such as lymphocytes utilize integrin $\alpha 4\beta 1$ to arrest on the endothelium and to extravasate from the circulation (Guan et al. (2990) Cell 60, 53-61;

and Elices et al. (1990) Cell 60, 577-584), while hematopoietic precursor cells use α4β1 to adhere to bone marrow endothelium (Simmons et al. (1992) Blood. 80, 388-395; Papayannopoulou et al. (2001) Blood 98, 2403-2411; Craddock et al. (1997) Blood 90, 4779-4788; Miyake et al. (1991) J. Cell Biol. 114, 557-565). To evaluate a role for α4β1 in stem cell homing, we examined the expression of α4β1 on circulating stem cells by FACs analysis. We found that the large majority of CD34+ cells express α4β1 and that substantially all of the CD34+CD133+ subset, which can differentiate into endothelium Peichev et al. (2000) Blood 95, 952-958), express integrin α4β1 (FIG. 34a).

Example 19

Integrin α4β1 is a Functionally Active Receptor on Stem Cells

Since integrins on circulating cells are often maintained in an inactive or low affinity state (Bartolome et al. (2003) Mol. Biol. Cell 14, 54-66), we next determined whether α4β1 on stem cells is functionally active. Integrin α4β1 is a receptor for cellular fibronectin (CS-1 fibronectin) (Elices et al. (1994) J. Clin. Invest. 93, 405-416) and for VCAM, an immunoglobulin superfamily molecule that is expressed on endothelium in inflamed tissues (Elices et al. (1990) Cell 60, 577-584). Stem cells readily attached to CS-1 fibronectin coated plates; this adhesion was blocked by anti-α4β1, but not control (anti-αvβ5) antibodies (FIG. 34b). These results indicate that integrin α4β1 is a functionally active receptor on many stem cells.

Example 20

Integrin α4β1 Interaction with VCAM and/or Fibronectin Mediates Attachment of Stem Cells to Endothelial Cells In Vitro To determine whether stem cells can attach to endothelial cells (ECs) in an α4β1 dependent manner, we plated fluorescently labeled stem cells on confluent EC monolayers, which express the α4β1 ligand VCAM (FIG. 34c). Stem cells bound strongly to ECs (FIG. 34d-e). This adhesion was blocked by antibody antagonists of (α4β1 but not by control antibodies (anti-αvβ5) (FIG. 34d-e). Attachment was also blocked by recombinant soluble VCAM, a competitive inhibitor of integrin α4β1 function. These studies demonstrate that α4β1 can mediate the attachment of stem cells to ECs in vitro and suggest the possibility that α4-VCAM or α4-fibronectin interactions can promote stem cell adhesion to the vasculature.

Example 21

Neovasculature Cells Express Integrin α4β1 Ligands VCAM and Fibronectin In Vitro We next examined whether tissues undergoing neovascularization express the α4β1 ligands VCAM and cellular fibronectin by examining mouse breast carcinomas or normal tissue for these molecules. Both molecules (green) are expressed in tumor endothelium (red, FIG. 35a), at much greater levels in the tumor periphery than in its center (FIG. 35a). These ligands are rarely expressed by normal endothelium, although fibronectin was occasionally observed around large vessels (FIG. 35a). These results demonstrate that the α4β1 ligands VCAM and fibronectin are in precisely the right location to promote the adhesion of α4β1+ stem cells.

Example 22

Integrin α4β1-Antibody Inhibits Stem Cell Migration to Neovasculature In Vivo

To determine if α4β1 mediates the attachment of stem cells to growing blood vessels in vivo, fluorescently labeled stem cells were introduced by tail vein injection into nude mice with established murine breast carcinoma (N202) or Lewis lung carcinoma (LLC) tumors. Tissues were removed for analysis within one hour of cell injection. Stem cells (red) arrested in or extravasated near the vessels (green) of both tumor types (FIG. 35b). Strikingly, when stem cells were co-injected with function-blocking anti-human α4β1 antibodies, they were unable to arrest in the vasculature of either tumor type (FIG. 35b-d). In contrast, saline or control antibodies had minimal effect on stem cell arrest and adhesion (FIG. 35b-d). Although stem cells homed to the tumor vasculature, they did not home to adjacent normal tissues or to other organs such as lung. These studies indicate that α4β1 regulates homing of stem cells to tumor neovasculature. These results discount nonspecific homing of cells to leaky tumor vessels, because stem cells do not lodge in central tumor vessels and antagonists of specific receptors block their adhesion in vessels.

Example 23

Integrin α4β1-Antibody Inhibits Stem Cell Differentiation into Vascular Endothelium In Vivo To determine whether α4β1 promotes stem cell homing and subsequent participation in blood vessel formation in vivo, we injected lineage negative (Lin−) bone marrow derived cells from EGFP (enhanced green fluorescent protein) mice[6] into animals with LLC tumors in the presence or absence of α4β1 antagonists and control antibodies. We found that after five days in vivo, EGFP+ cells in control treated animals had homed to tumors in significant numbers (arrowheads) and formed EGFP+ blood vessels (arrows, FIG. 36a-b). In contrast, few EGFP+ cells were observed in tumors of anti-α4β1 treated mice and no EGFP+ vessels were observed (FIG. 36a-b). These studies indicate that prevention of stem cell homing to the tumor vasculature inhibits their differentiation into vascular endothelium.

Example 24

Integrin α4β1-Antibody Inhibits Bone Marrow Stem Cell Migration to Neovasculature In Vivo The above data suggested that integrin α4β1 mediates the homing of stem cells arising directly from the bone marrow to tumors. To evaluate this, mice were transplanted with bone marrow from Tie2Lac Z mice. In these mice, bone marrow derived cells that differentiate into endothelium in vivo express beta-galactosidase under the control of the promoter of endothelial protein Tie2. Angiogenesis was stimulated in these mice by implantation of growth factor reduced Matrigel saturated with VEGF or bFGF. These growth factors induced an angiogenic response as well as the horning of beta galactosidase positive cells (FIG. 36c-d). Treatment of mice with anti-α4β1, but not anti-β2 integrin, antibodies, completely blocked the incorporation of beta-galactosidase positive cells into Matrigel (FIG. 36c-d). In control-treated animals, a majority of the beta-galactosidase positive cells incorporated into the neovasculature (arrows), as determined by anti-CD31 (red) and anti-beta galactosidase (green) immunostaining (FIG. 36e-f). Importantly, antagonists of α4β1 completely blocked this incorporation (FIG. 36e-f). Taken together, these studies indicate that α4β1, but not β2 integrin, potentiates stem cell trafficking by promoting their attachment to the neovasculature in remodeling tissues.

The invention claimed is:

1. A method for detecting an altered level of hematopoietic progenitor cell adhesion to target tissue, comprising:
 a) providing:
  i) a population of cells comprising hematopoietic progenitor cells that express integrin α4β1,
  ii) target tissue that is not bone marrow endothelial tissue, and
  iii) one or more agent that alters specific binding of integrin α4β1 to an integrin α4β1 ligand,
 b) treating one or more of said population of cells and said target tissue with said agent under conditions for specific binding of said integrin α4β1 with said integrin α4β1 ligand, wherein said treating is in vivo in a mammalian subject having a non-angiogenic disease, and
 c) detecting an altered level of adhesion of said hematopoietic progenitor cells to said target tissue that is not bone marrow endothelial tissue.

2. The method of claim 1, wherein said treating further comprises altering the level of trans-endothelial migration of said hematopoietic progenitor cells.

3. The method of claim 1, wherein said treating further comprises altering the level of differentiation of said hematopoietic progenitor cells into a second cell type.

4. The method of claim 3, wherein said second cell type is not a bone marrow endothelial cell.

5. The method of claim 4, wherein said second cell type comprises one or more of mesenchymal cell, epithelial cell, muscle cell, neuronal cell, immune cell, melanocyte cell, myoepithelial cell, and embryonic cell.

6. The method of claim 1, wherein said target tissue comprises one or more of vascular endothelial, muscle, neuronal, tumor, inflammatory, peripheral blood, cord blood, heart, ocular, skin, synovial, tumor, lung, breast, prostate, cervical, pancreatic, colon, ovarian, stomach, esophageal, mouth, tongue, gum, skin, liver, bronchial, cartilage, testis, kidney, endometrium, uterus, bladder, spleen, thymus, thyroid, brain, neuron, gall bladder, ocular, and joint tissues.

7. The method of claim 1, wherein said tissue is injured.

8. The method of claim 1, wherein said tissue is ischemic.

9. The method of claim 1, wherein said target tissue comprises fibronectin.

10. The method of claim 1, wherein said target tissue comprises vascular tissue.

11. The method of claim 1, wherein said mammalian subject is human.

12. The method of claim 1, wherein said agent comprises an antibody.

13. The method of claim 12, wherein said antibody comprises an anti-integrin α4β1 antibody.

14. The method of claim 12, wherein said antibody comprises an anti-vascular cell adhesion molecule antibody.

15. The method of claim 12, wherein said antibody comprises an anti-fibronectin antibody.

16. The method of claim 1, wherein said ligand comprises vascular cell adhesion molecule (VCAM).

17. The method of claim 1, wherein said ligand comprises fibronectin.

18. A method for detecting an altered level of hematopoietic progenitor cell adhesion to target tissue, comprising:
 a) providing:
  i) a population of cells comprising hematopoietic progenitor cells that express integrin α4β1,
  ii) target tissue that is not bone marrow endothelial tissue, and
  iii) one or more agent that alters specific binding of integrin α4β1 to an integrin α4β1 ligand,
 b) treating one or more of said population of cells and said target tissue with said agent under conditions that alter adhesion of said hematopoietic progenitor cell adhesion to target tissue, wherein said treating is in vivo in a mammalian subject having a non-angiogenic disease, and
 c) detecting an altered level of adhesion of said hematopoietic progenitor cells to said target tissue that is not bone marrow endothelial tissue.

19. A method for detecting an altered level of hematopoietic progenitor cell adhesion to target tissue, comprising:
 a) providing:
  i) a population of cells comprising hematopoietic progenitor cells that express integrin α4β1,
  ii) target tissue that is not bone marrow endothelial tissue, and
  iii) one or more agent that alters specific binding of integrin α4β1 to an integrin α4β1 ligand,
 b) treating one or more of said population of cells and said target tissue with said agent under conditions for specific binding of said integrin α4β1 with said integrin α4β1 ligand, wherein said treating is in vivo in a mammalian subject having a non-angiogenic disease that is selected from the group consisting of fibrosis and atherosclerosis, and
 c) detecting an altered level of adhesion of said hematopoietic progenitor cells to said target tissue that is not bone marrow endothelial tissue.

* * * * *